US012590118B2

(12) United States Patent
Li et al.

(10) Patent No.: US 12,590,118 B2
(45) Date of Patent: Mar. 31, 2026

(54) SALT AND CRYSTAL FORM OF STEROID DERIVATIVE REGULATOR

(71) Applicants: Shanghai Hansoh Biomedical Co., Ltd., Shanghai (CN); Jiangsu Hansoh Pharmaceutical Group Co., Ltd., Lianyungang (CN)

(72) Inventors: Zongbin Li, Shanghai (CN); Yuanzhuo Kuang, Shanghai (CN); Linsong Guo, Shanghai (CN)

(73) Assignees: Shanghai Hansoh Biomedical Co., Ltd., Shanghai (CN); Jiangsu Hansoh Pharmaceutical Group Co., Ltd., Lianyungang (CN)

( * ) Notice: Subject to any disclaimer, the term of this patent is extended or adjusted under 35 U.S.C. 154(b) by 999 days.

(21) Appl. No.: 17/597,919

(22) PCT Filed: Aug. 5, 2020

(86) PCT No.: PCT/CN2020/107061
§ 371 (c)(1),
(2) Date: Jan. 28, 2022

(87) PCT Pub. No.: WO2021/023213
PCT Pub. Date: Feb. 11, 2021

(65) Prior Publication Data

US 2022/0275020 A1 Sep. 1, 2022

(30) Foreign Application Priority Data

Aug. 7, 2019 (CN) ......................... 201910726659.8

(51) Int. Cl.

| | |
|---|---|
| ***C07J 43/00*** | (2006.01) |
| ***C07D 231/12*** | (2006.01) |
| ***C07D 231/14*** | (2006.01) |
| ***C07D 249/04*** | (2006.01) |
| ***C07D 257/04*** | (2006.01) |
| ***C07D 403/06*** | (2006.01) |
| ***C07D 403/08*** | (2006.01) |
| ***C07D 413/04*** | (2006.01) |
| ***C07J 53/00*** | (2006.01) |
| *A61K 31/58* | (2006.01) |
| *A61P 25/00* | (2006.01) |
| *A61P 25/24* | (2006.01) |

(52) U.S. Cl.
CPC ......... *C07J 43/003* (2013.01); *C07B 2200/13* (2013.01)

(58) Field of Classification Search
CPC .. C07J 43/003; C07B 2200/13; C07D 231/12; C07D 231/14; C07D 249/04; C07D 257/04; C07D 403/06; C07D 403/08; C07D 413/04
See application file for complete search history.

(56) References Cited

U.S. PATENT DOCUMENTS 10,435,431 B2 * 10/2019 Upasani ................. C07J 31/006
12,139,508 B2 * 11/2024 Su ............................. C07J 9/00

FOREIGN PATENT DOCUMENTS

| | | | |
|---|---|---|---|
| CN | 104136452 | A | 11/2014 |
| CN | 105339381 | A | 2/2016 |
| CN | 110088091 | A | 8/2019 |
| WO | WO-9303732 | A1 | 3/1993 |
| WO | WO-9521617 | A1 | 8/1995 |
| WO | WO-03077919 | A1 | 9/2003 |
| WO | WO-2015027227 | A1 | 2/2015 |
| WO | WO-2015180679 | A1 | 12/2015 |
| WO | WO-2014169833 | A9 | 3/2016 |
| WO | WO-2016061537 | A1 | 4/2016 |

(Continued)

OTHER PUBLICATIONS

Dorwald F. A. Side Reactions in Organic Synthesis, 2005, Wiley: VCH, Weinheim p. IX of Preface (Year: 2005).*

(Continued)

*Primary Examiner* — Bruck Kifle
*Assistant Examiner* — Kevin S Martin
(74) *Attorney, Agent, or Firm* — Foley Hoag LLP; Dana M. Gordon; Alexander J. Chatterley

(57) ABSTRACT

The present invention relates to a steroid derivative regulator, in particular to a compound of formula (I), a salt and crystal form thereof, a preparation method therefor, a pharmaceutical composition containing a therapeutically effective amount of the crystal form, and an application thereof as a $GABA_A$ receptor regulator in treatment of depression, convulsions, Parkinsonism and nervous system diseases.

(I)

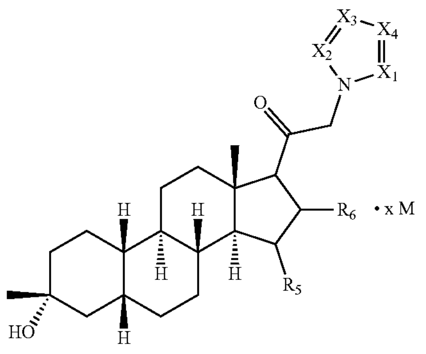

14 Claims, 11 Drawing Sheets

(56) References Cited

FOREIGN PATENT DOCUMENTS

| | | | | | |
|---|---|---|---|---|---|
| WO | WO-2016084790 | A1 | | 6/2016 | |
| WO | WO-2018013615 | A1 | | 1/2018 | |
| WO | WO-2019113494 | A1 | | 6/2019 | |
| WO | WO-2019126741 | A1 | | 6/2019 | |
| WO | WO-2019154247 | A1 | | 8/2019 | |
| WO | WO-2019154257 | A1 | | 8/2019 | |
| WO | WO-2021023213 | A1 | | 2/2021 | |
| WO | WO-2021195301 | A1 | * | 9/2021 | .............. A61P 31/14 |

OTHER PUBLICATIONS

"International Application No. PCT/CN2020/107061, International Search Report and Written Opinion mailed Nov. 5, 2020", (Nov. 5, 2020), 20 pgs.

* cited by examiner

SALT AND CRYSTAL FORM OF STEROID DERIVATIVE REGULATOR

PRIORITY CLAIM TO RELATED APPLICATIONS

This application is a U.S. national stage filing under 35 U.S.C. § 371 from International Application No. PCT/CN2020/107061, filed on 5 Aug. 2020, and published as WO2021/023213 on 11 Feb. 2021, which claims the benefit under 35 U.S.C. § 119 to Chinese Application No. 201910726659.8, filed 7 Aug. 2019, the benefit of priority of each of which is claimed herein, and which applications and publication are hereby incorporated herein by reference in their entirety.

FIELD OF THE INVENTION

The present invention belongs to the field of drug synthesis, and in particular relates to a salt of a steroid derivative regulator, a crystal form thereof, a method for preparing the same, and a use thereof.

BACKGROUND OF THE INVENTION $GABA_A$ receptor is a chemically-gated channel on the cell membrane and belongs to ionic receptors. $GABA_A$ receptor is widely distributed in the nervous system, and can bind to inhibitory neurotransmitter GABA (gamma-aminobutyric acid), leading to the opening of chloride channels and inhibition of neurons. $GABA_A$ receptor regulator (tetrahydroprogesterone) is a positive regulator of $GABA_A$ receptor. The binding of tetrahydroprogesterone to intrasynaptic $GABA_A$ receptor regulator can increase the opening frequency of chloride channel on the receptor and the influx of chloride ion, thereby increasing the Phasic current, producing a rapid inhibitory effect, reducing nerve excitability, and providing an anti-anxiety and anti-depression effect. The binding of tetrahydroprogesterone to extrasynaptic $GABA_A$ receptor provides a continuous chloride ion current, and mediates a lasting and sustained inhibitory effect. Tetrahydroprogesterone can also increase the content of brain derived neurotrophic factor (BDNF), promote the regeneration of hippocampal neurons, and provide a neuroprotective effect, thereby improving anxiety and depression symptoms; but the specific mechanism of action is not clear yet.

Major depressive disorder (MDD) is a common, chronic and recurrent disease. The burden and adverse consequence caused by it are becoming more and more serious. In the past 40 years, the research and clinical application of antidepressants have greatly developed. However, most antidepressants (fluoxetine, paroxetine, sertraline, fluvoxamine, citalopram, etc.) take 2 to 4 weeks to have an effect. The clinical treatment of major depressive disorder patients, especially patients with suicidal tendency, often needs to be prompt and rapid, thus there is an urgent need to develop fast-acting antidepressants.

In the past two decades, there has been little innovation in the research and development of depression treatment. The development goal of $GABA_A$ receptor regulators is to change the expectation of patients by changing the treatment regimen of MDD. If successfully developed, the $GABA_A$ receptor regulator may become the first drug that provides a truly new mechanism of action for the treatment of depression in more than two decades. At present, foreign pharmaceutical companies, including Sage Therapeutics and Marinus etc., are doing their best to develop $GABA_A$ receptor regulators.

Published patent applications related to $GABA_A$ receptor regulators include: WO2003077919, WO2014169833, WO2016061537, WO2015180679, and WO2015027227.

$GABA_A$ receptor regulators, as a popular target in the pharmaceutical industry, currently have a good application prospect.

First, $GABA_A$ receptor regulators can be applied to major depressive disorder (MDD). The annual incidence of MDD in China is about 2%, thus there is a huge market potential.

Second, existing antidepressants take a long time, commonly 3 to 4 weeks, to have an effect, have a high failure rate up to 40%, and require long-term medication. $GABA_A$ receptor regulators can provide a significant antidepressant effect within 24 hours, and the effect can last for several days to two weeks.

Third, $GABA_A$ receptor regulators can meet the treatment need of MDD patients with oral administration once a day.

The PCT patent applications (PCT/CN2019/074134 and PCT/CN2019/074108) of Jiangsu Hansoh Pharmaceutical Group Co., Ltd. disclose the structure of a series of steroid derivative regulators. In the subsequent research and development, in order to obtain a product that can be readily processed, filtered and dried and to achieve features such as convenient storage and long-term stability, the present invention has conducted a comprehensive study on the salts of the above substances, and is dedicated to obtaining the most suitable salts and crystal forms.

SUMMARY OF THE INVENTION

The objective of the present invention is to provide an acid addition salt of formula (Ia), having a structure as shown in formula (Ia):

(Ia)

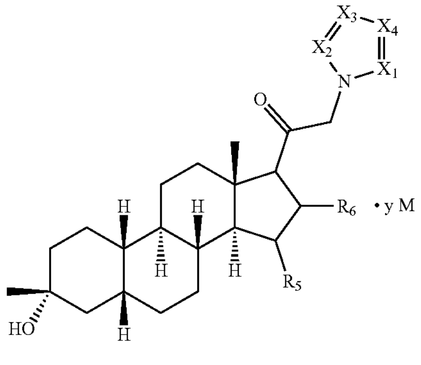

wherein:

$X_1$ is selected from the group consisting of $CR_1$ and N, and preferably N;

$X_2$ is selected from the group consisting of $CR_2$ and N;

$X_3$ is selected from the group consisting of $CR_3$ and N;

$X_4$ is selected from the group consisting of $CR_4$ and N;

$R_1$ and $R_2$ are each independently selected from the group consisting of hydrogen, deuterium, cyano, halogen, nitro, amino, $C_{1-8}$ alkyl, $C_{1-8}$ haloalkyl, $C_{1-8}$ alkoxy, $C_{1-8}$ hydroxyalkyl, cyano-substituted $C_{1-8}$ alkyl, $C_{3-8}$ cycloalkyl, cyano-substituted $C_{3-8}$ cycloalkyl, 3 to 8 membered heterocyclyl, $C_{6-10}$ aryl and 5 to 10 membered heteroaryl;

$R_3$ and $R_4$ are each independently selected from the group consisting of hydrogen, deuterium, cyano, halogen, nitro, amino, $C_{1-8}$ alkyl, $C_{1-8}$ haloalkyl, $C_{1-8}$ alkoxy, $C_{1-8}$ hydroxyalkyl, cyano-substituted $C_{1-8}$ alkyl, $C_{3-8}$ cycloalkyl, cyano-substituted $C_{3-8}$ cycloalkyl, 3 to 8 membered heterocyclyl, $C_{6-10}$ aryl, 5 to 10 membered heteroaryl, —$(CH_2)_nR_a$, —$(CH_2)_nOR_a$, —$(CH_2)_nSR_a$, —$(CH_2)_nC(O)R_a$, —$S(O)R_a$, —$S(O)_2R_a$, —S(O)(=NH)$R_a$, —C(O)$OR_a$ and —C(O)O$(CH_2)_nNR_aR_b$, wherein the $C_{1-8}$ alkyl, $C_{2-8}$ alkenyl, $C_{2-8}$ alkynyl, $C_{1-8}$ haloalkyl, $C_{1-8}$ hydroxyalkyl, cyano-substituted $C_{1-8}$ alkyl, $C_{1-8}$ alkoxy, $C_{3-8}$ cycloalkyl, cyano-substituted $C_{3-8}$ cycloalkyl, 3 to 8 membered heterocyclyl, $C_{6-10}$ aryl and 5 to 10 membered heteroaryl can be each optionally further substituted;

$R_5$ and $R_6$ are each independently selected from the group consisting of hydrogen, deuterium, cyano, halogen, nitro, amino, $C_{1-8}$ alkyl, $C_{2-8}$ alkenyl, $C_{2-8}$ alkynyl, $C_{1-8}$ haloalkyl, $C_{1-8}$ alkoxy, $C_{1-8}$ hydroxyalkyl, cyano-substituted $C_{1-8}$ alkyl, $C_{1-8}$ alkylthio, $C_{3-8}$ cycloalkyl, cyano-substituted $C_{3-8}$ cycloalkyl, 3 to 8 membered heterocyclyl, $C_{6-10}$ aryl, 5 to 10 membered heteroaryl, —$(CH_2)_nR_a$, —$(CH_2)_nOR_a$, —$S(O)R_a$, —$S(O)_2R_a$ and —$(CH_2)_nNR_aR_b$, wherein the $C_{1-8}$ alkyl, $C_{2-8}$ alkenyl, $C_{2-8}$ alkynyl, $C_{1-8}$ haloalkyl, $C_{1-8}$ hydroxyalkyl, cyano-substituted $C_{1-8}$ alkyl, $C_{1-8}$ alkoxy, $C_{3-8}$ cycloalkyl, cyano-substituted $C_{3-8}$ cycloalkyl, 3 to 8 membered heterocyclyl, $C_{6-10}$ aryl and 5 to 10 membered heteroaryl can be each optionally further substituted;

or, $R_5$ and $R_6$ together with the carbon atoms to which they are attached form a $C_{3-8}$ cycloalkyl or 3 to 8 membered heterocyclyl, wherein the $C_{3-8}$ cycloalkyl and 3 to 8 membered heterocyclyl can be each optionally further substituted;

wherein $R_5$ and $R_6$ are not hydrogen at the same time;

$R_a$ and $R_b$ are each independently selected from the group consisting of hydrogen, deuterium, halogen, cyano, hydroxy, amino, nitro, $C_{1-8}$ alkyl, $C_{1-8}$ alkoxy, $C_{1-8}$ hydroxyalkyl, $C_{1-8}$ deuterated alkyl, $C_{1-8}$ haloalkyl, $C_{3-8}$ cycloalkyl, 3 to 8 membered heterocyclyl, $C_{6-10}$ aryl and 5 to 10 membered heteroaryl, wherein the $C_{1-8}$ alkyl, $C_{1-8}$ deuterated alkyl, $C_{1-8}$ haloalkyl, $C_{3-8}$ cycloalkyl, 3 to 8 membered heterocyclyl, $C_{6-10}$ aryl and 5 to 10 membered heteroaryl can be each optionally further substituted;

M is an inorganic acid or organic acid, wherein the inorganic acid is selected from the group consisting of hydrochloric acid, sulfuric acid, nitric acid, hydrobromic acid, hydrofluoric acid, hydroiodic acid and phosphoric acid, and the organic acid is selected from the group consisting of 2,5-dihydroxybenzoic acid, 1-hydroxy-2-naphthoic acid, acetic acid, dichloroacetic acid, trichloroacetic acid, acetohydroxamic acid, adipic acid, benzenesulfonic acid, 4-chlorobenzenesulfonic acid, benzoic acid, 4-acetylaminobenzoic acid, 4-aminobenzoic acid, capric acid, caproic acid, caprylic acid, cinnamic acid, citric acid, cyclamic acid, camphorsulfonic acid, aspartic acid, camphor acid, gluconic acid, glucuronic acid, glutamic acid, erythorbic acid, lactic acid, malic acid, mandelic acid, pyroglutamic acid, tartaric acid, lauryl sulfuric acid, dibenzoyl tartaric acid, ethane-1,2-disulfonic acid, ethanesulfonic acid, formic acid, fumaric acid, galactonic acid, gentisic acid, glutaric acid, 2-ketoglutaric acid, glycolic acid, hippuric acid, isethionic acid, lactobionic acid, ascorbic acid, asparagic acid, lauric acid, camphor acid, maleic acid, malonic acid, D-tartaric acid, pamoic acid, methanesulfonic acid, 1,5-naphthalenedisulfonic acid, naphthalene-2-sulfonic acid, nicotinic acid, oleic acid, orotic acid, oxalic acid, palmitic acid, embonic acid, propionic acid, salicylic acid, 4-aminosalicylic acid, sebacic acid, stearic acid, succinic acid, thiocyanic acid, undecylenic acid, trifluoroacetic acid, benzenesulfonic acid, p-toluenesulfonic acid and L-malic acid; and y is selected from the group consisting of 0, 1, 2 and 3;

n is an integer from 0 to 6.

In a preferred embodiment of the present invention, in the acid addition salt of formula (Ia):

$R_1$ and $R_2$ are each independently selected from the group consisting of hydrogen, cyano, halogen, $C_{1-6}$ alkyl and $C_{3-6}$ cycloalkyl, and preferably hydrogen, cyano, halogen, $C_{1-3}$ alkyl and $C_{3-6}$ cycloalkyl;

$R_3$ and $R_4$ are each independently selected from the group consisting of hydrogen, cyano, halogen, nitro, $C_{1-6}$ alkyl, $C_{1-6}$ haloalkyl, $C_{1-6}$ hydroxyalkyl, cyano-substituted $C_{1-6}$ alkyl, $C_{3-6}$ cycloalkyl, cyano-substituted $C_{3-6}$ cycloalkyl, 5 or 6 membered heteroaryl, —$(CH_2)_nSR_a$, —$(CH_2)_nC(O)R_a$, —$S(O)R_a$, —$S(O)_2R_a$, —S(O)(=NH)$R_a$, —C(O)$OR_a$ and —C(O)O$(CH_2)_nNR_aR_b$;

$R_5$ is selected from the group consisting of hydrogen, cyano, halogen, $C_{1-6}$ alkyl, $C_{1-6}$ haloalkyl, $C_{1-6}$ hydroxyalkyl, cyano-substituted $C_{1-6}$ alkyl, $C_{1-6}$ alkoxy, $C_{1-6}$ alkylthio, $C_{3-6}$ cycloalkyl, cyano-substituted $C_{3-6}$ cycloalkyl, 3 to 6 membered heterocyclyl, $C_{6-10}$ aryl, 5 to 10 membered heteroaryl, —$(CH_2)_nR_a$, —$(CH_2)_nOR_a$, —$S(O)_2R_a$ and —$(CH_2)_nNR_aR_b$, wherein the 5 to 10 membered heteroaryl can be optionally further substituted;

$R_6$ is selected from the group consisting of hydrogen, halogen, cyano, $C_{1-6}$ alkyl and $C_{1-6}$ haloalkyl, and preferably hydrogen, halogen, cyano, $C_{1-3}$ alkyl and $C_{1-3}$ haloalkyl;

or, $R_5$ and $R_6$ together with the carbon atoms to which they are attached form a $C_{3-8}$ cycloalkyl, wherein the $C_{3-8}$ cycloalkyl can be optionally further substituted;

wherein $R_5$ and $R_6$ are not hydrogen at the same time;

$R_a$ and $R_b$ are each independently selected from the group consisting of hydrogen, halogen, cyano, nitro, $C_{1-6}$ alkyl, 3 to 6 membered heterocyclyl and 5 to 10 membered heteroaryl, wherein the $C_{1-6}$ alkyl, 3 to 6 membered heterocyclyl and 5 to 10 membered heteroaryl can be each optionally further substituted;

M is selected from the group consisting of hydrochloric acid, sulfuric acid, nitric acid, hydrobromic acid, phosphoric acid, methanesulfonic acid, 1,5-naphthalenedisulfonic acid and p-toluenesulfonic acid; and y is selected from the group consisting of 1 and 2;

n is an integer from 0 to 3.

In a preferred embodiment of the present invention, in the acid addition salt of formula (Ia):

$R_1$ and $R_2$ are each independently selected from the group consisting of hydrogen, fluorine, chlorine, cyano, methyl and cyclopropyl;

$R_3$ and $R_4$ are each independently selected from the group consisting of hydrogen, halogen, cyano, nitro, $C_{1-3}$ alkyl, cyano-substituted $C_{1-3}$ alkyl, halogen-substituted $C_{1-3}$ alkyl, $C_{1-3}$ hydroxyalkyl, $C_{3-6}$ cycloalkyl, cyano-substituted $C_{3-6}$ cycloalkyl, oxazolyl, —C(O)$R_a$, —$SC_{1-3}$ alkyl, —S(O)$C_{1-3}$ alkyl, —$S(O)_2C_{1-3}$ alkyl, —C(O)$OC_{1-3}$ alkyl, —S(O)(=NH)$C_{1-3}$ alkyl and —C(O)O$(CH_2)_nN(CH_3)C_{1-3}$ alkyl, and preferably hydrogen, fluorine, chlorine, cyano, nitro, trifluoromethyl, cyclopropyl, cyano-substituted cyclopropyl, cyano-substituted isopropyl, hydroxyisopropyl, oxazolyl, —C(O)$R_a$, —$SCH_3$, —S(O)$CH_3$, —$S(O)_2CH_3$, —C(O)$OCH_2CH_3$, —S(O)(=NH)$CH_3$ and —C(O)O$(CH_2)_2NCH_3(CH_3)$;

$R_5$ is selected from the group consisting of hydrogen, halogen, cyano, $C_{1-3}$ alkyl, $C_{1-3}$ haloalkyl, $C_{1-3}$ alkoxy, $C_{1-3}$ hydroxyalkyl, cyano-substituted $C_{1-3}$ alkyl, $C_{3-6}$ cycloalkyl, cyano-substituted $C_{3-6}$ cycloalkyl, 3 to 6 membered nitrogen-containing heterocyclyl, $C_{6-10}$ aryl, 5 to 10 membered heteroaryl, $C_{1-3}$ alkylthio, —$(CH_2)_n R_a$, —$(CH_2)_nOR_a$, —$S(O)_2R_a$ and —$(CH_2)_nN(R_a)_2$, and preferably hydrogen, fluorine, chlorine, cyano, methyl, ethyl, isopropyl, fluoromethyl, trifluoromethyl, methoxy, cyclopropyl, cyclobutyl, methyl-substituted pyrazolyl, phenyl, —$SCH_3$, —$(CH_2)_nR_a$, —$NC(CH_3)_2$, —$S(O)_2C(CH_3)_2$ and —$CH_2N(CH_3)_2$;

$R_6$ is selected from the group consisting of hydrogen, fluorine, cyano, methyl, ethyl and trifluoromethyl;

or, $R_5$ and $R_6$ together with the carbon atoms to which they are attached form a $C_{3-6}$ cycloalkyl, and preferably cyclopropyl, wherein the cyclopropyl is optionally substituted by fluorine;

$R_a$ is selected from the group consisting of hydrogen, nitro, $C_{1-3}$ alkyl, azetidinyl and pyrrolidinyl, wherein the azetidinyl and pyrrolidinyl are each optionally substituted by halogen, and preferably by fluorine;

M is selected from the group consisting of hydrochloric acid, sulfuric acid, methanesulfonic acid, p-toluenesulfonic acid, hydrobromic acid, nitric acid and 1,5-naphthalenedisulfonic acid, and preferably methanesulfonic acid;

y is 0, 1 or 2;

n is selected from the group consisting of 0, 1 and 2.

In a preferred embodiment of the present invention, the acid addition salt of formula (Ia) has a structure as shown in formula (IIa):

(IIa)

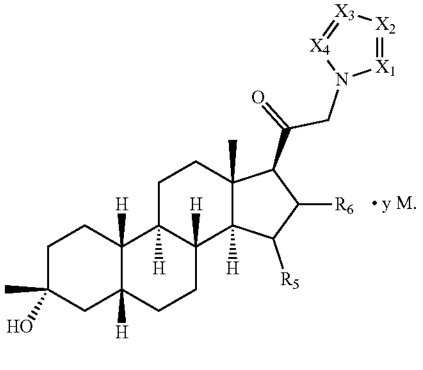

In a preferred embodiment of the present invention, the acid addition salt of formula (Ia) has a structure as shown in formula (IIIa):

(IIIa)

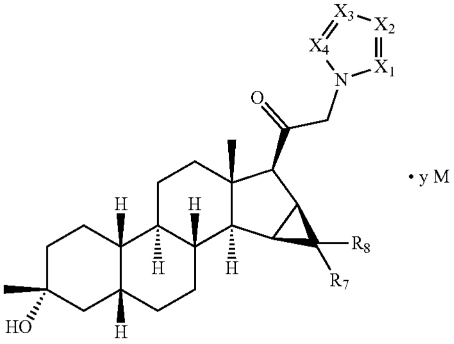

wherein:

$R_7$ and $R_8$ are each independently selected from the group consisting of hydrogen, fluorine, chlorine, bromine and methyl, and preferably hydrogen and fluorine.

In a preferred embodiment of the present invention, the acid addition salt of formula (Ia) has a structure as shown in formula (IVa):

(IVa)

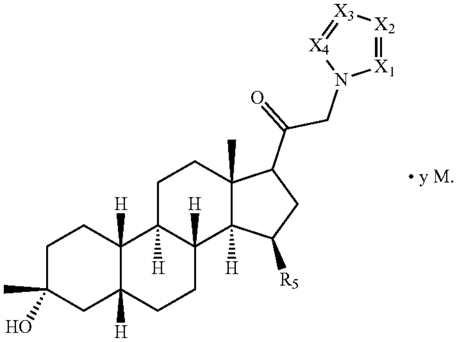

In a preferred embodiment of the present invention, the acid addition salt of formula (Ia) has a structure as shown in formula (Va):

(Va)

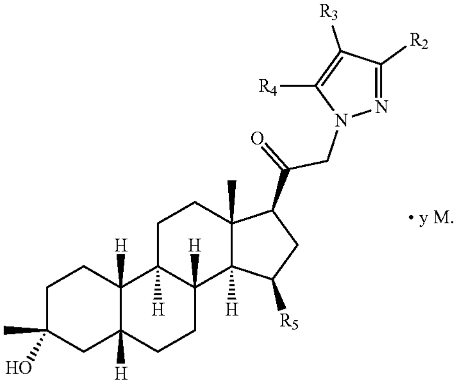

In a preferred embodiment of the present invention, the acid addition salt of formula (Ia) has a structure as follows:
1
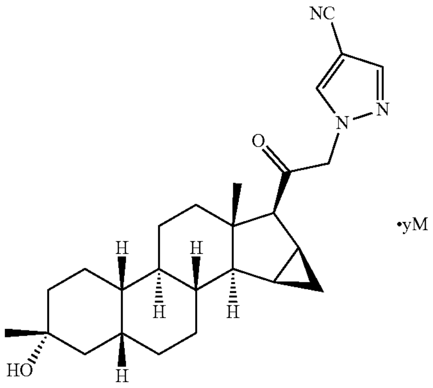
2
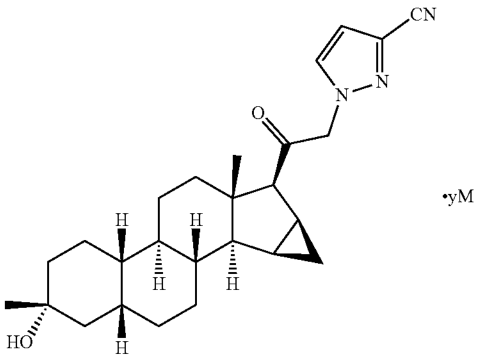
3
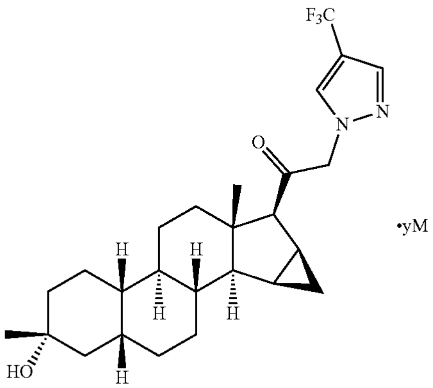
4
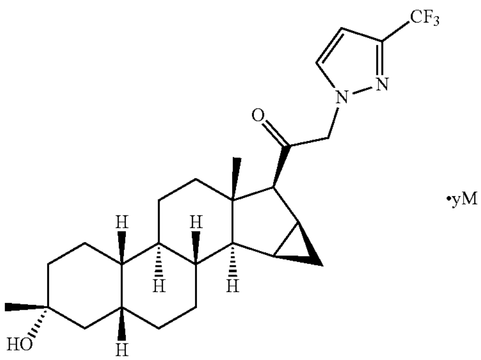
-continued
5
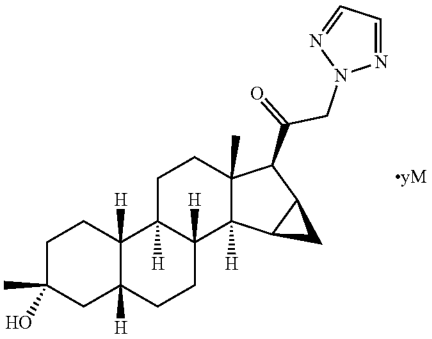
6
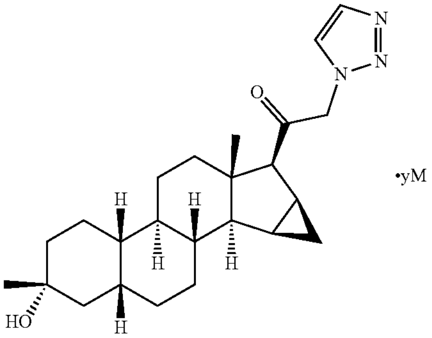
7
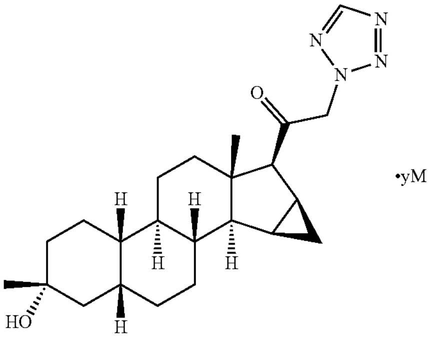
8
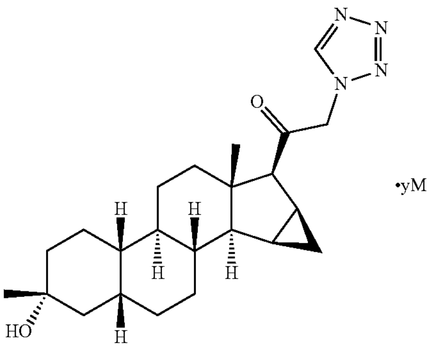

-continued
9
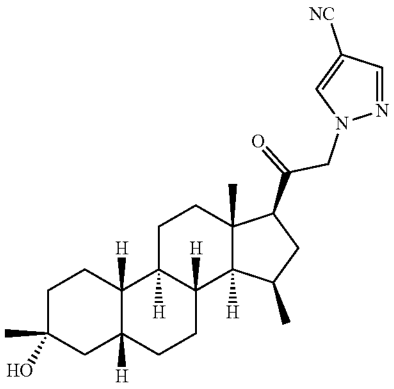
•yM
10
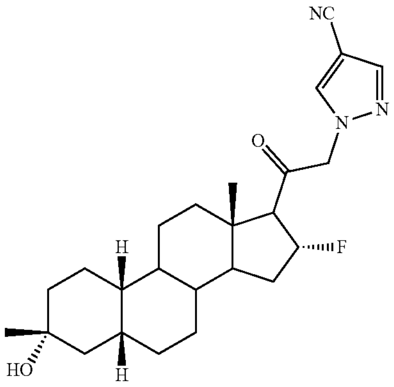
•yM
11
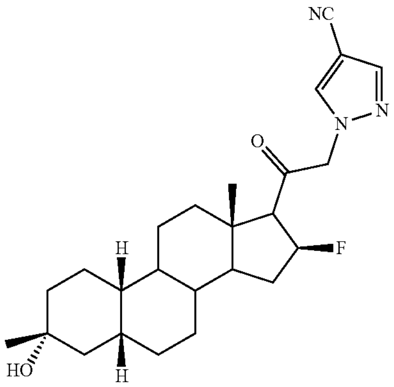
•yM
12
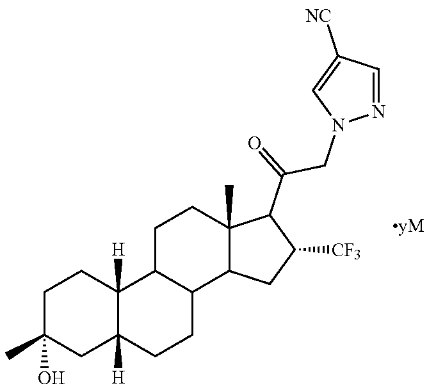
•yM
-continued
13
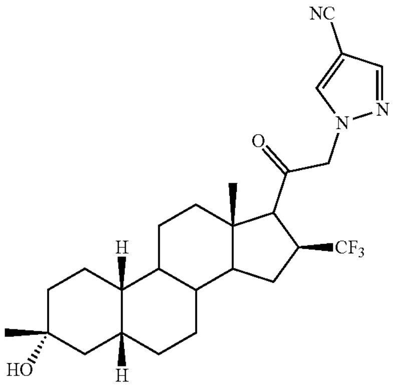
•yM
14
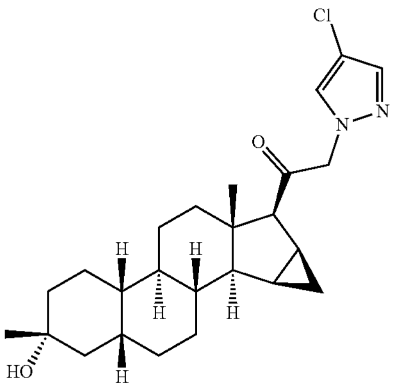
•yM
15
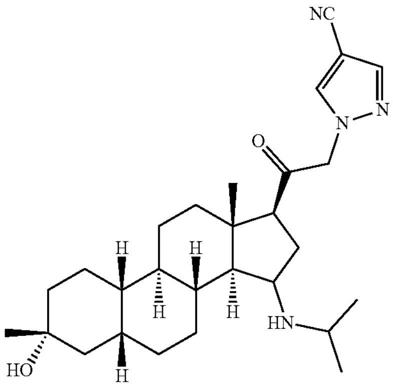
•yM
16
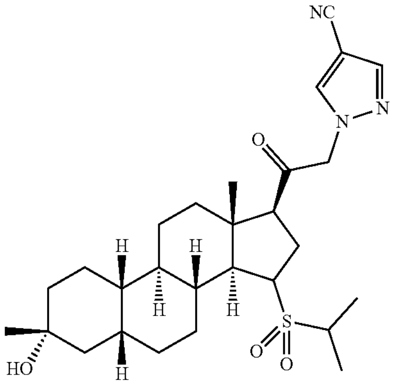
•yM -continued
17
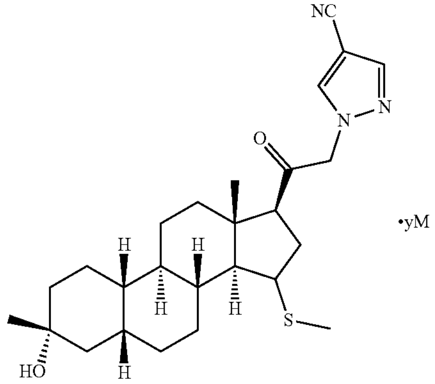
18
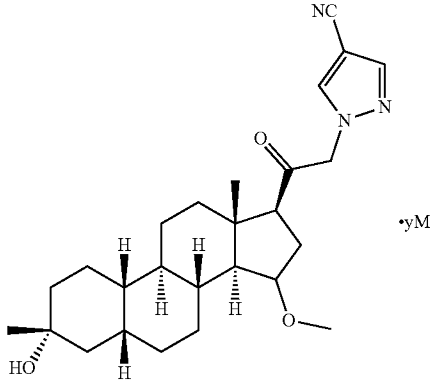
19
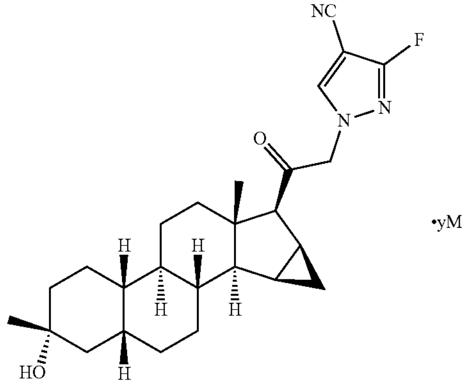
20
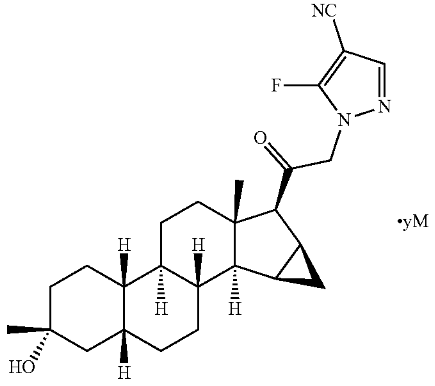
-continued
21
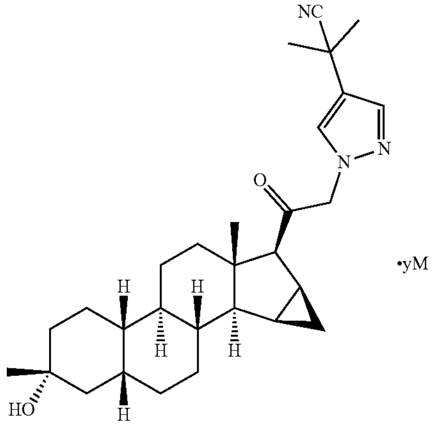
22
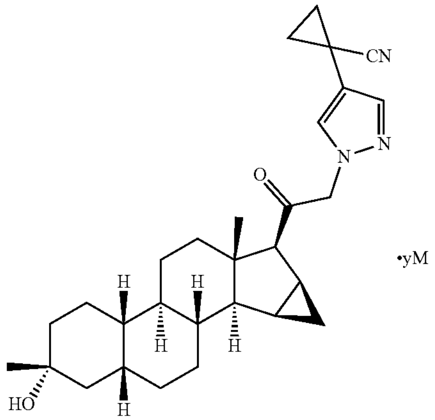
23
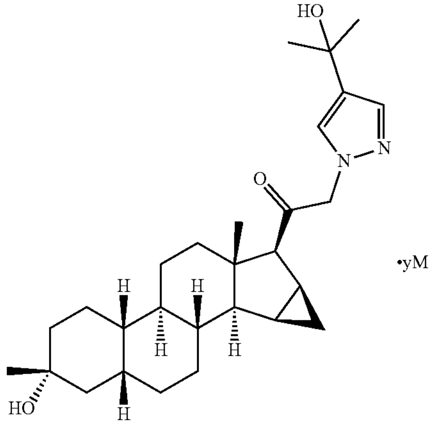

-continued
24
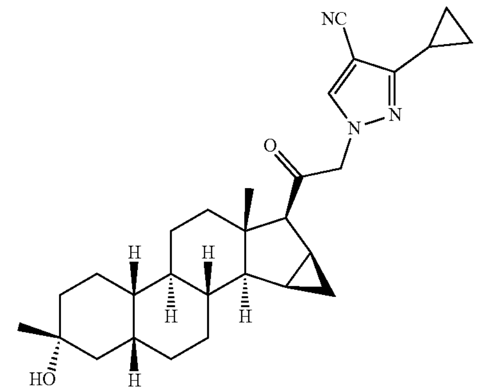
•yM
25
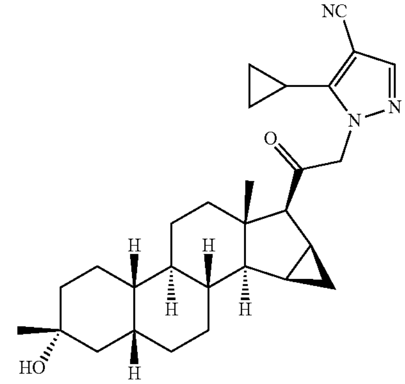
•yM
26
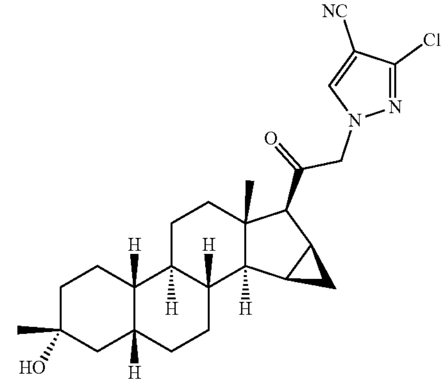
•yM
27
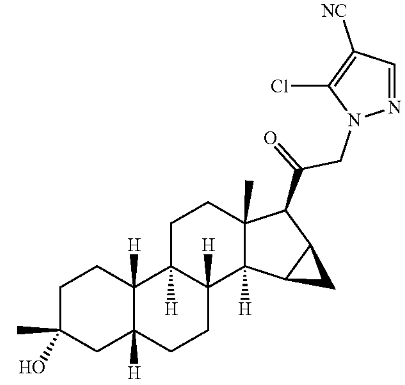
•yM
-continued
28
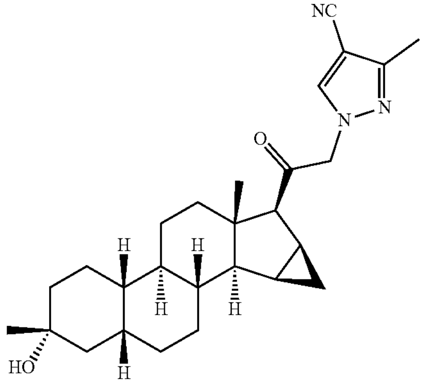
•yM
29
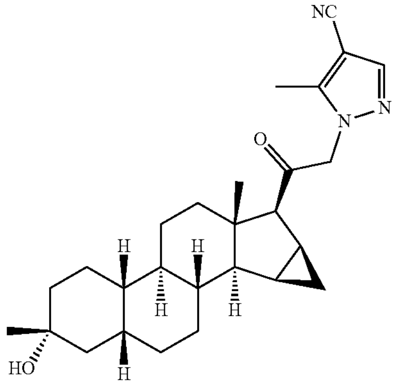
•yM
30
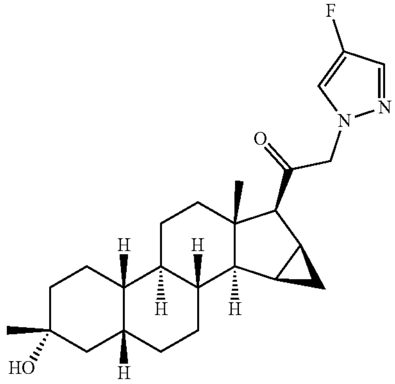
•yM
31
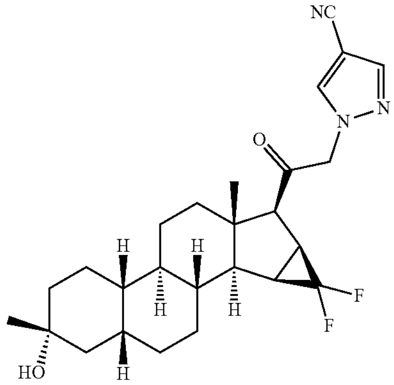
•yM -continued
32
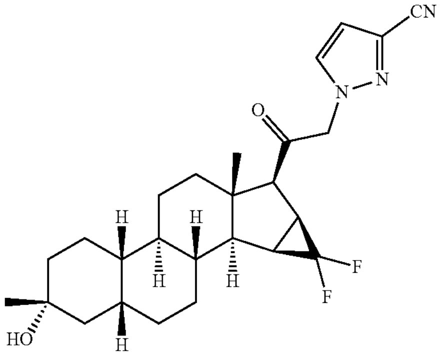
•yM
33
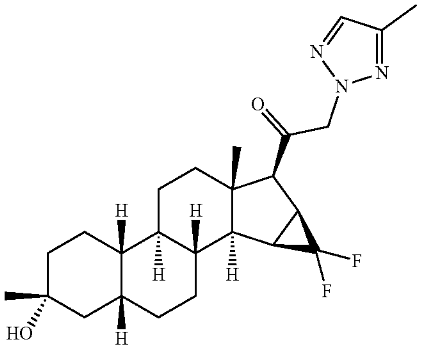
•yM
34
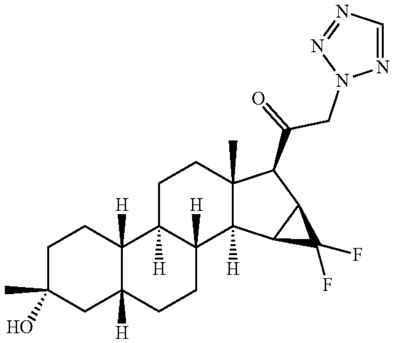
•yM
35
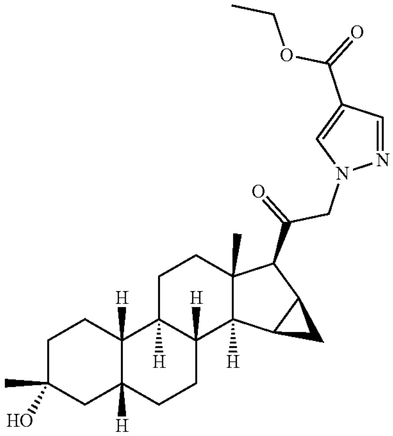
•yM
-continued
36
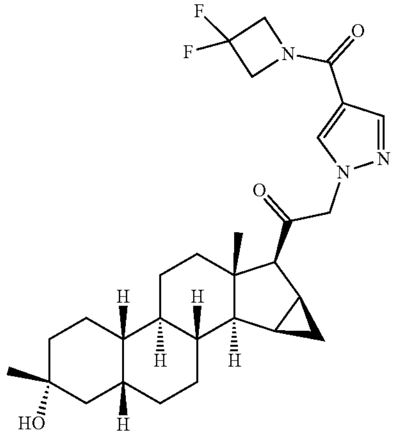
•yM
37
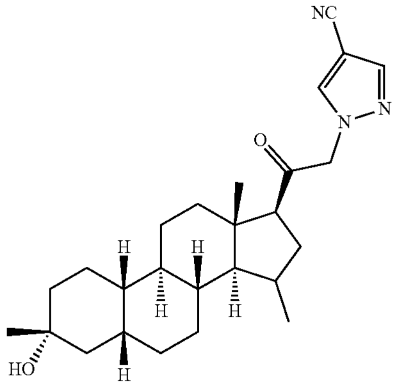
•yM
38
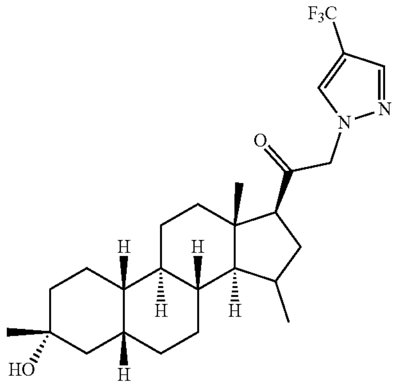
•yM
39
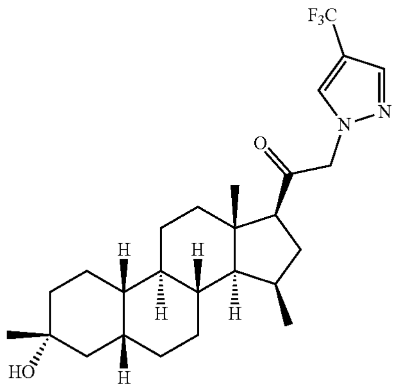
•yM -continued
40
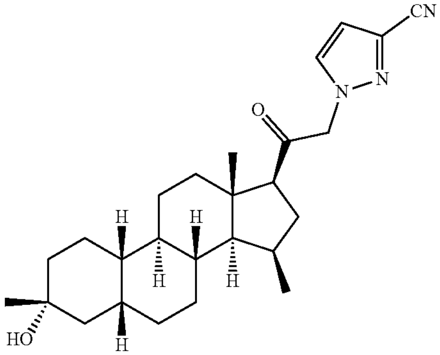
•yM
41
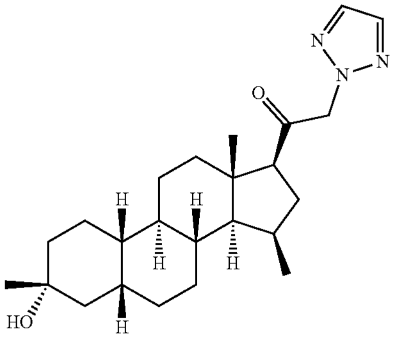
•yM
42
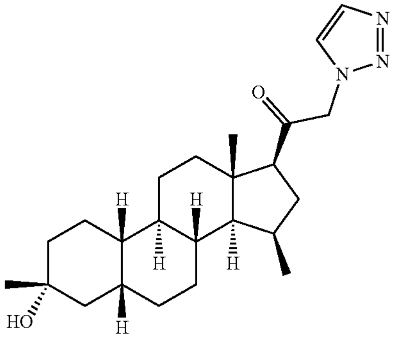
•yM
43
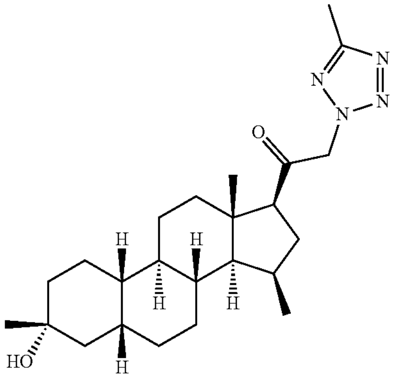
•yM
-continued
44
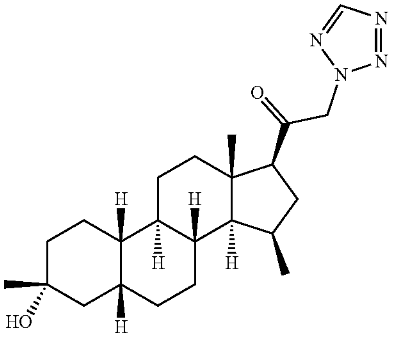
•yM
45
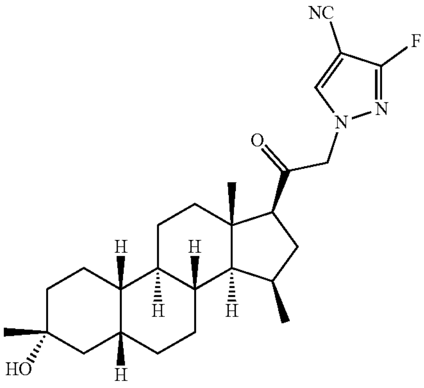
•yM
46
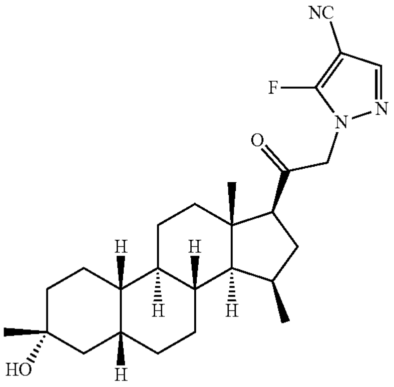
•yM
47
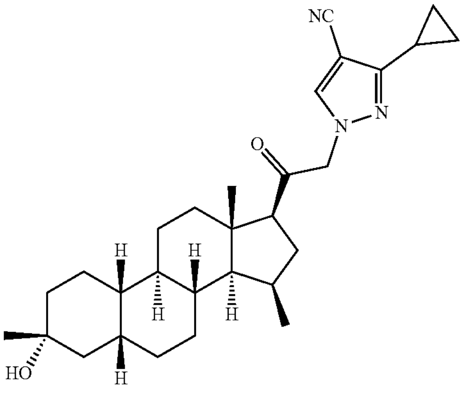
•yM -continued
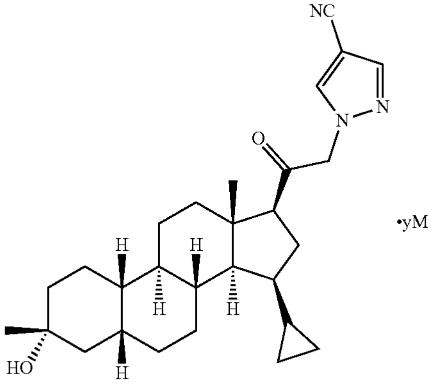
48
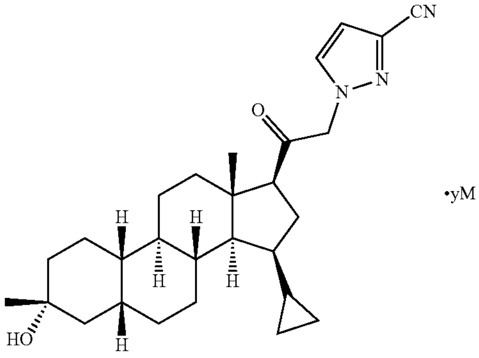
49
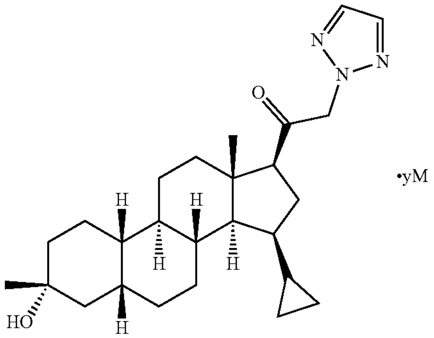
50
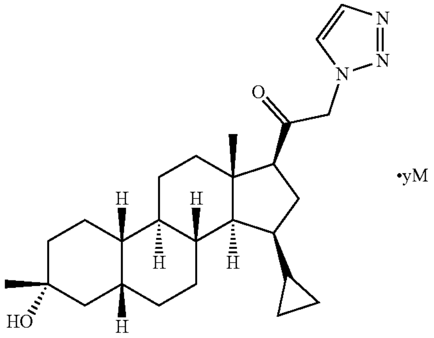
51
-continued
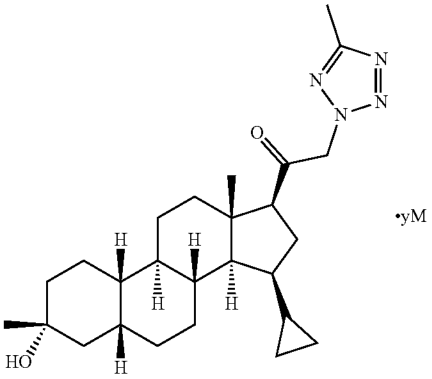
52
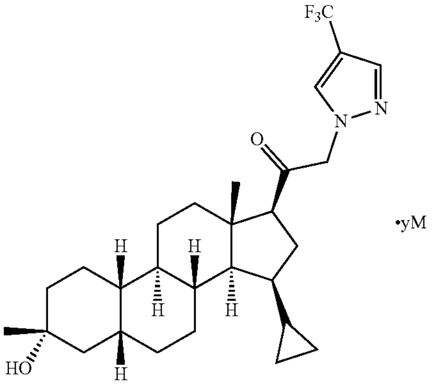
53
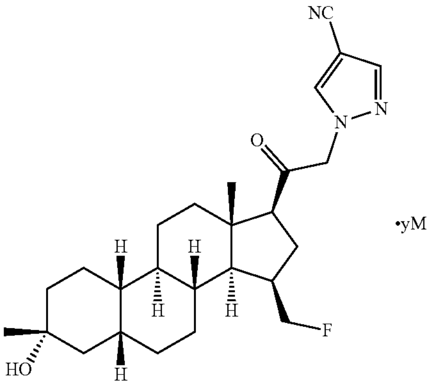
54
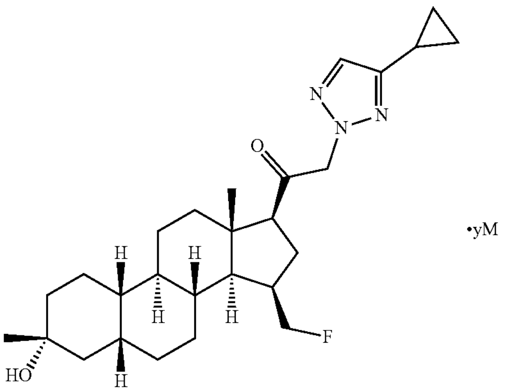
55

-continued
56
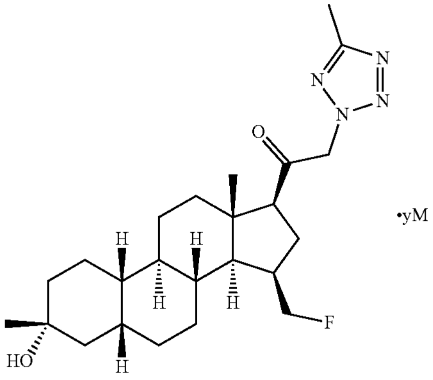
57
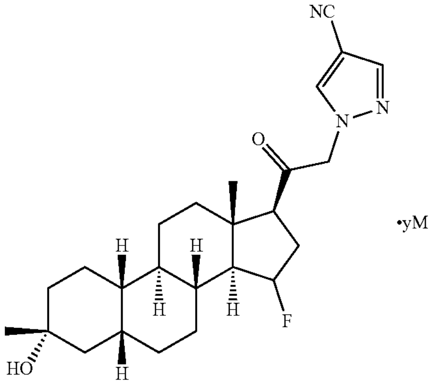
58
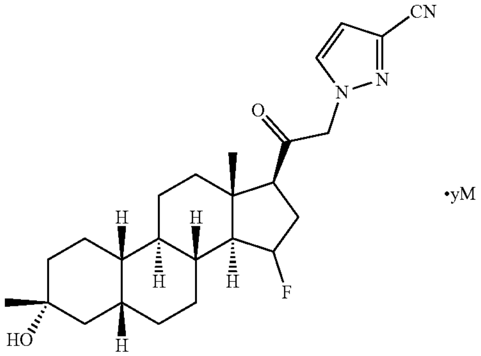
59
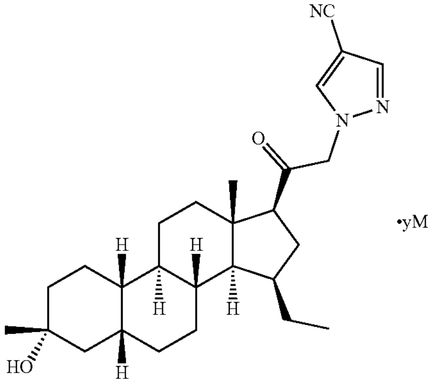
-continued
60
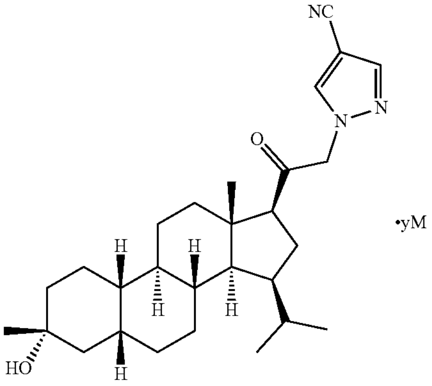
61
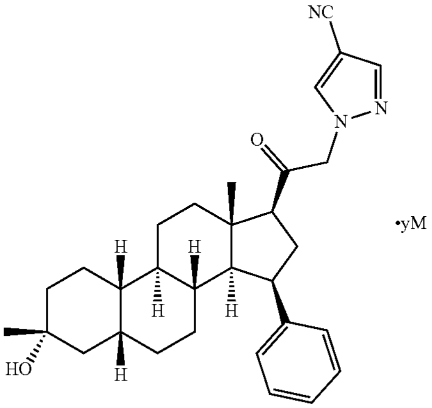
62
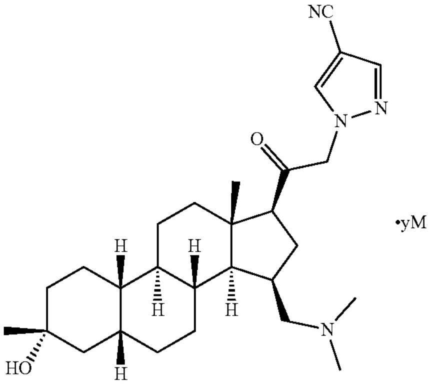
63
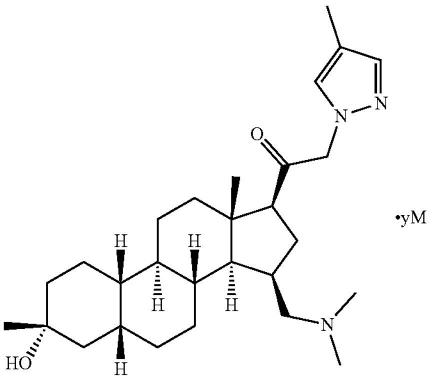

64
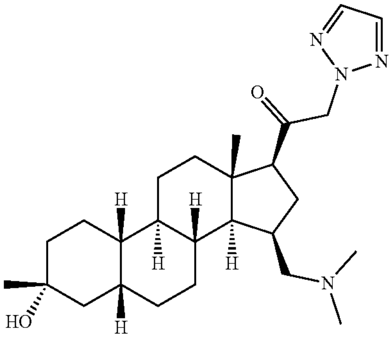
•yM
65
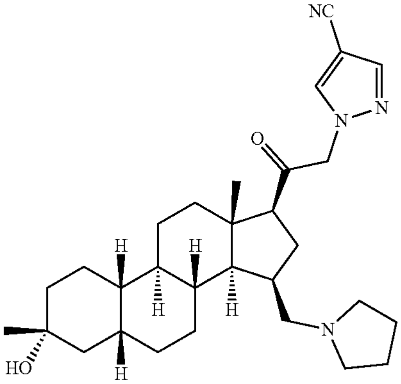
•yM
66
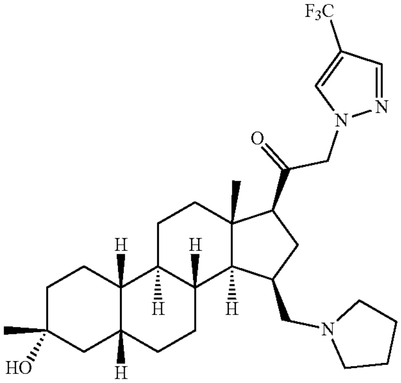
•yM
67
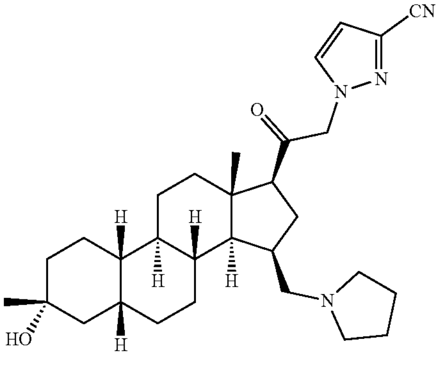
•yM
68
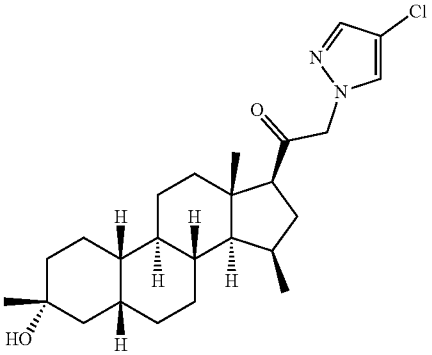
•yM
69
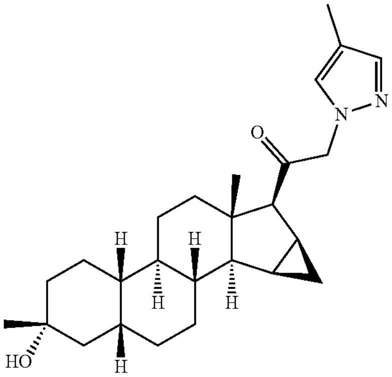
•yM
70
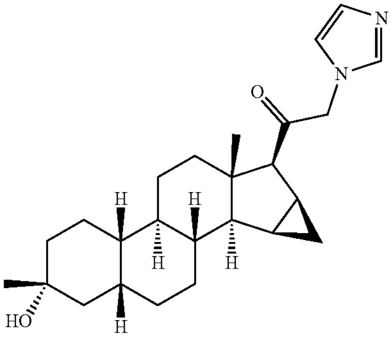
•yM
71
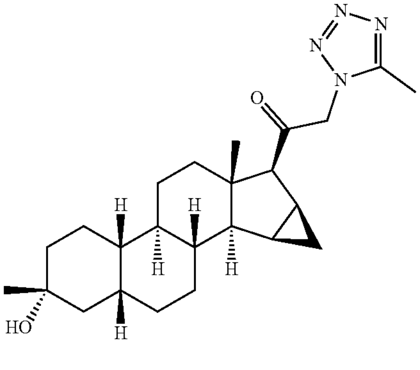
•yM -continued
72
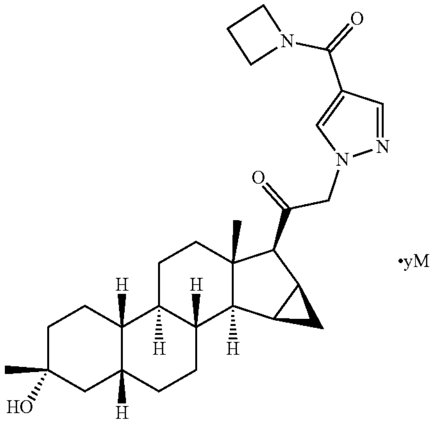
73
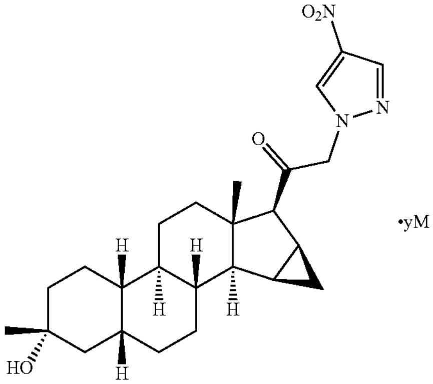
74
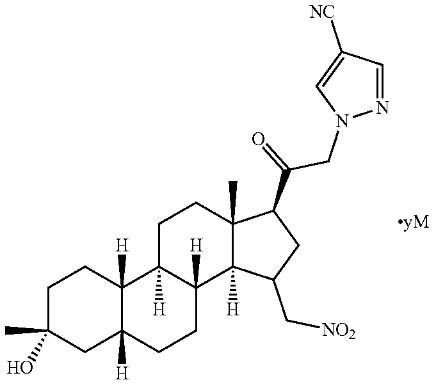
75
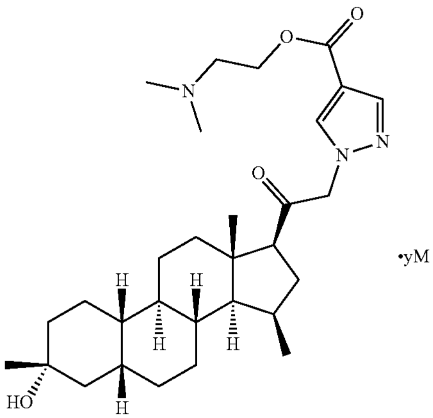
-continued
76
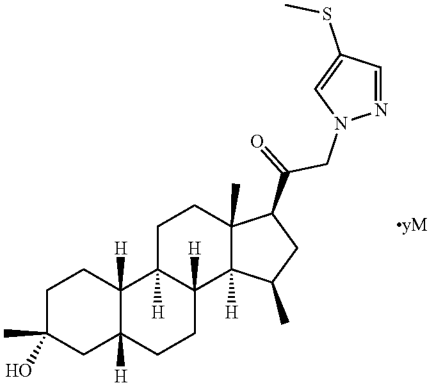
77
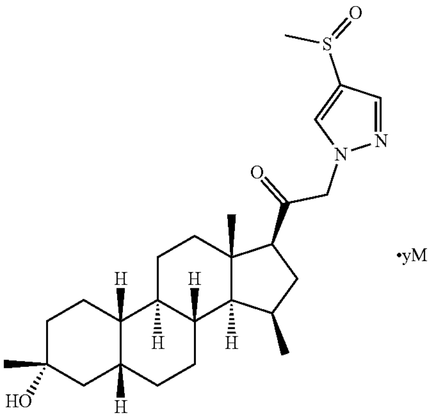
78
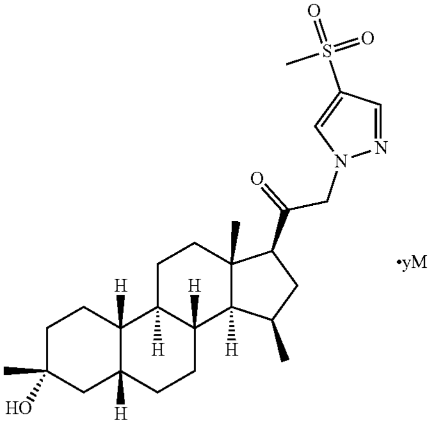

-continued
79
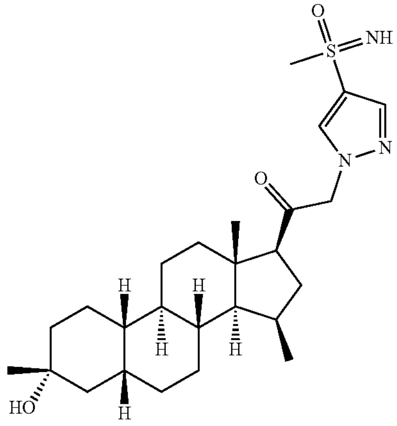
•yM
80
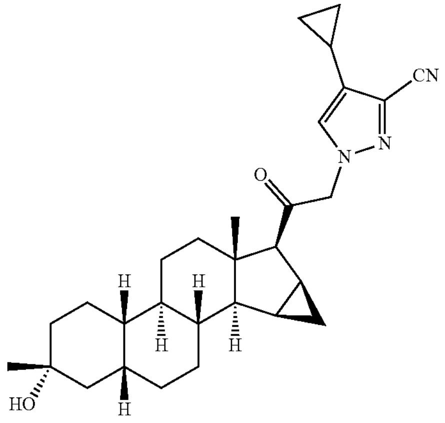
•yM
81
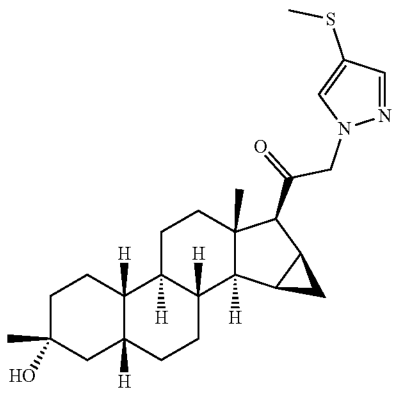
•yM
-continued
82
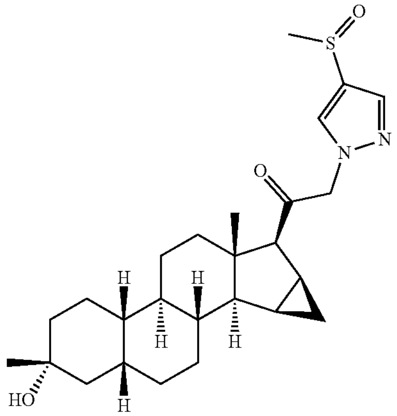
•yM
83
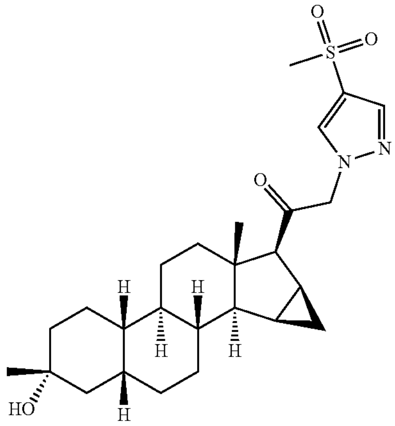
•yM
84
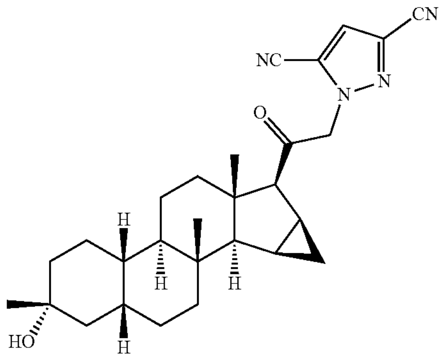
•yM
85
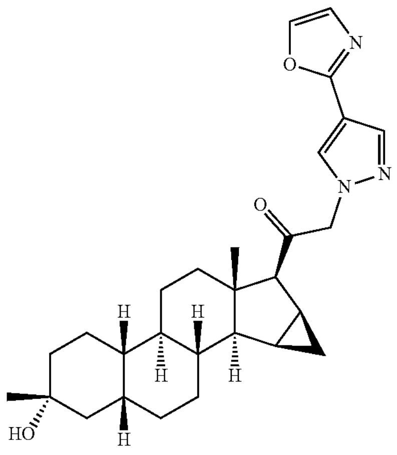
•yM -continued
86
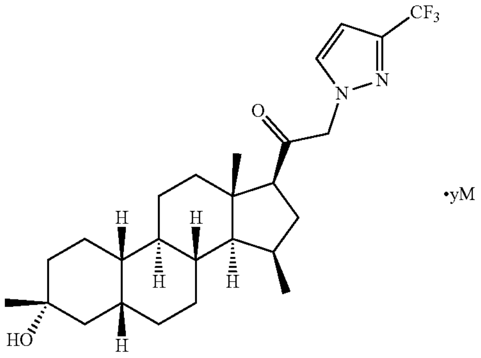
87
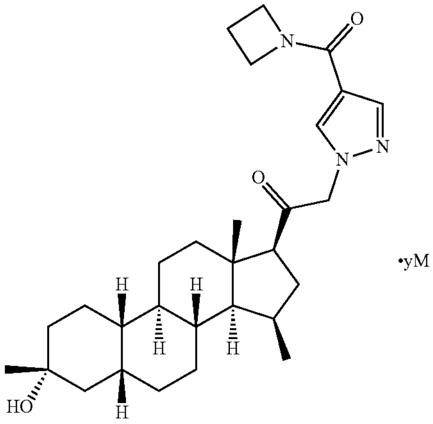
88
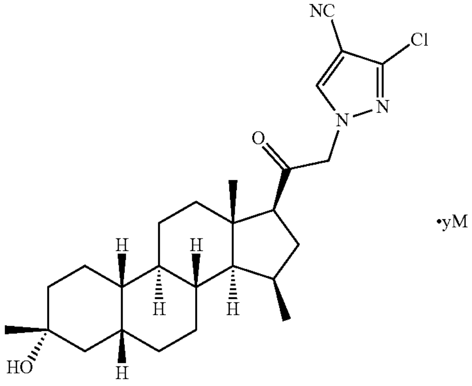
89
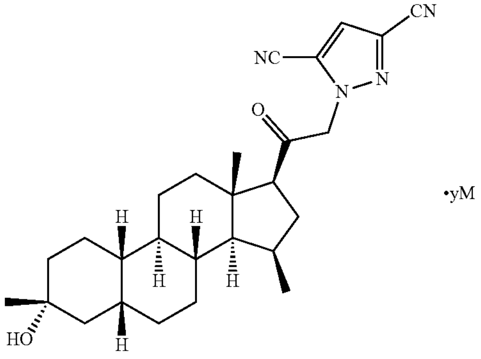
-continued
90
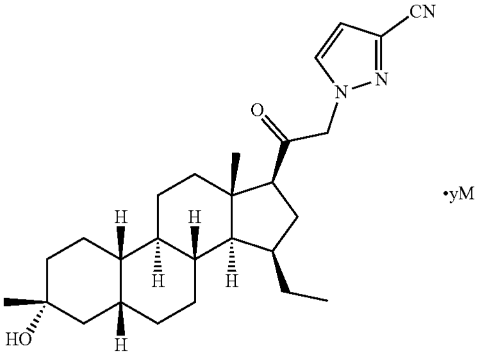
91
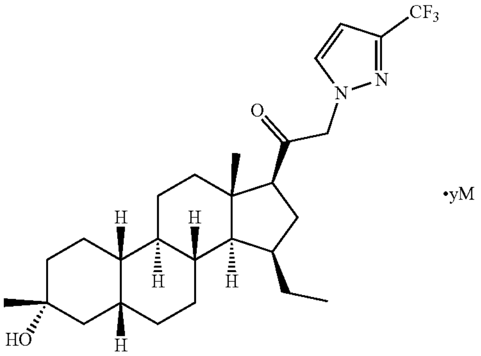
92
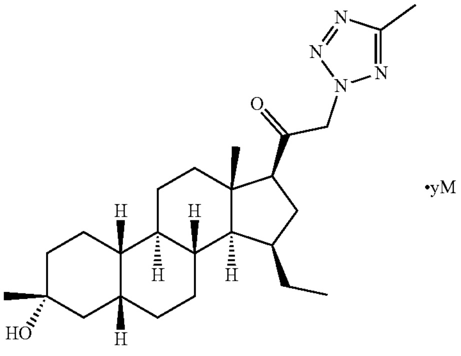
93
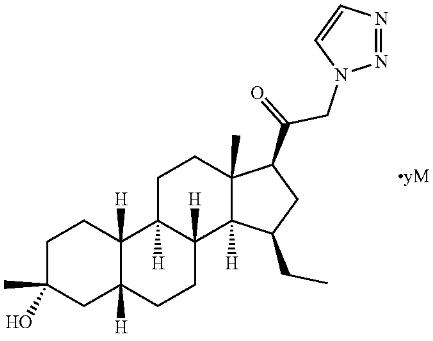

-continued
94
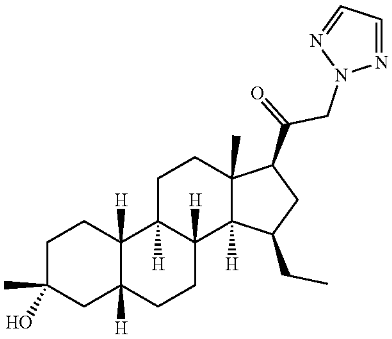
•yM
95
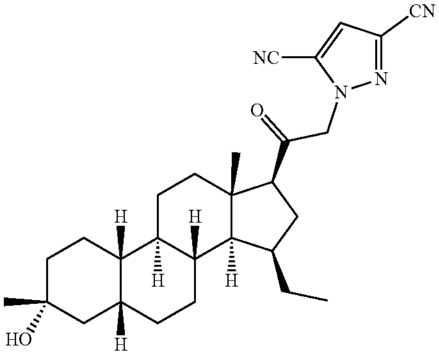
•yM
96
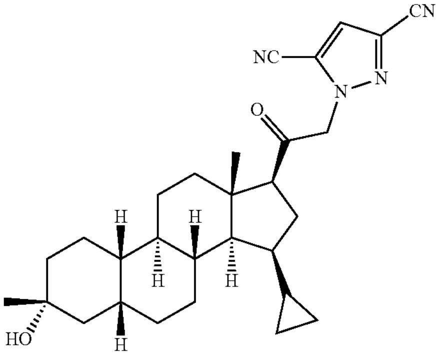
•yM
97
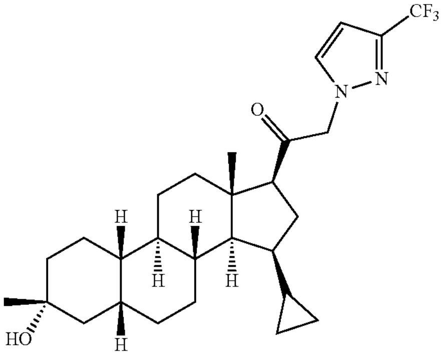
•yM
-continued
98
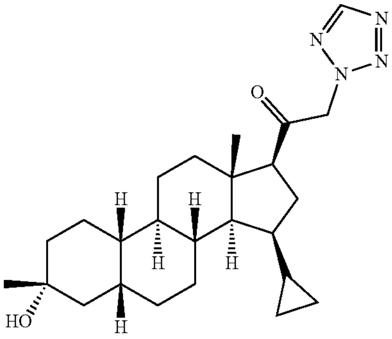
•yM
99
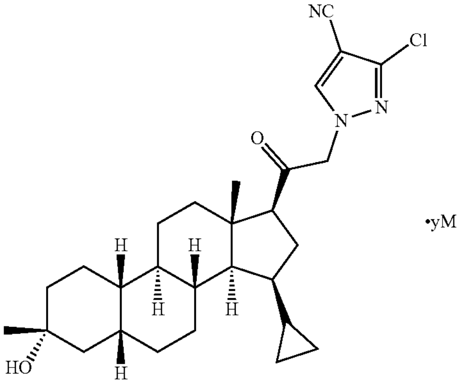
•yM
100
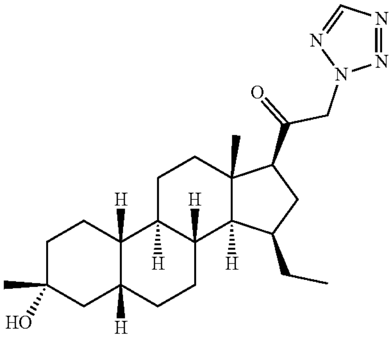
•yM
101
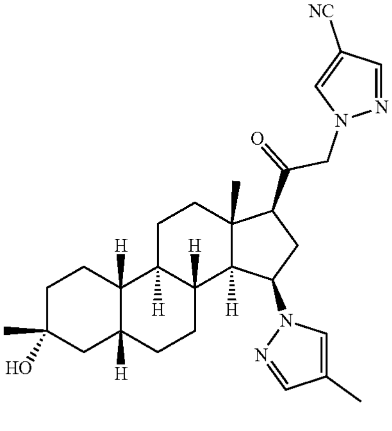
•yM -continued

102

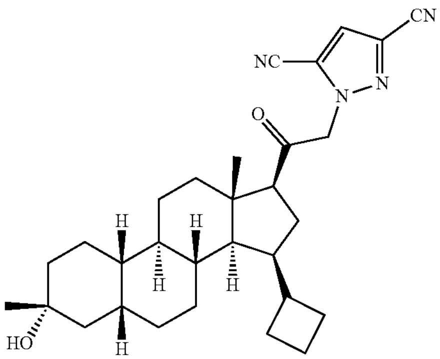

•yM or

103

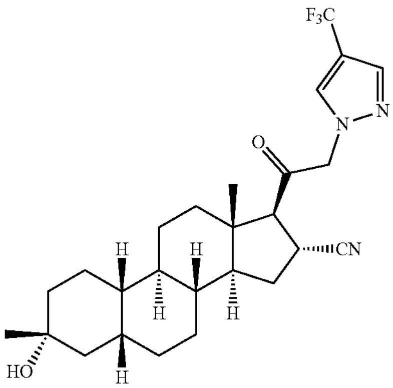

•yM.

In a preferred embodiment of the present invention, the acid addition salt of formula (Ia) has a structure as shown in formula (VIa):

(VIa)

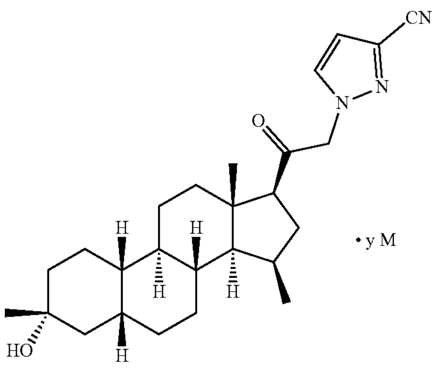

•y M

M is methanesulfonic acid, and y is 1.

In a preferred embodiment of the present invention, the compound of formula (Ia) is characterized in that the compound of formula (VIa) is amorphous.

The objective of the present invention is to provide a crystal form of the compound of formula (I), having a structure as shown in formula (I):

(I)

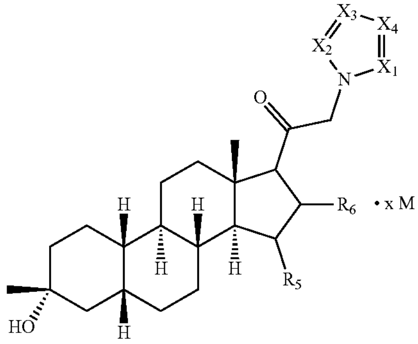

•x M wherein:

$X_1$ is selected from the group consisting of $CR_1$ and N, and preferably N;

$X_2$ is selected from the group consisting of $CR_2$ and N;

$X_3$ is selected from the group consisting of $CR_3$ and N;

$X_4$ is selected from the group consisting of $CR_4$ and N;

$R_1$ and $R_2$ are each independently selected from the group consisting of hydrogen, deuterium, cyano, halogen, nitro, amino, $C_{1-8}$ alkyl, $C_{1-8}$ haloalkyl, $C_{1-8}$ alkoxy, $C_{1-8}$ hydroxyalkyl, cyano-substituted $C_{1-8}$ alkyl, $C_{3-8}$ cycloalkyl, cyano-substituted $C_{3-8}$ cycloalkyl, 3 to 8 membered heterocyclyl, $C_{6-10}$ aryl and 5 to 10 membered heteroaryl;

$R_3$ and $R_4$ are each independently selected from the group consisting of hydrogen, deuterium, cyano, halogen, nitro, amino, $C_{1-8}$ alkyl, $C_{1-8}$ haloalkyl, $C_{1-8}$ alkoxy, $C_{1-8}$ hydroxyalkyl, cyano-substituted $C_{1-8}$ alkyl, $C_{3-8}$ cycloalkyl, cyano-substituted $C_{3-8}$ cycloalkyl, 3 to 8 membered heterocyclyl, $C_{6-10}$ aryl, 5 to 10 membered heteroaryl, $-(CH_2)_nR_a$, $-(CH_2)_nOR_a$, $-(CH_2)_nSR_a$, $-(CH_2)_nC(O)R_a$, $-S(O)R_a$, $-S(O)_2R_a$, $-S(O)(=NH)R_a$, $-C(O)OR_a$ and $-C(O)O(CH_2)_nNR_aR_b$, wherein the $C_{1-8}$ alkyl, $C_{2-8}$ alkenyl, $C_{2-5}$ alkynyl, $C_{1-8}$ haloalkyl, $C_{1-8}$ hydroxyalkyl, cyano-substituted $C_{1-8}$ alkyl, $C_{1-8}$ alkoxy, $C_{3-8}$ cycloalkyl, cyano-substituted $C_{3-8}$ cycloalkyl, 3 to 8 membered heterocyclyl, $C_{6-10}$ aryl and 5 to 10 membered heteroaryl can be each optionally further substituted;

$R_5$ and $R_6$ are each independently selected from the group consisting of hydrogen, deuterium, cyano, halogen, nitro, amino, $C_{1-8}$ alkyl, $C_{2-8}$ alkenyl, $C_{2-8}$ alkynyl, $C_{1-8}$ haloalkyl, $C_{1-8}$ alkoxy, $C_{1-8}$ hydroxyalkyl, cyano-substituted $C_{1-8}$ alkyl, $C_{1-8}$ alkylthio, $C_{3-8}$ cycloalkyl, cyano-substituted $C_{3-8}$ cycloalkyl, 3 to 8 membered heterocyclyl, $C_{6-10}$ aryl, 5 to 10 membered heteroaryl, $-(CH_2)_nR_a$, $-(CH_2)_nOR_a$, $-S(O)R_a$, $-S(O)_2R_a$ and $-(CH_2)_nNR_aR_b$, wherein the $C_{1-8}$ alkyl, $C_{2-8}$ alkenyl, $C_{2-8}$ alkynyl, $C_{1-8}$ haloalkyl, $C_{1-8}$ hydroxyalkyl, cyano-substituted $C_{1-8}$ alkyl, $C_{1-8}$ alkoxy, $C_{3-8}$ cycloalkyl, cyano-substituted $C_{3-8}$ cycloalkyl, 3 to 8 membered heterocyclyl, $C_{6-10}$ aryl and 5 to 10 membered heteroaryl can be each optionally further substituted;

or, $R_5$ and $R_6$ together with the carbon atoms to which they are attached form a $C_{3-8}$ cycloalkyl or 3 to 8 membered heterocyclyl, wherein the $C_{3-8}$ cycloalkyl and 3 to 8 membered heterocyclyl can be each optionally further substituted;

wherein $R_5$ and $R_6$ are not hydrogen at the same time;

$R_a$ and $R_b$ are each independently selected from the group consisting of hydrogen, deuterium, halogen, cyano, hydroxy, amino, nitro, $C_{1-8}$ alkyl, $C_{1-8}$ alkoxy, $C_{1-8}$ hydroxyalkyl, $C_{1-8}$ deuterated alkyl, $C_{1-8}$ haloalkyl, $C_{3-8}$ cycloalkyl, 3 to 8 membered heterocyclyl, $C_{6-10}$ aryl and 5 to 10 membered heteroaryl, wherein the $C_{1-8}$ alkyl, $C_{1-8}$ deuterated alkyl, $C_{1-8}$ haloalkyl, $C_{3-8}$ cycloalkyl, 3 to 8 membered heterocyclyl, $C_{6-10}$ aryl and 5 to 10 membered heteroaryl can be each optionally further substituted;

M is an inorganic acid or organic acid, wherein the inorganic acid is selected from the group consisting of hydrochloric acid, sulfuric acid, nitric acid, hydrobromic acid, hydrofluoric acid, hydroiodic acid and phosphoric acid, and the organic acid is selected from the group consisting of 2,5-dihydroxybenzoic acid, 1-hydroxy-2-naphthoic acid, acetic acid, dichloroacetic acid, trichloroacetic acid, acetohydroxamic acid, adipic acid, benzenesulfonic acid, 4-chlorobenzenesulfonic acid, benzoic acid, 4-acetylaminobenzoic acid, 4-aminobenzoic acid, capric acid, caproic acid, caprylic acid, cinnamic acid, citric acid, cyclamic acid, camphorsulfonic acid, aspartic acid, camphor acid, gluconic acid, glucuronic acid, glutamic acid, erythorbic acid, lactic acid, malic acid, mandelic acid, pyroglutamic acid, tartaric acid, lauryl sulfuric acid, dibenzoyl tartaric acid, ethane-1,2-disulfonic acid, ethanesulfonic acid, formic acid, fumaric acid, galactonic acid, gentisic acid, glutaric acid, 2-ketoglutaric acid, glycolic acid, hippuric acid, isethionic acid, lactobionic acid, ascorbic acid, asparagic acid, lauric acid, camphor acid, maleic acid, malonic acid, D-tartaric acid, pamoic acid, methanesulfonic acid, 1,5-naphthalenedisulfonic acid, naphthalene-2-sulfonic acid, nicotinic acid, oleic acid, orotic acid, oxalic acid, palmitic acid, embonic acid, propionic acid, salicylic acid, 4-aminosalicylic acid, sebacic acid, stearic acid, succinic acid, thiocyanic acid, undecylenic acid, trifluoroacetic acid, benzenesulfonic acid, p-toluenesulfonic acid and L-malic acid; and x is selected from the group consisting of 0, 1, 2 and 3;

n is an integer from 0 to 6.

In a preferred embodiment of the present invention, the crystal form of the compound of formula (I) is characterized in that, $R_1$ and $R_2$ are each independently selected from the group consisting of hydrogen, cyano, halogen, $C_{1-6}$ alkyl and $C_{3-6}$ cycloalkyl, and preferably hydrogen, cyano, halogen, $C_{1-3}$ alkyl and $C_{3-6}$ cycloalkyl;

$R_3$ and $R_4$ are each independently selected from the group consisting of hydrogen, cyano, halogen, nitro, $C_{1-6}$ alkyl, $C_{1-6}$ haloalkyl, $C_{1-6}$ hydroxyalkyl, cyano-substituted $C_{1-6}$ alkyl, $C_{3-6}$ cycloalkyl, cyano-substituted $C_{3-6}$ cycloalkyl, 5 or 6 membered heteroaryl, $-(CH_2)_nSR_a$, $-(CH_2)_nC(O)R_a$, $-S(O)R_a$, $-S(O)_2R_a$, $-S(O)(=NH)R_a$, $-C(O)OR_a$ and $-C(O)O(CH_2)_nNR_aR_b$;

$R_5$ is selected from the group consisting of hydrogen, cyano, halogen, $C_{1-6}$ alkyl, $C_{1-6}$ haloalkyl, $C_{1-6}$ hydroxyalkyl, cyano-substituted $C_{1-6}$ alkyl, $C_{1-6}$ alkoxy, $C_{1-6}$ alkylthio, $C_{3-6}$ cycloalkyl, cyano-substituted $C_{3-6}$ cycloalkyl, 3 to 6 membered heterocyclyl, $C_{6-10}$ aryl, 5 to 10 membered heteroaryl, $-(CH_2)_nR_a$, $-(CH_2)_nOR_a$, $-S(O)_2R_a$ and $-(CH_2)_nNR_aR_b$, wherein the 5 to 10 membered heteroaryl can be optionally further substituted;

$R_6$ is selected from the group consisting of hydrogen, halogen, cyano, $C_{1-6}$ alkyl and $C_{1-6}$ haloalkyl, and preferably hydrogen, halogen, cyano, $C_{1-3}$ alkyl and $C_{1-3}$ haloalkyl;

or, $R_5$ and $R_6$ together with the carbon atoms to which they are attached form a $C_{3-8}$ cycloalkyl, wherein the $C_{3-8}$ cycloalkyl can be optionally further substituted;

wherein $R_5$ and $R_6$ are not hydrogen at the same time;

$R_a$ and $R_b$ are each independently selected from the group consisting of hydrogen, halogen, cyano, nitro, $C_{1-6}$ alkyl, 3 to 6 membered heterocyclyl and 5 to 10 membered heteroaryl, wherein the $C_{1-6}$ alkyl, 3 to 6 membered heterocyclyl and 5 to 10 membered heteroaryl can be each optionally further substituted;

M is selected from the group consisting of hydrochloric acid, sulfuric acid, nitric acid, hydrobromic acid, phosphoric acid, methanesulfonic acid, 1,5-naphthalenedisulfonic acid and p-toluenesulfonic acid; and x is selected from the group consisting of 1 and 2;

n is an integer from 0 to 3.

In a preferred embodiment of the present invention, the crystal form of the compound of formula (I) is characterized in that, $R_1$ and $R_2$ are each independently selected from the group consisting of hydrogen, fluorine, chlorine, cyano, methyl and cyclopropyl;

$R_3$ and $R_4$ are each independently selected from the group consisting of hydrogen, halogen, cyano, nitro, $C_{1-3}$ alkyl, cyano-substituted $C_{1-3}$ alkyl, halogen-substituted $C_{1-3}$ alkyl, $C_{1-3}$ hydroxyalkyl, $C_{3-6}$ cycloalkyl, cyano-substituted $C_{3-6}$ cycloalkyl, oxazolyl, $-C(O)R_a$, $-SC_{1-3}$ alkyl, $-S(O)C_{1-3}$ alkyl, $-S(O)_2C_{1-3}$ alkyl, $-C(O)OC_{1-3}$ alkyl, $-S(O)(=NH)C_{1-3}$ alkyl and $-C(O)O(CH_2)_nN(CH_3)C_{1-3}$ alkyl, and preferably hydrogen, fluorine, chlorine, cyano, nitro, trifluoromethyl, cyclopropyl, cyano-substituted cyclopropyl, cyano-substituted isopropyl, hydroxyisopropyl, oxazolyl, $-C(O)R_a$, $-SCH_3$, $-S(O)CH_3$, $-S(O)_2CH_3$, $-C(O)OCH_2CH_3$, $-S(O)(=NH)CH_3$ and $-C(O)O(CH_2)_2NCH_3(CH_3)$;

$R_5$ is selected from the group consisting of hydrogen, halogen, cyano, $C_{1-3}$ alkyl, $C_{1-3}$ haloalkyl, $C_{1-3}$ alkoxy, $C_{1-3}$ hydroxyalkyl, cyano-substituted $C_{1-3}$ alkyl, $C_{3-6}$ cycloalkyl, cyano-substituted $C_{3-6}$ cycloalkyl, 3 to 6 membered nitrogen-containing heterocyclyl, $C_{6-10}$ aryl, 5 to 10 membered heteroaryl, $C_{1-3}$ alkylthio, $-(CH_2)_nR_a$, $-(CH_2)_nOR_a$, $-S(O)_2R_a$ and $-(CH_2)_nN(R_a)_2$, and preferably hydrogen, fluorine, chlorine, cyano, methyl, ethyl, isopropyl, fluoromethyl, trifluoromethyl, methoxy, cyclopropyl, cyclobutyl, methyl-substituted pyrazolyl, phenyl, $-SCH_3$, $-(CH_2)_nR_a$, $-NC(CH_3)_2$, $-S(O)_2C(CH_3)_2$ and $-CH_2N(CH_3)_2$;

$R_6$ is selected from the group consisting of hydrogen, fluorine, cyano, methyl, ethyl and trifluoromethyl;

or, $R_5$ and $R_6$ together with the carbon atoms to which they are attached form a $C_{3-6}$ cycloalkyl, and preferably cyclopropyl, wherein the cyclopropyl is optionally substituted by halogen, and preferably by fluorine;

$R_a$ is selected from the group consisting of hydrogen, nitro, $C_{1-3}$ alkyl, azetidinyl and pyrrolidinyl, wherein the azetidinyl and pyrrolidinyl are each optionally substituted by halogen, and preferably by fluorine;

M is selected from the group consisting of hydrochloric acid, sulfuric acid, methanesulfonic acid, p-toluenesulfonic acid, hydrobromic acid, nitric acid and 1,5-naphthalenedisulfonic acid, and preferably methanesulfonic acid;

x is 0, 1 or 2;

n is selected from the group consisting of 0, 1 and 2.

In a preferred embodiment of the present invention, the crystal form of the compound of formula (I) has a structure as shown in formula (II):

(II)

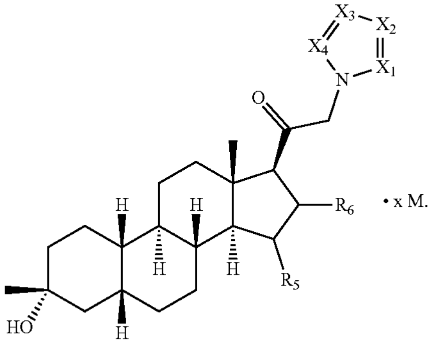

In a preferred embodiment of the present invention, the crystal form of the compound of formula (I) has a structure as shown in formula (III):

(III)

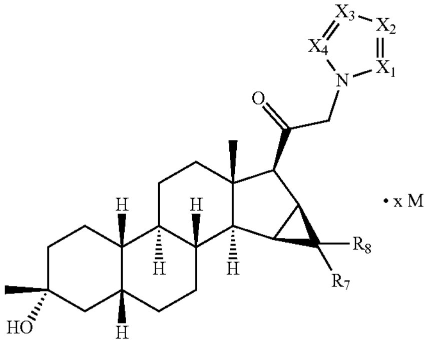

wherein:

$R_7$ and $R_8$ are each independently selected from the group consisting of hydrogen, fluorine, chlorine, bromine and methyl, and preferably hydrogen and fluorine.

In a preferred embodiment of the present invention, the crystal form of the compound of formula (I) has a structure as shown in formula (IV):

(IV)

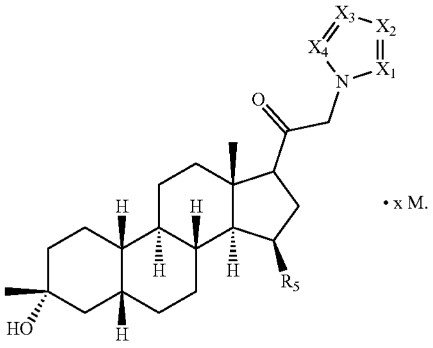

In a preferred embodiment of the present invention, the crystal form of the compound of formula (I) has a structure as shown in formula (V):

(V)

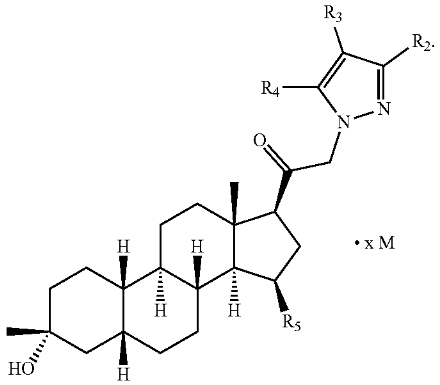

In a preferred embodiment of the present invention, in the crystal form of the compound of formula (I), the structure of the compound is as follows:

1

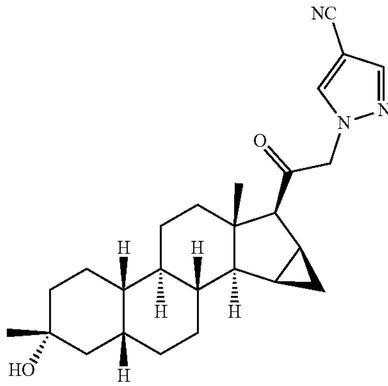

2

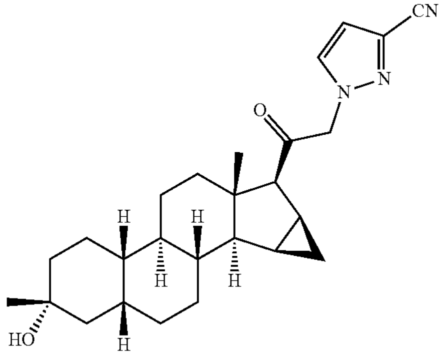

-continued
3
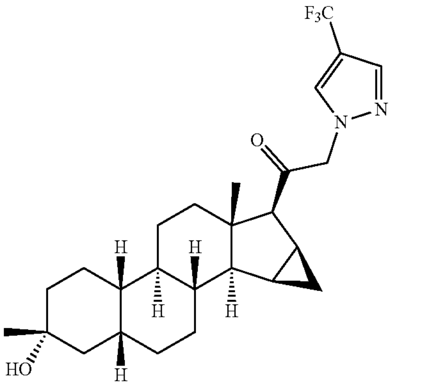
4
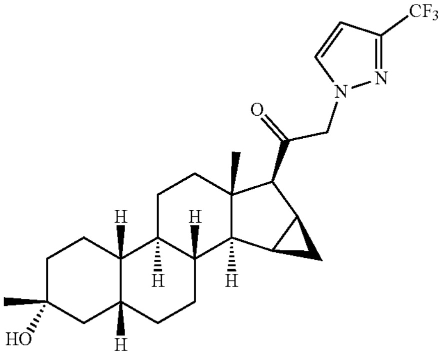
5
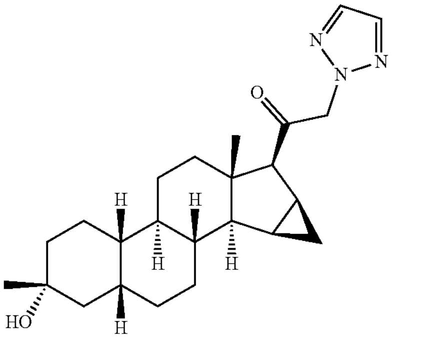
6
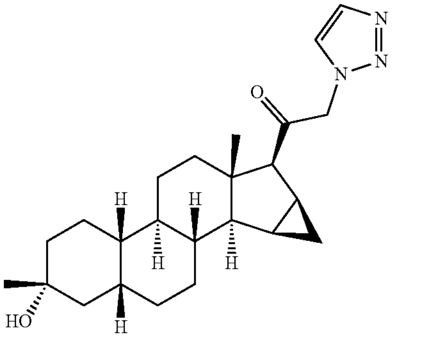
-continued
7
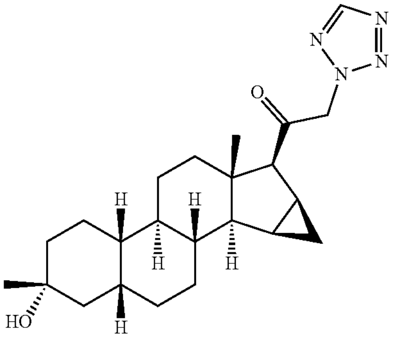
8
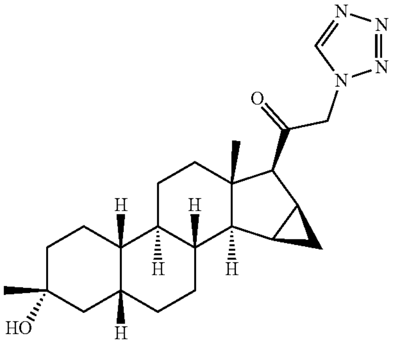
9
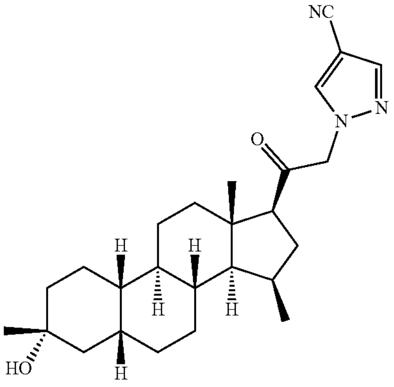
10
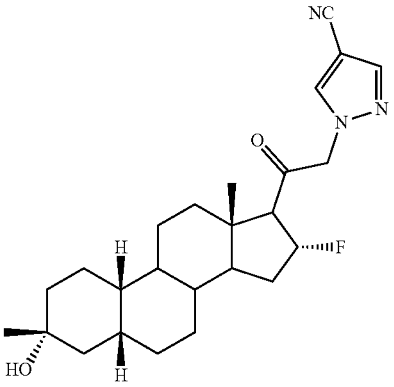

-continued
11
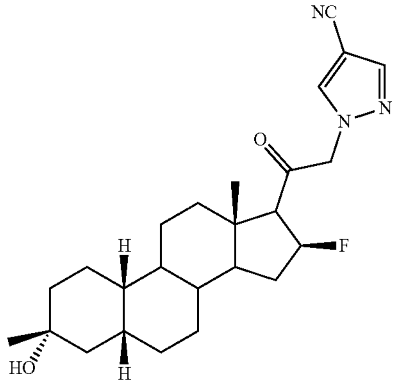
12
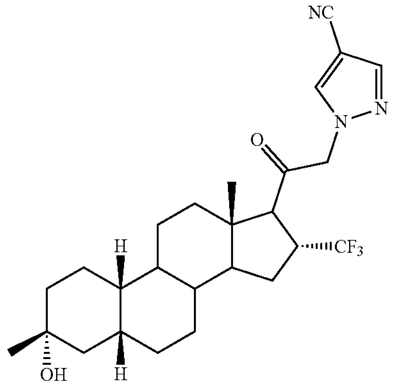
13
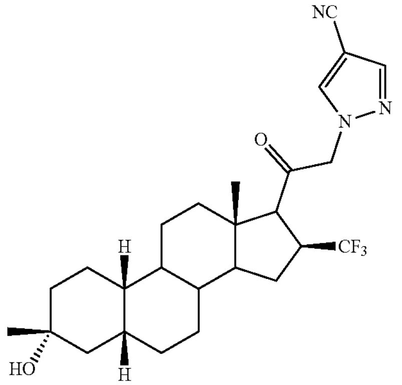
14
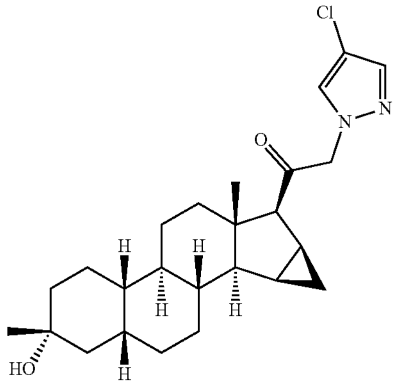
-continued
15
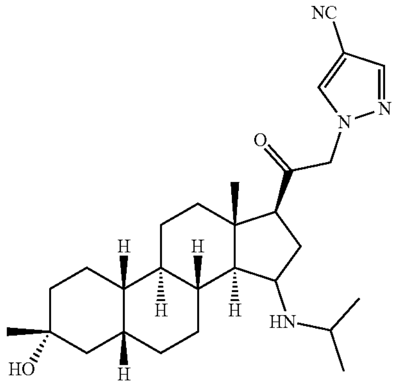
16
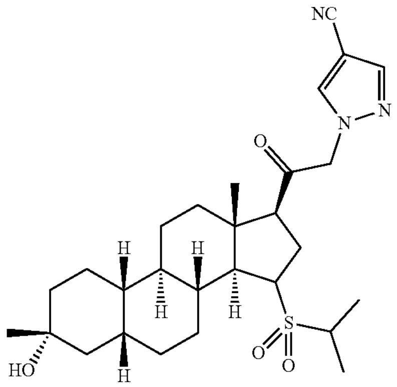
17
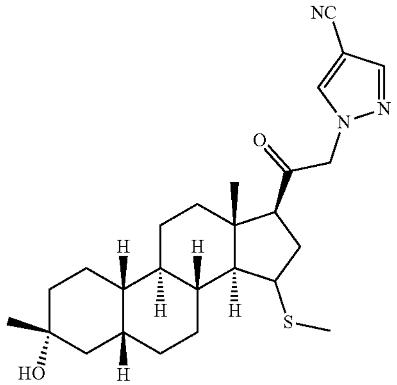
18
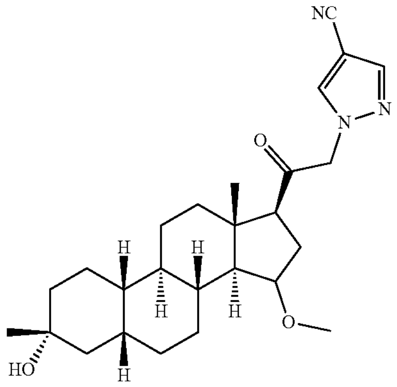

-continued
19
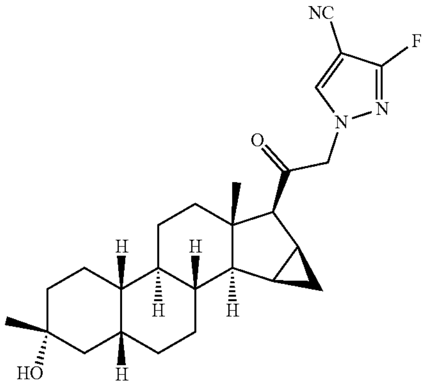
20
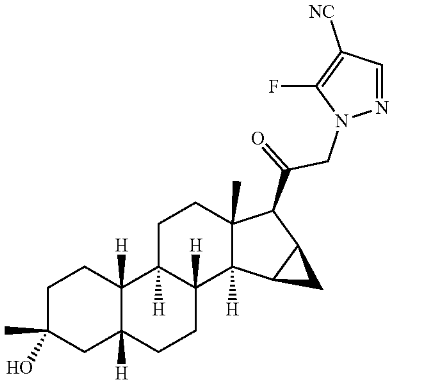
21
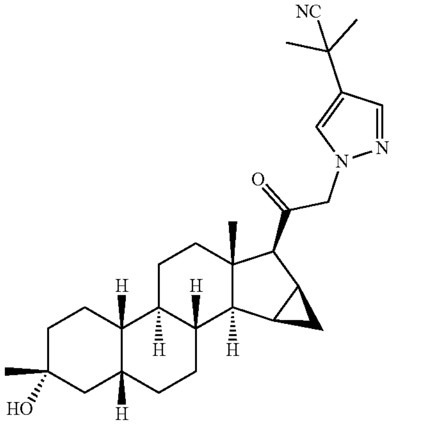
22
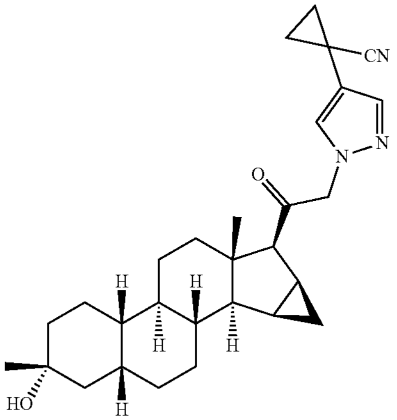
-continued
23
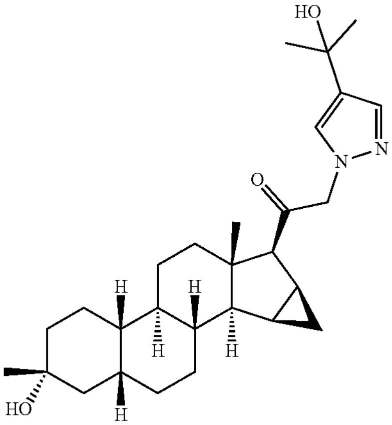
24
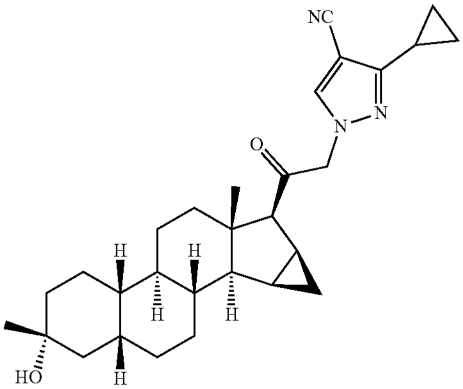
25
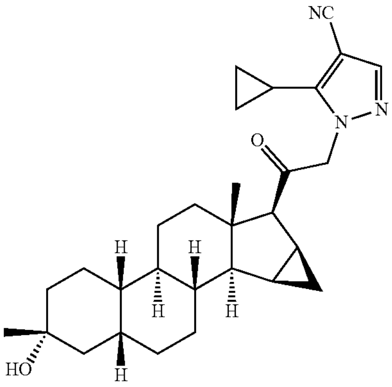
26
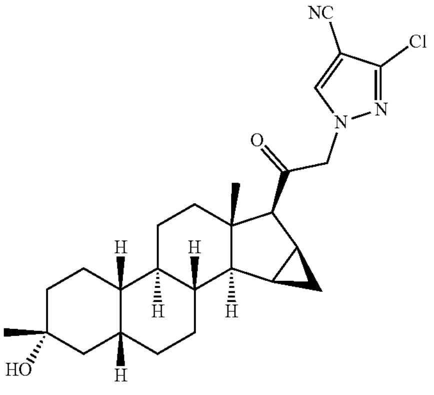

-continued
27
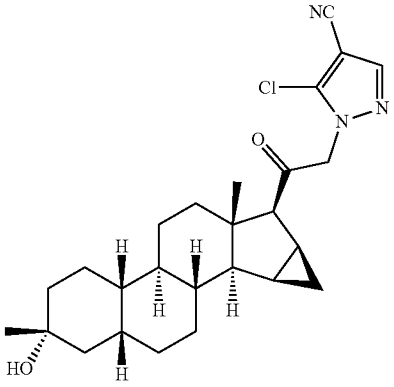
28
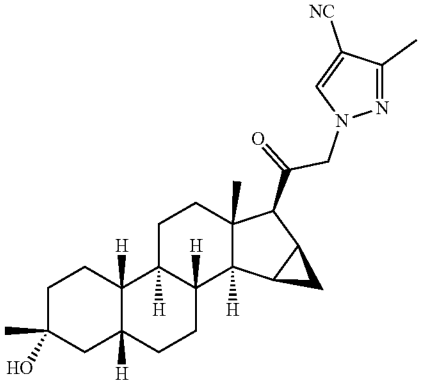
29
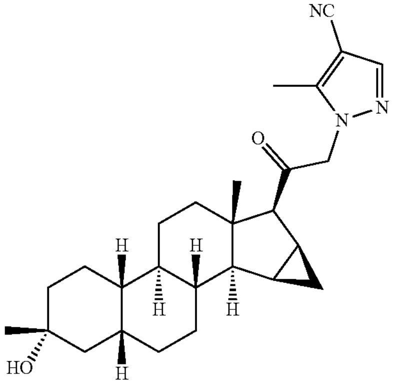
30
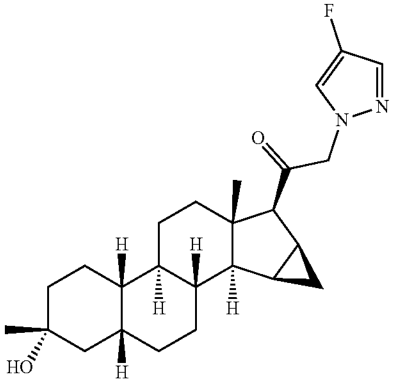
-continued
31
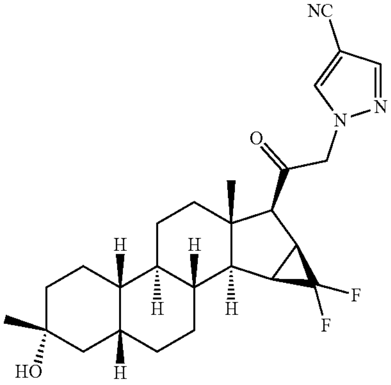
32
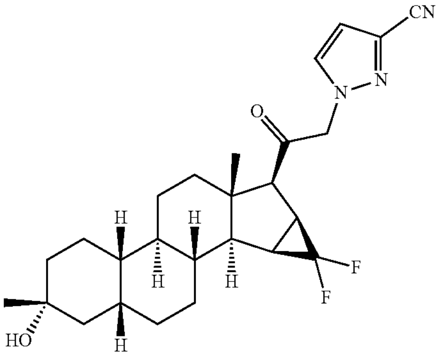
33
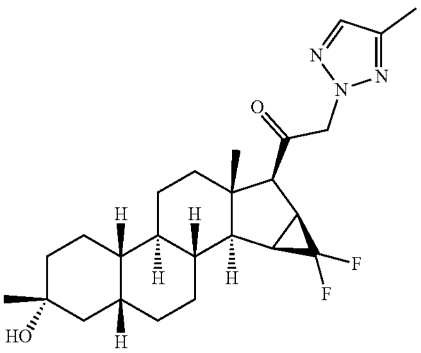
34
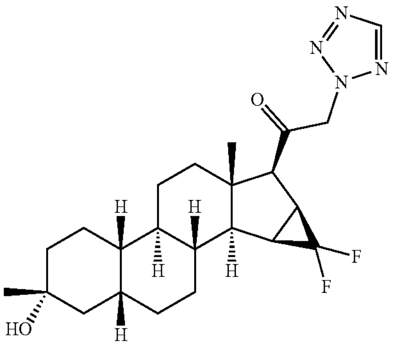

-continued
35
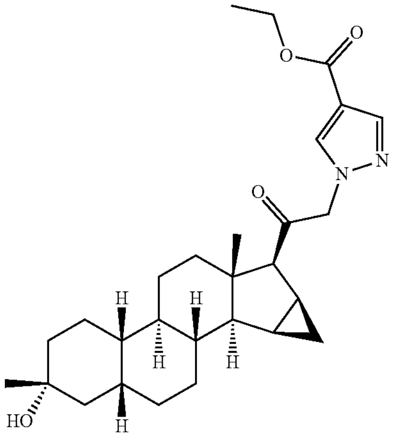
36
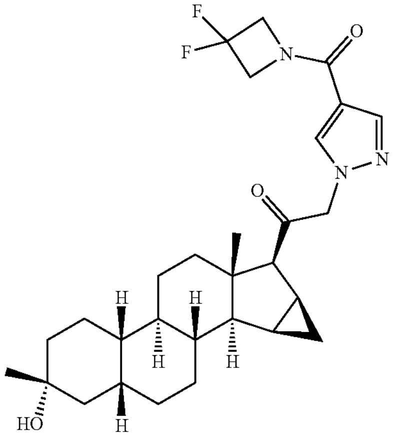
37
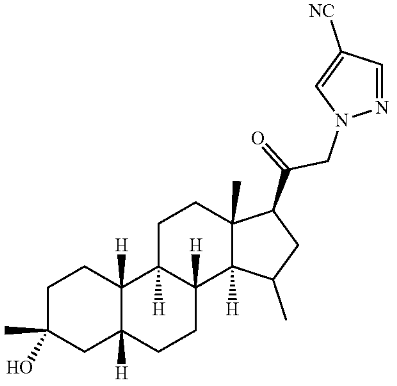
38
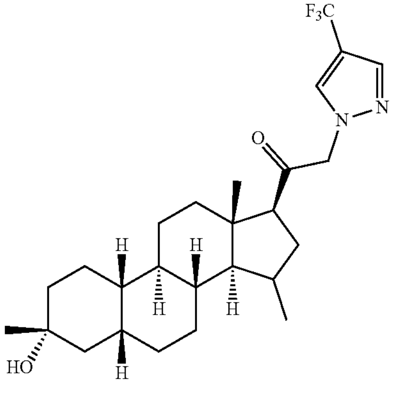
-continued
39
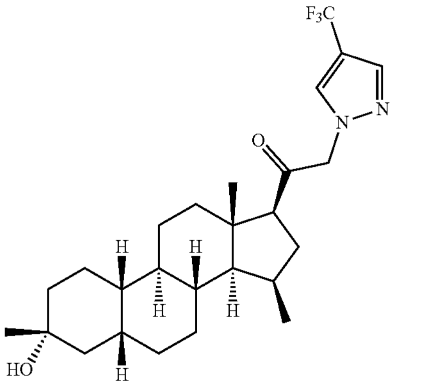
40
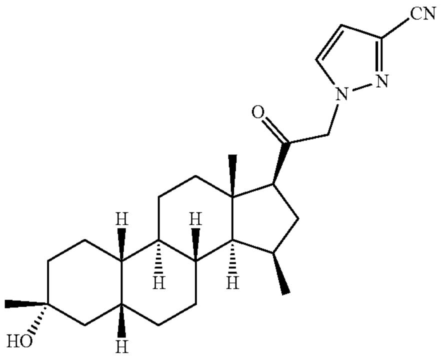
41
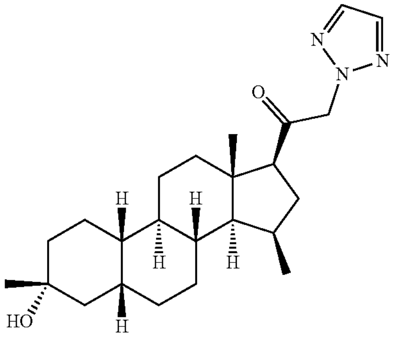
42
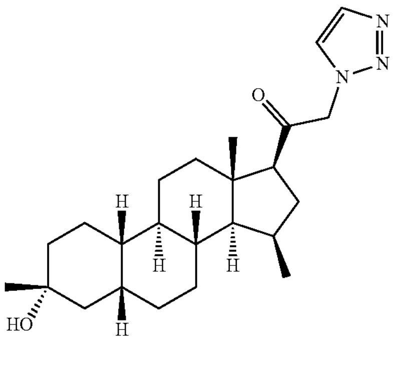

-continued
43
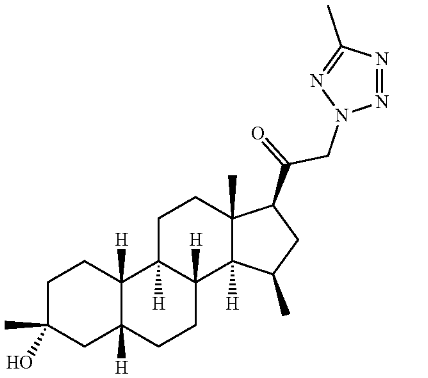
44
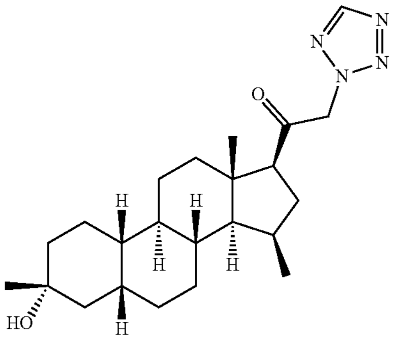
45
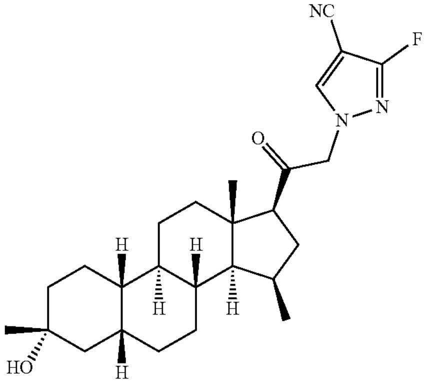
46
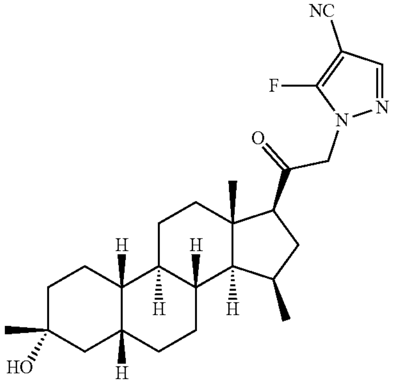
-continued
47
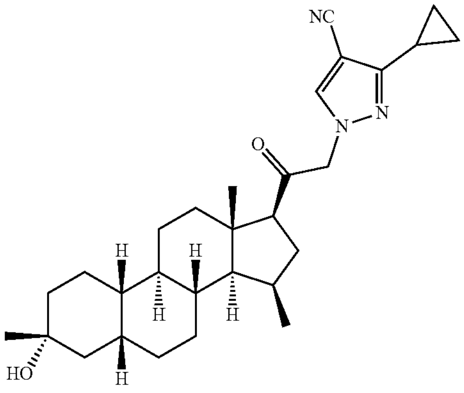
48
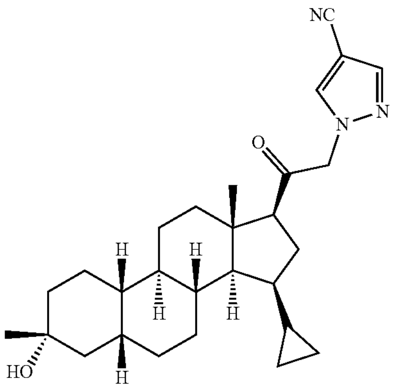
49
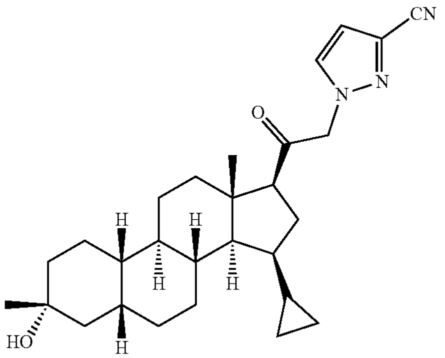
50
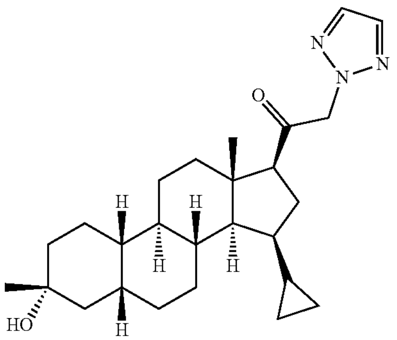

51
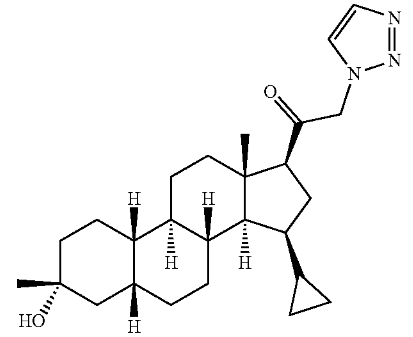
52
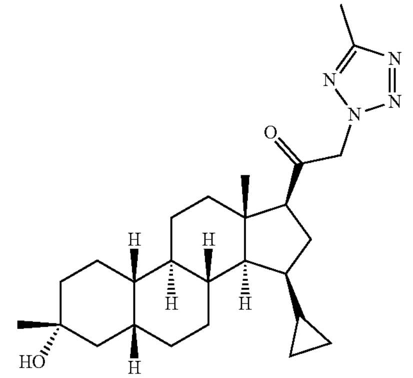
53
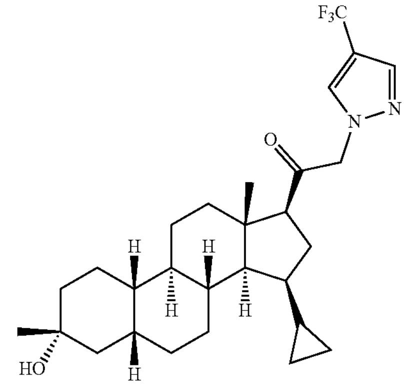
54
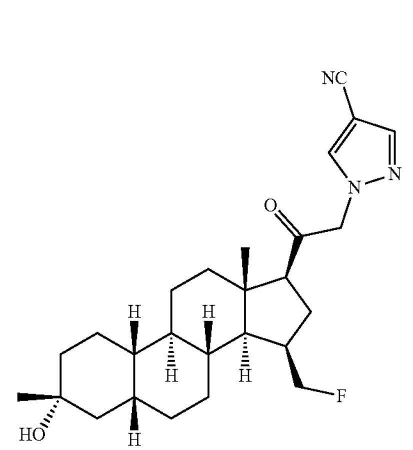
55
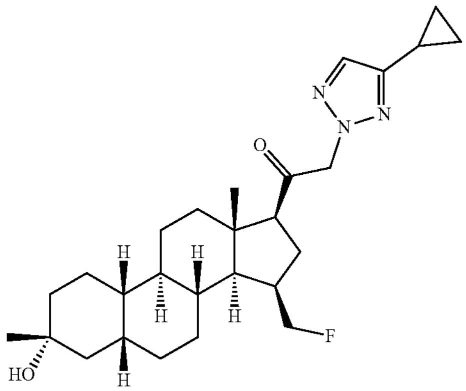
56
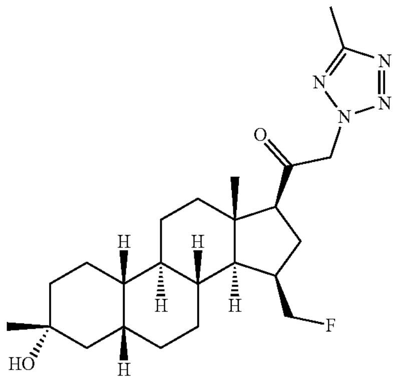
57
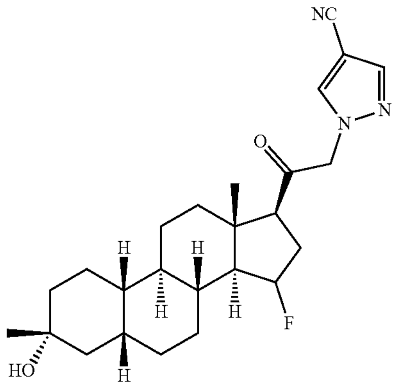
58
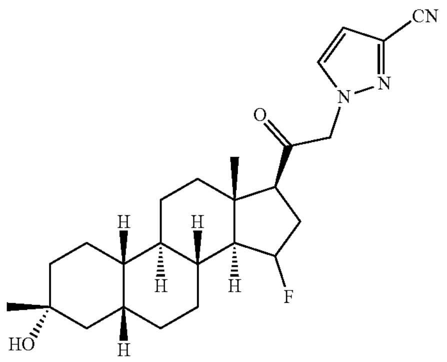

-continued
59
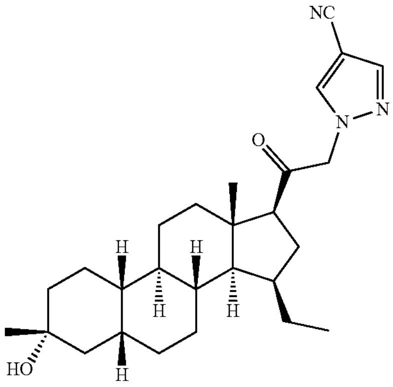
60
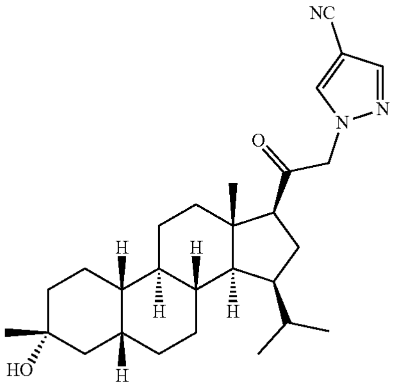
61
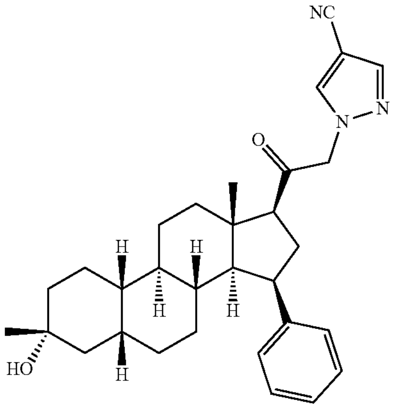
62
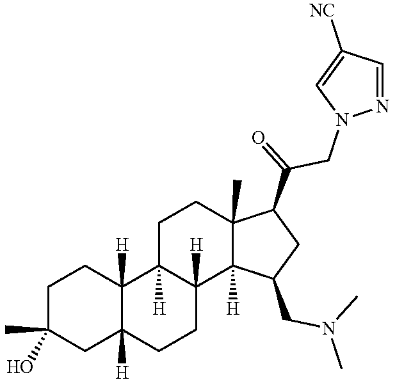
-continued
63
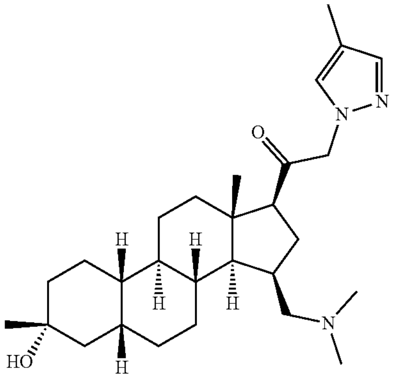
64
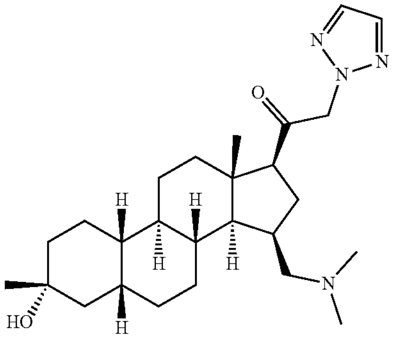
65
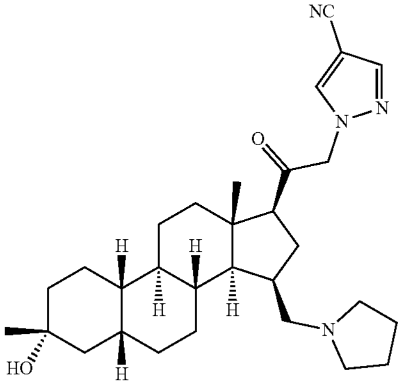
66
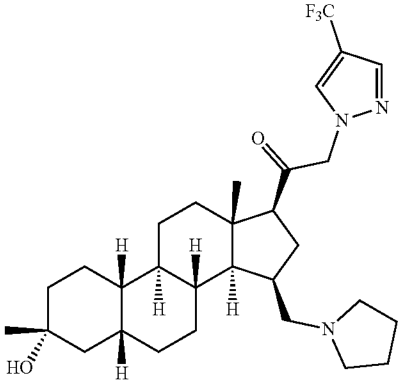

-continued
67
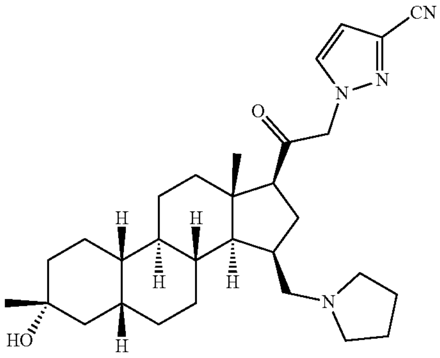
68
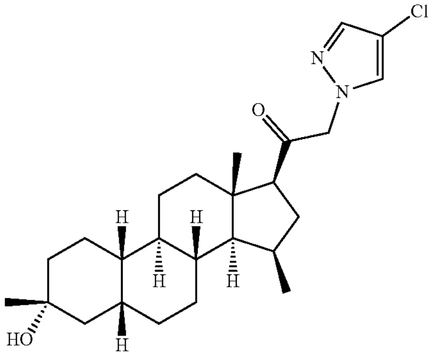
69
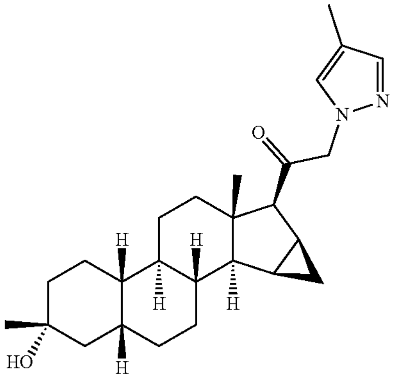
70
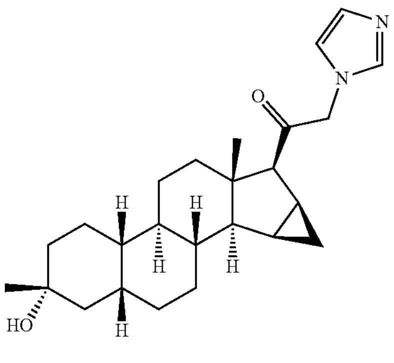
-continued
71
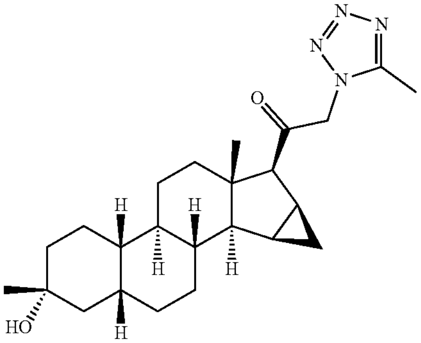
72
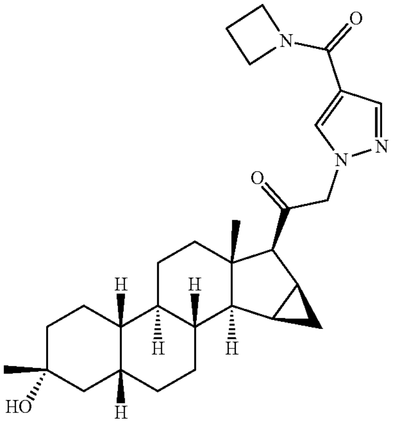
73
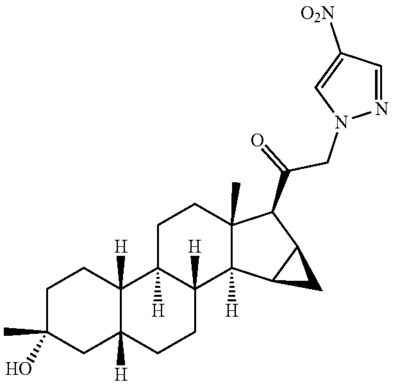
74
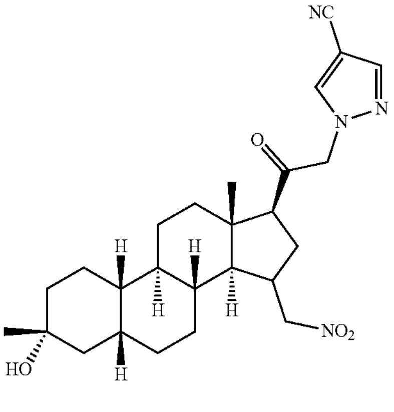

-continued
75
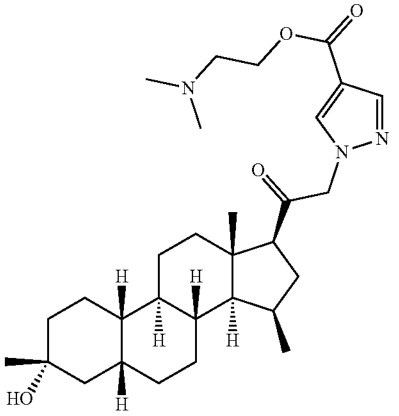
76
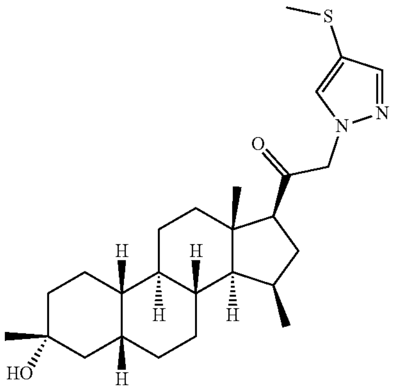
77
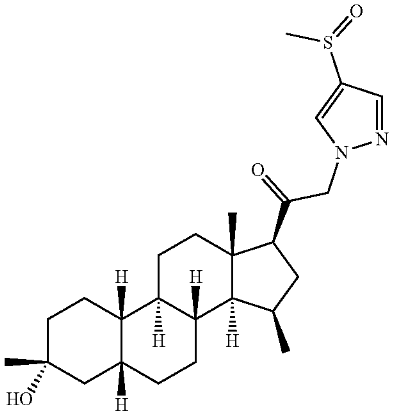
78
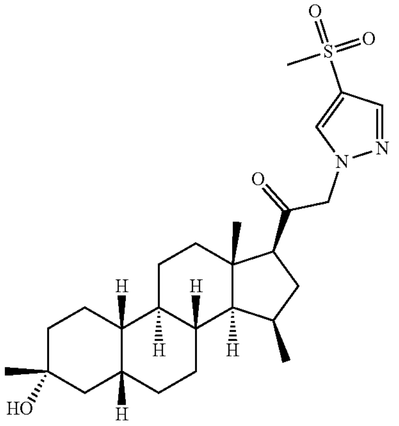
-continued
79
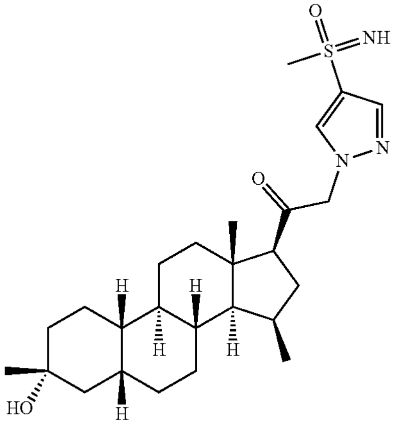
80
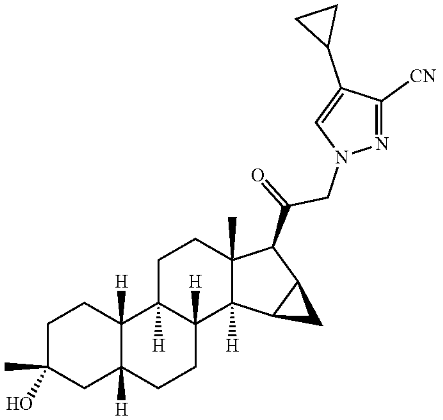
81
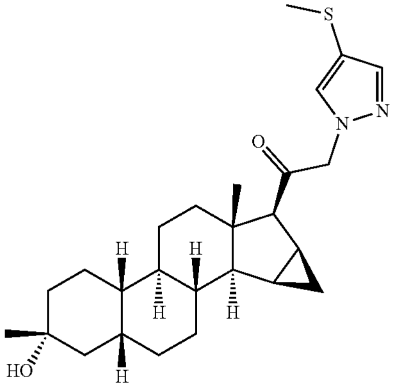

-continued
82
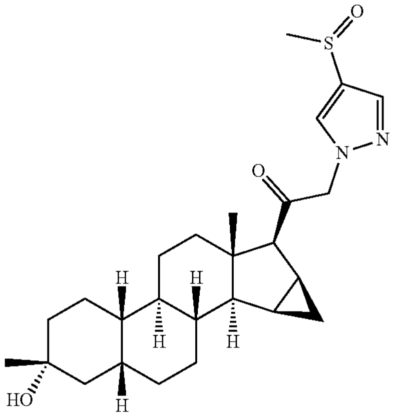
83
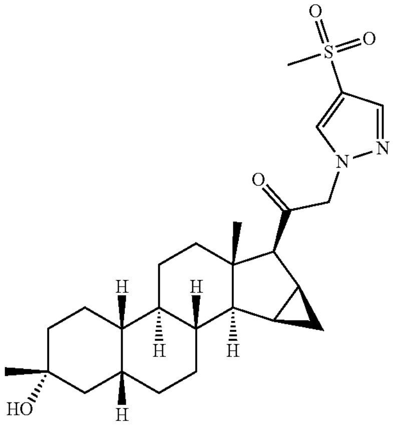
84
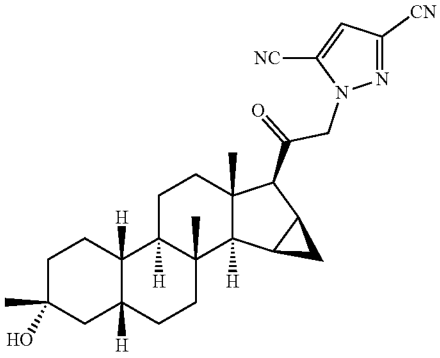
85
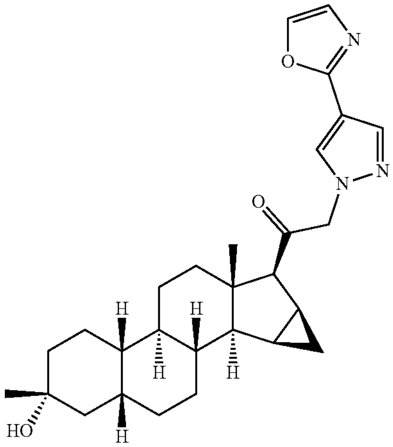
-continued
86
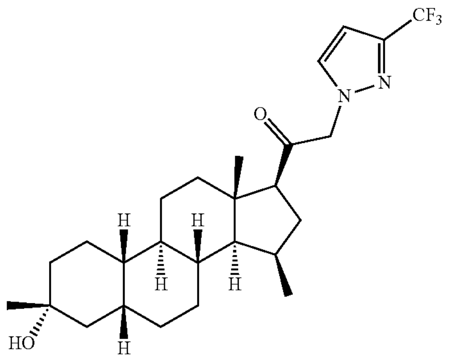
87
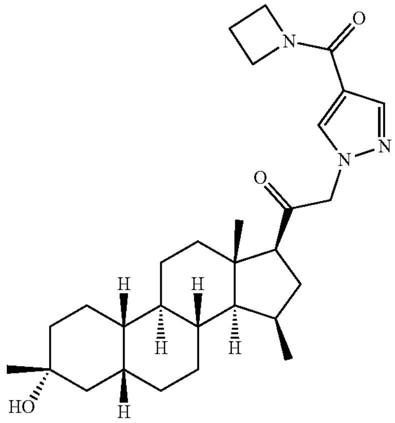
88
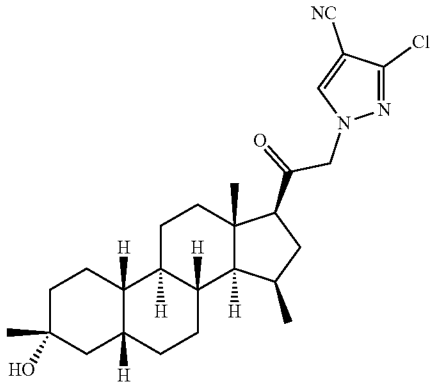
89
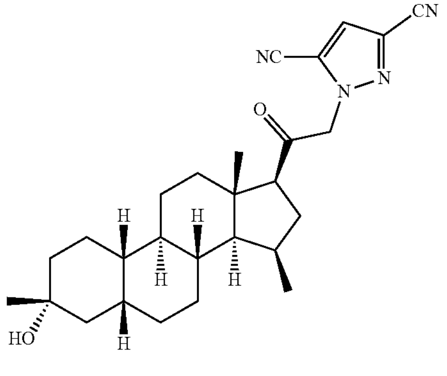

-continued
90
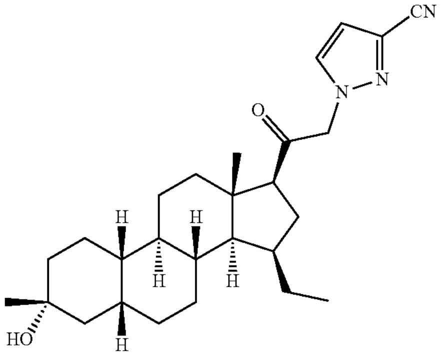
91
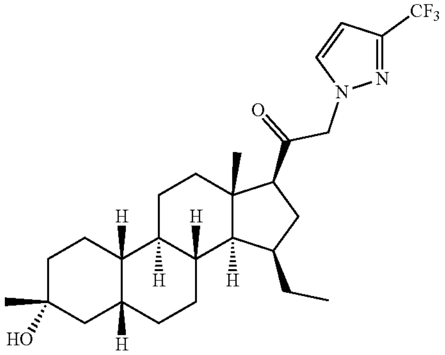
92
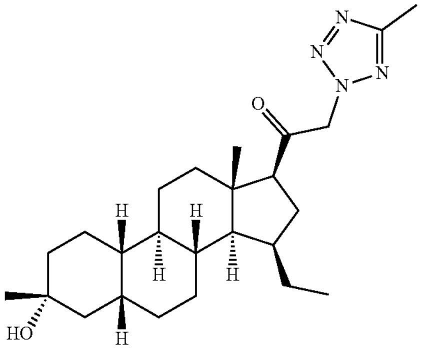
93
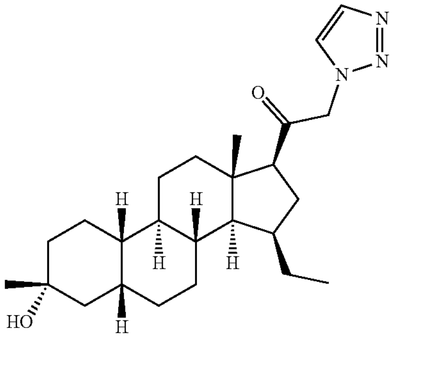
-continued
94
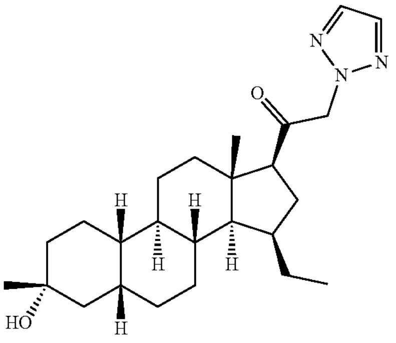
95
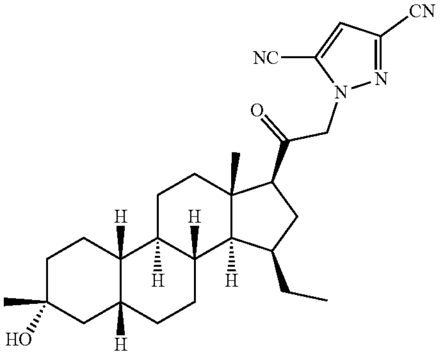
96
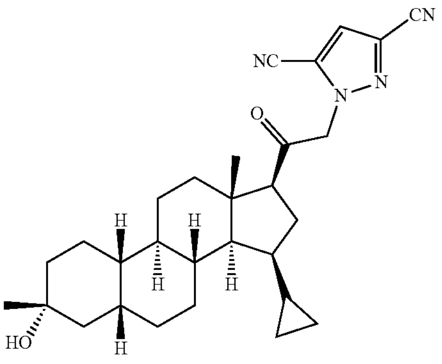
97
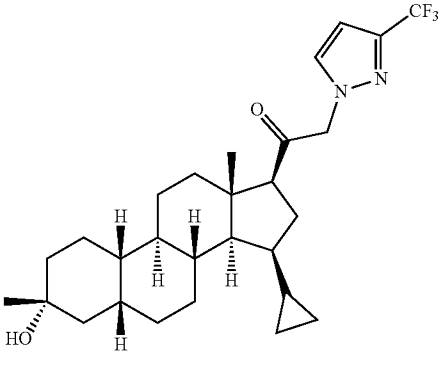

-continued

98

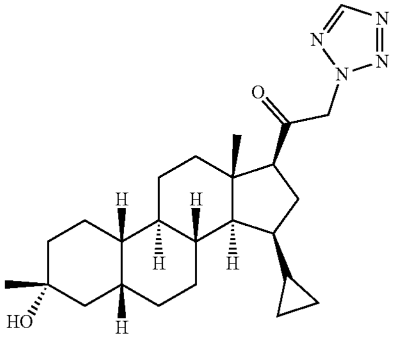

99

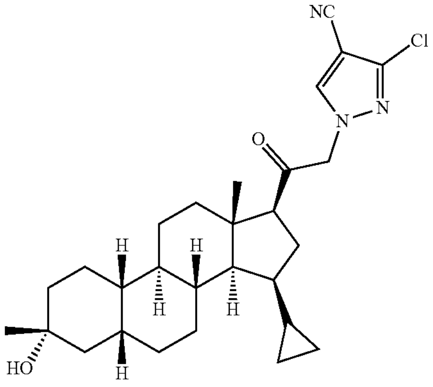

100

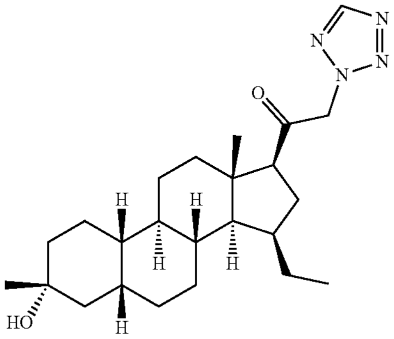

101

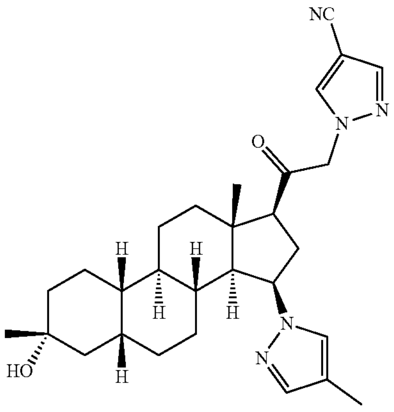

-continued

102

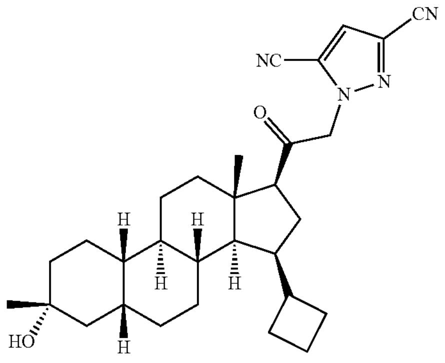

or

103

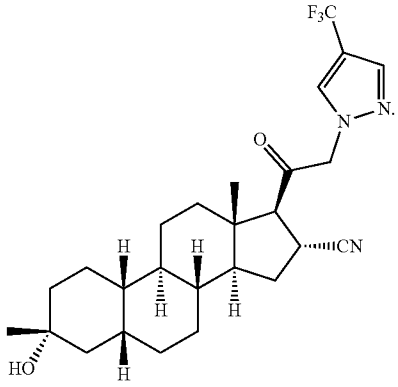

In a preferred embodiment of the present invention, the crystal form of the compound of formula (I) has a structure as shown in formula (VI):

(VI)

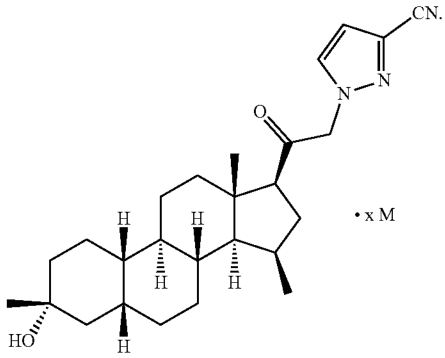

A further preferred embodiment of the present invention is characterized in that x is 0, and the compound of formula (VI) is a crystal form of free base.

A further preferred embodiment of the present invention is characterized in that when x is selected from the group consisting of 1, 2 and 3, the compound of formula (VI) is a crystal form of salt, and preferably x is 1.

A further preferred embodiment of the present invention is a crystal form of free base of the compound of formula (VI), characterized in that the compound of formula (VI) is a hydrate or an anhydrate.

The objective of the present invention is also to provide a method for preparing the crystal form of the compound of formula (I) or the compound of formula (Ia), specifically comprising the following steps of:

1) preparation of stock solution: the free base of the compound of the general formula is dissolved in an organic solvent to obtain a clear stock solution, the concentration of the solution is preferably 50 to 100 mg/mL, and more preferably 100 mg/mL;
2) preparation of counter ion acid solution: a counter ion acid is added to an organic solvent or water to obtain a clear counter ion acid solution; the organic solvent is preferably ethanol, and the concentration is preferably 1.2 to 2.2 mol/L;
3) preparation of salt of the compound: the stock solution is added to the counter ion acid solution to obtain a clear salt solution, the salt solution is stirred overnight to precipitate a solid, and then filtered, and the filter cake is dried in vacuum to obtain the salt of the compound of formula (I); the vacuum temperature is preferably 40° C., and the amount of counter ion acid is preferably 0.6 to 1.2 equivalents;

wherein:

the organic solvent is selected from the group consisting of 88% acetone, methanol, ethanol, ethyl acetate, dichloromethane, acetone, toluene, acetonitrile, tetrahydrofuran, heptane, methyl tert-butyl ether, isopropyl ether and N,N-dimethylformamide; and preferably ethyl acetate and ethanol;

the counter ion acid is selected from the group consisting of hydrochloric acid, sulfuric acid, nitric acid, hydrobromic acid, hydrofluoric acid, hydroiodic acid, phosphoric acid, 2,5-dihydroxybenzoic acid, 1-hydroxy-2-naphthoic acid, acetic acid, dichloroacetic acid, trichloroacetic acid, acetohydroxamic acid, adipic acid, benzenesulfonic acid, 4-chlorobenzenesulfonic acid, benzoic acid, 4-acetylaminobenzoic acid, 4-aminobenzoic acid, capric acid, caproic acid, caprylic acid, cinnamic acid, citric acid, cyclamic acid, camphorsulfonic acid, aspartic acid, camphor acid, gluconic acid, glucuronic acid, glutamic acid, erythorbic acid, lactic acid, malic acid, mandelic acid, pyroglutamic acid, D-tartaric acid, pamoic acid, lauryl sulfuric acid, dibenzoyl tartaric acid, ethane-1,2-disulfonic acid, ethanesulfonic acid, formic acid, fumaric acid, galactonic acid, gentisic acid, glutaric acid, 2-ketoglutaric acid, glycolic acid, hippuric acid, isethionic acid, lactobionic acid, ascorbic acid, asparagic acid, lauric acid, camphor acid, maleic acid, malonic acid, methanesulfonic acid, 1,5-naphthalenedisulfonic acid, naphthalene-2-sulfonic acid, nicotinic acid, oleic acid, orotic acid, oxalic acid, palmitic acid, embonic acid, propionic acid, salicylic acid, 4-aminosalicylic acid, sebacic acid, stearic acid, succinic acid, thiocyanic acid, undecylenic acid, trifluoroacetic acid, benzenesulfonic acid, p-toluenesulfonic acid and L-malic acid.

The objective of the present invention is also to provide a method for preparing the crystal form of the compound of formula (I) or the compound of formula (Ia), specifically comprising the following steps of:

1) weighing an appropriate amount of the free base of formula (VI) or the corresponding acid addition salt, followed by adding a good solvent and heating the mixture until dissolved;
2) after stirring for several hours, adding dropwise a poor solvent until turbidity appears;
3) stirring and cooling the mixture, followed by precipitating a crystal to obtain the target product;

wherein:

the good solvent is selected from the group consisting of 88% acetone, ethyl acetate, methanol, ethanol, dichloromethane, acetone and tetrahydrofuran; and preferably ethyl acetate;

the organic solvent is selected from the group consisting of 88% acetone, methanol, ethanol, ethyl acetate, dichloromethane, acetone, toluene, acetonitrile, tetrahydrofuran, heptane, methyl tert-butyl ether, isopropyl ether and N,N-dimethylformamide; and preferably tetrahydrofuran and ethanol; the good solvent and organic solution are miscible when used;

the poor solvent is selected from the group consisting of n-heptane, methyl tert-butyl ether and isopropyl ether; and preferably n-heptane and methyl tert-butyl ether; the poor solvent, good solvent and organic solution are miscible when used; in a preferred embodiment of the present invention, the crystal form of the compound of formula (VI) is crystal form I of the free base (crystal form I of the free base of Example 40), wherein x is 0, the crystal form is crystal form I of the free base, the X-ray powder diffraction pattern thereof has a diffraction peak at 2θ (±0.2°) of 16.7, or a diffraction peak at 2θ (±0.2°) of 12.6, or a diffraction peak at 2θ (±0.2°) of 17.4, or a diffraction peak at 2θ (±0.2°) of 7.3, or a diffraction peak at 2θ (±0.2°) of 20.2, or a diffraction peak at 2θ (±0.2°) of 20.6, or a diffraction peak at 2θ (±0.2°) of 11.9, or a diffraction peak at 2θ (±0.2°) of 11.1, or a diffraction peak at 2θ (±0.2°) of 23.9, or a diffraction peak at 2θ (±0.2°) of 21.9, or a diffraction peak at 2θ (±0.2°) of 38.4; preferably comprises any 3 to 11, or 5 to 8, or 6 to 8 of the above diffraction peaks, and more preferably comprises any 3, 6, 8, 10 or 11 of the above diffraction peaks.

In a preferred embodiment of the present invention, the X-ray powder diffraction pattern of crystal form I of the free base of Example 40 has diffraction peaks at 2θ (±0.2°) of 16.7, 12.6 and 17.4, and optionally further comprises one or more diffraction peaks at 2θ (±0.2°) of 7.3, 20.2, 20.6, 11.9, 11.1, 23.9, 21.9 and 38.4.

Preferably, the X-ray powder diffraction pattern of the crystal form has diffraction peaks at 2θ (±0.20) of 16.7, 12.6, 17.4, 7.3, 20.2 and 20.6.

Further preferably, the X-ray powder diffraction pattern of the crystal form has diffraction peaks at 2θ (±0.2) of 16.7, 12.6, 17.4, 7.3, 20.2, 20.6, 11.9 and 11.1.

Still further preferably, the X-ray powder diffraction pattern of the crystal form has diffraction peaks at 2θ (±0.20) of 16.7, 12.6, 17.4, 7.3, 20.2, 20.6, 11.9, 11.1, 23.9 and 21.9.

More further preferably, the X-ray powder diffraction pattern of the crystal form has diffraction peaks at 2θ (±0.24) of 16.7, 12.6, 17.4, 7.3, 20.2, 20.6, 11.9, 11.1, 23.9, 21.9 and 38.4.

In a preferred embodiment of the present invention, the crystal form of the compound of formula (VI) is crystal form I of the free base (i.e., crystal form I of the free base of Example 40), the X-ray powder diffraction pattern has diffraction peaks at 2θ (±0.20) of 16.7, 12.6 and 14.6, preferably has diffraction peaks at 2θ (±0.28) of 7.3, 13.2, 17.4, 19.4, 20.2 and 20.6, and more preferably has diffraction peaks at 2θ (±0.20) of 9.2, 11.1, 11.9, 19.6, 22.3 and 25.5.

Using Cu—Kα radiation, the characteristic X-ray diffraction peaks represented by 2θ angle and interplanar spacing d value are shown in Table 1.

TABLE 1

XRPD diffraction data of crystal form I of the free base of Example 40

| No. | 2θ (±0.2°) | d value | Peak height | Proportion (I %) | Area | Proportion (I %) |
|---|---|---|---|---|---|---|
| 1 | 7.288 | 12.1189 | 2551 | 37.8 | 22414 | 34.8 |
| 2 | 9.150 | 9.6575 | 870 | 12.9 | 7007 | 10.9 |
| 3 | 11.116 | 7.9532 | 903 | 13.4 | 8073 | 12.5 |
| 4 | 11.908 | 7.4258 | 1388 | 20.6 | 11394 | 17.7 |
| 5 | 12.596 | 7.0219 | 5007 | 74.1 | 47359 | 73.6 |
| 6 | 13.162 | 6.7210 | 1828 | 27.1 | 17604 | 27.4 |
| 7 | 14.600 | 6.0620 | 3880 | 57.5 | 48117 | 74.8 |
| 8 | 16.711 | 5.3008 | 6753 | 100.0 | 64337 | 100.0 |
| 9 | 17.399 | 5.0927 | 4992 | 73.9 | 44437 | 69.1 |
| 10 | 19.364 | 4.5801 | 2485 | 36.8 | 28292 | 44.0 |
| 11 | 19.606 | 4.5242 | 265 | 3.9 | 12347 | 19.2 |
| 12 | 20.220 | 4.3880 | 2717 | 40.2 | 23559 | 36.6 |
| 13 | 20.584 | 4.3114 | 2486 | 36.8 | 24247 | 37.7 |
| 14 | 21.923 | 4.0509 | 493 | 7.3 | 6503 | 10.1 |
| 15 | 22.266 | 3.9893 | 1498 | 22.2 | 17506 | 27.2 |
| 16 | 23.893 | 3.7212 | 429 | 6.4 | 4438 | 6.9 |
| 17 | 24.253 | 3.6667 | 558 | 8.3 | 5180 | 8.1 |
| 18 | 25.549 | 3.4836 | 880 | 13.0 | 14209 | 22.1 |
| 19 | 26.400 | 3.3733 | 501 | 7.4 | 5772 | 9.0 |
| 20 | 27.738 | 3.2135 | 712 | 10.5 | 6813 | 10.6 |
| 21 | 28.657 | 3.1125 | 382 | 5.7 | 4540 | 7.1 |
| 22 | 29.362 | 3.0393 | 699 | 10.4 | 6699 | 10.4 |
| 23 | 30.354 | 2.9422 | 179 | 2.7 | 3524 | 5.5 |
| 24 | 35.099 | 2.5546 | 303 | 4.5 | 3607 | 5.6 |
| 25 | 38.421 | 2.3410 | 506 | 7.5 | 6863 | 10.7 |
| 26 | 38.970 | 2.3093 | 246 | 3.6 | 3560 | 5.5 |

The compound of formula (VI) of the present invention is crystal form I of the free base compound (i.e., crystal form I of the free base of Example 40), the X-ray powder diffraction pattern thereof is substantially as shown in FIG. 1.

The compound of formula (VI) of the present invention is crystal form I of the free base compound (i.e., crystal form I of the free base of Example 40), the DSC spectrum thereof has an endothermic peak at 151.4±0.5° C., and the TGA spectrum shows a weight loss of 0.36% at 40 to 150° C., indicating that there is almost no residual solvent. The DSC spectrum thereof shows no thermal effect before 120° C., and the TGA spectrum shows no weight loss before 120° C., indicating that there is no crystal water in crystal form I of the free base. Specifically, the TGA-DSC spectrum thereof is substantially as shown in FIG. 2.

The compound of formula (VI) of the present invention is crystal form I of the free base compound (i.e., crystal form I of the free base of Example 40), the DVS spectrum thereof is substantially as shown in FIG. 8.

In a preferred embodiment of the present invention, the acid addition salt of the compound of formula (VI), and a hydrate form, stereoisomer, pharmaceutically acceptable salt and crystal form thereof, wherein x is 0, is crystal form II of the free base (i.e., crystal form II of the free base of Example 40), the X-ray powder diffraction pattern has diffraction peaks at 2θ (±0.2°) of 11.7, 13.4, 13.6, 16.6 and 18.9, further has diffraction peaks at 2θ (±0.2°) of 9.5, 10.1, 14.7, 19.3, and more further has diffraction peaks at 2θ (±0.2°) of 19.6, 20.6, 20.9, 21.6, 22.1, 22.5, 22.7 and 24.4.

The compound of formula (VI) of the present invention is crystal form II of the free base (i.e., crystal form II of the free base of Example 40), using Cu—Ku. radiation, the characteristic X-ray diffraction peaks represented by 2θ angle and interplanar spacing d value are shown in Table 2.

TABLE 2

XRPD diffraction data of crystal form II of the free base of Example 40

| No. | 2θ (±0.2°) | d value | Peak height | Proportion (I %) | Area | Proportion (I %) |
|---|---|---|---|---|---|---|
| 1 | 6.859 | 12.8757 | 247 | 3.2 | 1404 | 2.8 |
| 2 | 9.553 | 9.2509 | 549 | 7.0 | 3649 | 7.2 |
| 3 | 10.064 | 8.7818 | 919 | 11.7 | 6282 | 12.4 |
| 4 | 11.686 | 7.5667 | 7662 | 97.7 | 49042 | 96.9 |
| 5 | 13.447 | 6.5792 | 3825 | 48.8 | 36976 | 73.1 |
| 6 | 13.611 | 6.5004 | 4165 | 53.1 | 50588 | 100.0 |
| 7 | 14.687 | 6.0266 | 1032 | 13.2 | 6283 | 12.4 |
| 8 | 16.587 | 5.3401 | 7055 | 90.0 | 45926 | 90.8 |
| 9 | 18.135 | 4.8877 | 337 | 4.3 | 2153 | 4.3 |
| 10 | 18.904 | 4.6905 | 7841 | 100.0 | 50136 | 99.1 |
| 11 | 19.307 | 4.5936 | 2178 | 27.8 | 21273 | 42.1 |
| 12 | 19.593 | 4.5272 | 998 | 12.7 | 6508 | 12.9 |
| 13 | 20.601 | 4.3079 | 1793 | 22.9 | 12880 | 25.5 |
| 14 | 20.966 | 4.2336 | 1482 | 18.9 | 10103 | 20.0 |
| 15 | 21.555 | 4.1193 | 1425 | 18.2 | 9159 | 18.1 |
| 16 | 22.064 | 4.0254 | 1165 | 14.9 | 7826 | 15.5 |
| 17 | 22.468 | 3.9538 | 1088 | 13.9 | 8815 | 17.4 |
| 18 | 22.676 | 3.9181 | 1160 | 14.8 | 9277 | 18.3 |
| 19 | 23.402 | 3.7981 | 559 | 7.1 | 4389 | 8.7 |
| 20 | 24.437 | 3.6396 | 1187 | 15.1 | 9394 | 18.6 |
| 21 | 25.635 | 3.4721 | 582 | 7.4 | 5209 | 10.3 |

The compound of formula (VI) of the present invention is crystal form II of the free base (i.e., crystal form II of the free base of Example 40), the X-ray powder diffraction pattern thereof is substantially as shown in FIG. 3.

The compound of formula (VI) of the present invention is crystal form II of the free base (i.e., crystal form II of the free base of Example 40), the DSC spectrum thereof has an endothermic peak at 193.5±0.5° C., and the TGA spectrum shows a weight loss of 0.32% at 40 to 150° C., indicating that there is almost no residual solvent. The DSC spectrum thereof shows no thermal effect before 120° C., and the TGA spectrum shows no weight loss before 120° C., indicating that there is no crystal water in crystal form II of the free base. Specifically, the TGA-DSC spectrum thereof is substantially as shown in FIG. 4.

The compound of formula (VI) of the present invention is crystal form II of the free base (i.e., crystal form II of the free base of Example 40), the DVS spectrum thereof is substantially as shown in FIG. 9.

In a preferred embodiment of the present invention, the acid addition salt of the compound of formula (VI), and a hydrate form, stereoisomer, pharmaceutically acceptable salt and crystal form thereof, wherein x is 0, is crystal form III of the free base (i.e., crystal form III of the free base of Example 40), the X-ray powder diffraction pattern has diffraction peaks at 2θ (±0.2°) of 10.0, 11.7, 13.7, 16.6, 18.9 and 19.2, and further has diffraction peaks at 2θ (±0.2°) of 13.4, 19.6, 20.6, 20.9, 22.0, 22.7, 23.4 and 25.6.

The compound of formula (I) of the present invention is crystal form III of the free base (i.e., crystal form III of the free base of Example 40), using Cu—Kα radiation, the characteristic X-ray diffraction peaks represented by 2θ angle and interplanar spacing d value are shown in Table 3.

TABLE 3

XRPD diffraction data of crystal form III of the free base of Example 40

| No. | 2θ (±0.2°) | d value | Peak height | Proportion (I %) | Area | Proportion (I %) |
|---|---|---|---|---|---|---|
| 1 | 10.044 | 8.7990 | 2662 | 20.1 | 15303 | 20.3 |
| 2 | 11.663 | 7.5810 | 13229 | 100.0 | 75496 | 100.0 |
| 3 | 13.425 | 6.5899 | 634 | 4.8 | 4077 | 5.4 |

TABLE 3-continued

| XRPD diffraction data of crystal form III of the free base of Example 40 | | | | | | |
|---|---|---|---|---|---|---|
| No. | 2θ (±0.2°) | d value | Peak height | Proportion (I %) | Area | Proportion (I %) |
| 4 | 13.686 | 6.4649 | 1660 | 12.5 | 10588 | 14.0 |
| 5 | 16.553 | 5.3512 | 1365 | 10.3 | 9233 | 12.2 |
| 6 | 18.898 | 4.6921 | 1677 | 12.7 | 11100 | 14.7 |
| 7 | 19.242 | 4.6089 | 5126 | 38.7 | 34095 | 45.2 |
| 8 | 19.570 | 4.5324 | 735 | 5.6 | 5086 | 6.7 |
| 9 | 20.563 | 4.3156 | 781 | 5.9 | 5059 | 6.7 |
| 10 | 20.930 | 4.2408 | 922 | 7.0 | 5977 | 7.9 |
| 11 | 22.042 | 4.0294 | 740 | 5.6 | 4722 | 6.3 |
| 12 | 22.668 | 3.9194 | 524 | 4.0 | 3890 | 5.2 |
| 13 | 23.382 | 3.8013 | 579 | 4.4 | 4110 | 5.4 |
| 14 | 25.611 | 3.4754 | 524 | 4.0 | 3860 | 5.1 |

The compound of formula (VI) of the present invention is crystal form III of the free base (i.e., crystal form III of the free base of Example 40), the X-ray powder diffraction pattern thereof is substantially as shown in FIG. 5.

The compound of formula (VI) of the present invention is crystal form III of the free base (i.e., crystal form III of the free base of Example 40), the DSC spectrum thereof has an endothermic peak at 206.4±0.5° C., and the TGA spectrum shows a weight loss of 0.29% at 40 to 150° C., indicating that there is almost no residual solvent. The DSC spectrum thereof shows no thermal effect before 120° C., and the TGA spectrum shows no weight loss before 120° C., indicating that there is no crystal water in crystal form III of the free base. The TGA-DSC spectrum thereof is substantially as shown in FIG. 6.

The compound of formula (VI) of the present invention is crystal form III of the free base (i.e., crystal form III of the free base of Example 40), the DVS spectrum thereof is substantially as shown in FIG. 10.

In a preferred embodiment of the present invention, the acid addition salt of the compound of formula (VI), and a hydrate form, stereoisomer, pharmaceutically acceptable salt and crystal form thereof, wherein M is methanesulfonic acid, x is 1, is a crystal form of mesylate (i.e., crystal form of the mesylate of Example 40), the X-ray powder diffraction pattern has diffraction peaks at 2θ (±0.2°) of 12.5, 13.5, 19.4 and 19.9, further has diffraction peaks at 2θ (±0.2°) of 15.1, 15.8, 16.5, 17.3, 18.7 and 23.1, and more further has diffraction peaks at 2θ (±0.2°) of 11.1, 11.5, 13.9, 18.5, 21.3, 21.7, 26.5 and 28.9.

The compound of formula (VI) of the present invention is mesylate (i.e., the mesylate of Example 40), using Cu—Kα radiation, the characteristic X-ray diffraction peaks represented by 2θ angle and interplanar spacing d value are shown in Table 4.

TABLE 4

| XRPD diffraction data of the mesylate of formula (VI) (i.e., the mesylate of Example 40) | | | | | | |
|---|---|---|---|---|---|---|
| No. | 2θ (±0.2°) | d value | Peak height | Proportion (I %) | Area | Proportion (I %) |
| 1 | 11.095 | 7.9682 | 80 | 11.4 | 766 | 10.0 |
| 2 | 11.513 | 7.6794 | 71 | 10.1 | 802 | 10.5 |
| 3 | 12.453 | 7.1021 | 404 | 57.5 | 2870 | 37.5 |
| 4 | 13.469 | 6.5687 | 232 | 33.0 | 3530 | 46.1 |
| 5 | 13.936 | 6.3493 | 111 | 15.8 | 1324 | 17.3 |
| 6 | 15.088 | 5.8672 | 257 | 36.6 | 2126 | 27.8 |
| 7 | 15.839 | 5.5907 | 189 | 26.9 | 1459 | 19.0 |
| 8 | 16.477 | 5.3756 | 139 | 19.8 | 1696 | 22.1 |

TABLE 4-continued

| XRPD diffraction data of the mesylate of formula (VI) (i.e., the mesylate of Example 40) | | | | | | |
|---|---|---|---|---|---|---|
| No. | 2θ (±0.2°) | d value | Peak height | Proportion (I %) | Area | Proportion (I %) |
| 9 | 17.260 | 5.1335 | 360 | 51.3 | 2964 | 38.7 |
| 10 | 18.470 | 4.7997 | 157 | 22.4 | 1178 | 15.4 |
| 11 | 18.720 | 4.7363 | 154 | 21.9 | 1529 | 20.0 |
| 12 | 19.387 | 4.5748 | 702 | 100.0 | 7661 | 100.0 |
| 13 | 19.892 | 4.4596 | 245 | 34.9 | 3840 | 50.1 |
| 14 | 20.904 | 4.2461 | 70 | 10.0 | 268 | 3.5 |
| 15 | 21.252 | 4.1773 | 79 | 11.3 | 1703 | 22.2 |
| 16 | 21.653 | 4.1008 | 67 | 9.5 | 1915 | 25.0 |
| 17 | 21.825 | 4.0690 | 65 | 9.3 | 1119 | 14.6 |
| 18 | 22.211 | 3.9991 | 93 | 13.2 | 506 | 6.6 |
| 19 | 23.136 | 3.8412 | 202 | 28.8 | 3124 | 40.8 |
| 20 | 23.463 | 3.7883 | 84 | 12.0 | 651 | 8.5 |
| 21 | 24.006 | 3.7039 | 121 | 17.2 | 1078 | 14.1 |
| 22 | 25.142 | 3.5391 | 82 | 11.7 | 825 | 10.8 |
| 23 | 26.479 | 3.3634 | 116 | 16.5 | 1526 | 19.9 |
| 24 | 28.939 | 3.0828 | 93 | 13.2 | 1964 | 25.6 |

The compound of formula (VI) of the present invention is mesylate (i.e., the mesylate of Example 40), the X-ray powder diffraction pattern thereof is substantially as shown in FIG. 7.

The objective of the present invention is also to provide a pharmaceutical composition comprising a therapeutically effective amount of the acid addition salt of formula (Ia), and one or more pharmaceutically acceptable carriers.

The objective of the present invention is also to provide a use of the compound of formula (Ia) or the pharmaceutical composition comprising the same in the preparation of a $GABA_A$ receptor regulator medicament.

The objective of the present invention is also to provide a pharmaceutical composition comprising a therapeutically effective amount of the crystal form of the compound of formula (I), and one or more pharmaceutically acceptable carriers.

The objective of the present invention is also to provide a pharmaceutical composition comprising the compound of formula (I), (I)

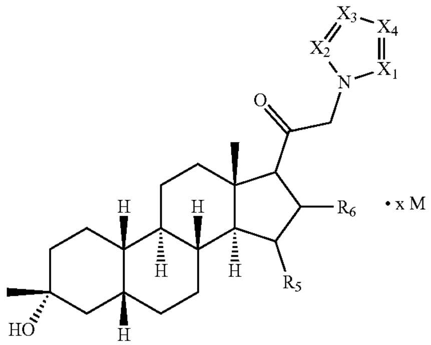

wherein:

- $X_1$ is selected from the group consisting of $CR_1$ and N, and preferably N;
- $X_2$ is selected from the group consisting of $CR_2$ and N;
- $X_3$ is selected from the group consisting of $CR_3$ and N;
- $X_4$ is selected from the group consisting of $CR_4$ and N;
- $R_1$ and $R_2$ are each independently selected from the group consisting of hydrogen, deuterium, cyano, halogen, nitro, amino, $C_{1-8}$ alkyl, $C_{1-8}$ haloalkyl, $C_{1-8}$ alkoxy, $C_{1-8}$ hydroxyalkyl, cyano-substituted $C_{1-8}$ alkyl, $C_{3-8}$ cycloalkyl, cyano-substituted $C_{3-8}$ cycloalkyl, 3 to 8 membered heterocyclyl, $C_{6-10}$ aryl and 5 to 10 membered heteroaryl;

$R_3$ and $R_4$ are each independently selected from the group consisting of hydrogen, deuterium, cyano, halogen, nitro, amino, $C_{1-8}$ alkyl, $C_{1-8}$ haloalkyl, $C_{1-8}$ alkoxy, $C_{1-8}$ hydroxyalkyl, cyano-substituted $C_{1-8}$ alkyl, $C_{3-8}$ cycloalkyl, cyano-substituted $C_{3-8}$ cycloalkyl, 3 to 8 membered heterocyclyl, $C_{6-10}$ aryl, 5 to 10 membered heteroaryl, $-(CH_2)_nR_a$, $-(CH_2)_nOR_a$, $-(CH_2)_nSR_a$, $-(CH_2)_nC(O)R_a$, $-S(O)R_a$, $-S(O)_2R_a$, $-S(O)(=NH)R_a$, $-C(O)OR_a$ and $-C(O)O(CH_2)_nNR_aR_b$, wherein the $C_{1-8}$ alkyl, $C_{2-5}$ alkenyl, $C_{2-8}$ alkynyl, $C_{1-8}$ haloalkyl, $C_{1-8}$ hydroxyalkyl, cyano-substituted $C_{1-8}$ alkyl, $C_{1-8}$ alkoxy, $C_{3-8}$ cycloalkyl, cyano-substituted $C_{3-8}$ cycloalkyl, 3 to 8 membered heterocyclyl, $C_{6-10}$ aryl and 5 to 10 membered heteroaryl can be each optionally further substituted;

$R_5$ and $R_6$ are each independently selected from the group consisting of hydrogen, deuterium, cyano, halogen, nitro, amino, $C_{1-8}$ alkyl, $C_{2-8}$ alkenyl, $C_{2-8}$ alkynyl, $C_{1-8}$ haloalkyl, $C_{1-8}$ alkoxy, $C_{1-8}$ hydroxyalkyl, cyano-substituted $C_{1-8}$ alkyl, $C_{1-8}$ alkylthio, $C_{3-8}$ cycloalkyl, cyano-substituted $C_{3-8}$ cycloalkyl, 3 to 8 membered heterocyclyl, $C_{6-10}$ aryl, 5 to 10 membered heteroaryl, $-(CH_2)_nR_a$, $-(CH_2)_nOR_a$, $-S(O)R_a$, $-S(O)_2R_a$ and $-(CH_2)_nNR_aR_b$, wherein the $C_{1-8}$ alkyl, $C_{2-8}$ alkenyl, $C_{2-8}$ alkynyl, $C_{1-8}$ haloalkyl, $C_{1-8}$ hydroxyalkyl, cyano-substituted $C_{1-8}$ alkyl, $C_{1-8}$ alkoxy, $C_{3-8}$ cycloalkyl, cyano-substituted $C_{3-8}$ cycloalkyl, 3 to 8 membered heterocyclyl, $C_{6-10}$ aryl and 5 to 10 membered heteroaryl can be each optionally further substituted;

or, $R_5$ and $R_6$ together with the carbon atoms to which they are attached form a $C_{3-8}$ cycloalkyl or 3 to 8 membered heterocyclyl, wherein the $C_{3-8}$ cycloalkyl and 3 to 8 membered heterocyclyl can be each optionally further substituted;

wherein $R_5$ and $R_6$ are not hydrogen at the same time;

$R_a$ and $R_b$ are each independently selected from the group consisting of hydrogen, deuterium, halogen, cyano, hydroxy, amino, nitro, $C_{1-8}$ alkyl, $C_{1-8}$ alkoxy, $C_{1-8}$ hydroxyalkyl, $C_{1-8}$ deuterated alkyl, $C_{1-8}$ haloalkyl, $C_{3-8}$ cycloalkyl, 3 to 8 membered heterocyclyl, $C_{6-10}$ aryl and 5 to 10 membered heteroaryl, wherein the $C_{1-8}$ alkyl, $C_{1-8}$ deuterated alkyl, $C_{1-8}$ haloalkyl, $C_{3-8}$ cycloalkyl, 3 to 8 membered heterocyclyl, $C_{6-10}$ aryl and 5 to 10 membered heteroaryl can be each optionally further substituted;

M is an inorganic acid or organic acid, wherein the inorganic acid is selected from the group consisting of hydrochloric acid, sulfuric acid, nitric acid, hydrobromic acid, hydrofluoric acid, hydroiodic acid and phosphoric acid, and the organic acid is selected from the group consisting of 2,5-dihydroxybenzoic acid, 1-hydroxy-2-naphthoic acid, acetic acid, dichloroacetic acid, trichloroacetic acid, acetohydroxamic acid, adipic acid, benzenesulfonic acid, 4-chlorobenzenesulfonic acid, benzoic acid, 4-acetylaminobenzoic acid, 4-aminobenzoic acid, capric acid, caproic acid, caprylic acid, cinnamic acid, citric acid, cyclamic acid, camphorsulfonic acid, aspartic acid, camphor acid, gluconic acid, glucuronic acid, glutamic acid, erythorbic acid, lactic acid, malic acid, mandelic acid, pyroglutamic acid, tartaric acid, lauryl sulfuric acid, dibenzoyl tartaric acid, ethane-1,2-disulfonic acid, ethanesulfonic acid, formic acid, fumaric acid, galactonic acid, gentisic acid, glutaric acid, 2-ketoglutaric acid, glycolic acid, hippuric acid, isethionic acid, lactobionic acid, ascorbic acid, asparagic acid, lauric acid, camphor acid, maleic acid, malonic acid, D-tartaric acid, pamoic acid, methanesulfonic acid, 1,5-naphthalenedisulfonic acid, naphthalene-2-sulfonic acid, nicotinic acid, oleic acid, orotic acid, oxalic acid, palmitic acid, embonic acid, propionic acid, salicylic acid, 4-aminosalicylic acid, sebacic acid, stearic acid, succinic acid, thiocyanic acid, undecylenic acid, trifluoroacetic acid, benzenesulfonic acid, p-toluenesulfonic acid and L-malic acid; and x is selected from the group consisting of 0, 1, 2 and 3;

n is an integer from 0 to 6.

In a preferred embodiment of the present invention, the pharmaceutical composition is characterized in that, $R_1$ and $R_2$ are each independently selected from the group consisting of hydrogen, cyano, halogen, $C_{1-6}$ alkyl and $C_{3-6}$ cycloalkyl, and preferably hydrogen, cyano, halogen, $C_{1-3}$ alkyl and $C_{3-6}$ cycloalkyl;

$R_3$ and $R_4$ are each independently selected from the group consisting of hydrogen, cyano, halogen, nitro, $C_{1-6}$ alkyl, $C_{1-6}$ haloalkyl, $C_{1-6}$ hydroxyalkyl, cyano-substituted $C_{1-6}$ alkyl, $C_{3-6}$ cycloalkyl, cyano-substituted $C_{3-6}$ cycloalkyl, 5 or 6 membered heteroaryl, $-(CH_2)_nSR_a$, $-(CH_2)_nC(O)R_a$, $-S(O)R_a$, $-S(O)_2R_a$, $-S(O)(=NH)R_a$, $-C(O)OR_a$ and $-C(O)O(CH_2)_nNR_aR_b$;

$R_5$ is selected from the group consisting of hydrogen, cyano, halogen, $C_{1-6}$ alkyl, $C_{1-6}$ haloalkyl, $C_{1-6}$ hydroxyalkyl, cyano-substituted $C_{1-6}$ alkyl, $C_{1-6}$ alkoxy, $C_{1-6}$ alkylthio, $C_{3-6}$ cycloalkyl, cyano-substituted $C_{3-6}$ cycloalkyl, 3 to 6 membered heterocyclyl, $C_{6-10}$ aryl, 5 to 10 membered heteroaryl, $-(CH_2)_nR_a$, $-(CH_2)_nOR_a$, $-S(O)_2R_a$ and $-(CH_2)_nNR_aR_b$, wherein the 5 to 10 membered heteroaryl can be optionally further substituted;

$R_6$ is selected from the group consisting of hydrogen, halogen, cyano, $C_{1-6}$ alkyl and $C_{1-6}$ haloalkyl, and preferably hydrogen, halogen, cyano, $C_{1-3}$ alkyl and $C_{1-3}$ haloalkyl;

or, $R_5$ and $R_6$ together with the carbon atoms to which they are attached form a $C_{3-8}$ cycloalkyl, wherein the $C_{3-8}$ cycloalkyl can be optionally further substituted;

wherein $R_5$ and $R_6$ are not hydrogen at the same time;

$R_a$ and $R_b$ are each independently selected from the group consisting of hydrogen, halogen, cyano, nitro, $C_{1-6}$ alkyl, 3 to 6 membered heterocyclyl and 5 to 10 membered heteroaryl, wherein the $C_{1-6}$ alkyl, 3 to 6 membered heterocyclyl and 5 to 10 membered heteroaryl can be each optionally further substituted;

M is selected from the group consisting of hydrochloric acid, sulfuric acid, nitric acid, hydrobromic acid, phosphoric acid, methanesulfonic acid, 1,5-naphthalenedisulfonic acid and p-toluenesulfonic acid; and x is selected from the group consisting of 1 and 2;

n is an integer from 0 to 3.

In a preferred embodiment of the present invention, $R_1$ and $R_2$ are each independently selected from the group consisting of hydrogen, fluorine, chlorine, cyano, methyl and cyclopropyl;

$R_3$ and $R_4$ are each independently selected from the group consisting of hydrogen, halogen, cyano, nitro, $C_{1-3}$ alkyl, cyano-substituted $C_{1-3}$ alkyl, halogen-substituted $C_{1-3}$ alkyl, $C_{1-3}$ hydroxyalkyl, $C_{3-6}$ cycloalkyl, cyano-substituted $C_{3-6}$ cycloalkyl, oxazolyl, $-C(O)R_a$, $-SC_{1-3}$ alkyl, $-S(O)C_{1-3}$ alkyl, $-S(O)_2C_{1-3}$ alkyl, $-C(O)OC_{1-3}$ alkyl, $-S(O)(=NH)C_{1-3}$ alkyl and —C(O)O$(CH_2)_n$N$(CH_3)$$C_{1-3}$ alkyl, and preferably hydrogen, fluorine, chlorine, cyano, nitro, trifluoromethyl, cyclopropyl, cyano-substituted cyclopropyl, cyano-substituted isopropyl, hydroxyisopropyl, oxazolyl, —C(O)$R_a$, —$SCH_3$, —S(O)$CH_3$, —$S(O)_2CH_3$, —C(O)$OCH_2CH_3$, —S(O)(=NH)$CH_3$ and —C(O)O$(CH_2)_2NCH_3(CH_3)$;

$R_5$ is selected from the group consisting of hydrogen, halogen, cyano, $C_{1-3}$ alkyl, $C_{1-3}$ haloalkyl, $C_{1-3}$ alkoxy, $C_{1-3}$ hydroxyalkyl, cyano-substituted $C_{1-3}$ alkyl, $C_{3-6}$ cycloalkyl, cyano-substituted $C_{3-6}$ cycloalkyl, 3 to 6 membered nitrogen-containing heterocyclyl, $C_{6-10}$ aryl, 5 to 10 membered heteroaryl, $C_{1-3}$ alkylthio, —$(CH_2)_n$$R_a$, —$(CH_2)_n$O$R_a$, —$S(O)_2R_a$ and —$(CH_2)_n$N$(R_a)_2$, and preferably hydrogen, fluorine, chlorine, cyano, methyl, ethyl, isopropyl, fluoromethyl, trifluoromethyl, methoxy, cyclopropyl, cyclobutyl, methyl-substituted pyrazolyl, phenyl, —$SCH_3$, —$(CH_2)_n$$R_a$, —N$C(CH_3)_2$, —$S(O)_2C(CH_3)_2$ and —$CH_2N(CH_3)_2$;

$R_6$ is selected from the group consisting of hydrogen, fluorine, cyano, methyl, ethyl and trifluoromethyl;

or, $R_5$ and $R_6$ together with the carbon atoms to which they are attached form a $C_{3-6}$ cycloalkyl, and preferably cyclopropyl, wherein the cyclopropyl is optionally substituted by halogen, and preferably by fluorine;

$R_a$ is selected from the group consisting of hydrogen, nitro, $C_{1-3}$ alkyl, azetidinyl and pyrrolidinyl, wherein the azetidinyl and pyrrolidinyl are each optionally substituted by halogen, and preferably by fluorine;

M is selected from the group consisting of hydrochloric acid, sulfuric acid, methanesulfonic acid, p-toluenesulfonic acid, hydrobromic acid, nitric acid and 1,5-naphthalenedisulfonic acid, and preferably methanesulfonic acid;

x is 0, 1 or 2;

n is selected from the group consisting of 0, 1 and 2.

In a preferred embodiment of the present invention, the structure of the compound of formula (I) is as shown in formula (II):

(II)

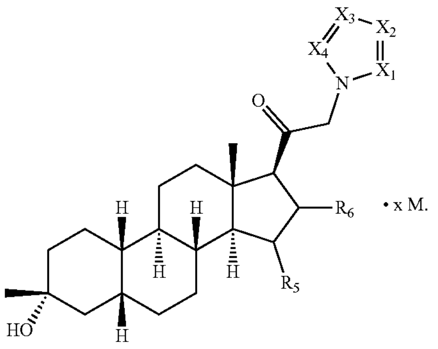

In a preferred embodiment of the present invention, the structure of the compound of formula (I) is as shown in formula (III):

(III)

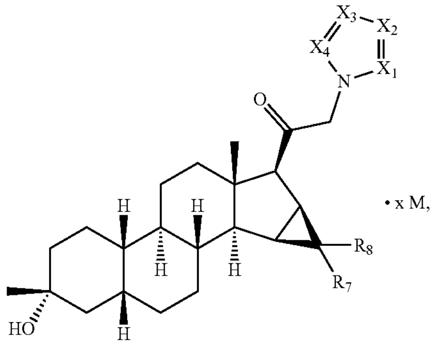

wherein $R_7$ and $R_8$ are each independently selected from the group consisting of hydrogen, fluorine, chlorine, bromine and methyl, and preferably hydrogen and fluorine.

In a preferred embodiment of the present invention, the structure of the compound of formula (I) is as shown in formula (IV):

(IV)

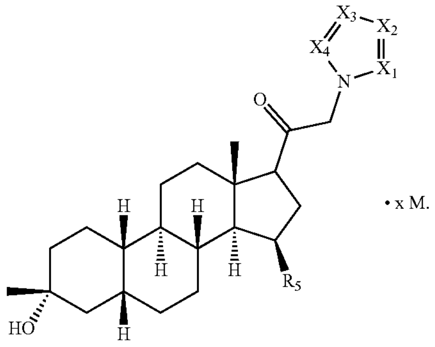

In a preferred embodiment of the present invention, the structure of the compound of formula (I) is as shown in formula (V):

(V)

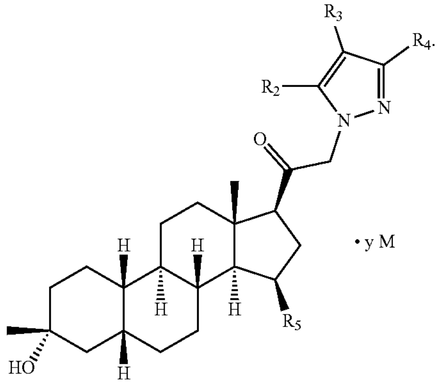

In a preferred embodiment of the present invention, the compound of formula (I) is selected from the group consisting of:

1
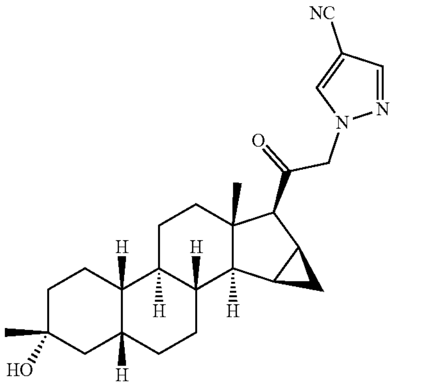
2
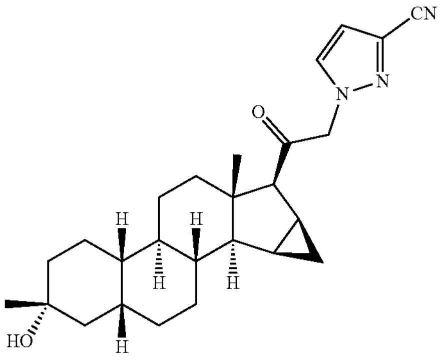
3
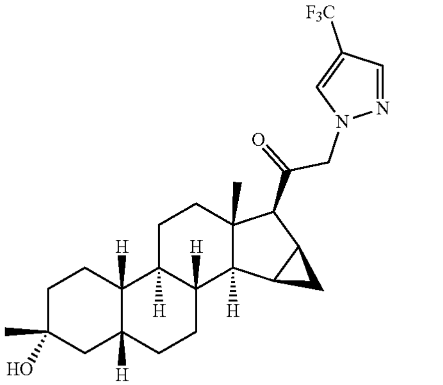
4
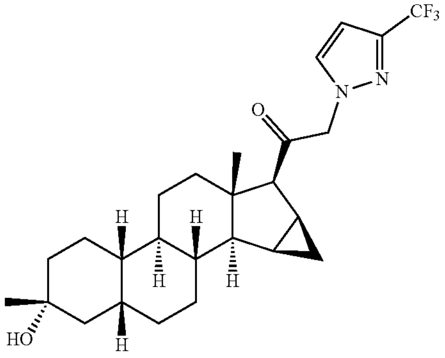
-continued
5
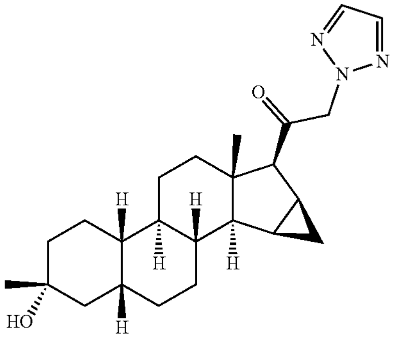
6
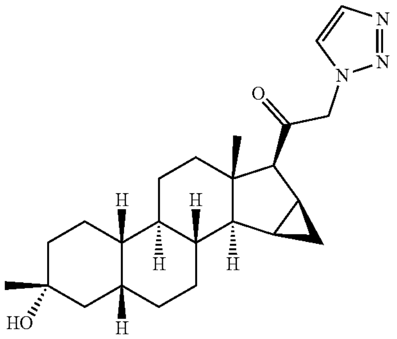
7
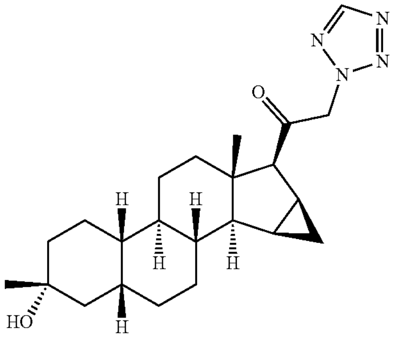
8
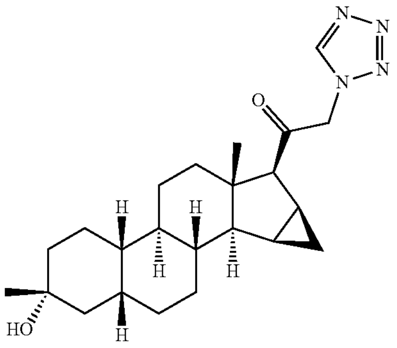

-continued
9
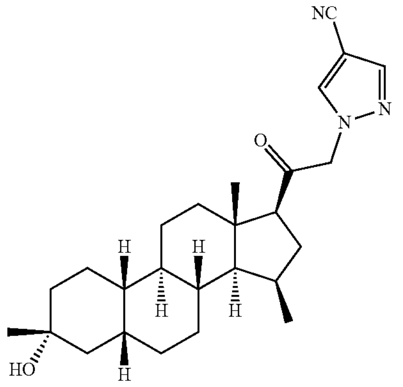
10
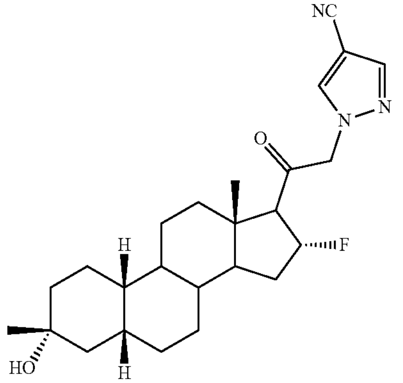
11
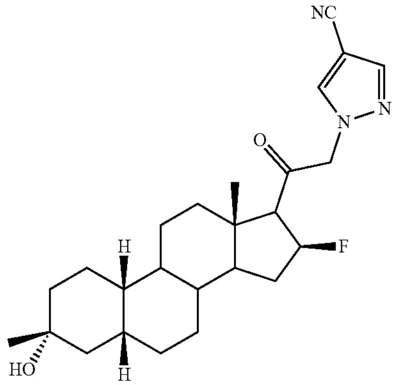
12
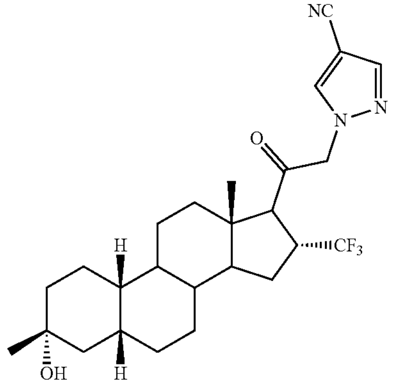
-continued
13
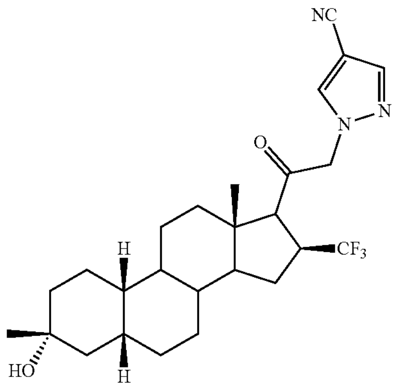
14
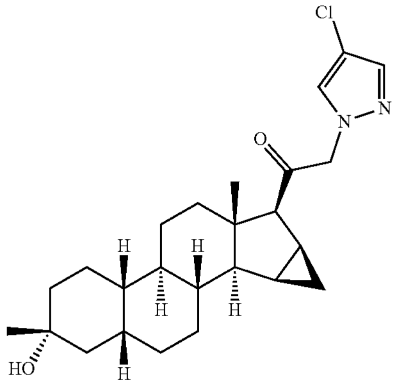
15
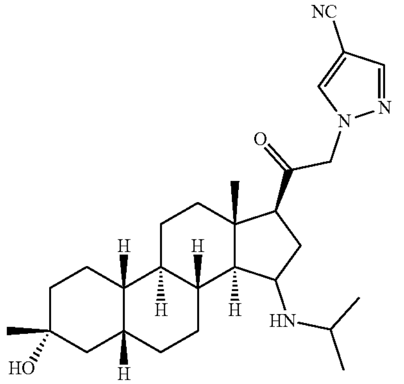
16
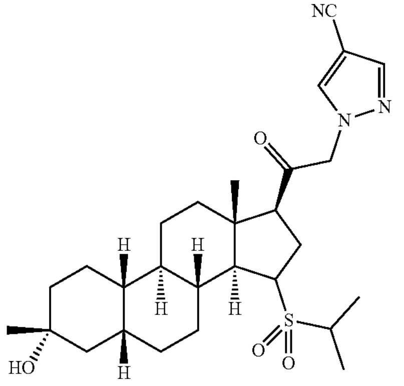

-continued
17
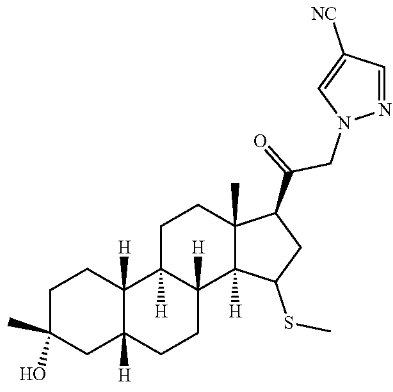
18
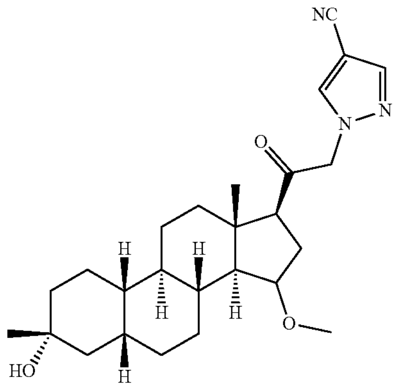
19
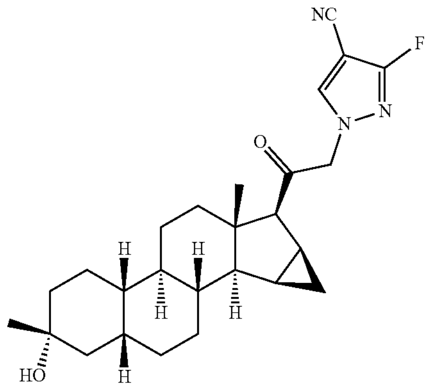
20
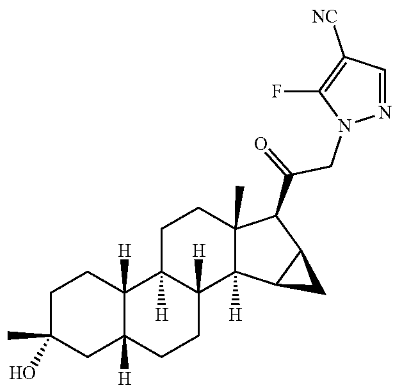
-continued
21
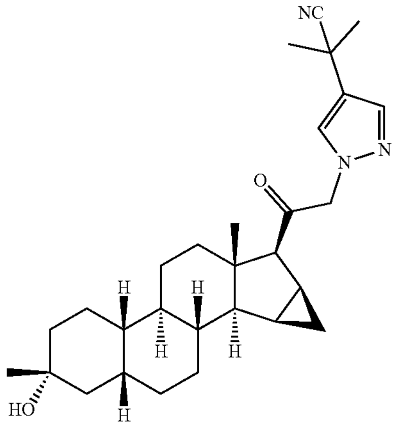
22
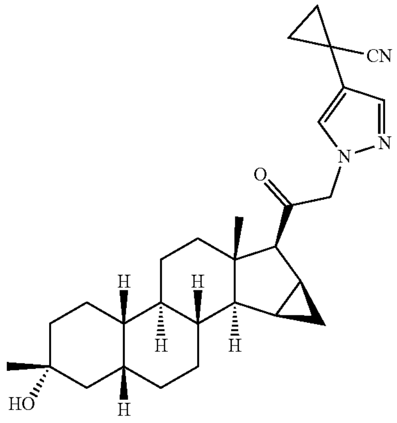
23
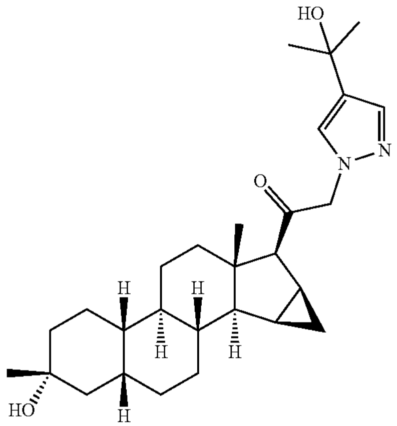

24
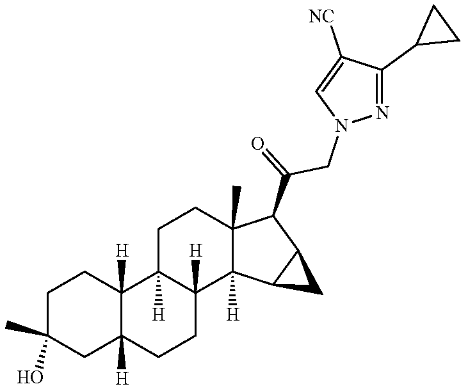
25
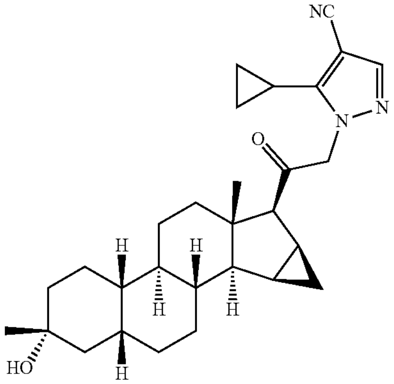
26
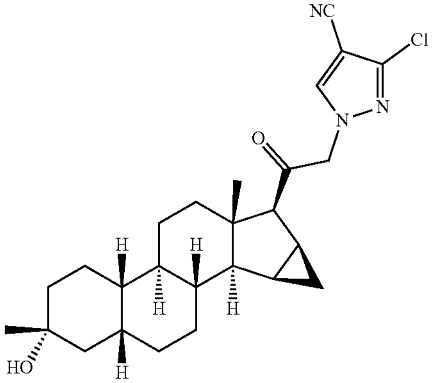
27
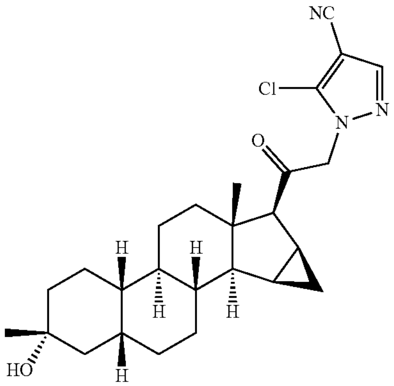
28
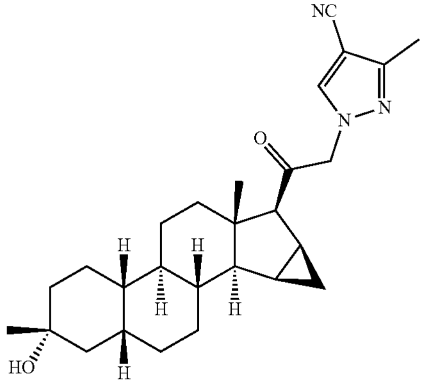
29
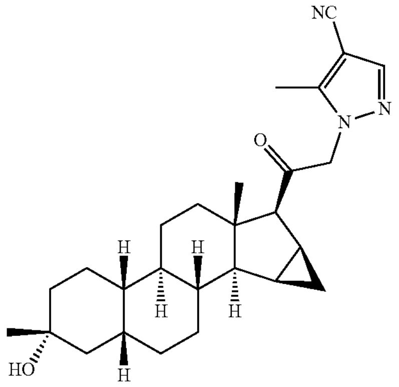
30
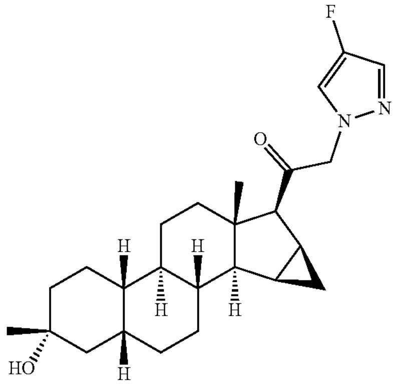
31
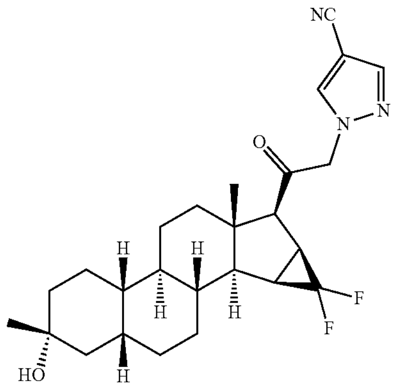

-continued
32
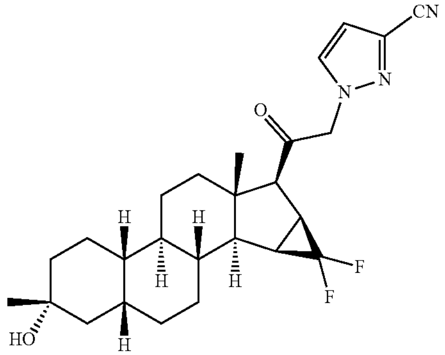
33
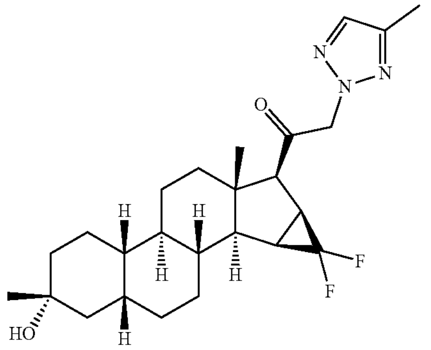
34
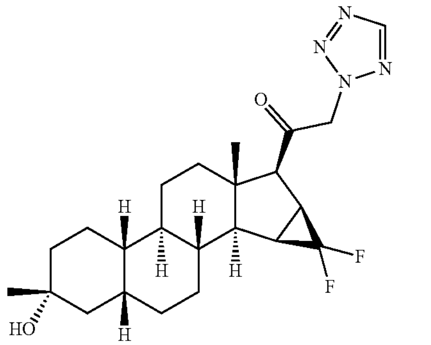
35
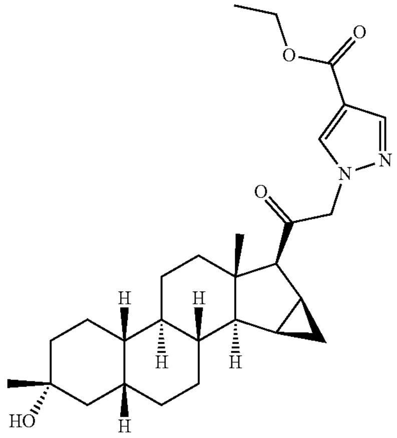
-continued
36
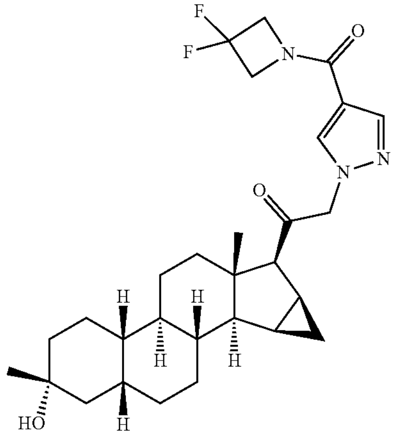
37
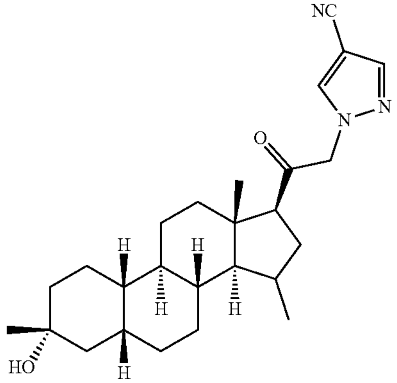
38
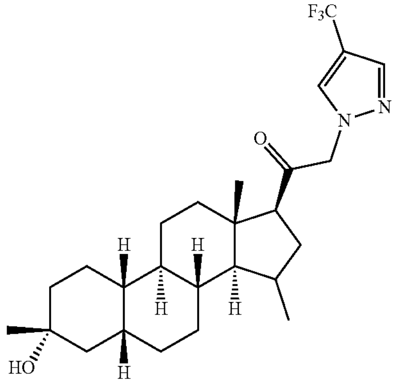
39
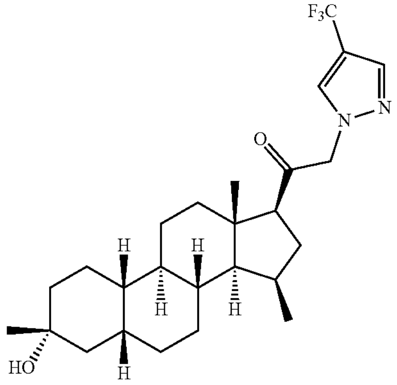

-continued
40
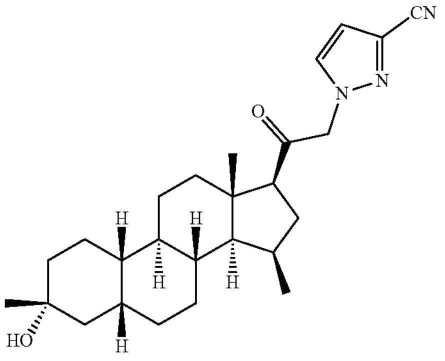
41
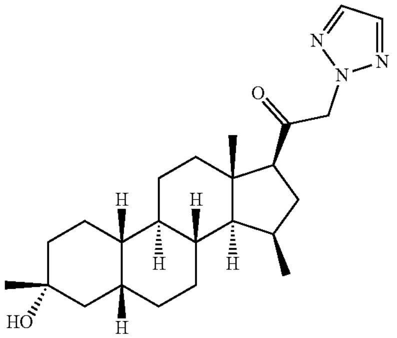
42
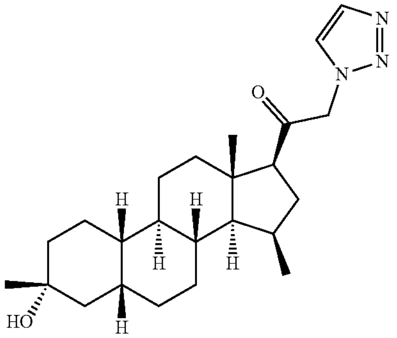
43
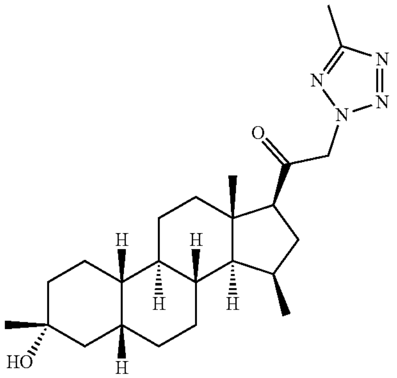
-continued
44
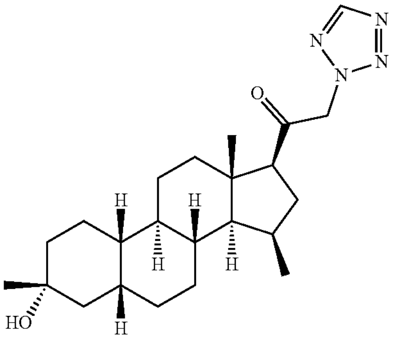
45
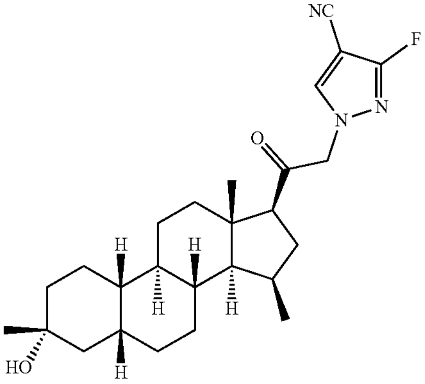
46
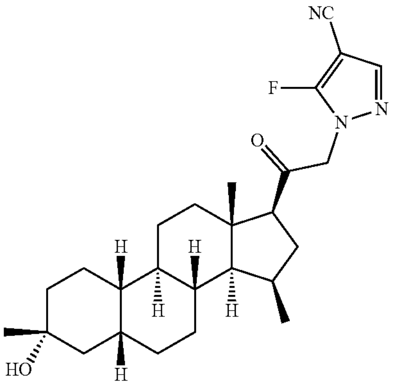
47
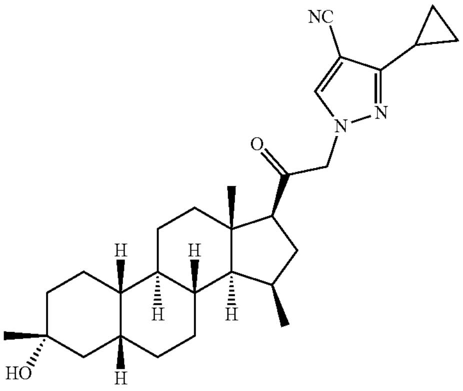

-continued
48
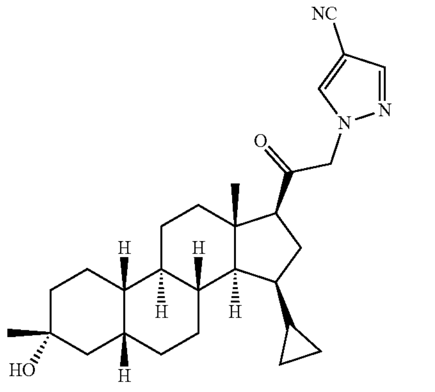
49
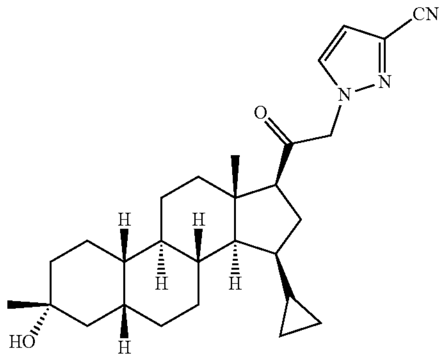
50
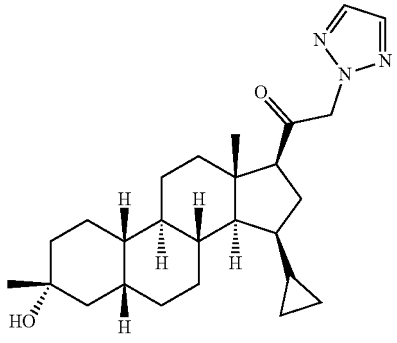
51
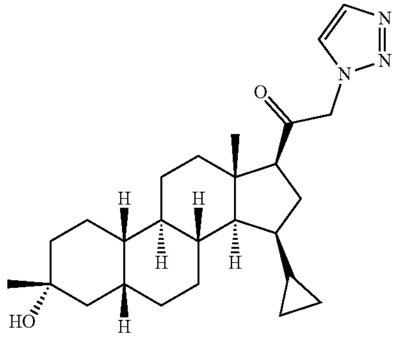
-continued
52
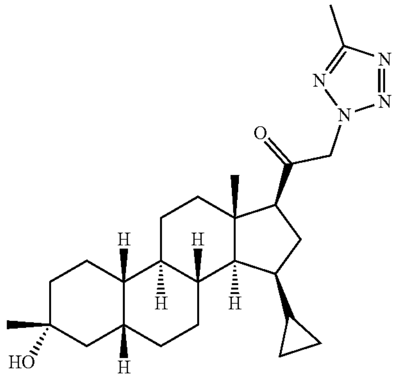
53
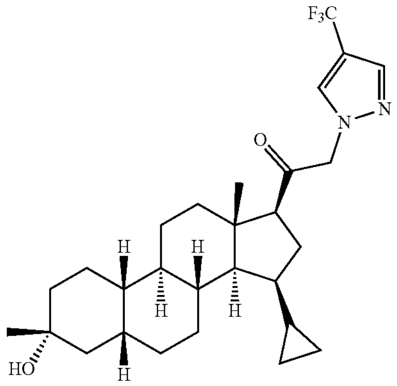
54
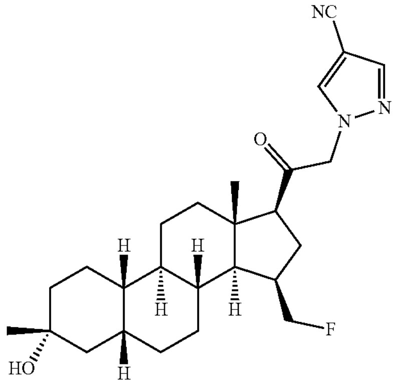
55
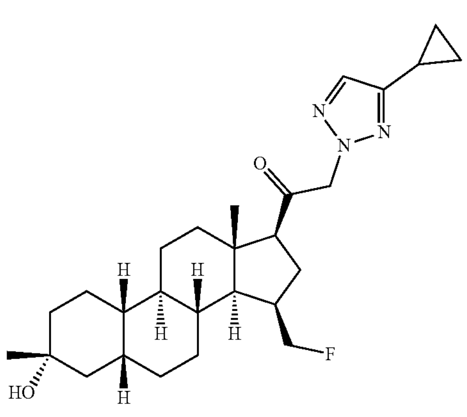

56
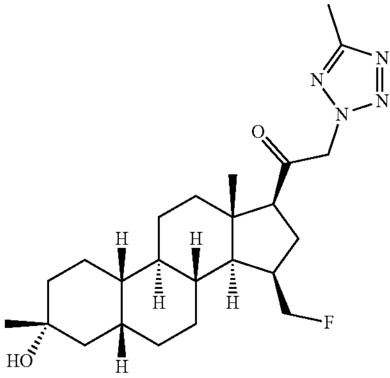
57
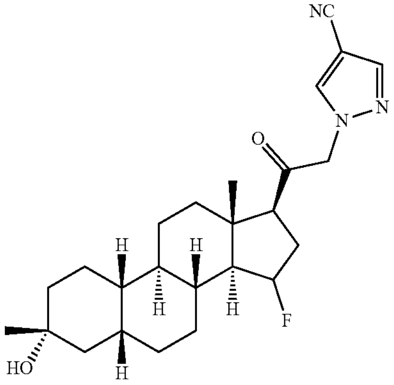
58
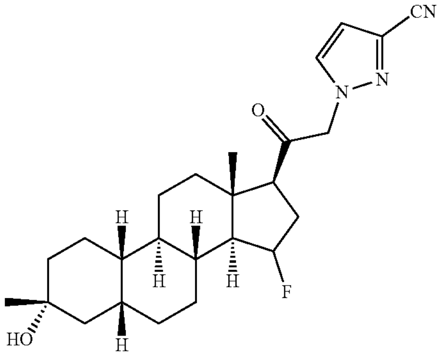
59
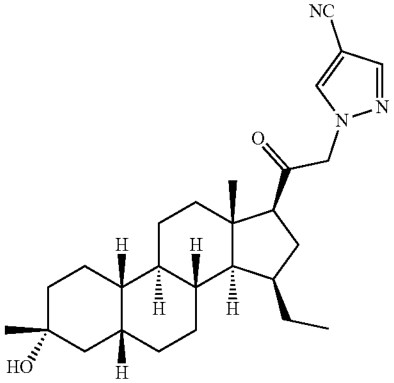
60
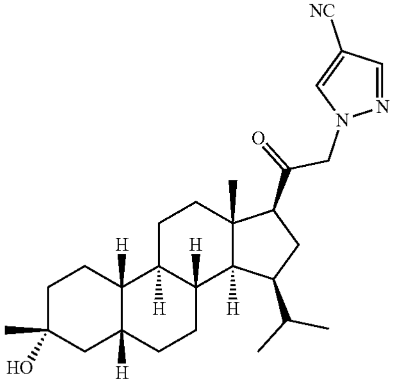
61
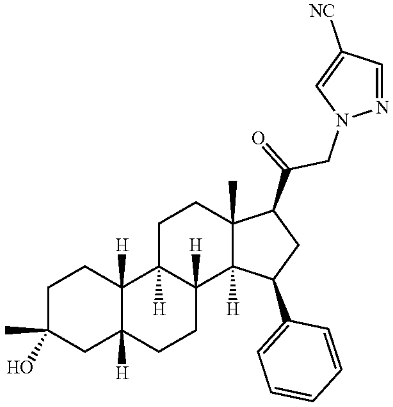
62
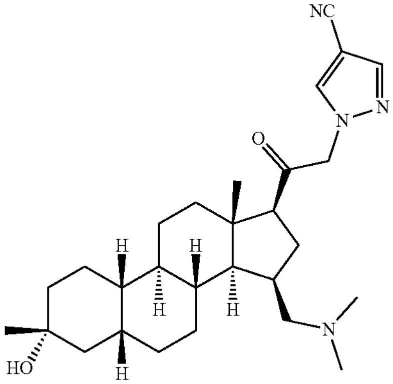
63
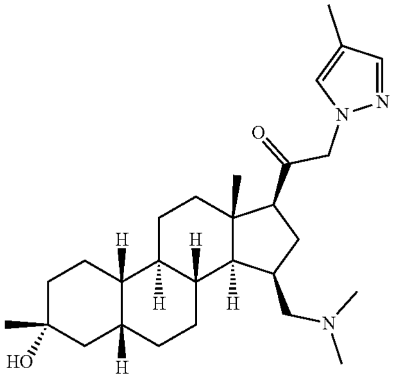

-continued
64
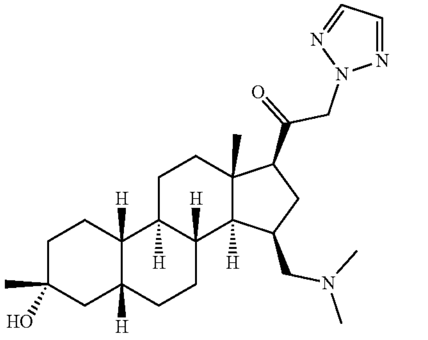
65
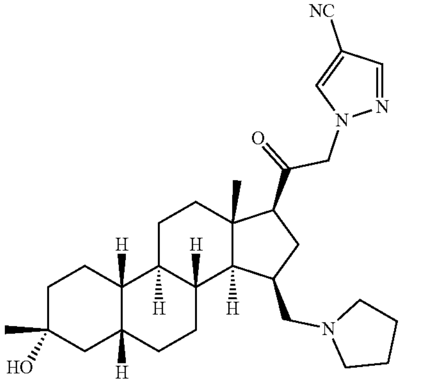
66
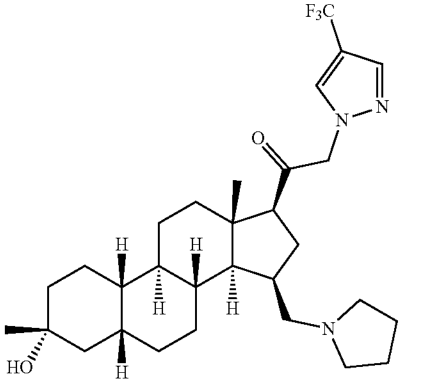
67
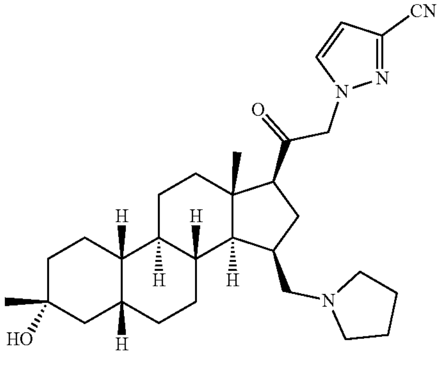
-continued
68
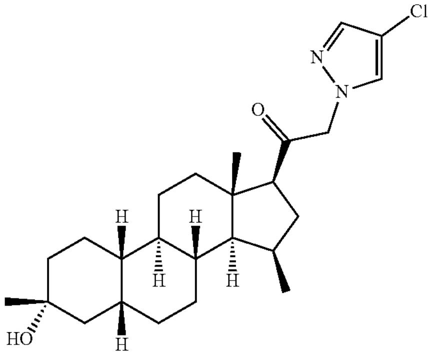
69
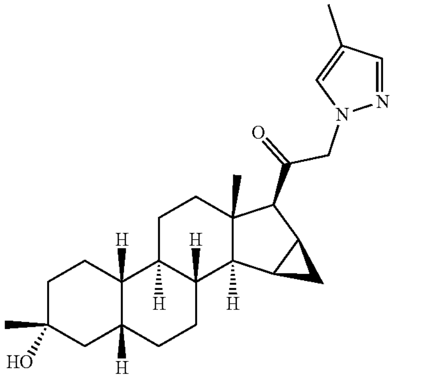
70
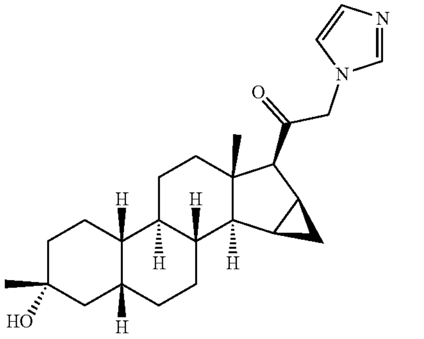
71
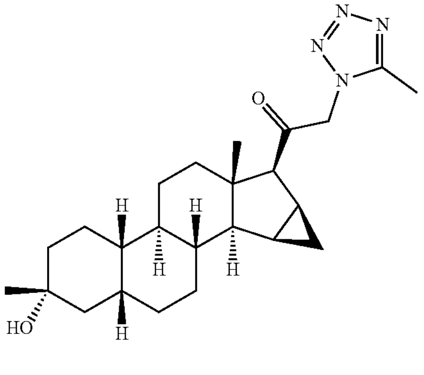

-continued
72
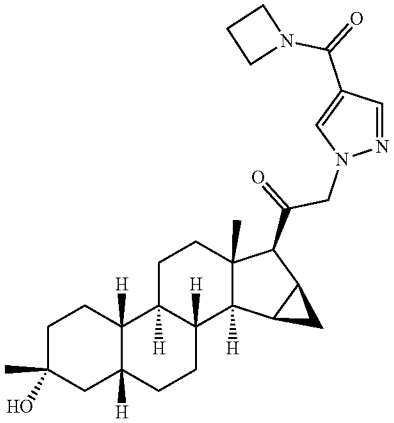
73
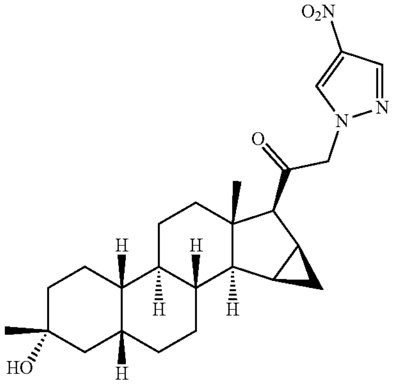
74
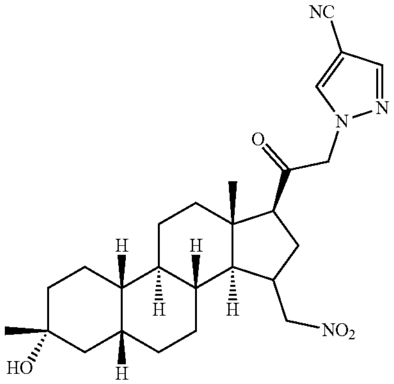
75
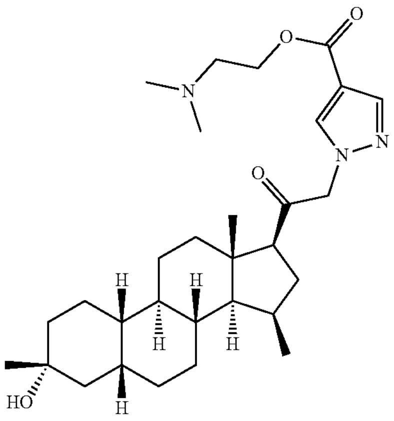
76
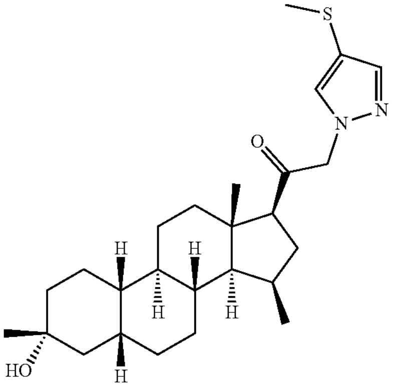
77
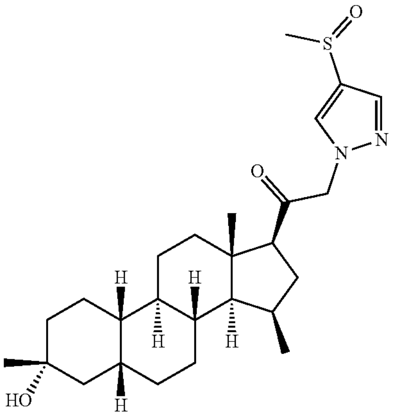
78
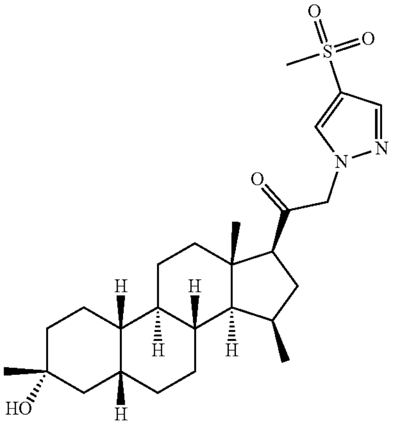

-continued
79
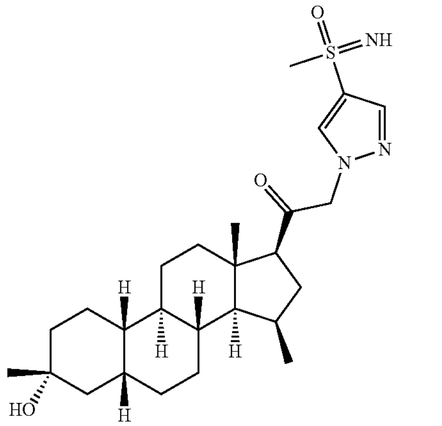
80
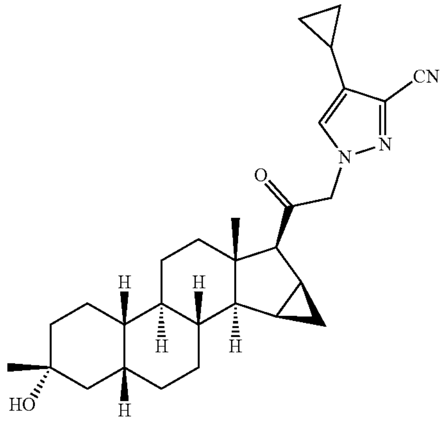
81
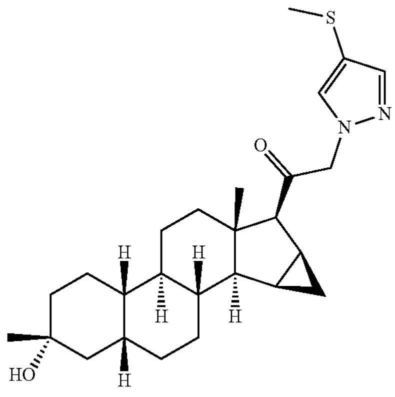
-continued
82
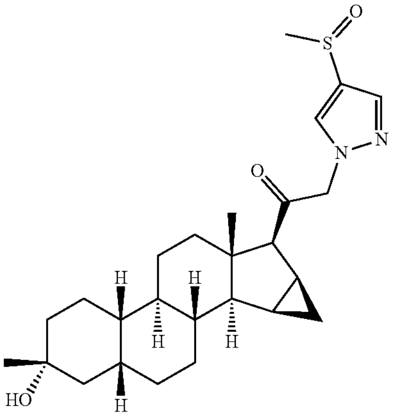
83
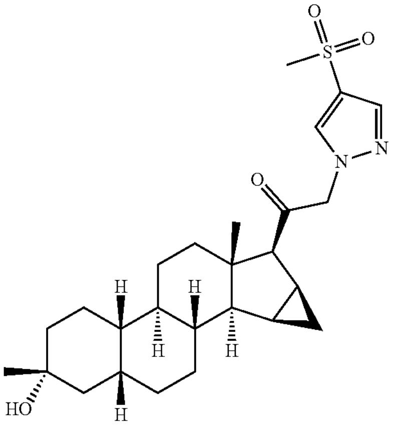
84
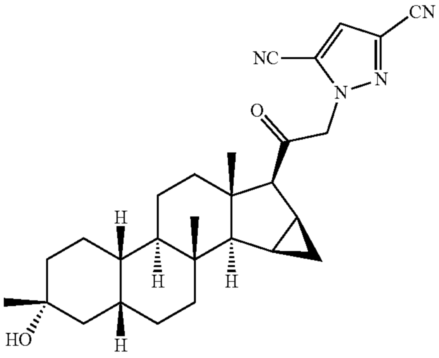
85
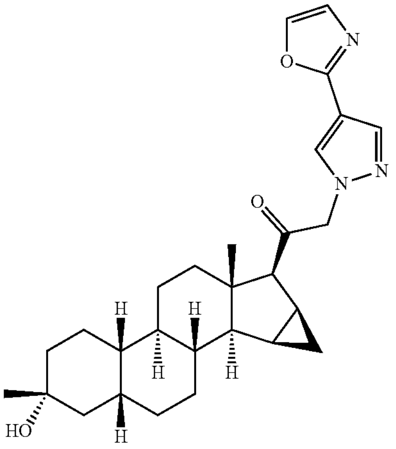

-continued
86
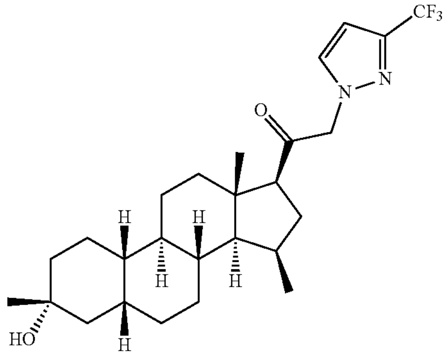
87
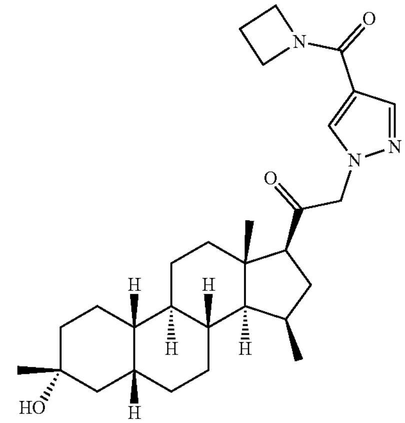
88
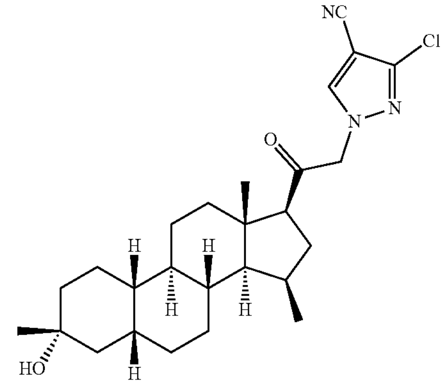
89
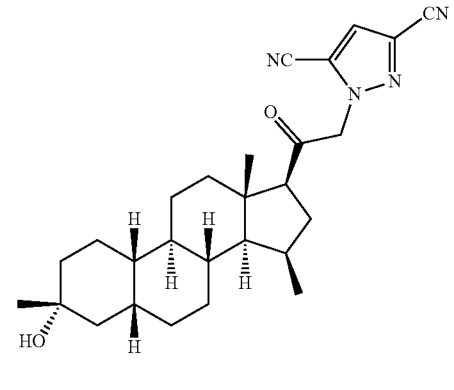
-continued
90
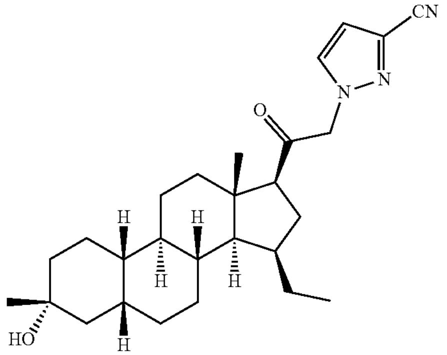
91
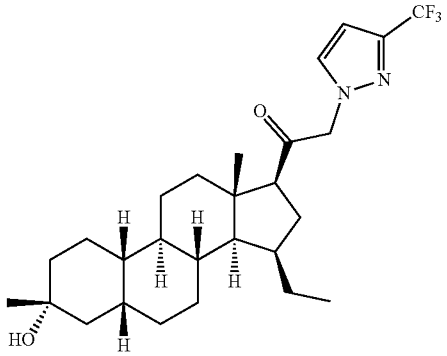
92
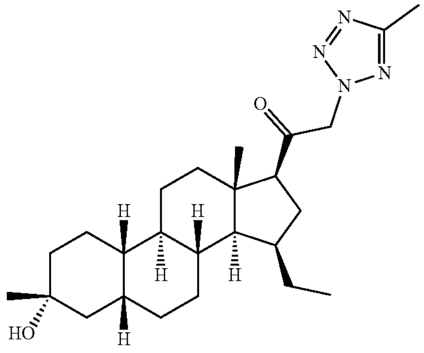
93
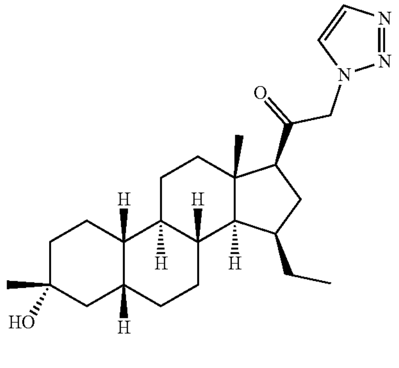

-continued
94
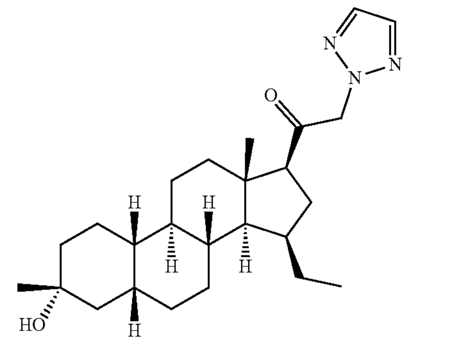
95
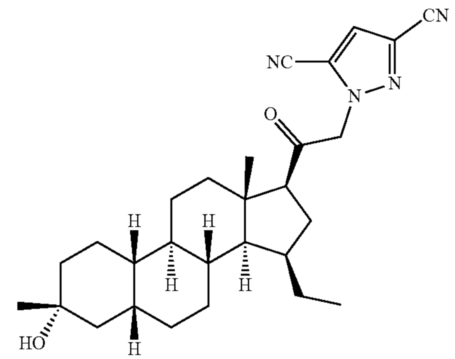
96
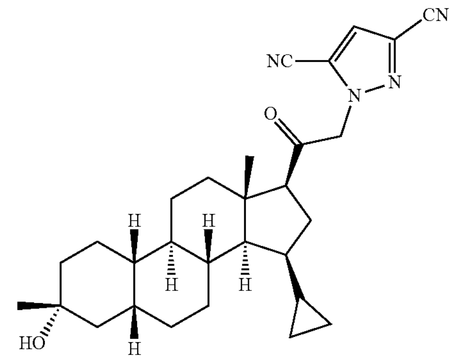
97
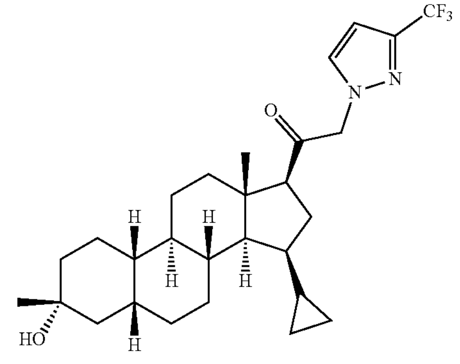
-continued
98
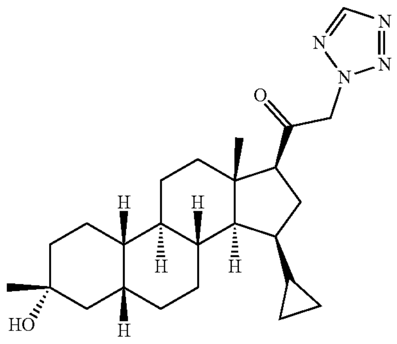
99
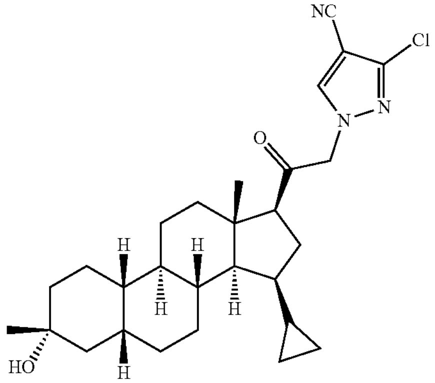
100
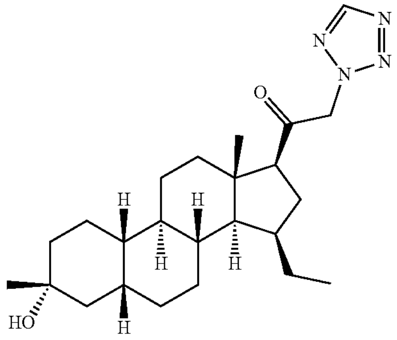
101
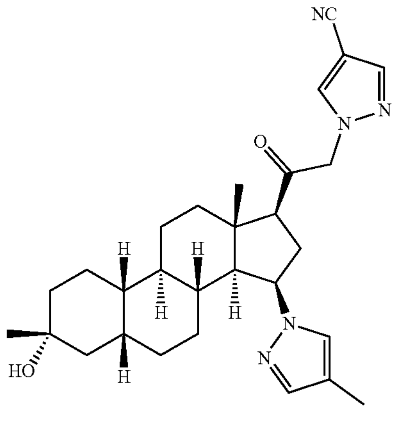

-continued

102

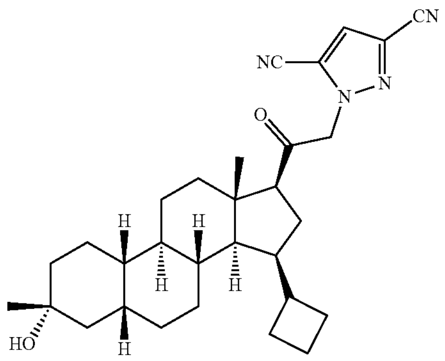

and

103

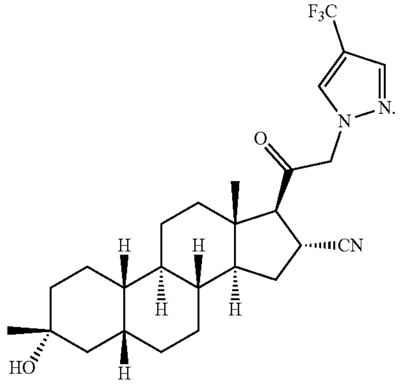

In a preferred embodiment of the present invention, it is the compound of formula (VI):

(VI)

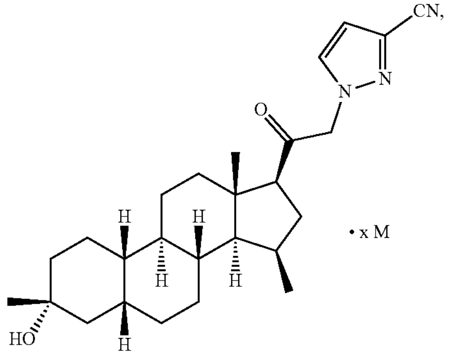

wherein x is selected from the group consisting of 0, 1 and 2.

In a preferred embodiment of the present invention, the pharmaceutical composition is an injection or an oral preparation, and preferably a tablet or a capsule.

In a preferred embodiment of the present invention, the unit dose is 1 to 200 mg, preferably 5 to 200 mg, further preferably 10 to 100 mg, and more preferably 10 to 50 mg.

In a preferred embodiment of the present invention, the unit dose can be 1 mg, 2 mg, 3 mg, 4 mg, 5 mg, 10 mg, 20 mg, 30 mg, 40 mg, 50 mg, 60 mg, 70 mg, 80 mg, 90 mg, 100 mg, 110 mg, 120 mg, 150 mg and the like, preferably 1 to 50 mg, or preferably 1 to 30 mg.

The objective of the present invention is also to provide a use of the crystal form of the compound of formula (I) or the corresponding pharmaceutical composition in the preparation of a $GABA_A$ receptor regulator medicament.

The objective of the present invention is also to provide the crystal form of the compound of formula (VI), and one or more pharmaceutically acceptable carriers.

The objective of the present invention is also to provide a use of the crystal form of the compound of formula (VI) or the corresponding pharmaceutical composition in the preparation of a $GABA_A$ receptor regulator medicament.

In a preferred embodiment of the present invention, the pharmaceutical composition of the $GABA_A$ receptor regulator medicament is used in treating a Central Nervous System (CNS)-related disease, wherein the CNS-related disease is selected from the group consisting of sleep disorder, mood disorder, schizophrenia spectrum disorder, spasmodic disorder, memory disorder and/or cognitive disorder, dyskinesia, personality disorder, autism spectrum disorder, pain, traumatic brain injury, vascular disease, substance abuse disorder and/or withdrawal syndrome or tinnitus.

DETAILED DESCRIPTION OF THE INVENTION

Figure 1:
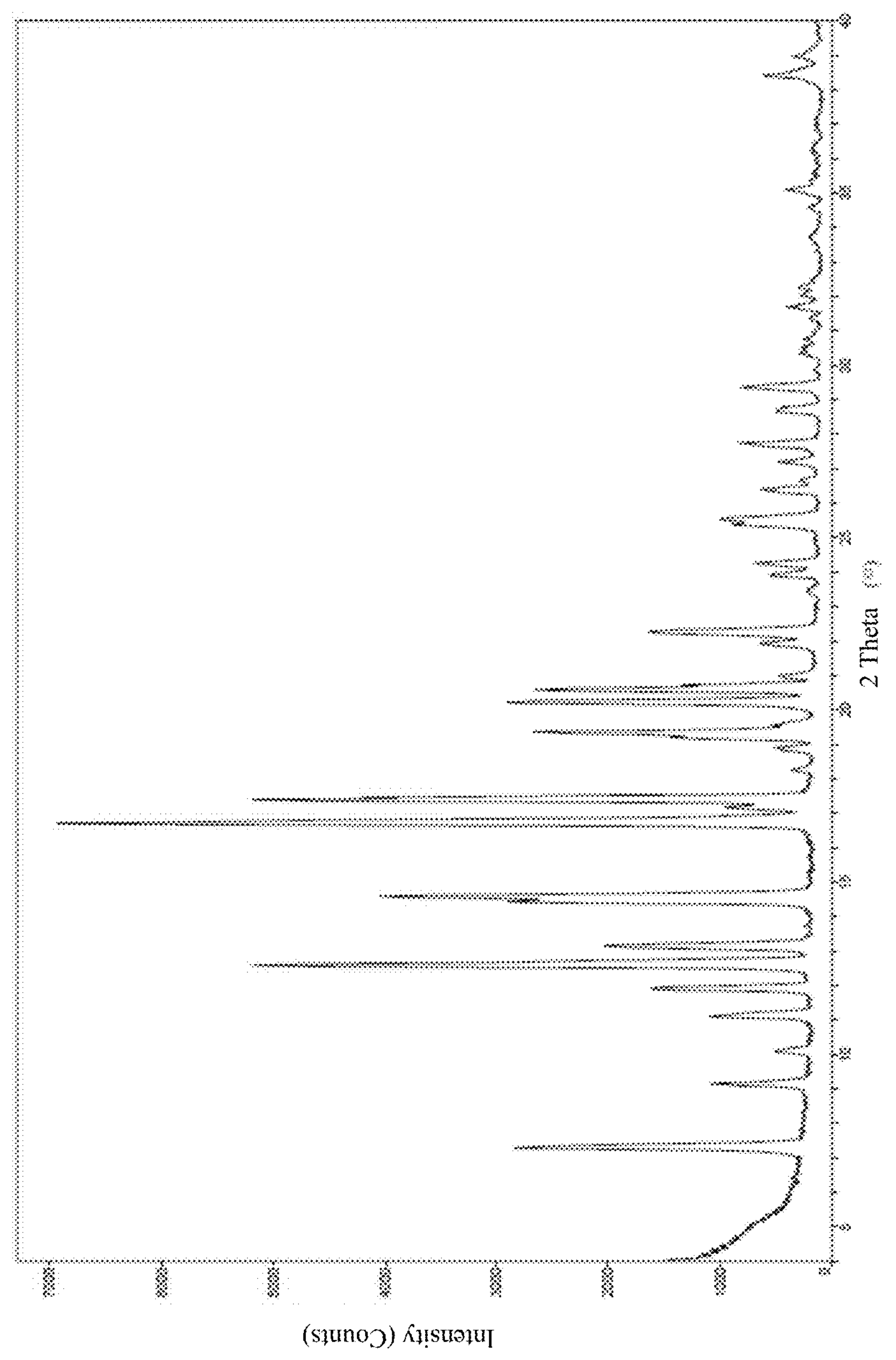
FIG. 1 is the XRPD pattern of crystal form I of the free base of formula (VI) (i.e., crystal form I of the free base of Example 40).

Unless otherwise stated, the terms used in the specification and claims have the meanings described below.

The term "alkyl" refers to a saturated aliphatic hydrocarbon group, which is a straight or branched chain group comprising 1 to 20 carbon atoms, preferably an alkyl having 1 to 8 carbon atoms, more preferably an alkyl having 1 to 6 carbon atoms, and most preferably an alkyl having 1 to 3 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various branched isomers thereof. The alkyl group can be substituted or unsubstituted. When substituted, the substituent group(s) can be substituted at any available connection point. The substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, oxo, carboxy and alkoxycarbonyl. The alkyl of the present invention is preferably selected from the group consisting of methyl, ethyl, isopropyl, tert-butyl, haloalkyl, deuterated alkyl, alkoxy-substituted alkyl and hydroxy-substituted alkyl.

The term "alkylene" refers to an alkyl of which a hydrogen atom is further substituted, for example, "methylene" refers to $—CH_2—$, "ethylene" refers to $—(CH_2)_2—$, "propylene" refers to $—(CH_2)_3—$, "butylene" refers to $—(CH_2)_4—$ and the like. The above substituents can be bonded to different carbon atoms to form a carbon chain, or can be bonded to one carbon atom to form a cycloalkyl. The term "alkenyl" refers to an alkyl as defined above that consists of at least two carbon atoms and at least one carbon-carbon double bond, for example, ethenyl, 1-propenyl, 2-propenyl, 1-, 2- or 3-butenyl and the like. The alkenyl group can be substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio and heterocyclylthio.

The term "cycloalkyl" refers to a saturated or partially unsaturated monocyclic or polycyclic hydrocarbon substituent group having 3 to 20 carbon atoms, preferably 3 to 8 carbon atoms, and more preferably 3 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl and the like. Polycyclic cycloalkyl includes a cycloalkyl having a spiro ring, fused ring or bridged ring. The cycloalkyl is preferably cyclopropyl, cyclobutyl, cyclohexyl, cyclopentyl and cycloheptyl.

The term "heterocyclyl" refers to a 3 to 20 membered saturated or partially unsaturated monocyclic or polycyclic hydrocarbon group, wherein one or more ring atoms are heteroatoms selected from the group consisting of N, O and $S(O)_m$ (wherein m is an integer of 0 to 2), but excluding —O—O—, —O—S— or —S—S— in the ring, with the remaining ring atoms being carbon atoms. Preferably, the heterocyclyl has 3 to 12 ring atoms wherein 1 to 4 atoms are heteroatoms; more preferably, 3 to 8 ring atoms; and most preferably 3 to 8 ring atoms. Non-limiting examples of monocyclic heterocyclyl include pyrrolidinyl, imidazolidinyl, tetrahydrofuranyl, tetrahydrothienyl, dihydroimidazolyl, dihydrofuranyl, dihydropyrazolyl, dihydropyrrolyl, piperidinyl, piperazinyl, morpholinyl, thiomorpholinyl, homopiperazinyl, pyranyl and the like, and preferably tetrahydrofuranyl, pyrazolidinyl, morpholinyl, piperazinyl and pyranyl. Polycyclic heterocyclyl includes a heterocyclyl having a spiro ring, fused ring or bridged ring. The heterocyclyl having a spiro ring, fused ring or bridged ring is optionally bonded to other group via a single bond, or further bonded to other cycloalkyl, heterocyclyl, aryl and heteroaryl via any two or more atoms on the ring. The heterocyclyl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, oxo, carboxy and alkoxycarbonyl.

The term "aryl" refers to a 6 to 14 membered all-carbon monocyclic ring or polycyclic fused ring (i.e., each ring in the system shares an adjacent pair of carbon atoms with another ring in the system) having a conjugated π-electron system, preferably a 6 to 10 membered aryl, for example, phenyl and naphthyl. The aryl is more preferably phenyl. The aryl ring can be fused to the ring of heteroaryl, heterocyclyl or cycloalkyl, wherein the ring bound to the parent structure is aryl ring. Non-limiting examples thereof include:

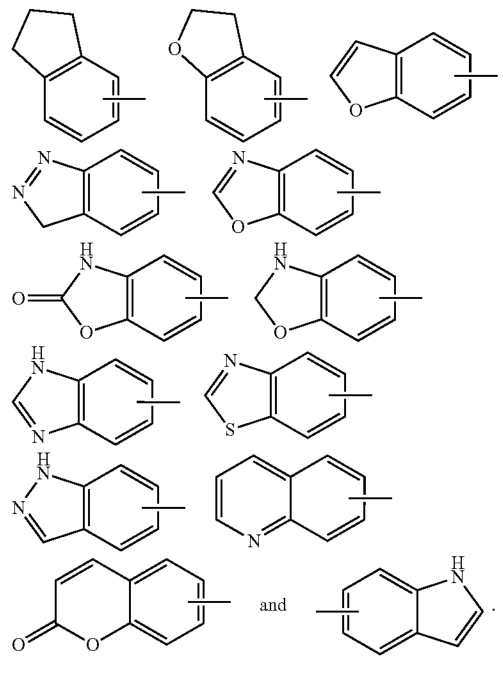

and .

The aryl can be substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy and alkoxycarbonyl.

The term "heteroaryl" refers to a 5 to 14 membered heteroaromatic system having 1 to 4 heteroatoms selected from the group consisting of O, S and N. The heteroaryl is preferably a 5 to 10 membered heteroaryl, and more preferably a 5 or 6 membered heteroaryl, for example imidazolyl, furyl, thienyl, thiazolyl, pyrazolyl, oxazolyl, pyrrolyl, triazolyl, tetrazolyl, pyridyl, pyrimidinyl, thiadiazolyl, pyrazinyl and the like, preferably triazolyl, thienyl, imidazolyl, pyrazolyl or pyrimidinyl, thiazolyl, and more preferably triazolyl, pyrrolyl, thienyl, thiazolyl and pyrimidinyl. The heteroaryl ring can be fused to the ring of aryl, heterocyclyl or cycloalkyl, wherein the ring bound to the parent structure is heteroaryl ring. Non-limiting examples thereof include:

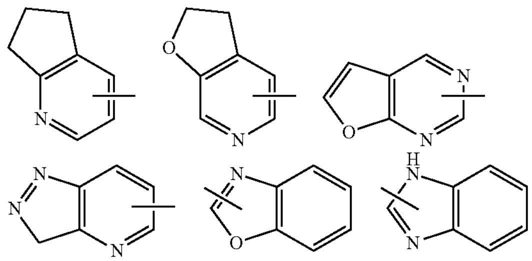

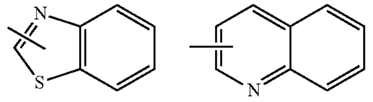

and

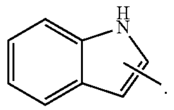

The heteroaryl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy and alkoxycarbonyl.

The term "alkoxy" refers to an —O-(alkyl) or an —O-(unsubstituted cycloalkyl) group, wherein the alkyl is as defined above. The alkoxy is preferably an alkoxy having 1 to 8 carbon atoms, more preferably an alkoxy having 1 to 6 carbon atoms, and most preferably an alkoxy having 1 to 3 carbon atoms. Non-limiting examples of alkoxy include methoxy, ethoxy, propoxy, butoxy, cyclopropyloxy, cyclobutyloxy, cyclopentyloxy, cyclohexyloxy. The alkoxy can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy and alkoxycarbonyl.

"Haloalkyl" refers to an alkyl group substituted by one or more halogens, wherein the alkyl is as defined above.

"Haloalkoxy" refers to an alkoxy group substituted by one or more halogens, wherein the alkoxy is as defined above.

"Hydroxyalkyl" refers to an alkyl group substituted by hydroxy(s), wherein the alkyl is as defined above.

"Alkenyl" refers to a chain alkenyl, also known as alkene group, which is preferably an alkenyl having 2 to 8 carbon atoms, more preferably an alkenyl having 2 to 6 carbon atoms, and most preferably an alkenyl having 2 to 3 carbon atoms. The alkenyl can be further substituted by other related group, for example alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy or alkoxycarbonyl.

"Alkynyl" refers to (CH≡C—), which is preferably an alkynyl having 2 to 8 carbon atoms, more preferably an alkynyl having 2 to 6 carbon atoms, and most preferably an alkynyl having 2 to 3 carbon atoms. The alkynyl can be further substituted by other related group, for example alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy or alkoxycarbonyl.

"Hydroxy" refers to an —OH group.

"Halogen" refers to fluorine, chlorine, bromine or iodine.

"Amino" refers to a $—NH_2$ group.

"Cyano" refers to a —CN group.

"Nitro" refers to a $—NO_2$ group.

"Carboxy" refers to a —C(O)OH group.

Different expressions such as "X is selected from the group consisting of A, B or C", "X is selected from the group consisting of A, B and C", "X is A, B or C", "X is A, B and C" and the like, express the same meaning, that is, X can be any one or more of A, B and C.

"Optional" or "optionally" means that the event or circumstance described subsequently can, but need not, occur, and such a description includes the situation in which the event or circumstance does or does not occur.

"Substituted" refers to one or more hydrogen atoms in a group, preferably up to 5, and more preferably 1 to 3 hydrogen atoms, independently substituted by a corresponding number of substituents. It goes without saying that the substituents only exist in their possible chemical position. The person skilled in the art is able to determine whether the substitution is possible or impossible by experiments or theory without excessive efforts. For example, the combination of amino or hydroxy having free hydrogen and carbon atoms having unsaturated bonds (such as olefinic) may be unstable.

"Stereoisomerism" includes geometric isomerism (cis-trans isomerism), optical isomerism, and conformational isomerism.

The hydrogen atom of the present invention can be substituted by its isotope deuterium. Any of the hydrogen atoms in the compounds of the examples of the present invention can also be substituted by deuterium atom.

A "pharmaceutical composition" refers to a mixture of one or more of the compounds according to the present invention or physiologically/pharmaceutically acceptable salts or prodrugs thereof with other chemical components, and other components such as physiologically/pharmaceutically acceptable carriers and excipients. The purpose of the pharmaceutical composition is to facilitate administration of a compound to an organism, which is conducive to the absorption of the active ingredient so as to exert biological activity.

A "pharmaceutically acceptable salt" refers to a salt of the compound of the present invention, which is safe and effective in mammals and has the desired biological activity.

"TGA" refers to thermogravimetric analysis (TGA) test.

"DSC" refers to differential scanning calorimetry (DSC) test.

"DVS" refers to dynamic vapour sorption (DVS) test.

"XRPD" refers to X-ray powder diffraction (XRPD) test.

"HPLC" refers to high performance liquid chromatography (HPLC) test.

"PK" refers to pharmacokinetic (PK) test.

The present invention will be further described with reference to the following examples, but the examples should not be considered as limiting the scope of the present invention.

1.1 Experimental Instruments 1.1.1 Some Parameters of Physical and Chemical Testing Instruments

| | | |
|---|---|---|
| XRPD | Instrument model | Bruker D8 Advance |
| | Diffraction ray | CuK (1.5418) (40 kV, 40 mA), step size 0.02, slit 2 mm |
| | Scan rate | 10°/min (2θ value) |
| | Scan range | 4°~40° (2θ value) |
| DSC | Instrument model | NETZSCH DSC 214 Polyma |
| | Purge gas | Nitrogen |
| | Purge rate | 40 mL/min |
| | Heating rate | 10° C. /min |
| | Temperature range | 25~250° C. |
| | Plate type | Aluminum plate |
| TGA | Instrument model | NETZSCH TG 209 F3 Tarsus |
| | Purge gas | Nitrogen |
| | Purge rate | 40 mL/min |
| | Heating rate | 10° C./min |
| | Temperature range | Room temperature ~300° C. |
| | Plate type | Ceramic pot |
| DVS | Instrument model | SMS Intrinsic |
| | Experiment temperature | 25° C. |
| | Drying time | 0% RH 120 min |
| | Balance dm/dt | 0.02%/min (minimum 10 min, maximum 180 min) |
| | RH (%) measurement step size | 10% |
| | Measuring gradient | 0-95-0% |
| | Cycles | 2 |
| Single crystal diffraction | Instrument model | Bruker Smart Apex 11 |
| | light source | Mo target |
| | X-ray | Mo——Kα (λ = 0.71073 Å) |
| | Detector | CCD area detector |
| | Resolution | 0.84 Å |
| | Current and voltage | 40 kV, 25 mA |
| | Exposure time | 5 s |
| | Distance from area detector to sample | 50 mm |
| | Test temperature | 173(2)K |

1.2 Instruments and Liquid Phase Analysis Conditions 1.2.1 Instruments and Devices

| Instrument name | Model |
|---|---|
| Analytical Balance | Sartorius BSA224S-CW |
| Analytical Balance | Mettler-Toledo XPR2 |
| Pure water machine | Milli-Q Plus, Millipore |
| High performance liquid chromatograph | Agilent1260 |
| Pump | Agilent G1311B |
| Injector | G1329B |
| Column thermostat | G1316A |
| Detector | G1315D |
| Dynamic vapour sorption analyser | SMS Intrinsic |

1.2.2 Chromatographic Conditions

Chromatographic column: Agilent ZORBAX® Bonus-RP (3.5 μm, 4.6*150 mm)

Flow rate: 1.0 mL/min

Column temperature: 40° C.

Detection wavelength: 230 nm

Injection volume: 10.0 μL

Running time: 30 min

Diluent: methanol-water (v/v, 3:1)

Mobile phase: A: water (0.05% trifluoroacetic acid); B: acetonitrile (0.05% trifluoroacetic acid)

| Elution time (min) | Mobile phase A (%) | Mobile phase B (%) |
|---|---|---|
| 0.0 | 60 | 40 |
| 20.0 | 5 | 95 |
| 25.0 | 5 | 95 |
| 25.1 | 60 | 40 |
| 30 | 60 | 40 |

Preparation of Free Base

Example 1

Preparation of 1-(2-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-oxoethyl)-1H-pyrazole-4-carbonitrile

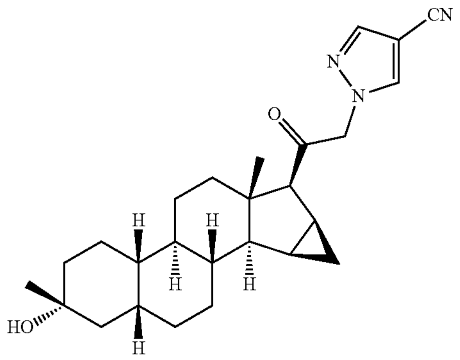

Step 1: Preparation of 2-bromo-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one

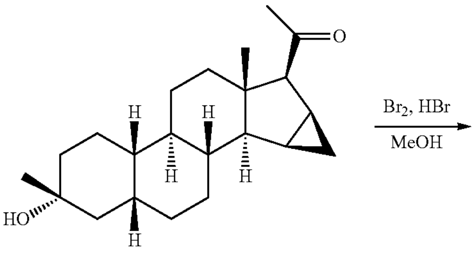

-continued

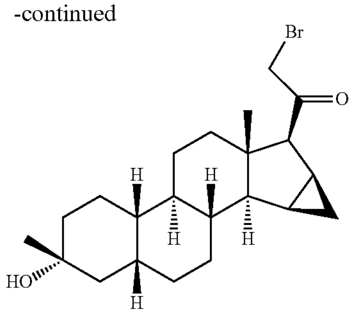

1-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)ethan-1-one (70 mg, 0.21 mmol) was dissolved in methanol (3 mL). A drop of hydrogen bromide was added to the solution, followed by the addition of liquid bromine (41 mg, 0.25 mmol), and then the reaction solution was stirred at room temperature for 1 hour. Water (20 mL) was added to the reaction solution, and the aqueous phase was extracted with ethyl acetate (20 mL×2). The organic phases were combined, dried over anhydrous sodium sulfate, filtrated and concentrated to obtain the crude product (87 mg, yield: 100%, crude), which was used directly in the next step.

Step 2: Preparation of 1-(2-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-oxoethyl)-1H-pyrazole-4-carbonitrile

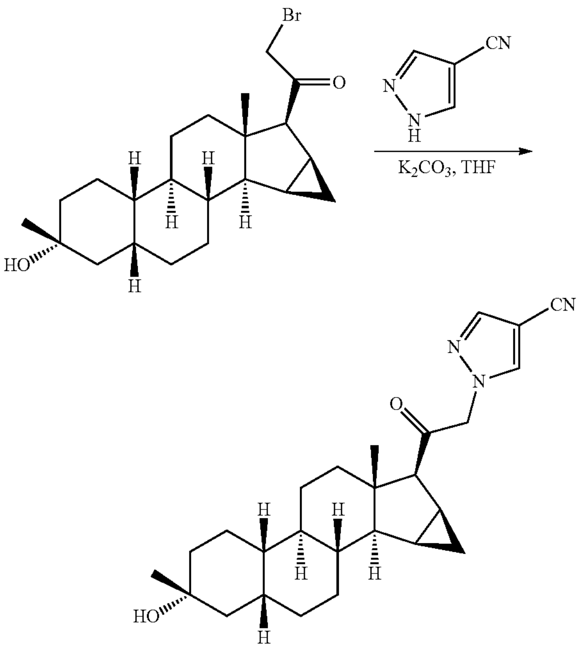

2-Bromo-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one (87 mg, 0.21 mmol), 1H-pyrazole-4-carbonitrile (59 mg, 0.64 mmol) and potassium carbonate (145 mg, 1.05 mmol) were dissolved in tetrahydrofuran (2 mL), and the resulting reaction solution was stirred at room temperature overnight. The reaction solution was filtrated, and the filtrate was concentrated. The resulting crude product was purified by high performance liquid chromatography to obtain 1-(2-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-oxoethyl)-1H-pyrazole-4-carbonitrile (33 mg, yield: 37%).

MS m/z (ESI): 404.2 $[M-H_2O+H]^+$.

$^1$H NMR (400 MHz, $CDCl_3$) δ 7.88 (s, 1H), 7.82 (s, 1H), 5.24-5.13 (m, 2H), 2.84 (d, J=2.7 Hz, 1H), 1.98-1.92 (m, 1H), 1.87-1.77 (m, 4H), 1.76-1.66 (m, 3H), 1.57-1.51 (m, 1H), 1.46-1.24 (m, 15H), 1.12-1.02 (m, 1H), 1.00-0.96 (m, 1H), 0.78 (s, 3H), 0.54-0.46 (m, 1H).

Example 2

1-(2-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-oxoethyl)-1H-pyrazole-3-carbonitrile

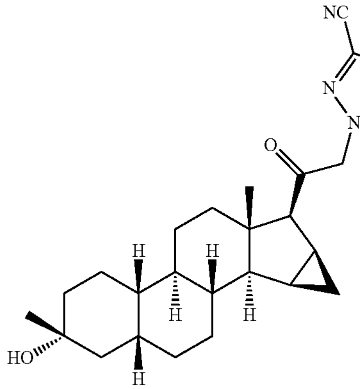

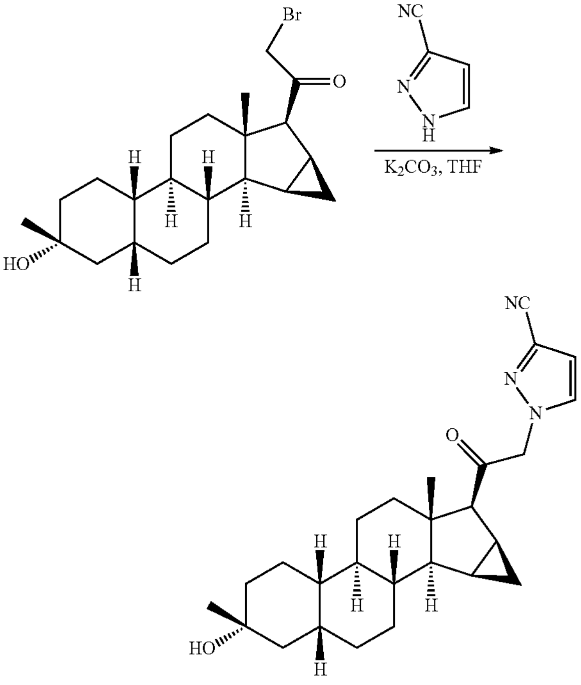

2-Bromo-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one (80 mg, 0.19 mmol), 1H-pyrazole-3-carbonitrile (55 mg, 0.58 mmol) and potassium carbonate (131 mg, 0.95 mmol) were dissolved in tetrahydrofuran (3 mL), and the resulting reaction solution was stirred at room temperature overnight. The reaction solution was filtrated, and the filtrate was concentrated. The resulting crude product was purified by high performance liquid chromatography to obtain 1-(2-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-oxoethyl)-1H-pyrazole-3-carbonitrile (34.7 mg, yield: 42%).

MS m/z (ESI): 404.2 $[M-H_2O+H]^+$ $^1$H NMR (400 MHz, $CDCl_3$) δ 7.50 (d, J=2.4 Hz, 1H), 6.74 (d, J=2.4 Hz, 1H), 5.29-5.13 (m, 2H), 2.83 (d, J=2.9 Hz, 1H), 1.97-1.92 (m, 1H), 1.86-1.79 (m, 4H), 1.73-1.64 (m, 3H), 1.58-1.52 (m, 1H), 1.43-1.27 (m, 15H), 1.12-0.96 (m, 2H), 0.79 (s, 3H), 0.53-0.44 (m, 1H).

Example 3

1-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-(4-(trifluoromethyl)-1H-pyrazol-1-yl)ethan-1-one

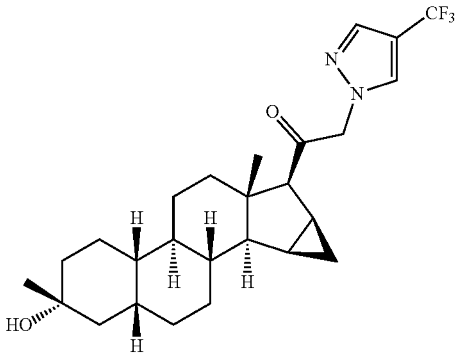

Step 1: Preparation of 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(4-(trifluoromethyl)-1H-pyrazol-1-yl)ethan-1-one

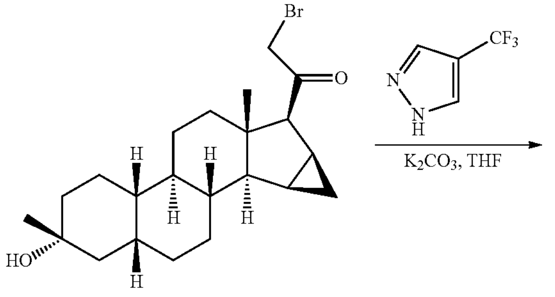

-continued

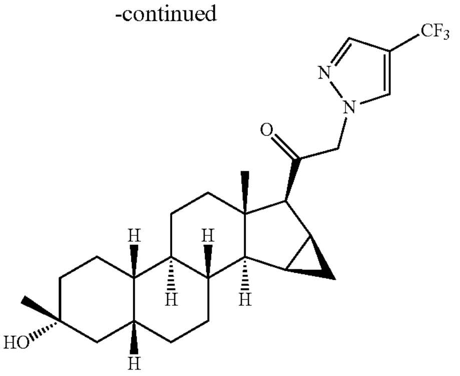

2-Bromo-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one (60 mg, 0.15 mmol), 4-(trifluoromethyl)-1H-pyrazole (60 mg, 0.44 mmol) and potassium carbonate (104 mg, 0.75 mmol) were dissolved in tetrahydrofuran (3 mL), and the resulting reaction solution was stirred at room temperature overnight. The reaction solution was filtrated, and the filtrate was concentrated. The resulting crude product was purified by high performance liquid chromatography to obtain 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(4-(trifluoromethyl)-1H-pyrazol-1-yl)ethan-1-one (22.2 mg, yield: 33%).

MS m/z (ESI): 465.3 $[M+H]^+$.

$^1$H NMR (400 MHz, $CDCl_3$) δ 7.74 (s, 1H), 7.73 (s, 1H), 5.25-5.09 (m, 2H), 2.83 (d, J=3.6 Hz, 1H), 2.00-1.91 (m, 1H), 1.89-1.79 (m, 4H), 1.78-1.65 (m, 3H), 1.58-1.52 (m, 1H), 1.47-1.22 (m, 15H), 1.15-0.95 (m, 2H), 0.79 (s, 3H), 0.52-0.44 (m, 1H).

Example 4

1-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-(3-(trifluoromethyl)-1H-pyrazol-1-yl)ethan-1-one

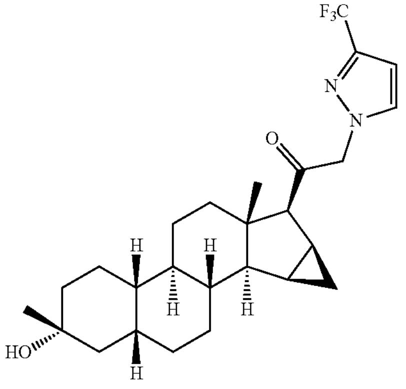

Step 1: Preparation of 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(3-(trifluoromethyl)-1H-pyrazol-1-yl)ethan-1-one

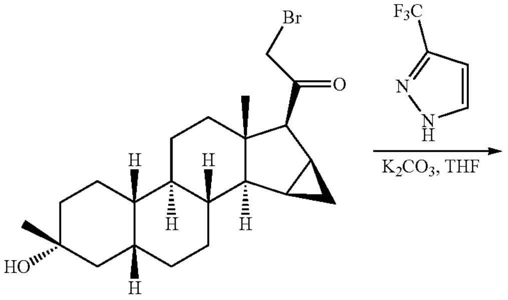

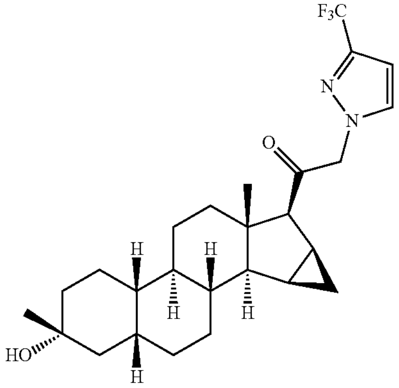

2-Bromo-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one (80 mg, 0.2 mmol), 3-(trifluoromethyl)-1H-pyrazole (80 mg, 0.6 mmol) and potassium carbonate (138 mg, 1.0 mmol) were dissolved in tetrahydrofuran (5 mL), and the resulting reaction solution was stirred at room temperature overnight. The reaction solution was filtrated, and the filtrate was concentrated. The resulting crude product was purified by high performance liquid chromatography to obtain 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(3-(trifluoromethyl)-1H-pyrazol-1-yl)ethan-1-one (17 mg, yield: 18%).

MS m/z (ESI): 447.3 $[M-H_2O+H]^+$.

$^1H$ NMR (400 MHz, $CDCl_3$) δ 7.49 (d, J=1.9 Hz, 1H), 6.60 (d, J=1.9 Hz, 1H), 5.27-5.13 (m, 2H), 2.83 (d, J=3.7 Hz, 1H), 1.99-1.90 (m, 1H), 1.89-1.76 (m, 4H), 1.75-1.61 (m, 3H), 1.58-1.50 (m, 1H), 1.50-1.21 (m, 15H), 1.13-0.96 (m, 2H), 0.79 (s, 3H), 0.52-0.45 (m, 1H).

Example 5 and Example 6

1-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-(2H-1,2,3-triazol-2-yl)ethan-1-one (5)

1-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-(1H-1,2,3-triazol-1-yl)ethan-1-one (6)

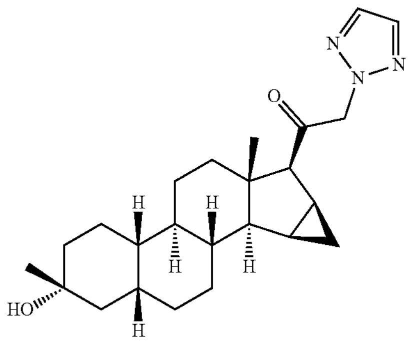

5

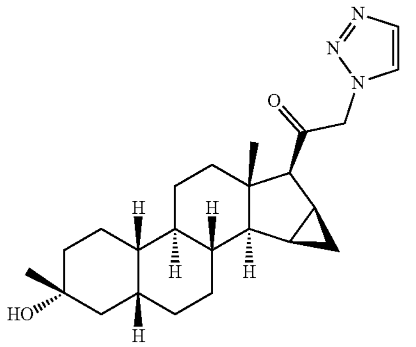

6

Step 1: Preparation of 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(2H-1,2,3-triazol-2-yl)ethan-1-one (5) and 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(1H-1,2,3-triazol-1-yl)ethan-1-one (6)

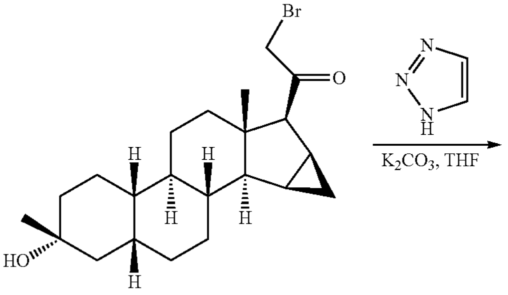

-continued

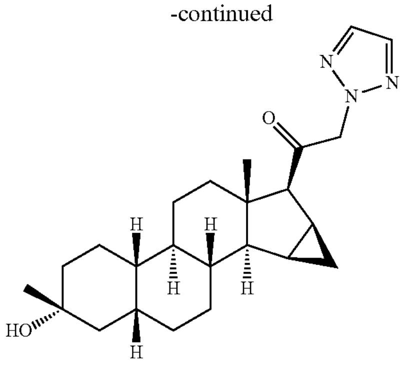

+

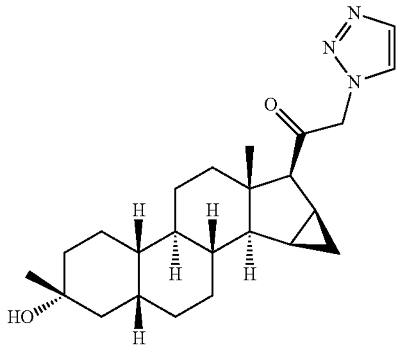

2-Bromo-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one (80 mg, 0.19 mmol), 1H-1,2,3-triazole (40 mg, 0.58 mmol) and potassium carbonate (131 mg, 0.95 mmol) were dissolved in tetrahydrofuran (3 mL), and the resulting reaction solution was stirred at room temperature overnight. The reaction solution was filtrated, and the filtrate was concentrated. The resulting crude product was purified by high performance liquid chromatography to obtain 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(2H-1,2,3-triazol-2-yl)ethan-1-one (5) (9.2 mg, yield: 12%) and 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(1H-1,2,3-triazol-1-yl)ethan-1-one (6) (17.8 mg, yield: 23%).

Example 5

MS m/z (ESI): 380.3 $[M-H_2O+H]^+$.

$^1$H NMR (400 MHz, $CDCl_3$) δ 7.69 (s, 2H), 5.55-5.36 (m, 2H), 2.82 (d, J=4.1 Hz, 1H), 1.99-1.92 (m, 1H), 1.87-1.74 (m, 4H), 1.73-1.52 (m, 5H), 1.47-1.26 (m, 14H), 1.14-0.98 (m, 2H), 0.84 (s, 3H), 0.52-0.43 (m, 1H).

Example 6

MS m/z (ESI): 398.3 $[M+H]^+$.

$^1$H NMR (400 MHz, $CDCl_3$) δ 7.76 (s, 1H), 7.66 (s, 1H), 5.52-5.35 (m, 2H), 2.87 (d, J=3.9 Hz, 1H), 2.02-1.92 (m, 1H), 1.89-1.78 (m, 4H), 1.76-1.65 (m, 3H), 1.59-1.52 (m, 1H), 1.48-1.23 (m, 15H), 1.15-0.98 (m, 2H), 0.80 (s, 3H), 0.56-0.45 (m, 1H).

Example 7 and Example 8

1-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-(2H-tetrazol-2-yl)ethan-1-one (7)

1-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-(1H-tetrazol-1-yl)ethan-1-one (8)

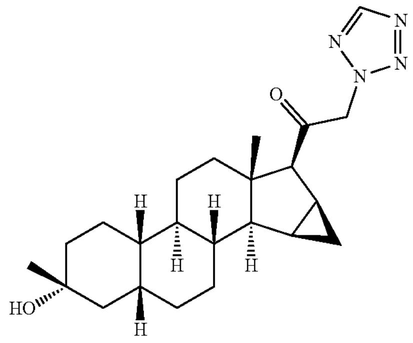

7

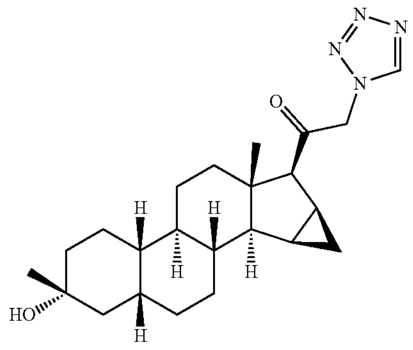

8

Step 1: Preparation of 1-((2R,4aS,4bR,6aS,7S,7aS, 8aR,8bR,8cR,10aR)-2-hydroxy-2,6a-dimethylocta-decahydrocyclopropa[4,5]cyclopenta[1,2-a] phenanthren-7-yl)-2-(2H-tetrazol-2-yl)ethan-1-one (7) and 1-((2R,4aS,4bR,6aS,7S,7aS,8aR,8bR,8cR, 10aR)-2-hydroxy-2,6a-dimethyloctadecahydrocyclo-propa[4,5]cyclopenta[1,2-a]phenanthren-7-yl)-2-(1H-tetrazol-1-yl)ethan-1-one (8)

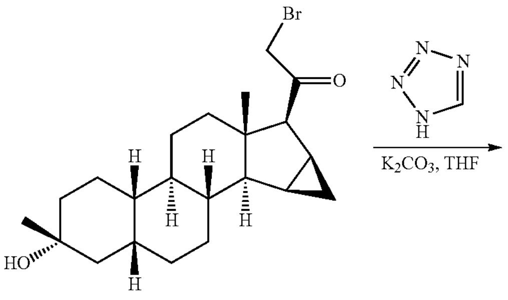

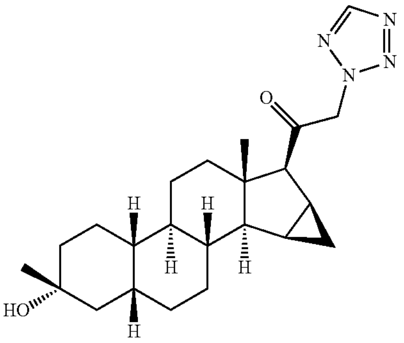

7

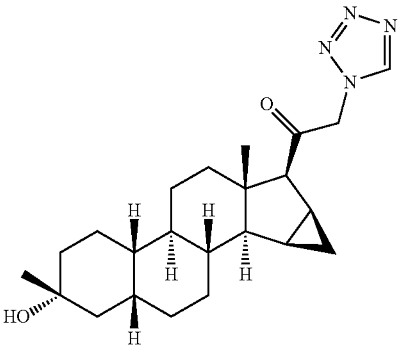

8

2-Bromo-1-((2R,4aS,4bR,6aS,7S,7aS,8aR,8bR,8cR, 10aR)-2-hydroxy-2,6a-dimethyloctadecahydrocyclopropa [4,5]cyclopenta[1,2-a]phenanthren-7-yl)ethan-1-one (50 mg, 0.12 mmol), 1H-tetrazole (26 mg, 0.37 mmol) and potassium carbonate (83 mg, 0.6 mmol) were dissolved in tetrahydrofuran (3 mL), and the resulting reaction solution was stirred at room temperature overnight. The reaction solution was filtrated, and the filtrate was concentrated. The resulting crude product was purified by high performance liquid chromatography to obtain 1-((2R,4aS,4bR,6aS,7S, 7aS,8aR,8bR,8cR,10aR)-2-hydroxy-2,6a-dimethylocta-decahydrocyclopropa[4,5]cyclopenta[1,2-a]phenanthren-7-yl)-2-(2H-tetrazol-2-yl)ethan-1-one (7) (11.6 mg, yield: 24%) and 1-((2R,4aS,4bR,6aS,7S,7aS,8aR,8bR,8cR,10aR)-2-hydroxy-2,6a-dimethyloctadecahydrocyclopropa[4,5]cy-clopenta[1,2-a]phenanthren-7-yl)-2-(1H-tetrazol-1-yl) ethan-1-one (8) (4.4 mg, yield: 9%).

Example 7

MS m/z (ESI): 381.2 $[M-H_2O+H]^+$ $^1$H NMR (400 MHz, $CDCl_3$) δ8.58 (s, 1H), 5.74-5.62 (m, 2H), 2.88 (d, J=3.8 Hz, 1H), 1.97-1.91 (m, 1H), 1.87-1.79 (m, 4H), 1.75-1.64 (m, 3H), 1.58-1.55 (m, 1H), 1.45-1.35 (m, 7H), 1.34-1.24 (m, 8H), 1.14-1.01 (m, 2H), 0.85 (s, 3H), 0.56-0.48 (m, 1H).

Example 8

MS m/z (ESI): 399.3 $[M+H]^+$ $^1$H NMR (400 MHz, $CDCl_3$) δ8.77 (s, 1H), 5.57-5.39 (m, 2H), 2.90 (s, 1H), 2.00-1.91 (m, 1H), 1.88-1.79 (m, 4H), 1.76-1.65 (m, 3H), 1.59-1.56 (m, 1H), 1.46-1.37 (m, 7H), 1.35-1.24 (m, 8H), 1.13-0.99 (m, 2H), 0.79 (s, 3H), 0.58-0.49 (m, 1H).

Example 9

1-(2-((3R,5R,8R,9R,10S,13S,14S,15R)-3-Hydroxy-3,13,15-trimethylhexadecahydro-1H-cyclopenta[a]phenanthren-17-yl)-2-oxoethyl)-1H-pyrazole-4-carbonitrile

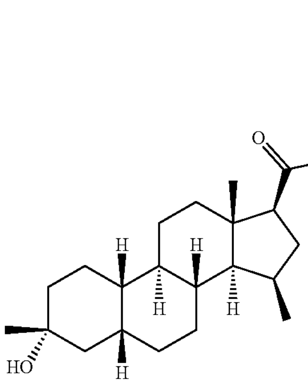

Step 1: (3R,5R,8R,9R,10S,13S,14S,15R)-3-Hydroxy-3,13,15-trimethylhexadecahydro-17H-cyclopenta[a]phenanthren-17-one

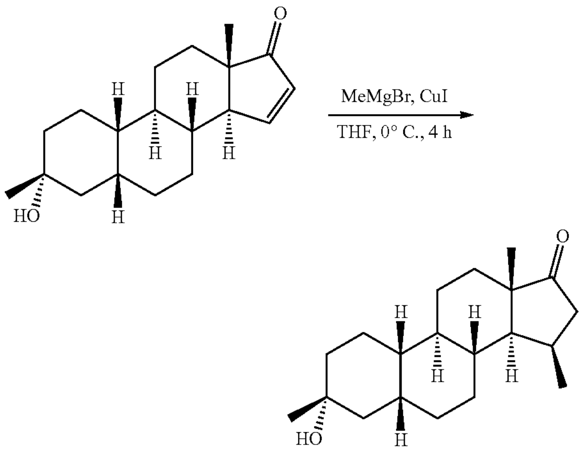

3.0 M methylmagnesium bromide (8.5 mL, 25.5 mmol) and 20 mL of anhydrous tetrahydrofuran were added to a dry 100 mL round bottom flask. The reaction system was purged with nitrogen, and cooled to 0° C. Cuprous iodide (3.94 g, 20.7 mmol) was added, and then the reaction solution was stirred at 0° C. for 1 hour. (3R,5R,8R,9R,10S,13S,14S)-3-Hydroxy-3,13-dimethyl-1,2,3,4,5,6,7,8,9,10,11,12,13,14-tetradecahydro-17H-cyclopenta[a]phenanthren-17-one (2 g, 6.9 mmol) was dissolved in 10 ml of anhydrous tetrahydrofuran, and the resulting solution was slowly added dropwise to the reaction system. The reaction solution was stirred for 3 hours, and TLC showed that the reaction was completed. Saturated ammonium chloride solution was added to quench the reaction, and the reaction solution was extracted with ethyl acetate. The organic phase was washed with water and saturated saline, dried over anhydrous sodium sulfate, filtrated and concentrated by rotary evaporation to dryness. The resulting crude product was purified by column chromatography (petroleum ether:ethyl acetate=2:1) to obtain (3R,5R,8R,9R,10S,13S,14S,15R)-3-hydroxy-3,13,15-trimethylhexadecahydro-17H-cyclopenta[a]phenanthren-17-one (1.56 g, yield: 75%).

$^{1}$H NMR (400 MHz, $CDCl_3$) δ 2.51-2.42 (m, 2H), 2.24 (d, J=17.6 Hz, 1H), 1.89-1.63 (m, 7H), 1.54-1.18 (m, 16H), 1.10 (d, J=7.6 Hz, 3H), 1.03 (s, 3H).

Step 2: (3R,5R,8R,9R,10S,13S,14S,15R,E)-17-Ethylidene-3,13,15-trimethylhexadecahydro-1H-cyclopenta[a]phenanthren-3-ol

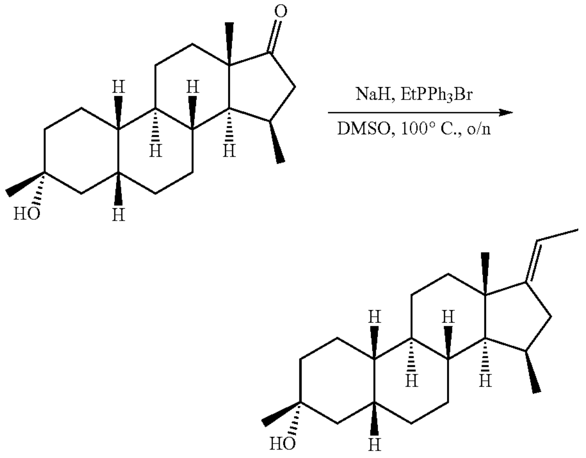

Ethyltriphenylphosphonium bromide (18.5 g, 50 mmol) was dissolved in anhydrous dimethyl sulfoxide (50 mL), and the reaction system was purged with nitrogen. Sodium hydride (2.0 g, 50 mmol) was added, and then the reaction solution was stirred at room temperature for 1 hour. (3R,5R,8R,9R,10S,13S,14S,15R)-3-Hydroxy-3,13,15-trimethylhexadecahydro-17H-cyclopenta[a]phenanthren-17-one (1.52 g, 5 mmol) was added, and then the reaction solution was stirred at 100° C. overnight. The reaction solution was cooled to room temperature. Water (200 mL) was added to the reaction solution to quench the reaction, and the aqueous phase was extracted with ethyl acetate (200 mL×2). The organic phases were combined, dried over anhydrous sodium sulfate, filtrated and concentrated. The resulting crude product was purified by column chromatography (petroleum ether/ethyl acetate: 50/1-3/1) to obtain (3R,5R,8R,9R,10S,13S,14S,15R,E)-17-ethylidene-3,13,15-trimethylhexadecahydro-1H-cyclopenta[a]phenanthren-3-ol (1.37 g, yield: 86%).

Step 3: (3R,5R,8R,9R,10S,13S,14S,15R,17S)-17-((R)-1-Hydroxyethyl)-3,13,15-trimethylhexadecahydro-1H-cyclopenta[a]phenanthren-3-ol

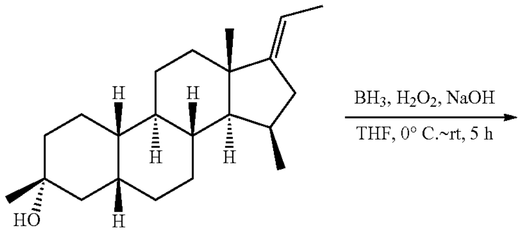

-continued

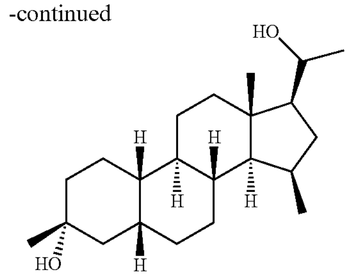

(3R,5R,8R,9R,10S,13S,14S,15R,E)-17-Ethylidene-3,13,15-trimethylhexadecahydro-1H-cyclopenta[a]phenanthren-3-ol (1.37 g, 4.33 mmol) was dissolved in anhydrous tetrahydrofuran (50 mL). The solution was cooled to 0° C., and then $BH_3$/THF (43 mL, 43 mmol) was added dropwise. The reaction solution was stirred at room temperature for 3 hours, and TLC showed that the reaction was completed. The reaction solution was cooled to 0° C., and then 3 M aqueous NaOH solution (40 mL) was slowly added, followed by the addition of $H_2O_2$ (30 mL). The reaction solution was stirred at room temperature for 2 hours, and TLC showed that the reaction was completed. Ethyl acetate (50 mL) was added, and then the reaction solution was washed with saturated aqueous $Na_2S_2O_3$ solution (30 mL) and water (30 mL) successively. The organic phase was dried over anhydrous sodium sulfate, filtrated and concentrated to obtain the crude product (1.37 g), which was used directly in the next step.

Step 4: 1-((3R,5R,8R,9R,10S,13S,14S,15R,17S)-3-Hydroxy-3,13,15-trimethylhexadecahydro-1H-cyclopenta[a]phenanthren-17-yl)ethan-1-one

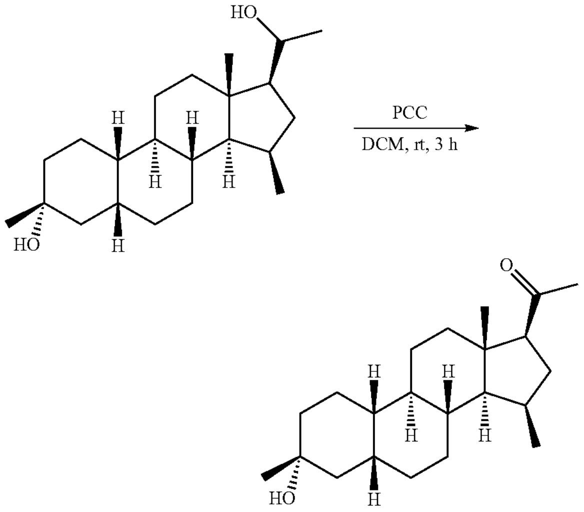

(3R,5R,8R,9R,10S,13S,14S,15R,17S)-17-((R)-1-Hydroxyethyl)-3,13,15-trimethylhexadecahydro-1H-cyclopenta[a]phenanthren-3-ol (1.37 g, crude) was dissolved in dichloromethane (30 mL). PCC (1.8 g, 8.66 mmol) was added, and then the reaction solution was stirred at room temperature for 2 hours. The reaction solution was filtrated, and the organic phase was concentrated. The resulting crude product was purified by column chromatography (petroleum ether/ethyl acetate: 1/1) to obtain 1-((3R,5R,8R,9R,10S,13S,14S,15R,17S)-3-hydroxy-3,13,15-trimethylhexadecahydro-1H-cyclopenta[a]phenanthren-17-yl)ethan-1-one (780 mg, yield of two steps: 54.3%).

$^1$H NMR (400 MHz, $CDCl_3$) δ 2.49 (dd, J=8.8, 10.4 Hz, 1H), 2.14-2.03 (m, 5H), 1.95-1.79 (m, 5H), 1.69-1.06 (m, 18H), 0.96 (d, J=7.2 Hz, 3H), 0.78 (s, 3H).

Step 5: 2-Bromo-1-((3R,5R,8R,9R,10S,13S,14S,15R,17S)-3-hydroxy-3,13,15-trimethylhexadecahydro-1H-cyclopenta[a]phenanthren-17-yl)ethan-1-one

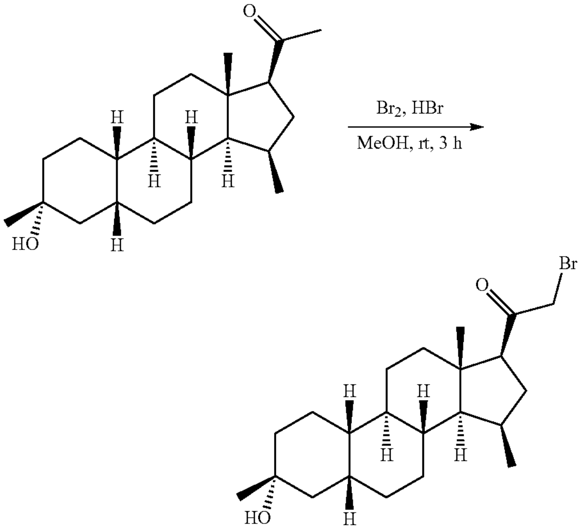

1-((3R,5R,8R,9R,10S,13S,14S,15R,17S)-3-Hydroxy-3,13,15-trimethylhexadecahydro-1H-cyclopenta[a]phenanthren-17-yl)ethan-1-one (333 mg, 1 mmol) was dissolved in methanol (10 mL). A drop of hydrogen bromide was added to the solution, followed by the addition of liquid bromine (176 mg, 1.1 mmol) was added, and then the reaction solution was stirred at room temperature for 1 hour. Water (20 mL) was added to the reaction solution, and the aqueous phase was extracted with ethyl acetate (20 mL×2). The organic phases were combined, dried over anhydrous sodium sulfate, filtrated and concentrated to obtain the crude product (413 mg, crude), which was used directly in the next step.

Step 6: 1-(2-((3R,5R,8R,9R,10S,13S,14S,15R)-3-Hydroxy-3,13,15-trimethylhexadecahydro-1H-cyclopenta[a]phenanthren-17-yl)-2-oxoethyl)-1H-pyrazole-4-carbonitrile

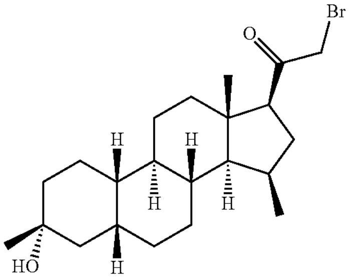

+

-continued

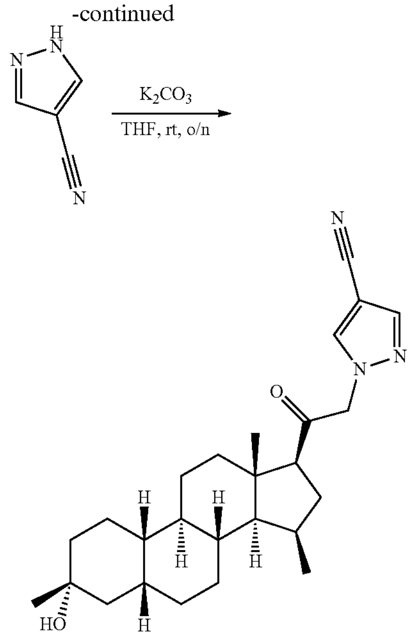

2-Bromo-1-((3R,5R,8R,9R,10S,13S,14S,15R,17S)-3-hydroxy-3,13,15-trimethylhexadecahydro-1H-cyclopenta[a]phenanthren-17-yl)ethan-1-one (82 mg, 0.2 mmol), 1H-pyrazole-4-carbonitrile (28 mg, 0.3 mmol) and potassium carbonate (54 mg, 0.3 mmol) were dissolved in anhydrous tetrahydrofuran (5 mL), and the resulting reaction solution was stirred at room temperature overnight. The reaction solution was filtrated, and the filtrate was concentrated. The resulting crude product was purified by high performance liquid chromatography to obtain 1-(2-((3R,5R,8R,9R,10S,13S,14S,15R)-3-hydroxy-3,13,15-trimethylhexadecahydro-1H-cyclopenta[a]phenanthren-17-yl)-2-oxoethyl)-1H-pyrazole-4-carbonitrile (41 mg, yield: 48%).

$^1H$ NMR (400 MHz, $CDCl_3$) δ 7.86 (s, 1H), 7.81 (s, 1H), 5.01 (d, J=17.9 Hz, 1H), 4.90 (d, J=17.9 Hz, 1H), 2.62-2.48 (m, 1H), 2.30-2.06 (m, 3H), 2.04-1.75 (m, 7H), 1.75-1.04 (m, 15H), 0.99 (d, J=7.1 Hz, 3H), 0.84 (s, 3H).

MS m/z (ESI): 424.6 $[M+H]^+$.

Example 14

2-(4-Chloro-1H-pyrazol-1-yl)-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one

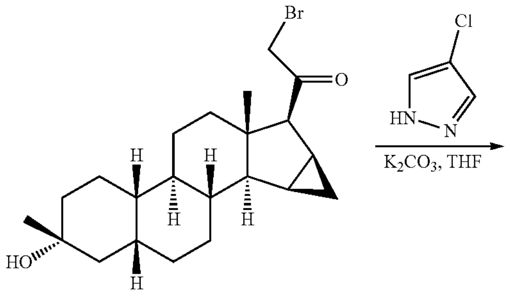

-continued

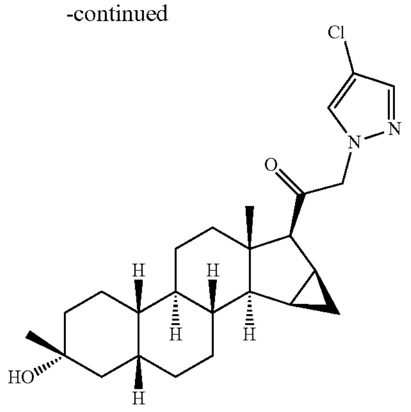

In accordance with Example 5, 2-bromo-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one and 4-chloro-1H-pyrazole were used as the starting materials, accordingly, 2-(4-chloro-1H-pyrazol-1-yl)-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one (21.9 mg, yield: 26%) was obtained.

MS m/z (ESI): 431.2 $[M+H]^+$ $^1H$ NMR (400 MHz, $CDCl_3$) δ7.45 (d, J=11.8 Hz, 2H), 5.17-5.01 (m, 2H), 2.81 (d, J=3.5 Hz, 1H), 1.99-1.91 (m, 1H), 1.86-1.79 (m, 3H), 1.77-1.62 (m, 3H), 1.57-1.49 (m, 3H), 1.44-1.20 (m, 14H), 1.12-0.96 (m, 2H), 0.78 (s, 3H), 0.51-0.44 (m, 1H).

Example 24 and Example 25

3-Cyclopropyl-1-(2-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-oxoethyl)-1H-pyrazole-4-carbonitrile (24)

5-Cyclopropyl-1-(2-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-oxoethyl)-1H-pyrazole-4-carbonitrile (25)

24

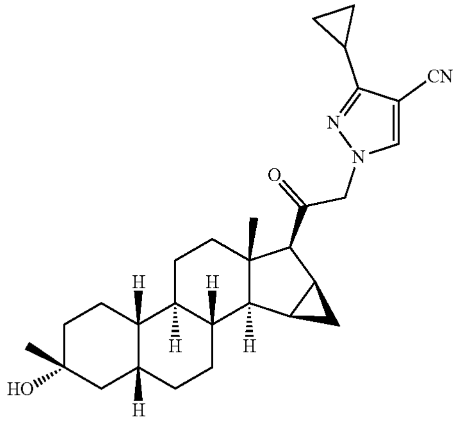

-continued

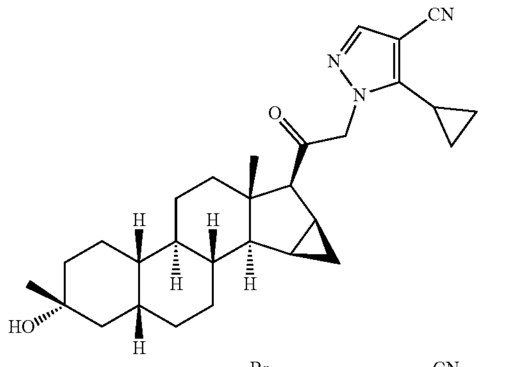

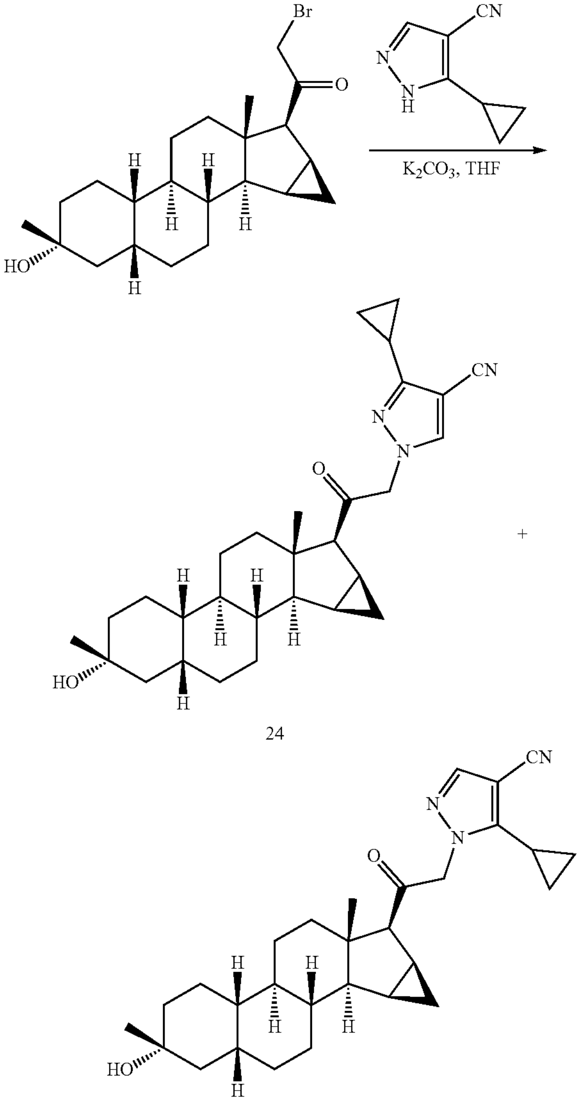

24

25

In accordance with Example 5, 2-bromo-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one and 5-cyclopropyl-1H-pyrazole-4-carbonitrile were used as the starting materials, accordingly, 3-cyclopropyl-1-(2-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-oxoethyl)-1H-pyrazole-4-carbonitrile (24) (19.2 mg, yield: 21%) and 5-cyclopropyl-1-(2-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-oxoethyl)-1H-pyrazole-4-carbonitrile (25) (3.0 mg, yield: 3.3%) were obtained.

Example 24

MS m/z (ESI): 462.3 [M+H]$^+$ $^1$H NMR (400 MHz, CDCl$_3$) δ7.73 (s, 1H), 5.14-4.98 (m, 2H), 2.80 (d, J=2.2 Hz, 1H), 2.05-1.89 (m, 2H), 1.86-1.78 (m, 4H), 1.75-1.64 (m, 3H), 1.58-1.52 (m, 2H), 1.46-1.33 (m, 7H), 1.33-1.20 (m, 7H), 1.14-0.92 (m, 6H), 0.76 (s, 3H), 0.53-0.43 (m, 1H).

Example 25

MS m/z (ESI): 462.3 [M+H]$^+$ $^1$H NMR (400 MHz, CDCl$_3$) δ7.69 (s, 1H), 5.33-5.13 (m, 2H), 2.85 (d, J=3.8 Hz, 1H), 2.00-1.92 (m, 1H), 1.86-1.79 (m, 3H), 1.76-1.62 (m, 4H), 1.60-1.51 (m, 2H), 1.45-1.34 (m, 7H), 1.34-1.22 (m, 7H), 1.17-0.94 (m, 7H), 0.81 (s, 3H), 0.54-0.45 (m, 1H).

Example 28 and Example 29

1-(2-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-oxoethyl)-3-methyl-1H-pyrazole-4-carbonitrile (28)

1-(2-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-oxoethyl)-5-methyl-1H-pyrazole-4-carbonitrile (29)

28

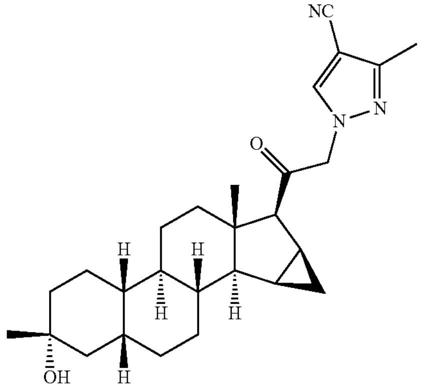

29

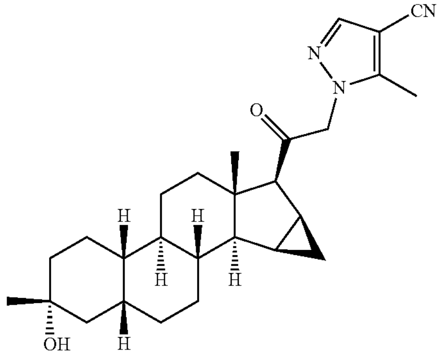

-continued

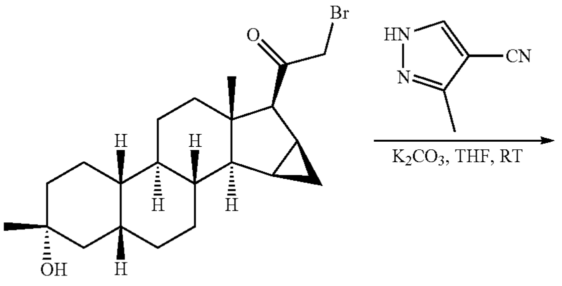

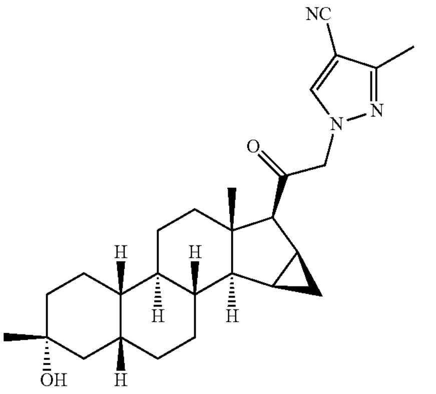

28

+

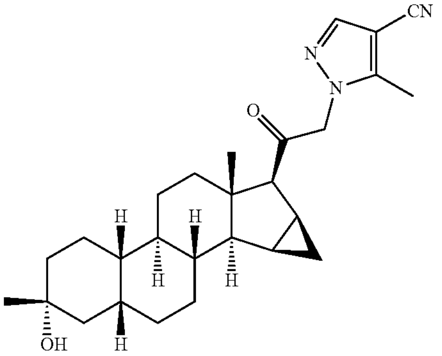

29

In accordance with Example 5, 2-bromo-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one and 3-methyl-1H-pyrazole-4-carbonitrile were used as the starting materials, accordingly, a mixture of Example 28 and Example 29 (approximately 3:1) (25.9 mg, white solid, yield: 39.3%) was obtained. The mixture was further separated by preparative chromatography to obtain 1-(2-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-oxoethyl)-3-methyl-1H-pyrazole-4-carbonitrile (28) and 1-(2-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-oxoethyl)-5-methyl-1H-pyrazole-4-carbonitrile (29).

Example 37A: MS m/z (ESI): 436.3[M+H]$^+$

Example 37B: MS m/z (ESI): 436.3[M+H]$^+$

Example 30

2-(4-Fluoro-1H-pyrazol-1-yl)-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one

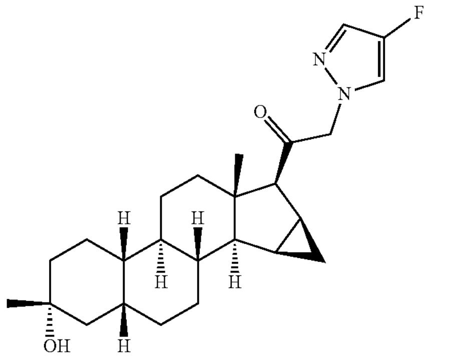

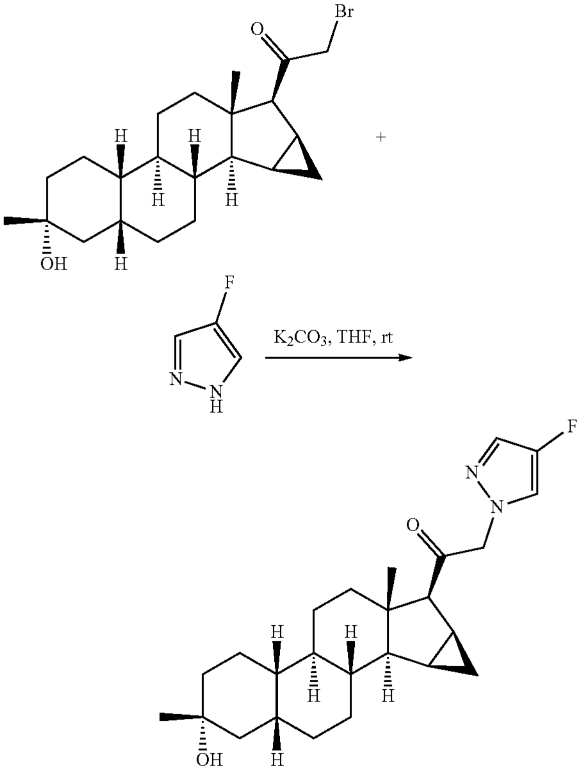

In accordance with Example 5, 2-bromo-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one and 4-fluoropyrazole were used as the starting materials, accordingly, 2-(4-fluoro-1H-pyrazol-1-yl)-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one (6.2 mg, white solid, yield: 7.7%) was obtained.

MS m/z (ESI): 415.2[M+H]$^+$ $^1$H NMR (400 MHz, $CDCl_3$) δ 7.37 (d, J=4.0 Hz, 1H), 7.32 (d, J=4.0 Hz, 1H), 5.03 (d, J=3.6 Hz, 2H), 2.80 (d, J=3.6 Hz, 1H), 2.01-1.93 (m, 2H), 1.85-1.80 (m, 3H), 1.73-1.61

(m, 6H), 1.41-1.32 (m, 9H), 1.27 (s, 3H), 1.12-1.02 (m, 2H), 0.99-0.96 (m, 1H), 0.78 (s, 3H), 0.50-0.44 (m, 1H).

Example 35

Ethyl 1-(2-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-oxoethyl)-1H-pyrazole-4-carboxylate

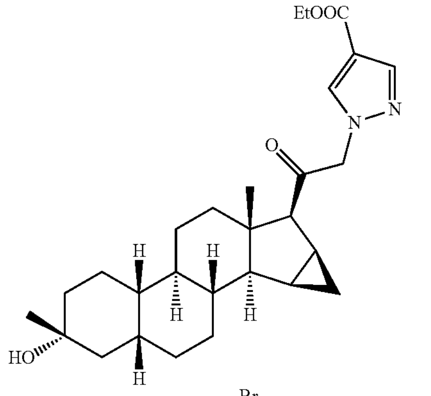

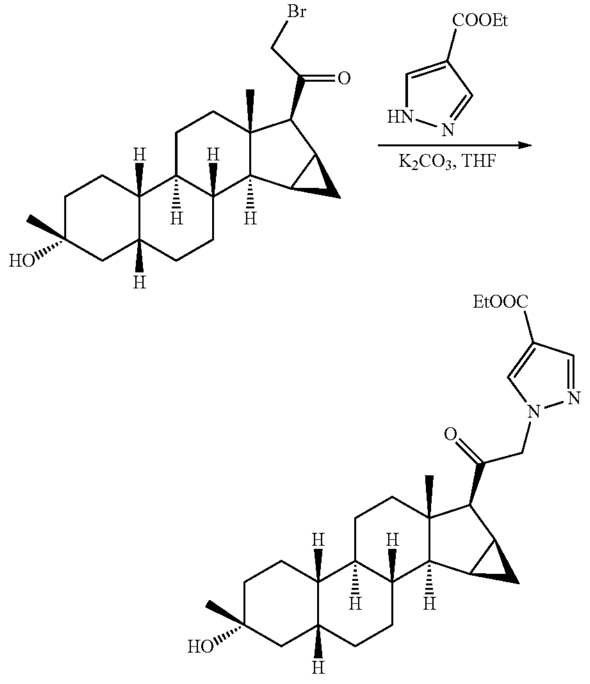

In accordance with Example 5, 2-bromo-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one and ethyl 1H-pyrazole-4-carboxylate were used as the starting materials, accordingly, ethyl 1-(2-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-oxoethyl)-1H-pyrazole-4-carboxylate (29.6 mg, white solid, yield: 43%) was obtained.

MS m/z (ESI): 469.3 $[M+H]^+$ $^1$H NMR (400 MHz, $CDCl_3$) δ 7.95 (s, 2H), 5.32-4.99 (m, 2H), 4.36-4.24 (m, 2H), 2.83 (s, 1H), 1.99-1.92 (m, 1H), 1.87-1.79 (m, 3H), 1.72-1.52 (m, 6H), 1.49-1.16 (m, 17H), 1.14-0.96 (m, 2H), 0.83 (s, 3H), 0.53-0.44 (m, 1H).

Example 39

1-((3R,5R,8R,9R,10S,13S,14S,15R,17S)-3-Hydroxy-3,13,15-trimethylhexadecahydro-1H-cyclopenta[a]phenanthren-17-yl)-2-(4-(trifluoromethyl)-1H-pyrazol-1-yl)ethan-1-one

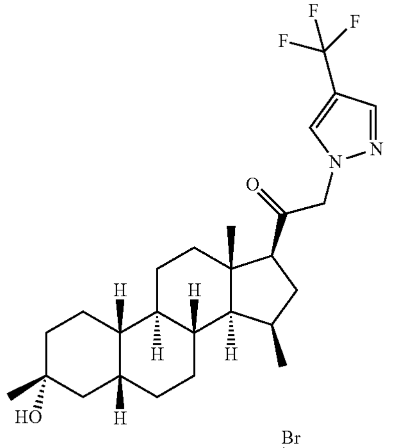

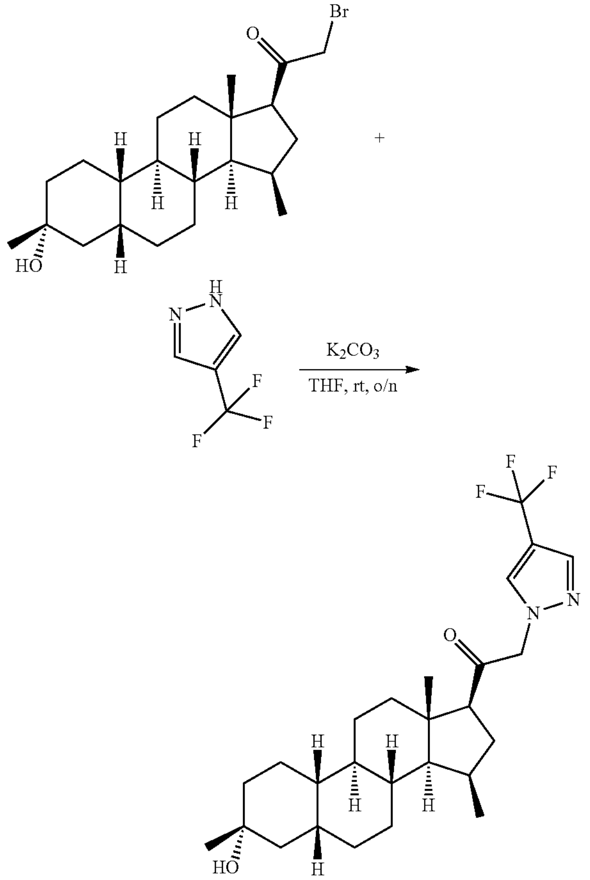

2-Bromo-1-((3R,5R,8R,9R,10S,13S,14S,15R,17S)-3-hydroxy-3,13,15-trimethylhexadecahydro-1H-cyclopenta[a]phenanthren-17-yl)ethan-1-one (82 mg, 0.2 mmol), 4-(trifluoromethyl)-1H-pyrazole (41 mg, 0.3 mmol) and potassium carbonate (54 mg, 0.3 mmol) were dissolved in anhydrous tetrahydrofuran (5 mL), and the resulting reaction solution was stirred at room temperature overnight. The reaction solution was filtrated, and the filtrate was concentrated. The resulting crude product was purified by high performance liquid chromatography to obtain 1-((3R,5R,8R,9R,10S,13S,14S,15R,17S)-3-hydroxy-3,13,15-trimethylhexadecahydro-1H-cyclopenta[a]phenanthren-17-yl)-2-(4-(trifluoromethyl)-1H-pyrazol-1-yl)ethan-1-one (24.6 mg, yield: 26%).

$^1$H NMR (400 MHz, $CDCl_3$) δ 7.72 (s, 2H), 5.00 (d, J=16 Hz, 1H), 4.90 (d, J=16 Hz, 1H), 2.58-2.54 (m, 1H), 1.88-1.83 (m, 2H), 1.69-1.58 (m, 5H), 1.50-1.25 (m, 19H), 0.98 (d, J=8.0 Hz, 3H), 0.85 (s, 3H).

MS m/z (ESI): 467.3 $[M+H]^+$

Example 40

1-(2-((3R,5R,8R,9R,10S,13S,14S,15R,17S)-3-Hydroxy-3,13,15-trimethylhexadecahydro-1H-cyclopenta[a]phenanthren-17-yl)-2-oxoethyl)-1H-pyrazole-3-carbonitrile

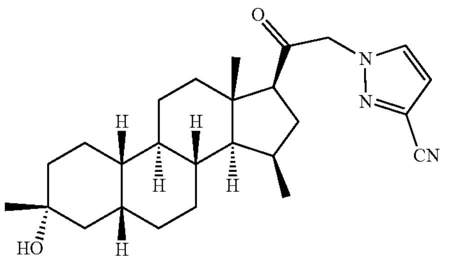

Step 1: Preparation of 1-(2-((3R,5R,8R,9R,10S,13S,14S,15R,17S)-3-hydroxy-3,13,15-trimethylhexadecahydro-1H-cyclopenta[a]phenanthren-17-yl)-2-oxoethyl)-1H-pyrazole-3-carbonitrile

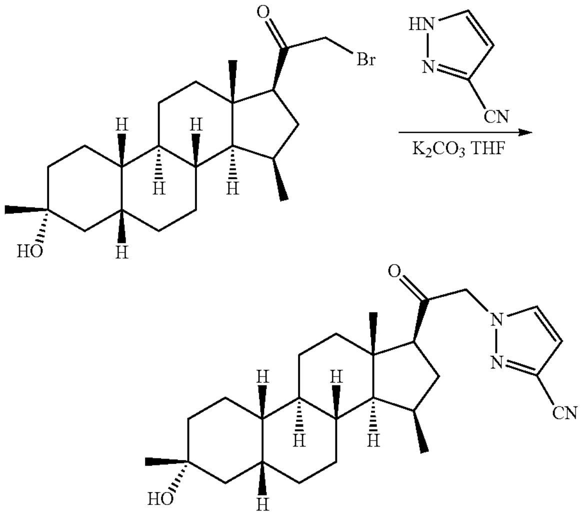

In accordance with Example 5, 2-bromo-1-((3R,5R,8R,9R,10S,13S,14S,15R,17S)-3-hydroxy-3,13,15-trimethylhexadecahydro-1H-cyclopenta[a]phenanthren-17-yl)ethan-1-one was used as the starting material, accordingly, 1-(2-((3R,5R,8R,9R,10S,13S,14S,15R,17S)-3-hydroxy-3,13,15-trimethylhexadecahydro-1H-cyclopenta[a]phenanthren-17-yl)-2-oxoethyl)-1H-pyrazole-3-carbonitrile (12.5 mg, yield: 20.2%) was obtained.

MS m/z (ESI): 424.1$[M+H]^+$.

$^1$H NMR (400 MHz, $CDCl_3$) δ 7.48 (d, J=2.4 Hz, 1H), 6.73 (d, J=2.4 Hz, 1H), 5.07-4.84 (m, 2H), 2.55 (t, J=8.1 Hz, 1H), 2.33-1.06 (m, 25H), 0.98 (d, J=7.0 Hz, 3H), 0.84 (s, 3H).

Example 41 and Example 42

1-((3R,5R,8R,9R,10S,13S,14S,15R,17S)-3-Hydroxy-3,13,15-trimethylhexadecahydro-1H-cyclopenta[a]phenanthren-17-yl)-2-(2H-1,2,3-triazol-2-yl)ethan-1-one (41)

1-((3R,5R,8R,9R,10S,13S,14S,15R,17S)-3-Hydroxy-3,13,15-trimethylhexadecahydro-1H-cyclopenta[a]phenanthren-17-yl)-2-(1H-1,2,3-triazol-1-yl)ethan-1-one (42)

41

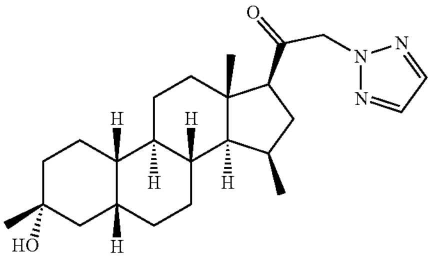

42

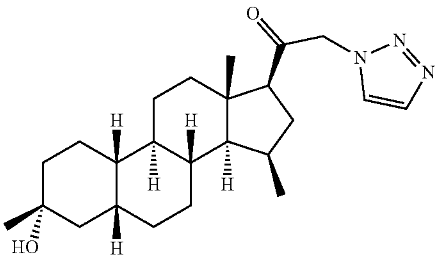

Step 1: Preparation of 1-((3R,5R,8R,9R,10S,13S,14S,15R,17S)-3-hydroxy-3,13,15-trimethylhexadecahydro-11H-cyclopenta[a]phenanthren-17-yl)-2-(2H-1,2,3-triazol-2-yl)ethan-1-one and 1-((3R,5R,8R,9R,10S,13S,14S,15R,17S)-3-hydroxy-3,13,15-trimethylhexadecahydro-1H-cyclopenta[a]phenanthren-17-yl)-2-(1H-1,2,3-triazol-1-yl)ethan-1-one

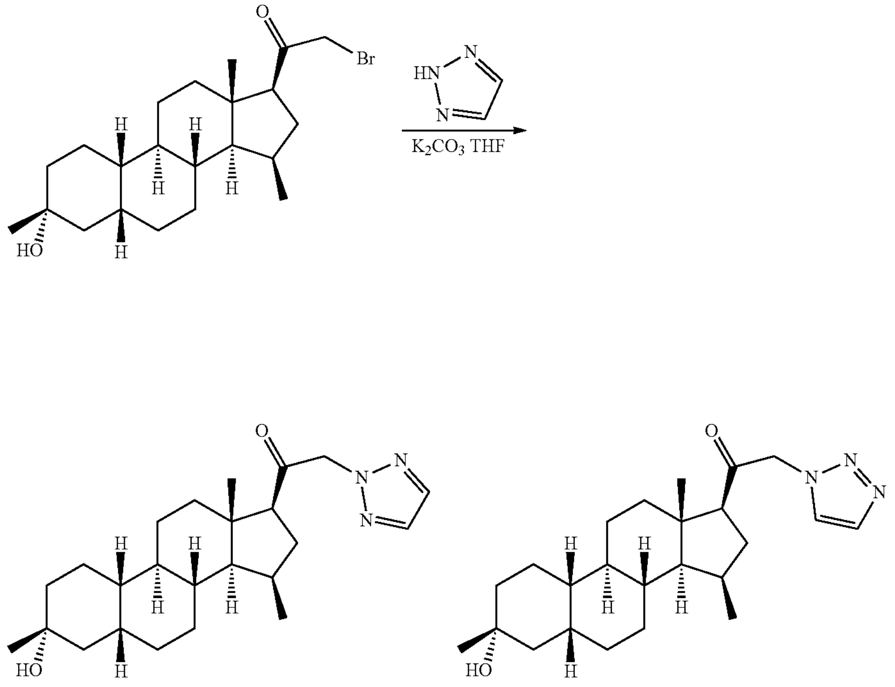

41

42

In accordance with Example 5, 2-bromo-1-((3R,5R,8R,9R,10S,13S,14S,15R,17S)-3-hydroxy-3,13,15-trimethylhexadecahydro-1H-cyclopenta[a]phenanthren-17-yl)ethan-1-one was used as the starting material, accordingly, 1-((3R,5R,8R,9R,10S,13S,14S,15R,17S)-3-hydroxy-3,13,15-trimethylhexadecahydro-1H-cyclopenta[a]phenanthren-17-yl)-2-(2H-1,2,3-triazol-2-yl)ethan-1-one (9.5 mg, yield: 16.3%) and 1-((3R,5R,8R,9R,10S,13S,14S,15R,17S)-3-hydroxy-3,13,15-trimethylhexadecahydro-1H-cyclopenta[a]phenanthren-17-yl)-2-(1H-1,2,3-triazol-1-yl)ethan-1-one (13 mg, yield: 22.3%) were obtained.

Example 41

MS m/z (ESI): 400.2[M+H]$^+$.

1H NMR (400 MHz, $CDCl_3$) δ 7.68 (s, 2H), 5.29-5.15 (m, 2H), 2.52 (t, J=8.0 Hz, 1H), 2.17-1.29 (m, 24H), 1.15-1.05 (m, 1H), 0.97 (d, J=7.0 Hz, 3H), 0.87 (s, 3H).

Example 42

MS m/z (ESI): 400.2[M+H]$^+$.

1H NMR (400 MHz, $CDCl_3$) δ7.77 (s, 1H), 7.65 (s, 1H), 5.32-5.02 (m, 2H), 2.60 (t, J=9.1 Hz, 1H), 2.30-2.12 (m, 2H), 1.99-1.27 (m, 22H), 1.17-1.06 (m, 1H), 0.99 (d, J=6.9 Hz, 3H), 0.84 (s, 3H)

Example 43

1-((3R,5R,8R,9R,10S,13S,14S,15R,17S)-3-Hydroxy-3,13,15-trimethylhexadecahydro-1H-cyclopenta[a]phenanthren-17-yl)-2-(5-methyl-2H-tetrazol-2-yl)ethan-1-one

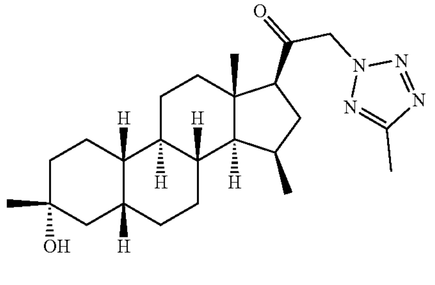

Step 1: Preparation of 1-((3R,5R,8R,9R,10S,13S,14S,15R,17S)-3-hydroxy-3,13,15-trimethylhexadecahydro-1H-cyclopenta[a]phenanthren-17-yl)-2-(5-methyl-2H-tetrazol-2-yl)ethan-1-one

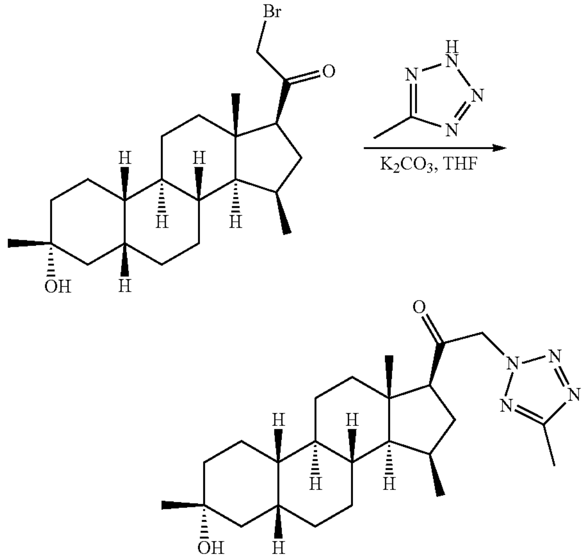

In accordance with Example 5, 2-bromo-1-((3R,5R,8R,9R,10S,13S,14S,15R,17S)-3-hydroxy-3,13,15-trimethylhexadecahydro-1H-cyclopenta[a]phenanthren-17-yl)ethan-1-one was used as the starting material, accordingly, 1-((3R,5R,8R,9R,10S,13S,14S,15R,17S)-3-hydroxy-3,13,15-trimethylhexadecahydro-1H-cyclopenta[a]phenanthren-17-yl)-2-(5-methyl-2H-tetrazol-2-yl)ethan-1-one (4.7 mg, yield: 7%) was obtained.

MS m/z (ESI): 415.3[M+H]$^+$ $^1$H NMR (400 MHz, $CDCl_3$) δ 5.36 (s, 2H), 2.57 (s, 3H), 2.27-2.11 (m, 2H), 2.00-198 (m, 1H), 1.87-1.83 (m, 5H), 1.77-1.57 (m, 6H), 1.52-1.30 (m, 12H), 1.11 (s, 2H), 0.98 (d, J=7.0 Hz, 3H), 0.88 (s, 3H).

Example 44

1-((3R,5R,8R,9R,10S,13S,14S,15R,17S)-3-Hydroxy-3,13,15-trimethylhexadecahydro-1H-cyclopenta[a]phenanthren-17-yl)-2-(2H-tetrazol-2-yl)ethan-1-one

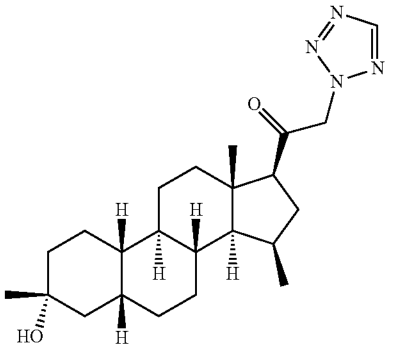

-continued

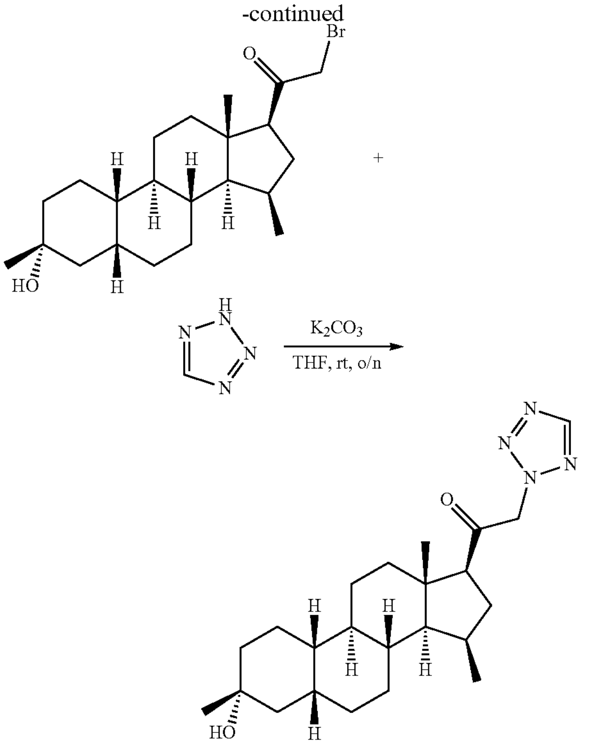

2-Bromo-1-((3R,5R,8R,9R,10S,13S,14S,15R,17S)-3-hydroxy-3,13,15-trimethylhexadecahydro-1H-cyclopenta[a]phenanthren-17-yl)ethan-1-one (82 mg, 0.2 mmol), 2H-tetrazole (21 mg, 0.3 mmol) and potassium carbonate (54 mg, 0.3 mmol) were dissolved in anhydrous tetrahydrofuran (5 mL), and the resulting reaction solution was stirred at room temperature overnight. The reaction solution was filtrated, and the filtrate was concentrated. The resulting crude product was purified by high performance liquid chromatography to obtain 1-((3R,5R,8R,9R,10S,13S,14S,15R,17S)-3-hydroxy-3,13,15-trimethylhexadecahydro-1H-cyclopenta[a]phenanthren-17-yl)-2-(2H-tetrazol-2-yl)ethan-1-one (15.7 mg, yield: 20%).

MS m/z (ESI): 401.3 [M+H]$^+$ $^1$H NMR (400 MHz, $CDCl_3$) δ 8.58 (s, 1H), 4.46 (s, 2H), 2.62-2.58 (m, 1H), 1.89-1.84 (m, 2H), 1.70-1.26 (m, 23H), 0.99 (d, J=8.0 Hz, 3H), 0.88 (s, 3H).

Example 47

3-Cyclopropyl-1-(2-((3R,5R,8R,9R,10S,13S,14S,15R,17S)-3-hydroxy-3,13,15-trimethylhexadecahydro-1H-cyclopenta[a]phenanthren-17-yl)-2-oxoethyl)-1H-pyrazole-4-carbonitrile

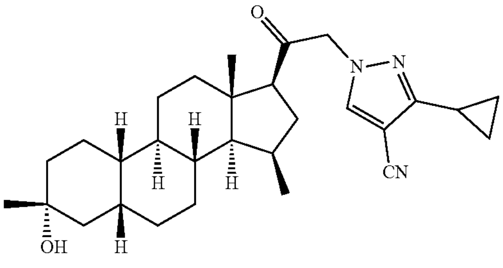

Step 1: Preparation of 3-cyclopropyl-1-(2-((3R,5R,8R,9R,10S,13S,14S,15R,17S)-3-hydroxy-3,13,15-trimethylhexadecahydro-1H-cyclopenta[a]phenanthren-17-yl)-2-oxoethyl)-1H-pyrazole-4-carbonitrile

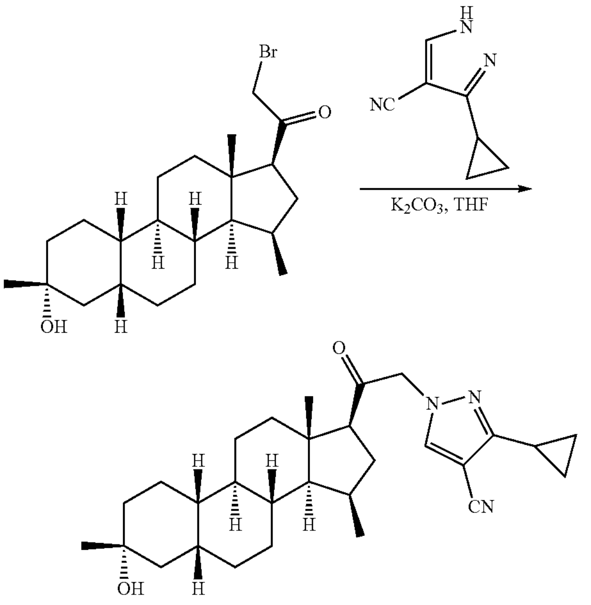

In accordance with Example 5, 2-bromo-1-((3R,5R,8R,9R,10S,13S,14S,15R,17S)-3-hydroxy-3,13,15-trimethylhexadecahydro-1H-cyclopenta[a]phenanthren-17-yl)ethan-1-one was used as the starting material, accordingly, 3-cyclopropyl-1-(2-((3R,5R,8R,9R,10S,13S,14S,15R,17S)-3-hydroxy-3,13,15-trimethylhexadecahydro-1H-cyclopenta[a]phenanthren-17-yl)-2-oxoethyl)-1H-pyrazole-4-carbonitrile (30 mg, yield: 41%) was obtained.

MS m/z (ESI): 464.3[M+H]$^+$ $^1$H NMR (400 MHz, $CDCl_3$) δ 7.71 (s, 1H), 4.82 (q, J=17.9 Hz, 2H), 2.51-2.46 (m, 1H), 2.27-2.18 (m, 1H), 2.19-2.08 (m, 1H), 2.04-1.91 (m, 2H), 1.90-1.80 (m, 4H), 1.68-1.60 (m, 4H), 1.57 (s, 3H), 1.51-1.29 (m, 8H), 1.18-1.03 (m, 3H), 1.02-0.95 (m, 7H), 0.82 (s, 3H).

Example 48

1-(2-((3R,5R,8R,9R,10S,13S,14S,15S)-15-Cyclopropyl-3-hydroxy-3,13-dimethylhexadecahydro-1H-cyclopenta[a]phenanthren-17-yl)-2-oxoethyl)-1H-pyrazole-4-carbonitrile

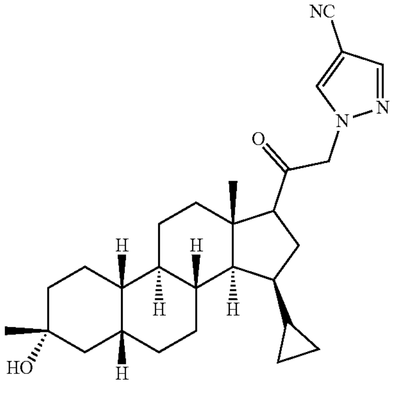

Step 1: (3R,5R,8R,9R,10S,13S,14S,15S)-15-Cyclopropyl-3-hydroxy-3,13-dimethylhexadecahydro-17H-cyclopenta[a]phenanthren-17-one

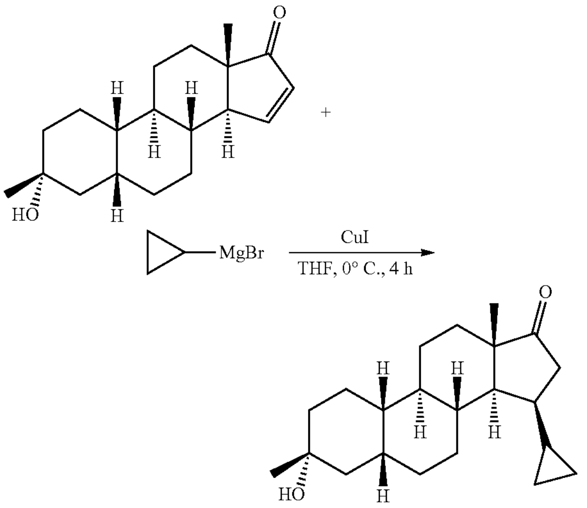

1.0 M cyclopropylmagnesium bromide (12.7 mL, 12.7 mmol) and 20 mL of anhydrous tetrahydrofuran were added to a dry 100 mL round bottom flask. The reaction system was purged with nitrogen, and cooled to 0° C. Cuprous iodide (1.97 g, 10.4 mmol) was added, and then the reaction solution was stirred at 0° C. for 1 hour. (3R,5R,8R,9R,10S,13S,14S)-3-Hydroxy-3,13-dimethyl-1,2,3,4,5,6,7,8,9,10,11,12,13,14-tetradecahydro-17H-cyclopenta[a]phenanthren-17-one (1 g, 3.5 mmol) was dissolved in 10 ml of anhydrous tetrahydrofuran, and the resulting solution was slowly added dropwise to the reaction system. The reaction solution was stirred for 3 hours, and TLC showed that the reaction was completed. Saturated ammonium chloride solution was added to quench the reaction, and the reaction solution was extracted with ethyl acetate. The organic phase was washed with water and saturated saline, dried over anhydrous sodium sulfate, filtrated and concentrated by rotary evaporation to dryness. The resulting crude product was purified by column chromatography (eluent: petroleum ether/ethyl acetate=2/1) to obtain (3R,5R,8R,9R,10S,13S,14S,15S)-15-cyclopropyl-3-hydroxy-3,13-dimethylhexadecahydro-17H-cyclopenta[a]phenanthren-17-one (1.11 g, 96%).

$^1$H NMR (400 MHz, $CDCl_3$) δ 2.45-2.30 (m, 2H), 1.85-1.76 (m, 9H), 1.59-1.52 (m, 5H), 1.59-1.27 (m, 12H), 1.11-0.98 (m, 1H), 0.67-0.64 (m, 1H), 0.47-0.43 (m, 1H), 0.22-0.18 (m, 1H), 0.09-0.07 (m, 1H)..

Step 2: (3R,5R,8R,9R,10S,13S,14S,15S,E)-15-Cyclopropyl-17-ethylidene-3,13-dimethylhexadecahydro-1H-cyclopenta[a]phenanthren-3-ol

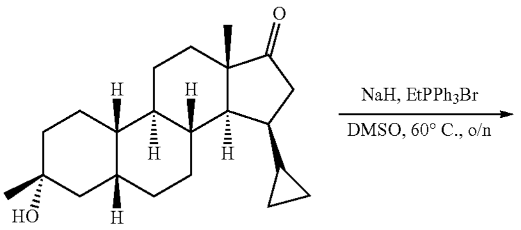

-continued

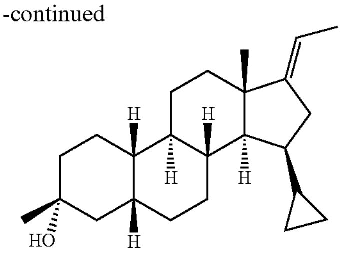

Ethyltriphenylphosphonium bromide (12.5 g, 33 mmol) was dissolved in anhydrous dimethyl sulfoxide (50 mL), and the reaction system was purged with nitrogen. Sodium hydride (1.32 g, 33 mmol) was added, and then the reaction solution was stirred at room temperature for 1 hour. (3R,5R,8R,9R,10S,13S,14S,15S)-15-Cyclopropyl-3-hydroxy-3,13-dimethylhexadecahydro-17H-cyclopenta[a]phenanthren-17-one (1.1 g, 3.3 mmol) was added, and then the reaction solution was stirred at 60° C. overnight. The reaction solution was cooled to room temperature. Water (200 mL) was added to the reaction solution to quench the reaction, and the aqueous phase was extracted with ethyl acetate (200 mL×2). The organic phases were combined, dried over anhydrous sodium sulfate, filtrated and concentrated. The resulting crude product was purified by column chromatography (petroleum ether/ethyl acetate: 50/1~3/1) to obtain (3R,5R,8R,9R,10S,13S,14S,15S,E)-15-cyclopropyl-17-ethylidene-3,13-dimethylhexadecahydro-1H-cyclopenta[a]phenanthren-3-ol (0.67 g, yield: 59%).

$^1$H NMR (400 MHz, $CDCl_3$) 35.15-5.09 (m, 1H), 2.45-2.38 (m, 1H), 2.38-2.18 (m, 2H), 1.90-1.07 (m, 28H), 0.86-0.78 (m, 1H), 0.56-0.50 (m, 1H), 0.38-0.32 (m, 1H), 0.12-0.02 (m, 2H).

Step 3: (3R,5R,8R,9R,10S,13S,14S,15S,17S)-15-Cyclopropyl-17-((R)-1-hydroxyethyl)-3,13-dimethylhexadecahydro-1H-cyclopenta[a]phenanthren-3-ol

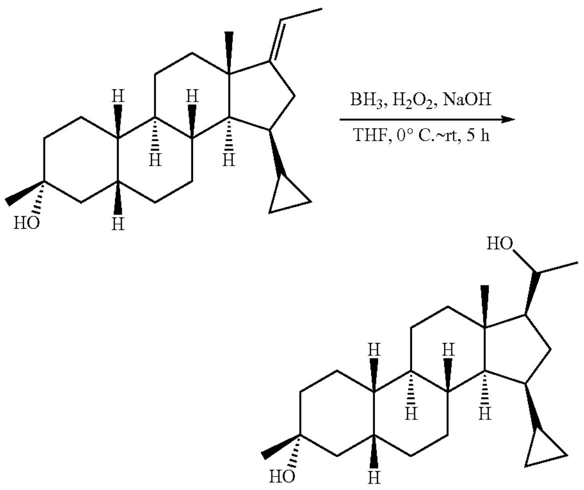

(3R,5R,8R,9R,10S,13S,14S,15S,E)-15-Cyclopropyl-17-ethylidene-3,13-dimethylhexadecahydro-1H-cyclopenta[a]phenanthren-3-ol (0.67 g, 1.96 mmol) was dissolved in anhydrous tetrahydrofuran (20 mL). The solution was cooled to 0° C., and then $BH_3$/THF (9.8 mL, 9.8 mmol) was added dropwise. The reaction solution was stirred at room temperature for 3 hours, and TLC showed that the reaction was completed. The reaction solution was cooled to 0° C., and then 3 M aqueous NaOH solution (10 mL) was slowly added, followed by the addition of 30% hydrogen peroxide (8 mL). The reaction solution was stirred at room temperature for 2 hours, and TLC showed that the reaction was completed. Ethyl acetate (50 mL) was added, and then the reaction solution was washed with saturated aqueous $Na_2S_{203}$ solution (30 mL) and water (30 mL) successively. The organic phase was dried over anhydrous sodium sulfate, filtrated and concentrated to obtain the crude product (0.71 g), which was used directly in the next step.

Step 4: 1-((3R,5R,8R,9R,10S,13S,14S,15S,17S)-15-Cyclopropyl-3-hydroxy-3,13-dimethylhexadecahydro-1H-cyclopenta[a]phenanthren-17-yl)ethan-1-one

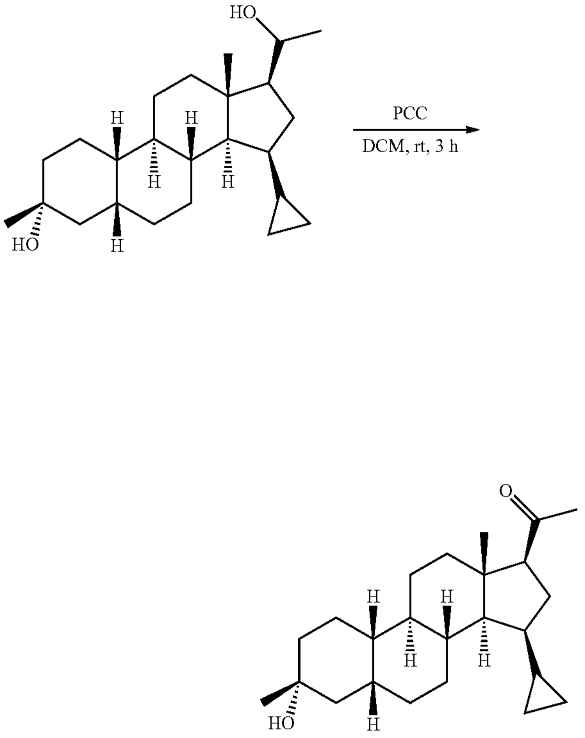

(3R,5R,8R,9R,10S,13S,14S,15S,17S)-15-Cyclopropyl-17-((R)-1-hydroxyethyl)-3,13-dimethylhexadecahydro-1H-cyclopenta[a]phenanthren-3-ol (0.71 g, crude) was dissolved in dichloromethane (20 mL). Pyridinium chlorochromate (1.27 g, 5.88 mmol) was added, and then the reaction solution was stirred at room temperature for 2 hours. The reaction solution was filtrated, and the organic phase was concentrated. The resulting crude product was purified by column chromatography (petroleum ether/ethyl acetate: 1/1) to obtain 1-((3R,5R,8R,9R,10S,13S,14S,15S,17S)-15-cyclopropyl-3-hydroxy-3,13-dimethylhexadecahydro-1H-cyclopenta[a]phenanthren-17-yl)ethan-1-one (480 mg, yield of two steps: 68.3%).

$^1$H NMR (400 MHz, $CDCl_3$) δ 2.45-2.40 (m, 1H), 2.18-2.10 (m, 4H), 1.99-1.03 (m, 24H), 0.84-0.79 (m, 4H), 0.60-0.53 (m, 1H), 0.43-0.38 (m, 1H), 0.14-0.02 (m, 2H).

Step 5: 2-Bromo-1-((3R,5R,8R,9R,10S,13S,14S,15S,17S)-15-cyclopropyl-3-hydroxy-3,13-dimethylhexadecahydro-1H-cyclopenta[a]phenanthren-17-yl) ethan-1-one

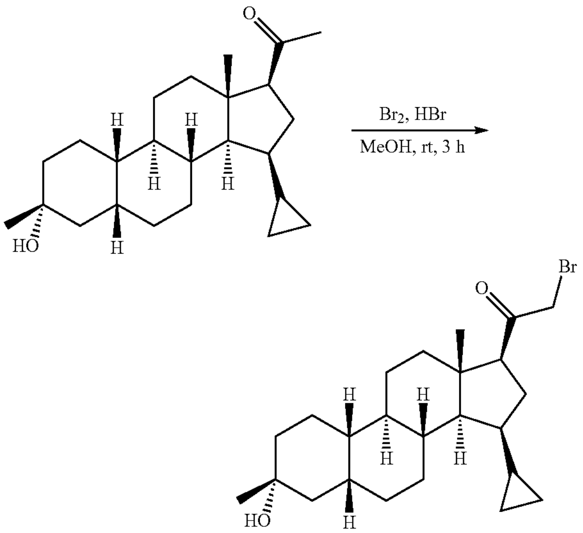

1-((3R,5R,8R,9R,10S,13S,14S,15S,17S)-15-Cyclopropyl-3-hydroxy-3,13-dimethylhexadecahydro-1H-cyclopenta[a]phenanthren-17-yl)ethan-1-one (107 mg, 0.3 mmol) was dissolved in methanol (5 mL). A drop of hydrogen bromide was added to the solution, followed by the addition of liquid bromine (56 mg, 0.35 mmol), and then the reaction solution was stirred at room temperature for 1 hour. Water (20 mL) was added to the reaction solution, and the aqueous phase was extracted with ethyl acetate (20 mL×2). The organic phases were combined, dried over anhydrous sodium sulfate, filtrated and concentrated to obtain the crude product (120 mg, crude), which was used directly in the next step.

Step 6: 1-(2-((3R,5R,8R,9R,10S,13S,14S,15S)-15-Cyclopropyl-3-hydroxy-3,13-dimethylhexadecahydro-1H-cyclopenta[a]phenanthren-17-yl)-2-oxoethyl)-1H-pyrazole-4-carbonitrile

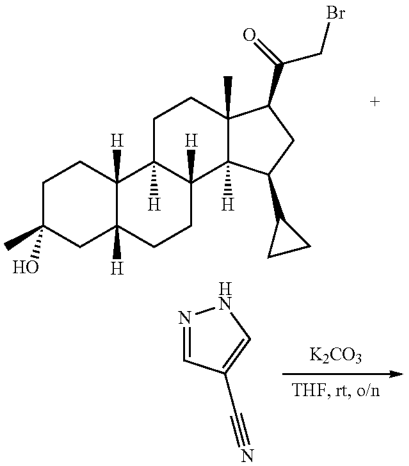

-continued

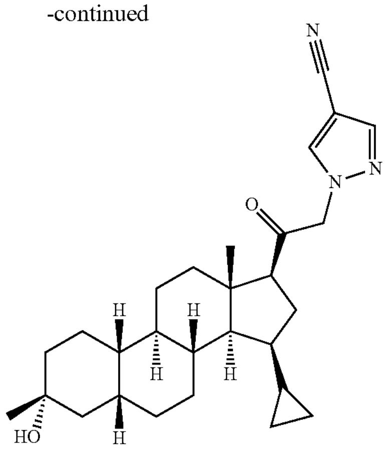

1-((3R,5R,8R,9R,10S,13S,14S,15S,17S)-15-Cyclopropyl-3-hydroxy-3,13-dimethylhexadecahydro-1H-cyclopenta[a]phenanthren-17-yl)ethan-1-one (60 mg, 0.14 mmol), 1H-pyrazole-4-carbonitrile (28 mg, 0.3 mmol) and potassium carbonate (54 mg, 0.3 mmol) were dissolved in anhydrous tetrahydrofuran (5 mL), and the resulting reaction solution was stirred at room temperature overnight. The reaction solution was filtrated, and the filtrate was concentrated. The resulting crude product was purified by high performance liquid chromatography to obtain 1-(2-((3R,5R,8R,9R,10S,13S,14S,15S)-15-cyclopropyl-3-hydroxy-3,13-dimethylhexadecahydro-1H-cyclopenta[a]phenanthren-17-yl)-2-oxoethyl)-1H-pyrazole-4-carbonitrile (31 mg, yield: 49%).

MS m/z (ESI): 450.3 $[M+H]^+$ $^1$H NMR (400 MHz, $CDCl_3$) δ 7.86 (s, 1H), 7.81 (s, 1H), 5.02 (d, J=16.0 Hz, 1H), 4.92 (d, J=16.0 Hz, 1H), 2.51-2.47 (m, 1H), 2.09-1.71 (m, 9H), 1.48-1.10 (m, 16H), 0.90 (s, 3H), 0.83-0.79 (m, 1H), 0.62-0.58 (m, 1H), 0.45-0.40 (m, 1H), 0.14-0.11 (m, 1H), 0.05-0.02 (m, 1H).

Example 49

1-(2-((3R,5R,8R,9R,10S,13S,14S,15S,17S)-15-Cyclopropyl-3-hydroxy-3,13-dimethylhexadecahydro-1H-cyclopenta[a]phenanthren-17-yl)-2-oxoethyl)-1H-pyrazole-3-carbonitrile

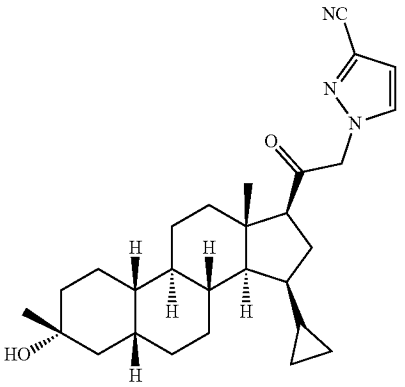

Step 1: Preparation of 1-(2-((3R,5R,8R,9R,10S,13S,14S,15S,17S)-15-cyclopropyl-3-hydroxy-3,13-dimethylhexadecahydro-1H-cyclopenta[a]phenanthren-17-yl)-2-oxoethyl)-1H-pyrazole-3-carbonitrile

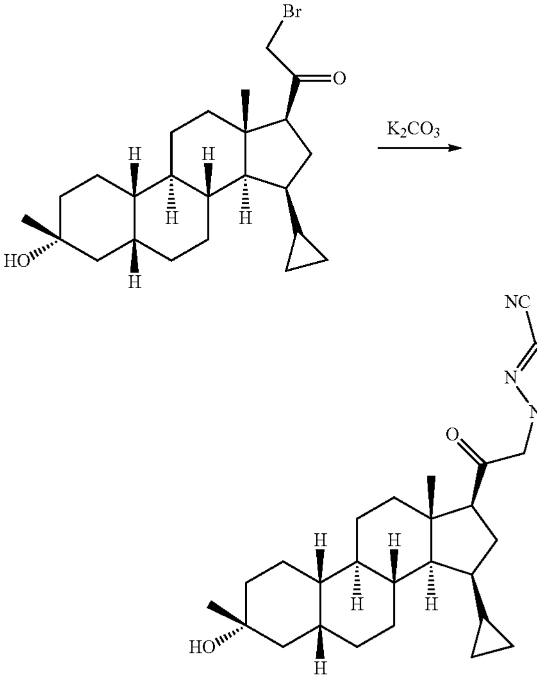

In accordance with Example 3, 1-((3R,5R,8R,9R,10S,13S,14S,15S,17S)-15-cyclopropyl-3-hydroxy-3,13-dimethylhexadecahydro-1H-cyclopenta[a]phenanthren-17-yl)ethan-1-one was used as the starting material, accordingly, 1-(2-((3R,5R,8R,9R,10S,13S,14S,15S,17S)-15-cyclopropyl-3-hydroxy-3,13-dimethylhexadecahydro-1H-cyclopenta[a]phenanthren-17-yl)-2-oxoethyl)-1H-pyrazole-3-carbonitrile (20 mg, yield 20%) was obtained.

MS m/z (ESI): 432.2$[M-H_2O+H]^+$ $^1$H NMR (400 MHz, $CDCl_3$) δ 7.49 (d, J=2.4 Hz, 1H), 6.73 (d, J=2.4 Hz, 1H), 4.98 (dd, J=40.0, 17.8 Hz, 2H), 2.52-2.45 (m, 1H), 2.24-2.13 (m, 1H), 2.11-2.03 (m, 1H), 2.04-1.95 (m, 2H), 1.90-1.82 (m, 2H), 1.75-1.66 (m, 2H), 1.54-1.23 (m, 16H), 1.18-1.05 (m, 2H), 0.93-0.79 (m, 4H), 0.63-0.55 (m, 1H), 0.45-0.37 (m, 1H), 0.18-0.09 (m, 1H), 0.08-0.01 (m, 1H).

Example 50 and Example 51

1-((3R,5R,8R,9R,10S,13S,14S,15S,17S)-15-Cyclopropyl-3-hydroxy-3,13-dimethylhexadecahydro-1H-cyclopenta[a]phenanthren-17-yl)-2-(2H-1,2,3-triazol-2-yl)ethan-1-one (50)

1-((3R,5R,8R,9R,10S,13S,14S,15S,17S)-15-Cyclopropyl-3-hydroxy-3,13-dimethylhexadecahydro-1H-cyclopenta[a]phenanthren-17-yl)-2-(1H-1,2,3-triazol-1-yl)ethan-1-one (51)

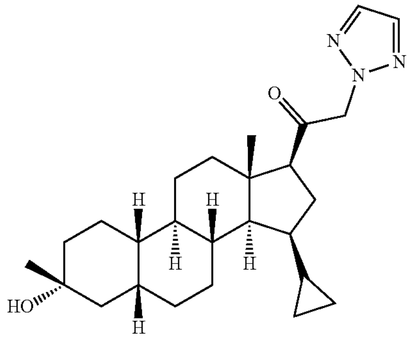

50

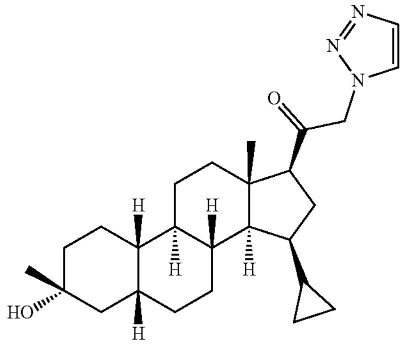

51

Step 1: Preparation of 1-((3R,5R,8R,9R,10S,13S,14S,15S,17S)-15-cyclopropyl-3-hydroxy-3,13-dimethylhexadecahydro-1H-cyclopenta[a]phenanthren-17-yl)-2-(2H-1,2,3-triazol-2-yl)ethan-1-one and 1-((3R,5R,8R,9R,10S,13S,14S,15S,17S)-15-Cyclopropyl-3-hydroxy-3,13-dimethylhexadecahydro-1H-cyclopenta[a]phenanthren-17-yl)-2-(1H-1,2,3-triazol-1-yl)ethan-1-one

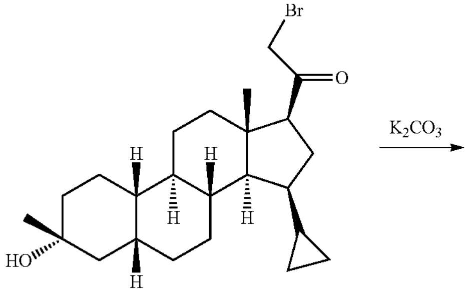

-continued

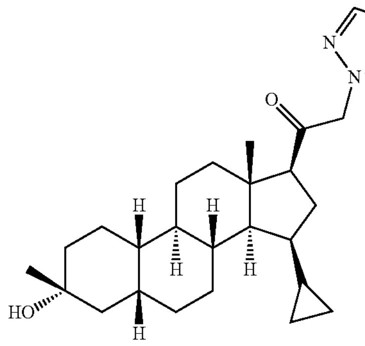

50

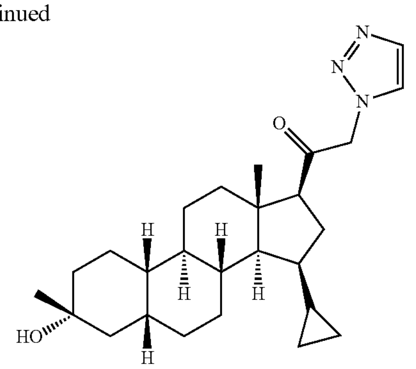

51

In accordance with Example 3, 1-((3R,5R,8R,9R,10S,13S,14S,15S,17S)-15-cyclopropyl-3-hydroxy-3,13-dimethylhexadecahydro-1H-cyclopenta[a]phenanthren-17-yl)ethan-1-one was used as the starting material, accordingly, 1-((3R,5R,8R,9R,10S,13S,14S,15S,17S)-15-cyclopropyl-3-hydroxy-3,13-dimethylhexadecahydro-1H-cyclopenta[a]phenanthren-17-yl)-2-(2H-1,2,3-triazol-2-yl)ethan-1-one (7.6 mg, yield: 7.8%) and 1-((3R,5R,8R,9R,10S,13S,14S,15S,17S)-15-cyclopropyl-3-hydroxy-3,13-dimethylhexadecahydro-1H-cyclopenta[a]phenanthren-17-yl)-2-(1H-1,2,3-triazol-1-yl)ethan-1-one (11.6 mg, yield: 11.9%) were obtained.

Example 50

MS m/z (ESI): 408.3[M−$H_2$O+H]$^+$ $^1$H NMR (400 MHz, $CDCl_3$) δ 7.68 (s, 2H), 5.24 (s, 2H), 2.49-2.42 (m, 1H), 2.23-2.14 (m, 1H), 2.10-1.94 (m, 3H), 1.91-1.81 (m, 3H), 1.75-1.66 (m, 2H), 1.48-1.24 (m, 15H), 1.17-1.04 (m, 2H), 0.94 (s, 3H), 0.86-0.76 (m, 1H), 0.63-0.54 (m, 1H), 0.45-0.38 (m, 1H), 0.14-0.01 (m, 2H).

Example 51

MS m/z (ESI): 426.3[M+H]$^+$ $^1$H NMR (400 MHz, $CDCl_3$) δ 7.78 (s, 1H), 7.67 (s, 1H), 5.22 (dd, J=47.1, 17.8 Hz, 2H), 2.59-2.50 (m, 1H), 2.25-2.15 (m, 1H), 2.14-1.98 (m, 2H), 1.96-1.79 (m, 3H), 1.76-1.58 (m, 6H), 1.56-1.25 (m, 12H), 1.22-1.04 (m, 2H), 0.91 (s, 3H), 0.87-0.77 (m, 1H), 0.62-0.55 (m, 1H), 0.47-0.36 (m, 1H), 0.18-0.02 (m, 2H).

Example 52

1-((3R,5R,8R,9R,10S,13S,14S,15S,17S)-15-Cyclopropyl-3-hydroxy-3,13-dimethylhexadecahydro-1H-cyclopenta[a]phenanthren-17-yl)-2-(5-methyl-2H-tetrazol-2-yl)ethan-1-one

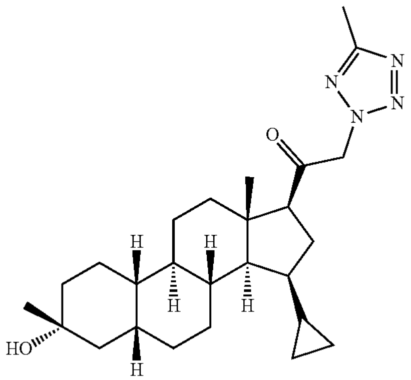

Step 1: Preparation of 1-((3R,5R,8R,9R,10S,13S,14S,15S,17S)-15-cyclopropyl-3-hydroxy-3,13-dimethylhexadecahydro-1H-cyclopenta[a]phenanthren-17-yl)-2-(5-methyl-2H-tetrazol-2-yl)ethan-1-one

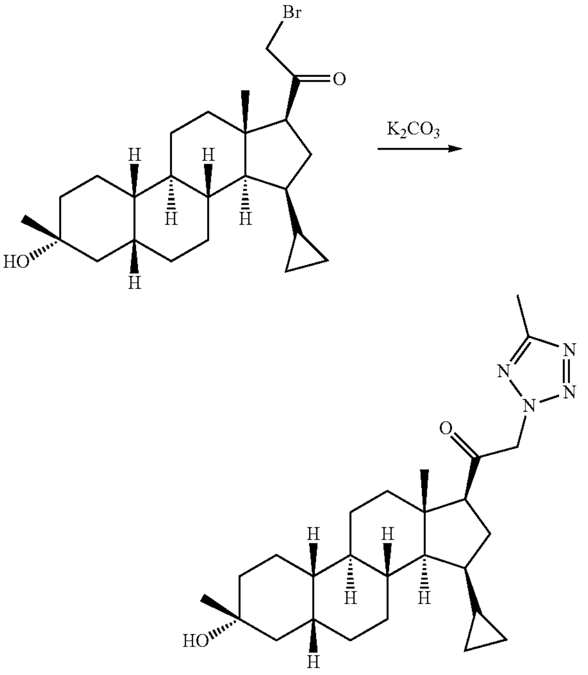

In accordance with Example 3, 1-((3R,5R,8R,9R,10S,13S,14S,15S,17S)-15-cyclopropyl-3-hydroxy-3,13-dimethylhexadecahydro-1H-cyclopenta[a]phenanthren-17-yl)ethan-1-one was used as the starting material, accordingly, 1-((3R,5R,8R,9R,10S,13S,14S,15S,17S)-15-cyclopropyl-3-hydroxy-3,13-dimethylhexadecahydro-1H-cyclopenta[a]phenanthren-17-yl)-2-(5-methyl-2H-tetrazol-2-yl)ethan-1-one (8.5 mg, yield: 9%) was obtained.

MS m/z (ESI): 441.3[M+H]$^+$ $^1$H NMR (400 MHz, $CDCl_3$) δ 5.36 (s, 2H), 2.57 (s, 3H), 2.54-2.47 (m, 1H), 2.25-2.15 (m, 1H), 2.13-1.95 (m, 3H), 1.92-1.79 (m, 3H), 1.77-1.66 (m, 2H), 1.50-1.24 (m, 15H), 1.18-1.05 (m, 2H), 0.94 (s, 3H), 0.87-0.78 (m, 1H), 0.63-0.55 (m, 1H), 0.45-0.37 (m, 1H), 0.17-0.02 (m, 2H).

Example 59

1-(2-((3R,5R,8R,9R,10S,13S,14S,15R,17S)-15-Ethyl-3-hydroxy-3,13-dimethylhexadecahydro-1H-cyclopenta[a]phenanthren-17-yl)-2-oxoethyl)-1H-pyrazole-4-carbonitrile

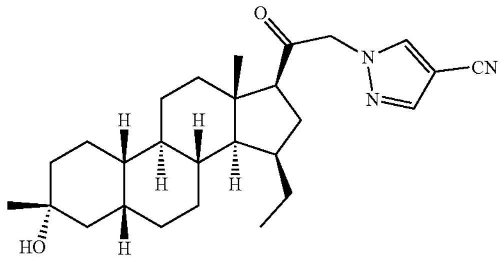

Step 1: (3R,5R,8R,9R,10S,13S,14S,15R)-15-Ethyl-3-hydroxy-3,13-dimethylhexadecahydro-17H-cyclopenta[a]phenanthren-17-one

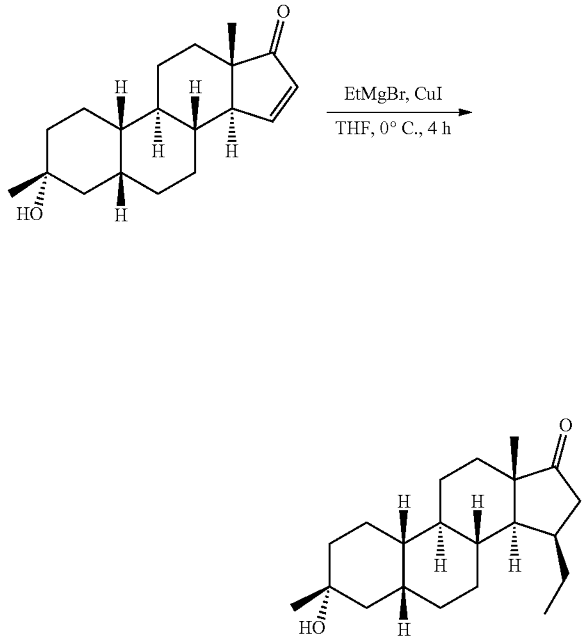

Tetrahydrofuran (15 mL) was added to a 100 mL three-neck flask, and ethyl magnesium bromide (10 mL, 1M, 10 mmol) was then added at 0° C. under a nitrogen atmosphere, followed by the addition of cuprous iodide (1.6 g, 8.4 mmol). The reaction solution was stirred at 0° C. for 1 hour. (3R,5R,8R,9R,10S,13S,14S)-3-Hydroxy-3,13-dimethyl-1,2,3,4,5,6,7,8,9,10,11,12,13,14-tetradecahydro-17H-cyclopenta[a]phenanthren-17-one (800 mg, 2.8 mmol) was dissolved in tetrahydrofuran (5 mL), and the resulting solution was slowly added dropwise to the reaction solution, which was then stirred at 0° C. for 4 hours. Saturated aqueous ammonium chloride solution was added to quench the reaction, and the reaction solution was extracted with ethyl acetate (20 mL). The organic phase was washed with saline (10 mL×3), dried over anhydrous sodium sulfate, filtrated and concentrated by rotary evaporation to dryness. The resulting crude product was purified by column chromatography (petroleum ether/ethyl acetate: 3/1) to obtain (3R,5R,8R,9R,10S,13S,14S,15R)-15-ethyl-3-hydroxy-3,13-dimethylhexadecahydro-17H-cyclopenta[a]phenanthren-17-one (750 mg, yield: 84.9%).

$^1$H NMR (400 MHz, $CDCl_3$) δ 2.37-2.30 (m, 1H), 2.15-2.02 (m, 2H), 1.91-1.31 (m, 17H), 1.27 (s, 3H), 1.24-1.03 (m, 4H), 0.98 (s, 3H), 0.90 (t, J=7.3 Hz, 3H).

Step 2: (3R,5R,8R,9R,10S,13S,14S,15R)-15-Ethyl-17-ethylidene-3,13-dimethylhexadecahydro-1H-cyclopenta[a]phenanthren-3-ol

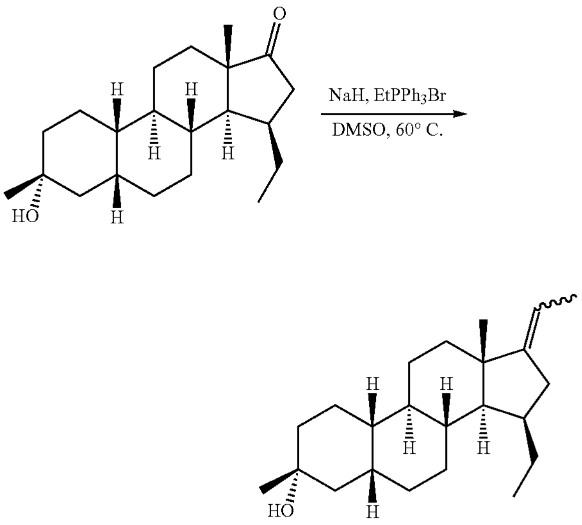

Dimethyl sulfoxide (20 mL) was added to a 100 mL three-neck flask, and ethyltriphenylphosphonium bromide (8.7 g, 23.5 mmol) was then added under a nitrogen atmosphere. Sodium hydride (60%) (940 mg, 23.5 mmol) was added in batches, and the reaction solution was stirred at room temperature for 1 hour. (3R,5R,8R,9R,10S,13S,14S,15R)-15-Ethyl-3-hydroxy-3,13-dimethylhexadecahydro-17H-cyclopenta[a]phenanthren-17-one (750 mg, 2.35 mmol) was dissolved in dimethyl sulfoxide (5 mL), and the resulting solution was slowly added dropwise to the reaction solution, which was then stirred under a nitrogen atmosphere at 80° C. for 5 hours. The reaction solution was cooled to room temperature. Saturated aqueous ammonium chloride solution was added to quench the reaction, and the reaction solution was extracted with ethyl acetate (50 mL). The organic phase was washed with saline (20 mL×3), dried over anhydrous sodium sulfate, filtrated and concentrated by rotary evaporation to dryness. The resulting crude product was purified by column chromatography (petroleum ether/ethyl acetate: 3/1) to obtain (3R,5R,8R,9R,10S,13S,14S,15R)-15-ethyl-17-ethylidene-3,13-dimethylhexadecahydro-1H-cyclopenta[a]phenanthren-3-ol (580 mg, yield: 71.7%).

$^1$H NMR (400 MHz, $CDCl_3$) δ 5.22-5.06 (m, 1H), 2.54-2.39 (m, 1H), 2.28-2.09 (m, 2H), 1.96-1.80 (m, 4H), 1.78-1.59 (m, 6H), 1.55-1.33 (m, 11H), 1.26 (s, 3H), 1.20-1.08 (m, 3H), 1.05 (s, 3H), 0.82 (t, J=7.3 Hz, 3H).

Step 3: (3R,5R,8R,9R,10S,13S,14S,15R,17R)-15-Ethyl-17-(1-hydroxyethyl)-3,13-dimethylhexadecahydro-1H-cyclopenta[a]phenanthren-3-ol

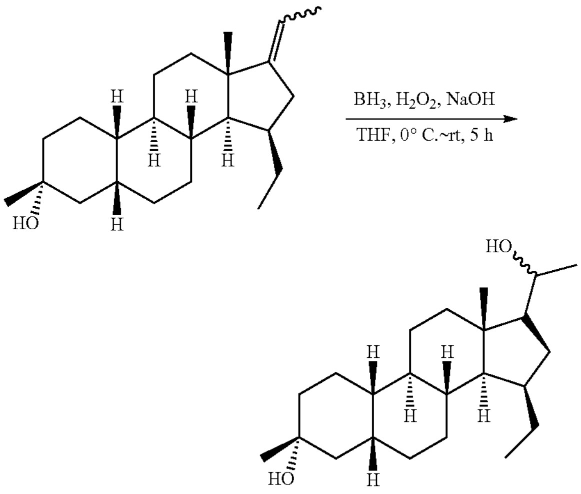

In accordance with Step 3 of Example 71, (3R,5R,8R,9R,10S,13S,14S,15R)-15-ethyl-17-ethylidene-3,13-dimethylhexadecahydro-1H-cyclopenta[a]phenanthren-3-ol was used as the starting material, accordingly, (3R,5R,8R,9R,10S,13S,14S,15R,17R)-15-ethyl-17-(1-hydroxyethyl)-3,13-dimethylhexadecahydro-1H-cyclopenta[a]phenanthren-3-ol (600 mg, yield: 98.1%) was obtained.

Step 4: 1-((3R,5R,8R,9R,10S,13S,14S,15R,17S)-15-Ethyl-3-hydroxy-3,13-dimethylhexadecahydro-1H-cyclopenta[a]phenanthren-17-yl)ethan-1-one

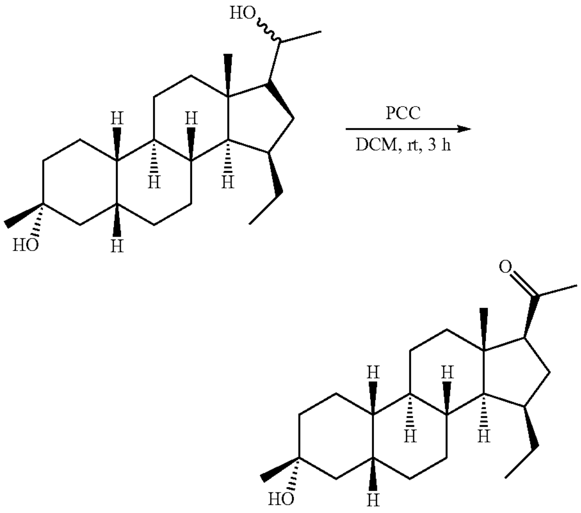

In accordance with Step 4 of Example 71, (3R,5R,8R,9R,10S,13S,14S,15R,17R)-15-ethyl-17-(1-hydroxyethyl)-3,13-dimethylhexadecahydro-1H-cyclopenta[a]phenanthren-3-ol was used as the starting material, accordingly, 1-((3R,5R,8R,9R,10S,13S,14S,15R,17S)-15-ethyl-3-hydroxy-3,13-dimethylhexadecahydro-1H-cyclopenta[a]phenanthren-17-yl)ethan-1-one (500 mg, yield: 83.8%) was obtained.

1H NMR (400 MHz, $CDCl_3$) δ 2.51 (t, J=8.0 Hz, 1H), 2.12 (s, 3H), 2.00-1.30 (m, 20H), 1.28 (s, 3H), 1.25-1.00 (m, 4H), 0.84 (t, J=7.2 Hz, 3H), 0.73 (s, 3H).

Step 5: 2-Bromo-1-((3R,5R,8R,9R,10S,13S,14S,15R,17S)-15-ethyl-3-hydroxy-3,13-dimethylhexadecahydro-1H-cyclopenta[a]phenanthren-17-yl)ethan-1-one

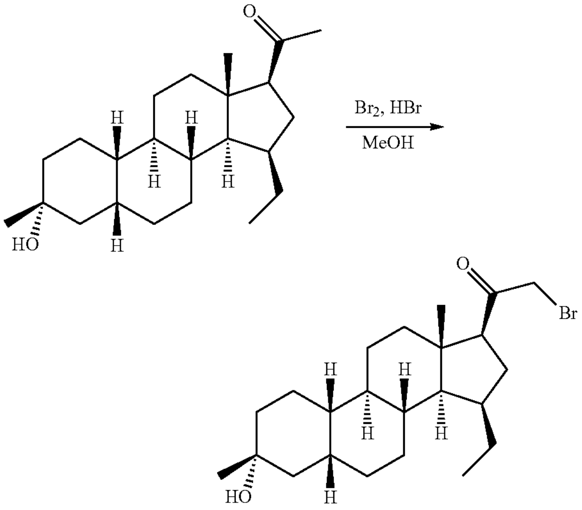

In accordance with Step 5 of Example 71, 1-((3R,5R,8R,9R,10S,13S,14S,15R,17S)-15-ethyl-3-hydroxy-3,13-dimethylhexadecahydro-1H-cyclopenta[a]phenanthren-17-yl)ethan-1-one was used as the starting material, accordingly, 2-bromo-1-((3R,5R,8R,9R,10S,13S,14S,15R,17S)-15-ethyl-3-hydroxy-3,13-dimethylhexadecahydro-1H-cyclopenta[a]phenanthren-17-yl)ethan-1-one (500 mg, yield: 81.4%) was obtained.

Step 6: 1-(2-((3R,5R,8R,9R,10S,13S,14S,15R,17S)-15-Ethyl-3-hydroxy-3,13-dimethylhexadecahydro-1H-cyclopenta[a]phenanthren-17-yl)-2-oxoethyl)-1H-pyrazole-4-carbonitrile

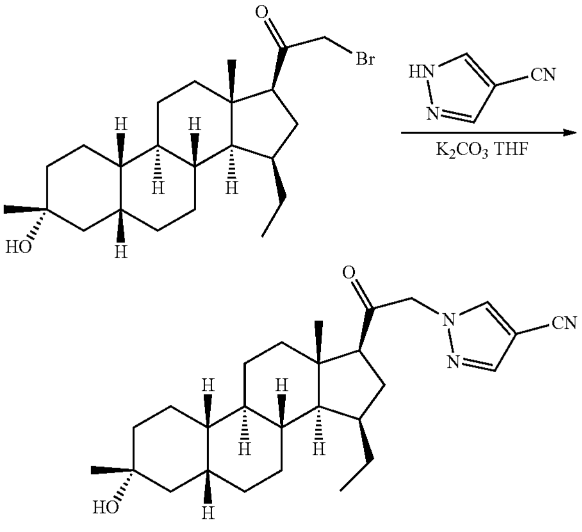

In accordance with Step 6 of Example 71, 2-bromo-1-((3R,5R,8R,9R,10S,13S,14S,15R,17S)-15-ethyl-3-hydroxy-3,13-dimethylhexadecahydro-1H-cyclopenta[a]phenanthren-17-yl)ethan-1-one was used as the starting material, accordingly, 1-(2-((3R,5R,8R,9R,10S,13S,14S,15R,17S)-15-ethyl-3-hydroxy-3,13-dimethylhexadecahydro-1H-cyclopenta[a]phenanthren-17-yl)-2-oxoethyl)-1H-pyrazole-4-carbonitrile (24 mg, yield: 38.8%) was obtained.

MS m/z (ESI): 438.2[M+H]$^+$.

$^1$H NMR (400 MHz, $CDCl_3$) δ 7.86 (s, 1H), 7.81 (s, 1H), 5.08-4.78 (m, 2H), 2.58 (t, J=8.0 Hz, 1H), 2.07-1.29 (m, 20H), 1.28 (s, 3H), 1.27-1.06 (m, 4H), 0.85 (t, J=7.3 Hz, 3H), 0.79 (s, 3H).

Example 68

2-(4-Chloro-1H-pyrazol-1-yl)-1-((3R,5R,8R,9R,10S,13S,14S,15R,17S)-3-hydroxy-3,13,15-trimethylhexadecahydro-1H-cyclopenta[a]phenanthren-17-yl)ethan-1-one

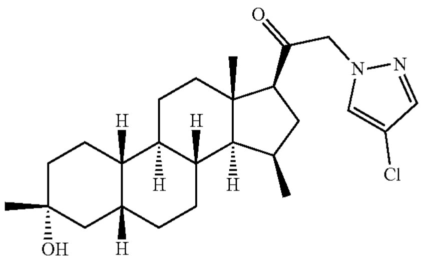

Step 1: Preparation of 2-(4-chloro-1H-pyrazol-1-yl)-1-((3R,5R,8R,9R,10S,13S,14S,15R,17S)-3-hydroxy-3,13,15-trimethylhexadecahydro-1H-cyclopenta[a]phenanthren-17-yl)ethan-1-one

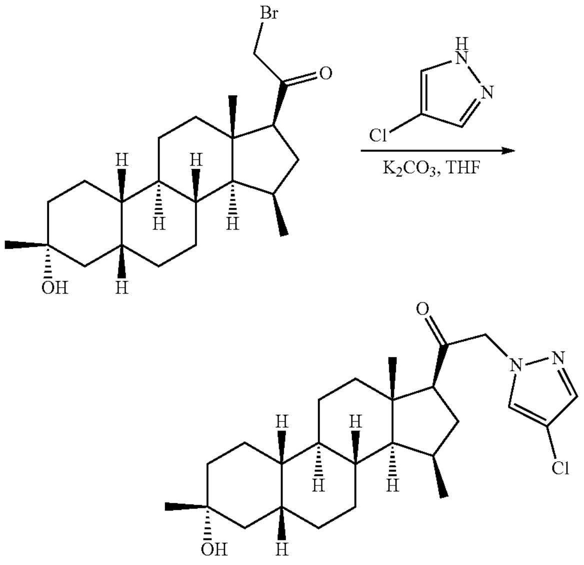

In accordance with Example 5, 2-bromo-1-((3R,5R,8R,9R,10S,13S,14S,15R,17S)-3-hydroxy-3,13,15-trimethylhexadecahydro-1H-cyclopenta[a]phenanthren-17-yl)ethan-1-one was used as the starting material, accordingly, 2-(4-chloro-1H-pyrazol-1-yl)-1-((3R,5R,8R,9R,10S,13S,14S,15R,17S)-3-hydroxy-3,13,15-trimethylhexadecahydro-1H-cyclopenta[a]phenanthren-17-yl)ethan-1-one (10 mg, yield: 14%) was obtained.

MS m/z (ESI): 433.3[M+H]$^+$ $^1$H NMR (400 MHz, $CDCl_3$) δ 7.45 (s, 1H), 7.41 (s, 1H), 4.86 (q, J=17.9 Hz, 2H), 2.61-2.44 (m, 1H), 2.30-2.07 (m, 2H), 2.02-1.91 (m, 1H), 1.86-1.80 (m, 4H), 1.76-1.57 (m, 4H), 1.51-1.38 (m, 6H), 1.37-1.20 (m, 6H), 1.20-1.03 (m, 2H), 0.98 (d, J=7.1 Hz, 3H), 0.83 (s, 3H).

Example 69

1-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-(4-methyl-1H-pyrazol-1-yl)ethan-1-one

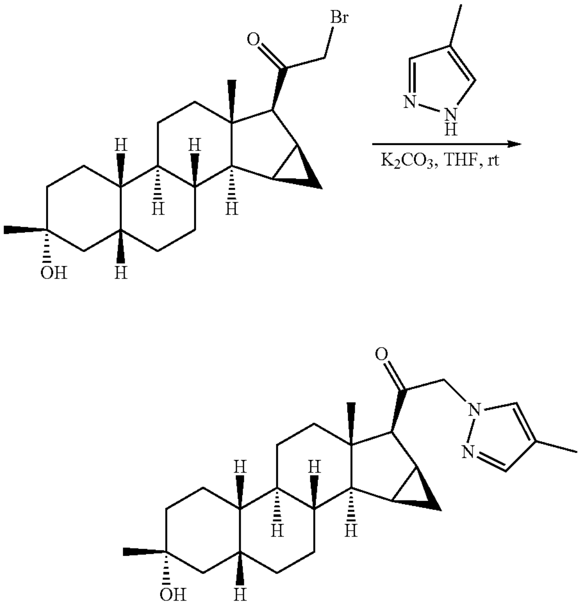

In accordance with Example 5, 2-bromo-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one and 4-methylpyrazole were used as the starting materials, accordingly, 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(4-methyl-1H-pyrazol-1-yl)ethan-1-one (12.6 mg, white solid, yield: 15.7%) was obtained.

MS m/z (ESI): 411.3[M+H]$^+$ $^1$H NMR (400 MHz, $CDCl_3$) δ 7.44 (s, 1H), 7.26 (s, 1H), 5.23 (m, 2H), 2.83 (d, J=4.4 Hz, 1H), 2.13 (s, 3H), 1.98-1.85 (m, 2H), 1.83-1.69 (m, 9H), 1.60-1.56 (m, 1H), 1.40-1.27 (m, 12H), 1.09-1.01 (m, 2H), 0.80 (s, 3H), 0.48-0.45 (m, 1H).

Example 70

1-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-(1H-imidazol-1-yl)ethan-1-one

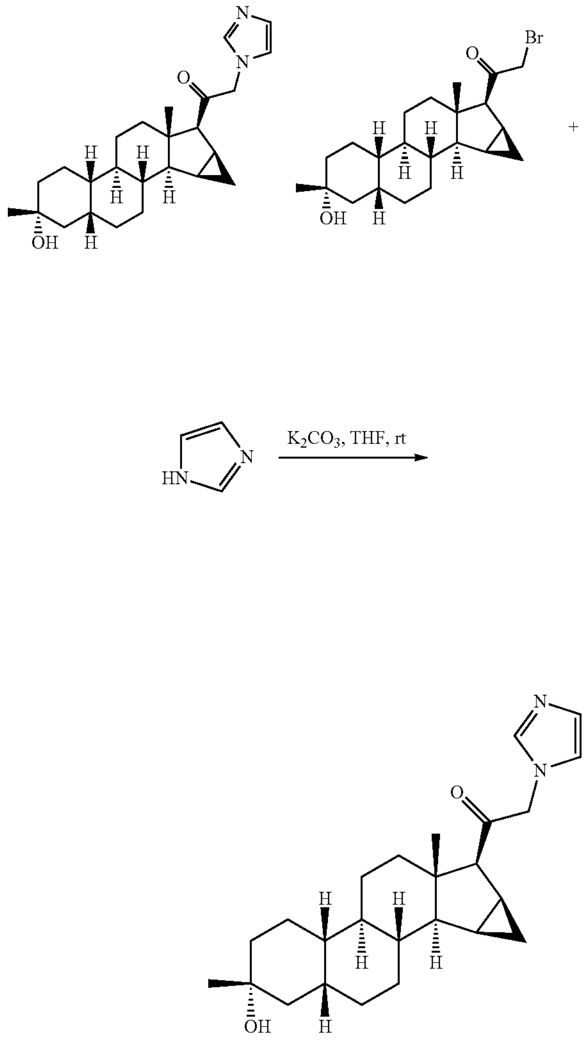

In accordance with Example 63, 2-bromo-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one and imidazole were used as the starting materials, accordingly, 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(1H-imidazol-1-yl)ethan-1-one (23.3 mg, white solid, yield: 34.4%) was obtained.

MS m/z (ESI): 397.2$[M+H]^+$ $^1$H NMR (400 MHz, $CDCl_3$) δ 7.48 (s, 1H), 7.12 (s, 1H), 6.88 (s, 1H), 4.98-4.87 (m, 2H), 2.82 (d, J=2.8 Hz, 1H), 1.94-1.91 (m, 1H), 1.85-1.81 (m, 4H), 1.70-1.53 (m, 10H), 1.41-1.28 (m, 9H), 1.13-0.95 (m, 2H), 0.78 (s, 3H), 0.52-0.46 (m, 1H).

Example 71

1-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-(5-methyl-1H-tetrazol-1-yl)ethan-1-one

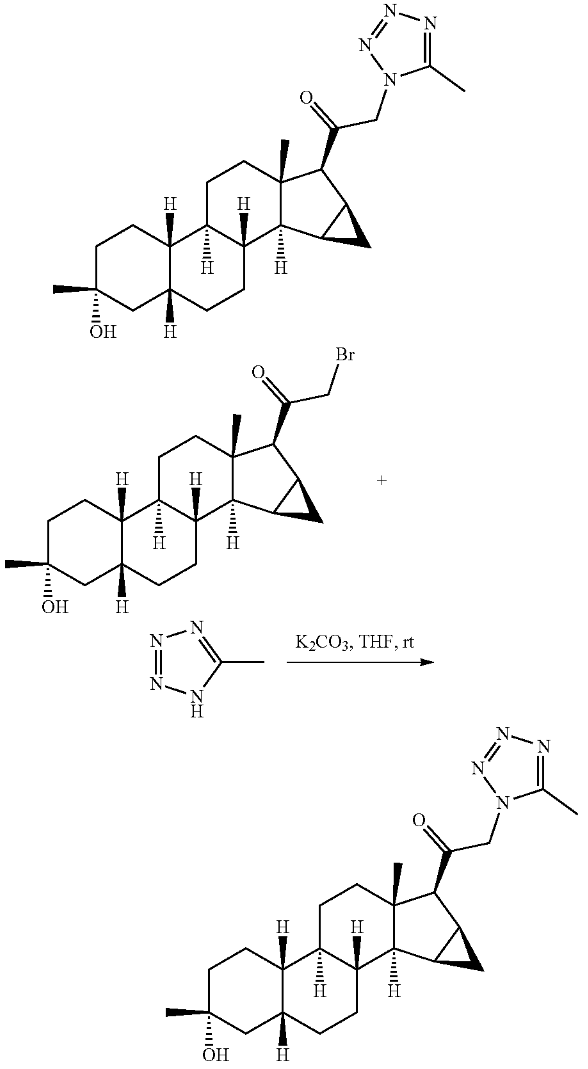

In accordance with Example 5, 2-bromo-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one and 5-methyl-1H-4-tetrazole were used as the starting materials, accordingly, 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(5-methyl-1H-tetrazol-1-yl)ethan-1-one (19 mg, white solid, yield: 23.5%) was obtained.

MS m/z (ESI): 413.2$[M+H]^+$ $^1$H NMR (400 MHz, $CDCl_3$) δ 5.58 (dd, $J_1$=17.6 Hz, $J_2$=7.6 Hz, 2H), 2.86 (d, J=4.0 Hz, 1H), 2.57 (s, 3H), 1.96-1.93 (m, 1H), 1.89-1.61 (m, 8H), 1.55-1.22 (m, 14H), 1.14-0.97 (m, 3H), 0.84 (s, 3H), 0.47-0.53 (m, 1H).

Example 72

2-(4-(Azetidine-1-carbonyl)-1H-pyrazol-1-yl)-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one

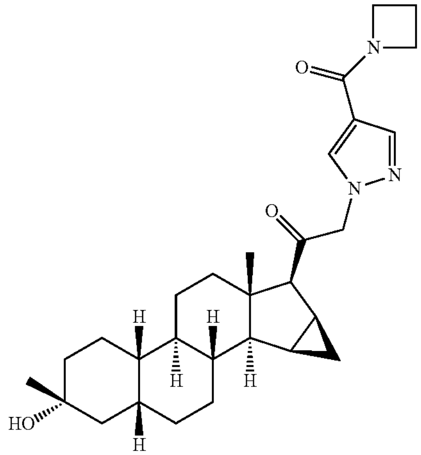

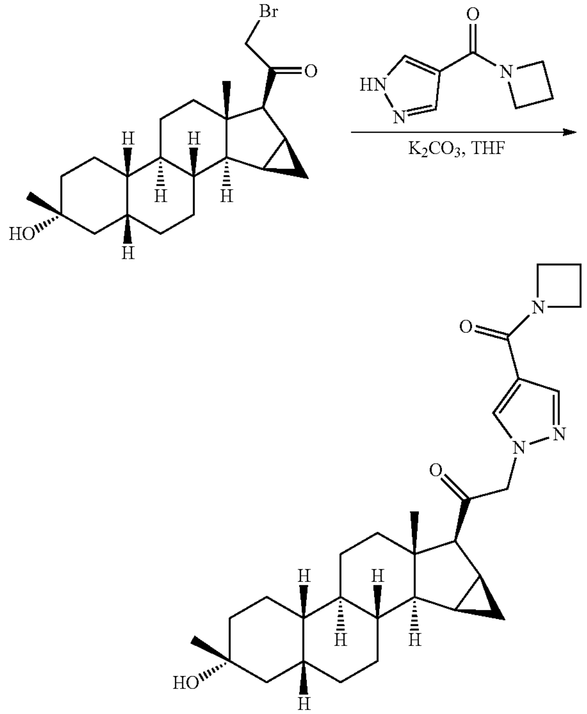

In accordance with Example 5, 2-bromo-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one and azetidin-1-yl(1H-pyrazol-4-yl)methanone were used as the starting materials, accordingly, 2-(4-(azetidine-1-carbonyl)-1H-pyrazol-1-yl)-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one (10.0 mg, yield: 14.3%) was obtained.

MS m/z (ESI): 480.3 $[M+H]^+$ $^1$H NMR (400 MHz, $CDCl_3$) δ 7.85-7.80 (m, 1H), 7.80-7.74 (m, 1H), 5.20-5.05 (m, 2H), 4.53-4.10 (m, 4H), 2.82 (d, J=3.3 Hz, 1H), 2.44-2.31 (m, 2H), 1.98-1.90 (m, 1H), 1.86-1.79 (m, 3H), 1.74-1.64 (m, 3H), 1.57-1.53 (m, 2H), 1.44-1.24 (m, 15H), 1.13-0.97 (m, 2H), 0.79 (s, 3H), 0.51-0.44 (m, 1H).

Example 73

1-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-(4-nitro-1H-pyrazol-1-yl)ethan-1-one

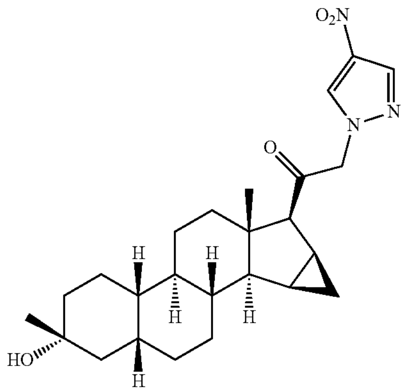

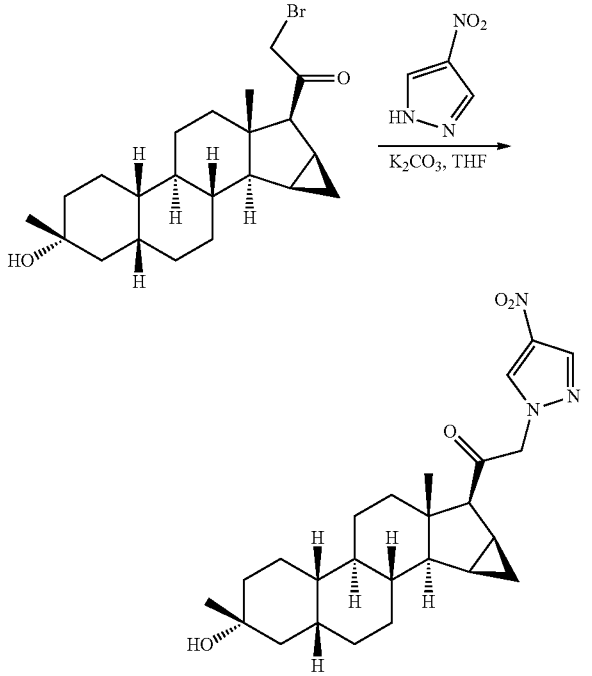

In accordance with Example 5, 2-bromo-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one and 4-nitro-1H-pyrazole were used as the starting materials, accordingly, 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(4-nitro-1H-pyrazol-1-yl)ethan-1-one (32.5 mg, yield: 60%) was obtained.

MS m/z (ESI): 424.2 $[M+H-H_2O]^+$ $^1$H NMR (400 MHz, $CDCl_3$) δ8.20 (s, 1H), 8.09 (s, 1H), 5.26-5.09 (m, 2H), 2.85 (s, 1H), 1.98-1.91 (m, 1H), 1.87-

1.79 (m, 4H), 1.74-1.65 (m, 3H), 1.56-1.52 (m, 2H), 1.47-1.35 (m, 7H), 1.34-1.24 (m, 7H), 1.13-0.97 (m, 2H), 0.79 (s, 3H), 0.55-0.47 (m, 1H).

Example 80

3-Cyclopropyl-1-(2-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-oxoethyl)-1H-pyrazole-4-carbonitrile

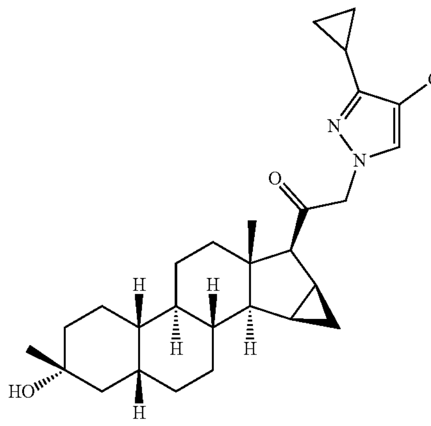

Step 1: Preparation of 3-cyclopropyl-1-(2-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-oxoethyl)-1H-pyrazole-4-carbonitrile

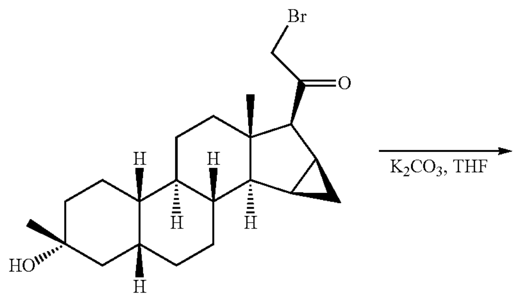

-continued

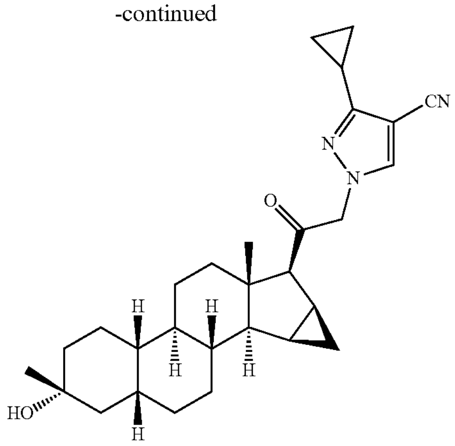

In accordance with Example 5, 2-bromo-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one was used as the starting material, accordingly, 3-cyclopropyl-1-(2-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-oxoethyl)-1H-pyrazole-4-carbonitrile (19.2 mg, yield: 21%) was obtained.

MS m/z (ESI): 462.3 $[M+H]^+$ $^1H$ NMR (400 MHz, $CDCl_3$) δ 7.73 (s, 1H), 5.13-4.95 (m, 2H), 2.80 (d, J=2.2 Hz, 1H), 2.04-1.89 (m, 2H), 1.86-1.79 (m, 3H), 1.76-1.63 (m, 3H), 1.58-1.49 (m, 3H), 1.46-1.21 (m, 14H), 1.12-0.93 (m, 6H), 0.76 (s, 3H), 0.51-0.43 (m, 1H).

Example 81

1-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-(4-(methylthio)-1H-pyrazol-1-yl)ethan-1-one

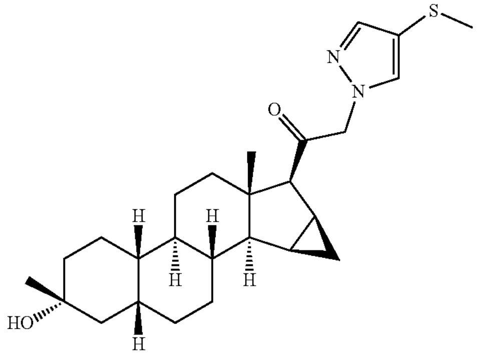

Step 1: Preparation of 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(4-(methylthio)-1H-pyrazol-1-yl)ethan-1-one

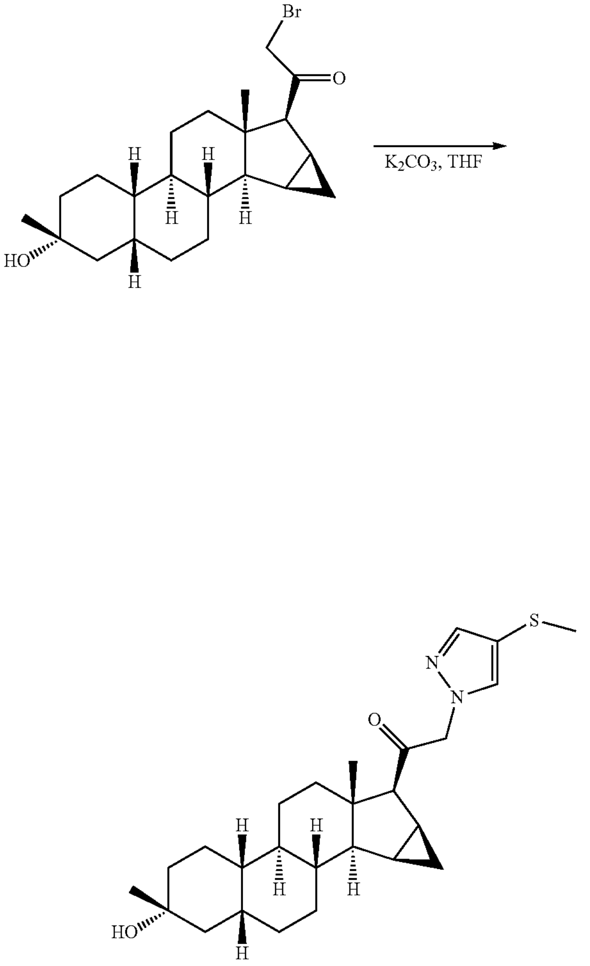

In accordance with Example 5, 2-bromo-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one was used as the starting material, accordingly, 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(4-(methylthio)-1H-pyrazol-1-yl)ethan-1-one (8.7 mg, yield: 16%) was obtained.

MS m/z (ESI): 443.2 $[M+H]^+$ $^1$H NMR (400 MHz, $CDCL_3$) δ 7.54 (s, 1H), 7.45 (s, 1H), 5.17-5.00 (m, 2H), 2.81 (d, J=3.8 Hz, 1H), 2.35 (s, 3H), 1.99-1.91 (m, 1H), 1.88-1.76 (m, 4H), 1.73-1.63 (m, 3H), 1.55-1.50 (m, 1H), 1.43-1.18 (m, 15H), 1.12-0.97 (m, 2H), 0.79 (s, 3H), 0.50-0.41 (m, 1H).

Example 82 and Example 83

1-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-(4-(methylsulfinyl)-1H-pyrazol-1-yl)ethan-1-one (82)

1-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-(4-(methylsulfonyl)-1H-pyrazol-1-yl)ethan-1-one (83)

82

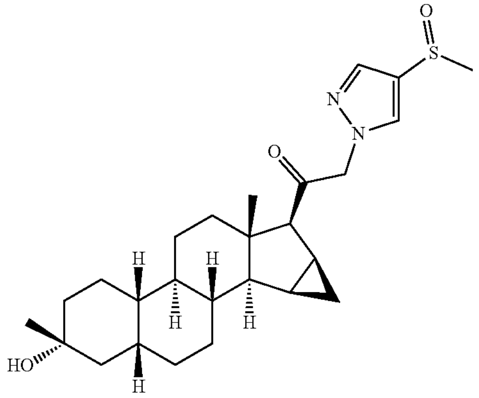

83

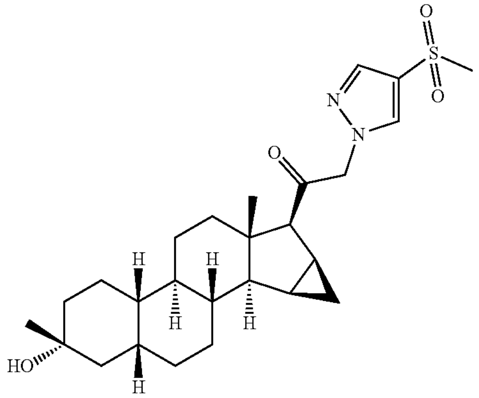

Step 1: Preparation of 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(4-(methylsulfinyl)-1H-pyrazol-1-yl)ethan-1-one and 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(4-(methylsulfonyl)-1H-pyrazol-1-yl)ethan-1-one

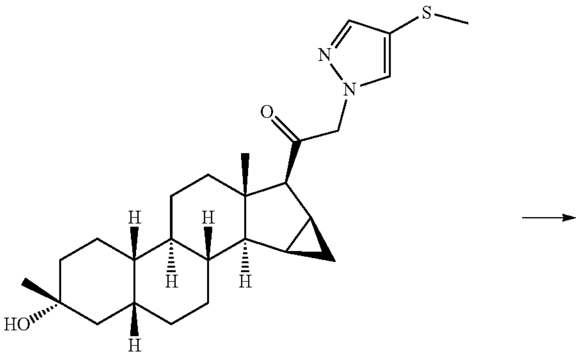

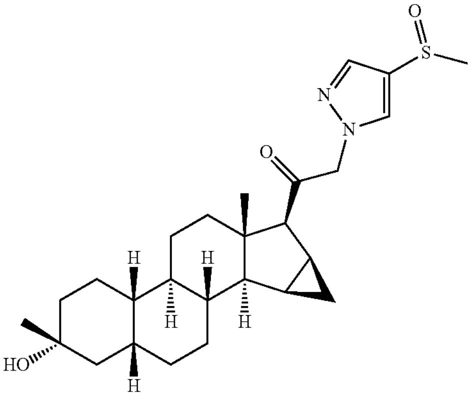

82

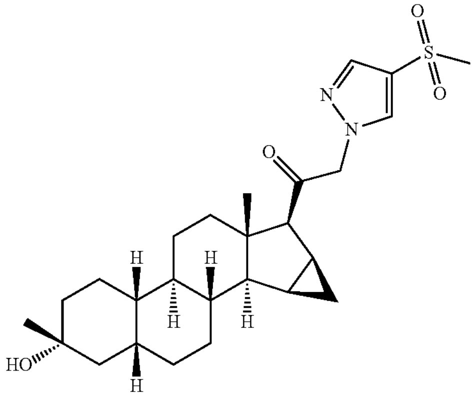

83

1-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-(4-(methylthio)-1H-pyrazol-1-yl)ethan-1-one (80 mg, 0.18 mmol) was dissolved in dichloromethane (10 mL), and the solution was cooled to −78° C. m-Chloroperoxybenzoic acid (55 mg, 0.27 mmol) was added, and the reaction solution was stirred for 1 hour. Water (10 mL) was added, and then the reaction solution was washed with saturated aqueous sodium bicarbonate solution (10 mL). The organic phase was separated, dried over anhydrous sodium sulfate, filtrated and concentrated by rotary evaporation to dryness. The resulting crude product was purified by high performance liquid chromatography to obtain 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(4-(methylsulfinyl)-1H-pyrazol-1-yl)ethan-1-one (17.2 mg, yield: 20%) and 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(4-(methylsulfonyl)-1H-pyrazol-1-yl)ethan-1-one (20.4 mg, yield: 25%).

Example 82

MS m/z (ESI): 441.3 $[M-H_2O+H]^+$ $^1H$ NMR (400 MHz, $CDCl_3$) δ 7.85 (s, 1H), 7.83 (s, 1H), 5.30-5.09 (m, 2H), 2.91 (s, 3H), 2.85-2.82 (m, 1H), 1.98-1.90 (m, 1H), 1.87-1.78 (m, 3H), 1.75-1.50 (m, 8H), 1.47-1.21 (m, 12H), 1.13-0.96 (m, 2H), 0.79 (s, 3H), 0.54-0.45 (m, 1H).

Example 83

MS m/z (ESI): 457.2 $[M-H_2O+H]^+$ $^1H$ NMR (400 MHz, $CDCl_3$) δ 7.94 (s, 1H), 7.87 (s, 1H), 5.26-5.10 (m, 2H), 3.14 (s, 3H), 2.85 (d, J=2.7 Hz, 1H), 1.98-1.91 (m, 1H), 1.87-1.79 (m, 3H), 1.76-1.64 (m, 3H), 1.59-1.52 (m, 1H), 1.50-1.18 (m, 16H), 1.15-0.96 (m, 2H), 0.79 (s, 3H), 0.55-0.46 (m, 1H).

Example 84

1-(2-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-oxo-ethyl)-1H-pyrazole-3,5-dicarbonitrile

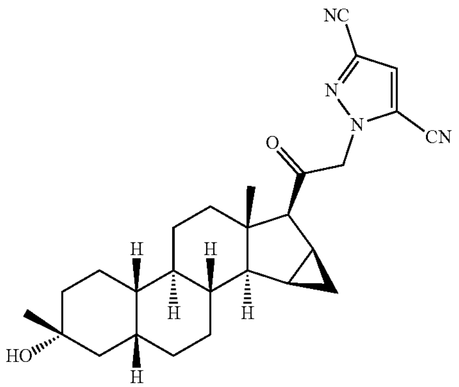

Step 1: Preparation of 1-(2-((2R,4aS,4bR,6aS,7S,7aS,8aR,8bR,8cR,10aR)-2-hydroxy-2,6a-dimethyl-octadecahydrocyclopropa[4,5]cyclopenta[1,2-a]phenanthren-7-yl)-2-oxoethyl)-1H-pyrazole-3,5-dicarbonitrile

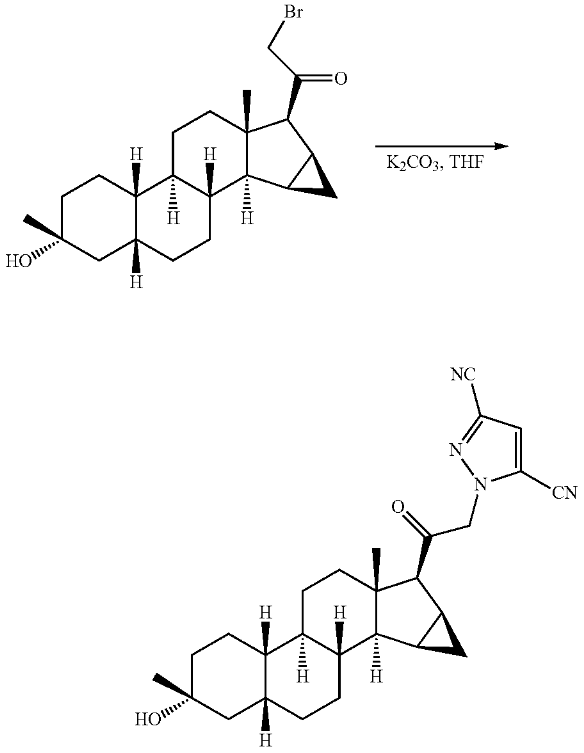

In accordance with Example 5, 2-bromo-1-((2R,4aS,4bR,6aS,7S,7aS,8aR,8bR,8cR,10aR)-2-hydroxy-2,6a-dimethyl-octadecahydrocyclopropa[4,5]cyclopenta[1,2-a]phenanthren-7-yl)ethan-1-one was used as the starting material, accordingly, 1-(2-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-oxo-ethyl)-1H-pyrazole-3,5-dicarbonitrile (18.0 mg, yield: 31.8%) was obtained.

MS m/z (ESI): 429.2 $[M-H_2O+H]^+$ $^1$H NMR (400 MHz, $CDCl_3$) δ 7.21 (s, 1H), 5.38 (q, J=18.0 Hz, 2H), 2.87 (d, J=3.0 Hz, 1H), 1.97-1.91 (m, 1H), 1.88-1.75 (m, 4H), 1.76-1.64 (m, 3H), 1.58-1.51 (m, 1H), 1.48-1.26 (m, 15H), 1.15-0.99 (m, 2H), 0.83 (s, 3H), 0.58-0.48 (m, 1H).

Example 85

1-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-(4-(oxazol-2-yl)-1H-pyrazol-1-yl)ethan-1-one

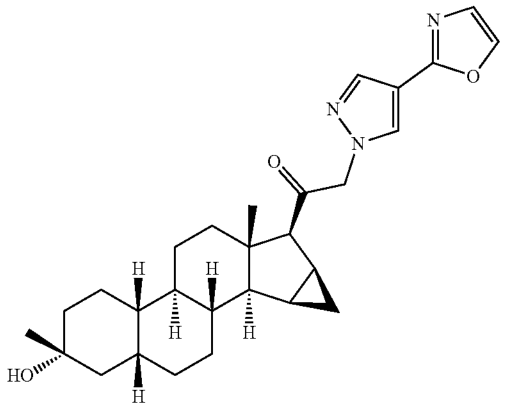

Step 1: Preparation of 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(4-(oxazol-2-yl)-1H-pyrazol-1-yl)ethan-1-one

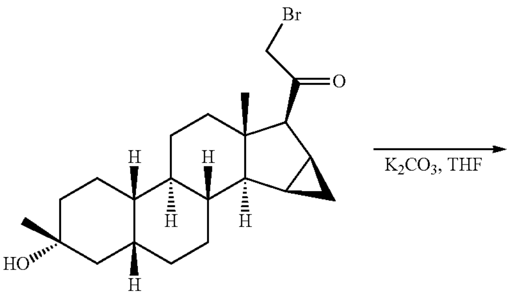

-continued

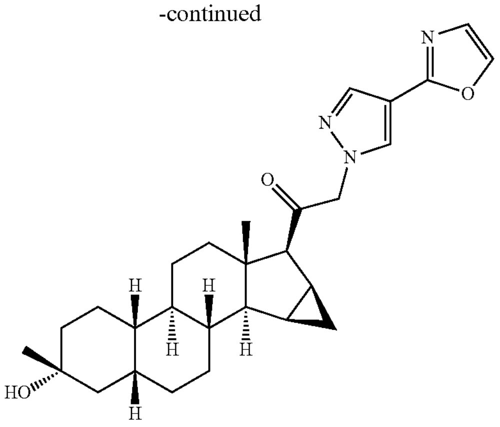

In accordance with Example 5, 2-bromo-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one was used as the starting material, accordingly, 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(4-(oxazol-2-yl)-1H-pyrazol-1-yl)ethan-1-one (16.0 mg, yield: 14%) was obtained.

MS m/z (ESI): 464.3 $[M+H]^+$ $^1$H NMR (400 MHz, $CDCl_3$) δ 7.89 (s, 1H), 7.79 (s, 1H), 7.73 (s, 1H), 7.13 (s, 1H), 5.27-5.13 (m, 2H), 2.85 (d, J=4.0 Hz, 1H), 2.01-1.93 (m, 1H), 1.87-1.65 (m, 11H), 1.58-1.50 (m, 1H), 1.44-1.22 (m, 11H), 1.14-0.98 (m, 2H), 0.81 (s, 3H), 0.53-0.44 (m, 1H).

Example 86

1-((3R,5R,8R,9R,10S,13S,14S,15R,17S)-3-Hydroxy-3,13,15-trimethylhexadecahydro-1H-cyclopenta[a]phenanthren-17-yl)-2-(3-(trifluoromethyl)-1H-pyrazol-1-yl)ethan-1-one

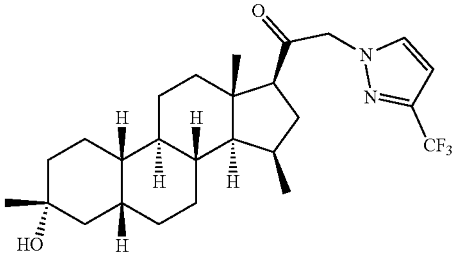

Step 1: 1-((3R,5R,8R,9R,10S,13S,14S,15R,17S)-3-hydroxy-3,13,15-trimethylhexadecahydro-1H-cyclopenta[a]phenanthren-17-yl)-2-(3-(trifluoromethyl)-1H-pyrazol-1-yl)ethan-1-one

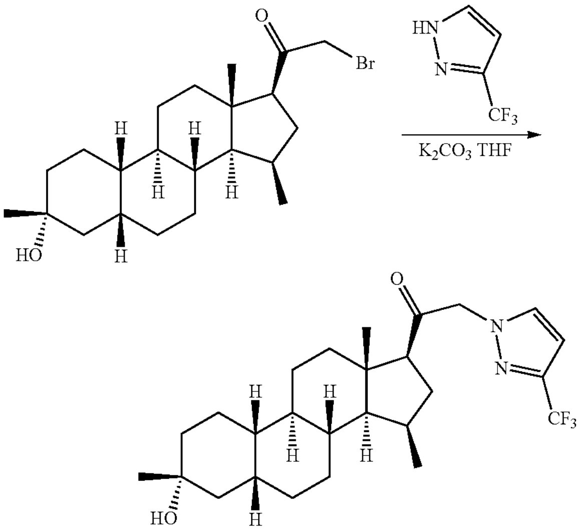

In accordance with Example 5, 2-bromo-1-((3R,5R,8R,9R,10S,13S,14S,15R,17S)-3-hydroxy-3,13,15-trimethylhexadecahydro-1H-cyclopenta[a]phenanthren-17-yl)ethan-1-one was used as the starting material, accordingly, 1-((3R,5R,8R,9R,10S,13S,14S,15R,17S)-3-hydroxy-3,13,15-trimethylhexadecahydro-1H-cyclopenta[a]phenanthren-17-yl)-2-(3-(trifluoromethyl)-1H-pyrazol-1-yl)ethan-1-one (20.5 mg, yield: 30.1%) was obtained.

MS m/z (ESI): 467.2$[M+H]^+$.

$^1$H NMR (400 MHz, $CDCl_3$) δ 7.49-7.43 (m, 1H), 6.59 (d, J=2.4 Hz, 1H), 5.14-4.85 (m, 2H), 2.54 (t, J=8.1 Hz, 1H), 2.26-2.08 (m, 2H), 2.02-1.93 (m, 1H), 1.90-1.79 (m, 4H), 1.74-1.59 (m, 3H), 1.57-1.19 (m, 14H), 1.21-1.04 (m, 1H), 0.98 (d, J=7.0 Hz, 3H), 0.84 (s, 3H).

Example 87

2-(4-(Azetidine-1-carbonyl)-1H-pyrazol-1-yl)-1-((3R,5R,8R,9R,10S,13S,14S,15R,17S)-3-hydroxy-3,13,15-trimethylhexadecahydro-1H-cyclopenta[a]phenanthren-17-yl)ethan-1-one

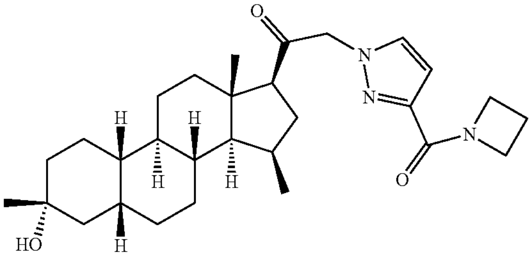

Step 1: Preparation of 2-(4-(azetidine-1-carbonyl)-1H-pyrazol-1-yl)-1-((3R,5R,8R,9R,10S,13S,14S,15R,17S)-3-hydroxy-3,13,15-trimethylhexadecahydro-1H-cyclopenta[a]phenanthren-17-yl)ethan-1-one

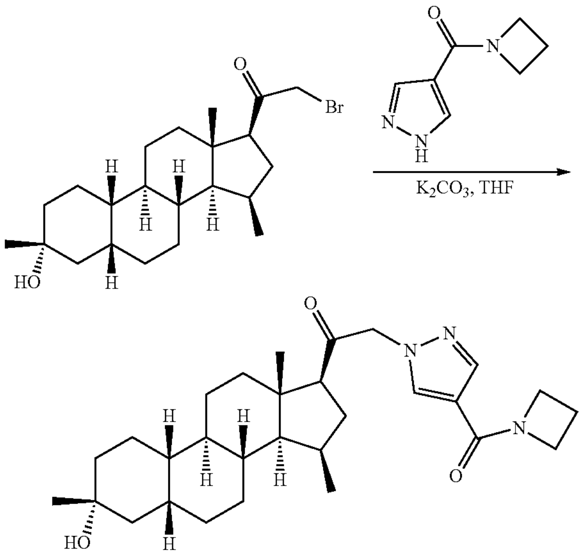

In accordance with Example 5, 2-bromo-1-((3R,5R,8R,9R,10S,13S,14S,15R,17S)-3-hydroxy-3,13,15-trimethylhexadecahydro-1H-cyclopenta[a]phenanthren-17-yl)ethan-1-one was used as the starting material, accordingly, 2-(4-(azetidine-1-carbonyl)-1H-pyrazol-1-yl)-1-((3R,5R,8R,9R,10S,13S,14S,15R,17S)-3-hydroxy-3,13,15-trimethylhexadecahydro-1H-cyclopenta[a]phenanthren-17-yl)ethan-1-one (12.0 mg, yield: 21%) was obtained.

MS m/z (ESI): 482.3[M+H]$^+$.

$^1$H NMR (400 MHz, $CDCl_3$) δ 7.78 (s, 2H), 5.00-4.77 (m, 2H), 4.38-4.25 (m, 4H), 2.54 (t, J=7.6 Hz, 1H), 2.43-2.32 (m, 2H), 2.26-2.08 (m, 2H), 1.98-1.96 (m, 1H), 1.88-1.83 (m, 3H), 1.69-1.62 (m, 5H), 1.48-1.42 (m, 4H), 1.38-1.26 (m, 9H), 1.16-1.07 (m, 2H), 0.98 (d, J=7.0 Hz, 3H), 0.84 (s, 3H).

Example 88

3-Chloro-1-(2-((3R,5R,8R,9R,10S,13S,14S,15R,17S)-3-hydroxy-3,13,15-trimethylhexadecahydro-1H-cyclopenta[a]phenanthren-17-yl)-2-oxoethyl)-1H-pyrazole-4-carbonitrile

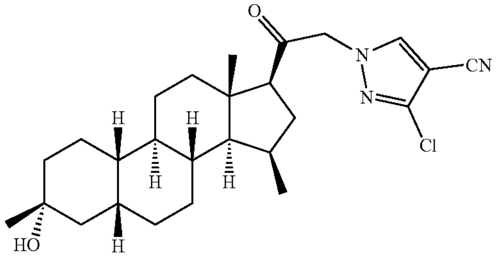

Step 1: Preparation of 3-chloro-1-(2-((3R,5R,8R,9R,10S,13S,14S,15R,17S)-3-hydroxy-3,13,15-trimethylhexadecahydro-1H-cyclopenta[a]phenanthren-17-yl)-2-oxoethyl)-1H-pyrazole-4-carbonitrile

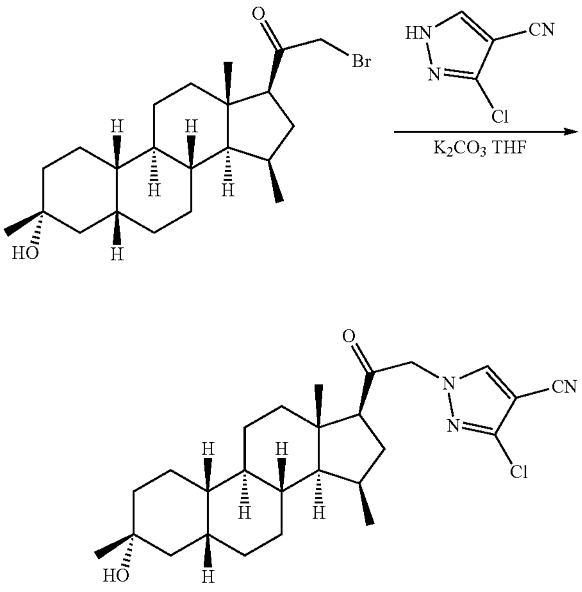

In accordance with Example 5, 2-bromo-1-((3R,5R,8R,9R,10S,13S,14S,15R,17S)-3-hydroxy-3,13,15-trimethylhexadecahydro-1H-cyclopenta[a]phenanthren-17-yl)ethan-1-one was used as the starting material, accordingly, the product 3-chloro-1-(2-((3R,5R,8R,9R,10S,13S,14S,15R,17S)-3-hydroxy-3,13,15-trimethylhexadecahydro-1H-cyclopenta[a]phenanthren-17-yl)-2-oxoethyl)-1H-pyrazole-4-carbonitrile (37 mg, yield: 55.3%) was obtained.

MS m/z (ESI): 456.2[M−H]−.

$^1$H NMR (400 MHz, $CDCl_3$) δ 7.81 (s, 1H), 5.03-4.75 (m, 2H), 2.54 (t, J=8.0 Hz, 1H), 2.31-2.13 (m, 2H), 1.93-1.06 (m, 23H), 0.99 (d, J=7.1 Hz, 3H), 0.83 (s, 3H).

Example 89

1-(2-((3R,5R,8R,9R,10S,13S,14S,15R,17S)-3-Hydroxy-3,13,15-trimethylhexadecahydro-1H-cyclopenta[a]phenanthren-17-yl)-2-oxoethyl)-1H-pyrazole-3,5-dicarbonitrile

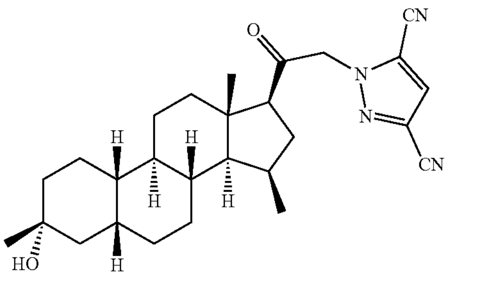

Step 1: Preparation of 1-(2-((3R,5R,8R,9R,10S,13S,14S,15R,17S)-3-hydroxy-3,13,15-trimethylhexadecahydro-1H-cyclopenta[a]phenanthren-17-yl)-2-oxoethyl)-1H-pyrazole-3,5-dicarbonitrile

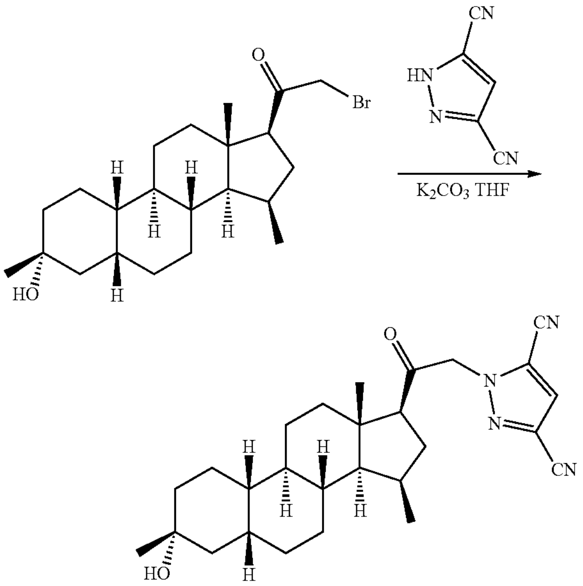

In accordance with Example 5, 2-bromo-1-((3R,5R,8R,9R,10S,13S,14S,15R,17S)-3-hydroxy-3,13,15-trimethylhexadecahydro-1H-cyclopenta[a]phenanthren-17-yl)ethan-1-one was used as the starting material, accordingly, the product 1-(2-((3R,5R,8R,9R,10S,13S,14S,15R,17S)-3-hydroxy-3,13,15-trimethylhexadecahydro-1H-cyclopenta[a]phenanthren-17-yl)-2-oxoethyl)-1H-pyrazole-3,5-dicarbonitrile (18 mg, yield 27.5%) was obtained.

MS m/z (ESI): 447.2[M−H]$^-$.

$^1$H NMR (400 MHz, $CDCl_3$) δ7.20 (s, 1H), 5.23-5.07 (m, 2H), 2.68-2.52 (m, 1H), 2.28-1.36 (m, 21H), 1.28 (s, 3H), 1.18-1.08 (m, 1H), 1.00 (d, J=6.9 Hz, 3H), 0.88 (s, 3H).

Example 90

1-(2-((3R,5R,8R,9R,10S,13S,14S,15R,17S)-15-Ethyl-3-hydroxy-3,13-dimethylhexadecahydro-1H-cyclopenta[a]phenanthren-17-yl)-2-oxoethyl)-1H-pyrazole-3-carbonitrile

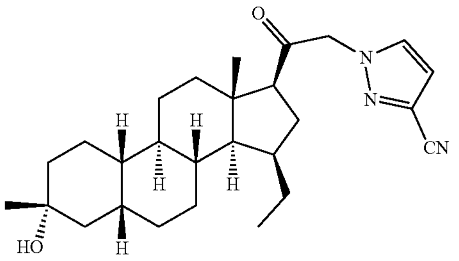

Step 1: Preparation of 1-(2-((3R,5R,8R,9R,10S,13S,14S,15R,17S)-15-ethyl-3-hydroxy-3,13-dimethylhexadecahydro-1H-cyclopenta[a]phenanthren-17-yl)-2-oxoethyl)-1H-pyrazole-3-carbonitrile

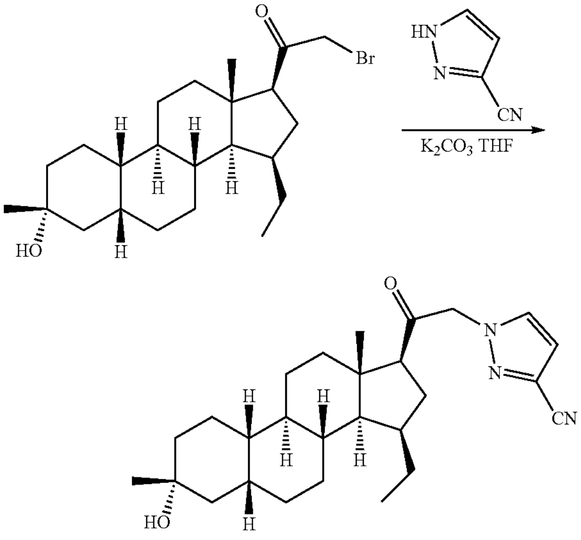

In accordance with Example 5, 2-bromo-1-((3R,5R,8R,9R,10S,13S,14S,15R,17S)-15-ethyl-3-hydroxy-3,13-dimethylhexadecahydro-1H-cyclopenta[a]phenanthren-17-yl)ethan-1-one was used as the starting material, accordingly, the product 1-(2-((3R,5R,8R,9R,10S,13S,14S,15R,17S)-15-ethyl-3-hydroxy-3,13-dimethylhexadecahydro-1H-cyclopenta[a]phenanthren-17-yl)-2-oxoethyl)-1H-pyrazole-3-carbonitrile (16 mg, yield: 25.9%) was obtained.

MS m/z (ESI): 438.2[M+H]$^+$.

$^1$H NMR (400 MHz, $CDCl_3$) δ 7.49 (d, J=2.5 Hz, 1H), 6.73 (d, J=2.4 Hz, 1H), 5.22-4.78 (m, 2H), 2.57 (t, J=8.0 Hz, 1H), 2.15-1.30 (m, 20H), 1.28 (s, 3H), 1.16-1.03 (m, 4H), 0.84 (t, J=7.3 Hz, 3H), 0.79 (s, 3H).

Example 91

1-((3R,5R,8R,9R,10S,13S,14S,15R,17S)-15-Ethyl-3-hydroxy-3,13-dimethylhexadecahydro-1H-cyclopenta[a]phenanthren-17-yl)-2-(3-(trifluoromethyl)-1H-pyrazol-1-yl)ethan-1-one

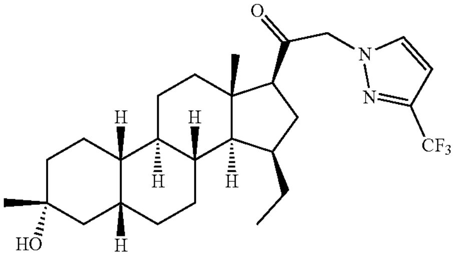

Step 1: Preparation of 1-((3R,5R,8R,9R,10S,13S,14S,15R,17S)-15-Ethyl-3-hydroxy-3,13-dimethylhexadecahydro-1H-cyclopenta[a]phenanthren-17-yl)-2-(3-(trifluoromethyl)-1H-pyrazol-1-yl)ethan-1-one

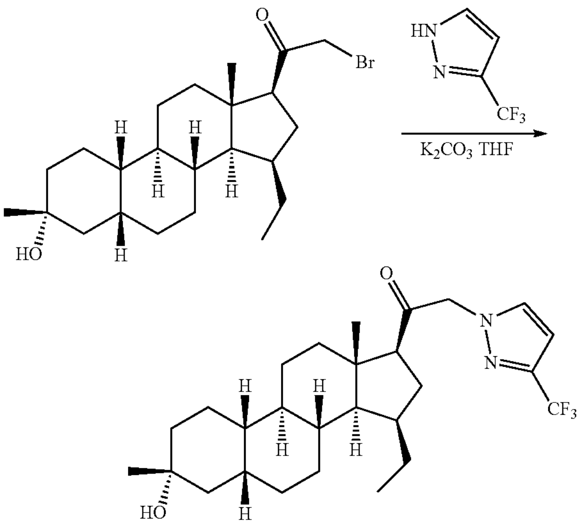

In accordance with Example 5, 2-bromo-1-((3R,5R,8R,9R,10S,13S,14S,15R,17S)-15-ethyl-3-hydroxy-3,13-dimethylhexadecahydro-1H-cyclopenta[a]phenanthren-17-yl)ethan-1-one was used as the starting material, accordingly, the product 1-((3R,5R,8R,9R,10S,13S,14S,15R,17S)-15-ethyl-3-hydroxy-3,13-dimethylhexadecahydro-1H-cyclopenta[a]phenanthren-17-yl)-2-(3-(trifluoromethyl)-1H-pyrazol-1-yl)ethan-1-one (23 mg, yield: 33.9%) was obtained.

MS m/z (ESI): 481.3[M+H]$^+$.

$^1$H NMR (400 MHz, $CDCl_3$) δ 7.47 (d, J=4.0 Hz, 1H), 6.59 (d, J=4.0 Hz 1H), 5.07-4.89 (m, 2H), 2.56 (t, J=9.3 Hz, 1H), 2.20-1.29 (m, 20H), 1.28 (s, 3H), 1.27-1.03 (m, 4H), 0.84 (t, J=7.3 Hz, 3H), 0.80 (s, 3H).

Example 92

1-((3R,5R,8R,9R,10S,13S,14S,15R,17S)-15-Ethyl-3-hydroxy-3,13-dimethylhexadecahydro-1H-cyclopenta[a]phenanthren-17-yl)-2-(5-methyl-2H-tetrazol-2-yl)ethan-1-one

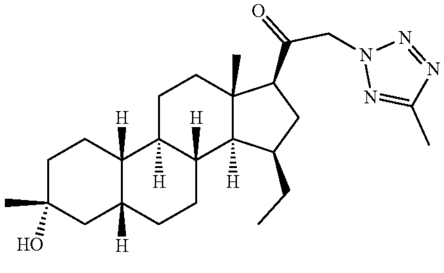

Step 1: Preparation of 1-((3R,5R,8R,9R,10S,13S,14S,15R,17S)-15-ethyl-3-hydroxy-3,13-dimethylhexadecahydro-1H-cyclopenta[a]phenanthren-17-yl)-2-(5-methyl-2H-tetrazol-2-yl)ethan-1-one

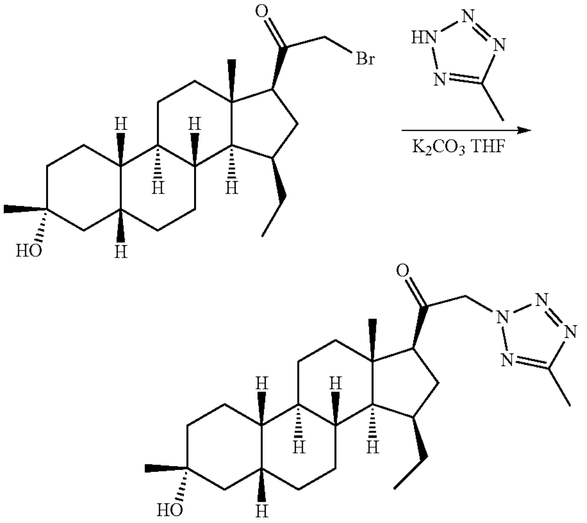

In accordance with Example 5, 2-bromo-1-((3R,5R,8R,9R,10S,13S,14S,15R,17S)-15-ethyl-3-hydroxy-3,13-dimethylhexadecahydro-1H-cyclopenta[a]phenanthren-17-yl)ethan-1-one was used as the starting material, accordingly, the product 1-((3R,5R,8R,9R,10S,13S,14S,15R,17S)-15-ethyl-3-hydroxy-3,13-dimethylhexadecahydro-1H-cyclopenta[a]phenanthren-17-yl)-2-(5-methyl-2H-tetrazol-2-yl)ethan-1-one (13.5 mg, yield: 22.3%) was obtained.

MS m/z (ESI): 429.3[M+H]$^+$.

$^1$H NMR (400 MHz, $CDCl_3$) δ 5.39-5.29 (m, 2H), 2.63-2.57 (m, 1H), 2.56 (s, 3H), 2.10-1.30 (m, 20H), 1.28 (s, 3H), 1.27-1.05 (m, 4H), 0.87-0.81 (m, 6H).

Example 93 and Example 94

1-((3R,5R,8R,9R,10S,13S,14S,15R,17S)-15-Ethyl-3-hydroxy-3,13-dimethylhexadecahydro-1H-cyclopenta[a]phenanthren-17-yl)-2-(1H-1,2,3-triazol-1-yl)ethan-1-one (93)

1-((3R,5R,8R,9R,10S,13S,14S,15R,17S)-15-Ethyl-3-hydroxy-3,13-dimethylhexadecahydro-1H-cyclopenta[a]phenanthren-17-yl)-2-(2H-1,2,3-triazol-2-yl)ethan-1-one (94)

93

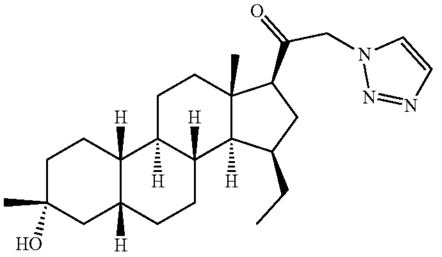

-continued

94

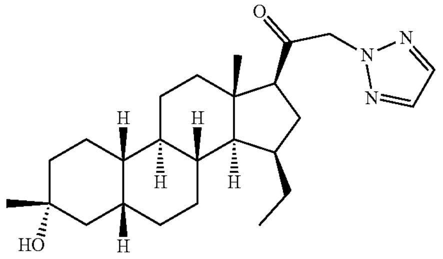

Step 1: Preparation of 1-((3R,5R,8R,9R,10S,13S,14S,15R,17S)-15-ethyl-3-hydroxy-3,13-dimethylhexadecahydro-1H-cyclopenta[a]phenanthren-17-yl)-2-(1H-1,2,3-triazol-1-yl)ethan-1-one and 1-((3R,5R,8R,9R,10S,13S,14S,15R,17S)-15-ethyl-3-hydroxy-3,13-dimethylhexadecahydro-1H-cyclopenta[a]phenanthren-17-yl)-2-(2H-1,2,3-triazol-2-yl)ethan-1-one

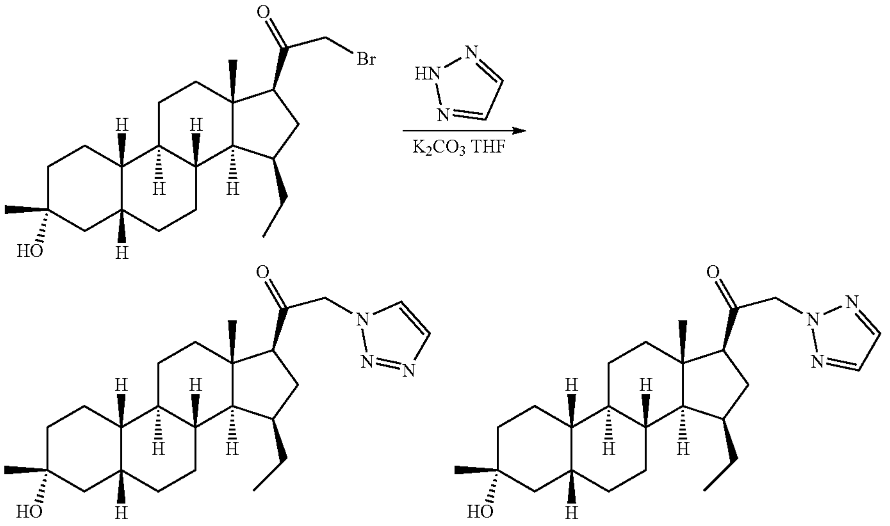

In accordance with Example 5, 2-bromo-1-((3R,5R,8R,9R,10S,13S,14S,15R,17S)-15-ethyl-3-hydroxy-3,13-dimethylhexadecahydro-1H-cyclopenta[a]phenanthren-17-yl)ethan-1-one was used as the starting material, accordingly, the products 1-((3R,5R,8R,9R,10S,13S,14S,15R,17S)-15-ethyl-3-hydroxy-3,13-dimethylhexadecahydro-1H-cyclopenta[a]phenanthren-17-yl)-2-(1H-1,2,3-triazol-1-yl)ethan-1-one (17 mg, yield: 29.1%) and 1-((3R,5R,8R,9R,10S,13S,14S,15R,17S)-15-ethyl-3-hydroxy-3,13-dimethylhexadecahydro-1H-cyclopenta[a]phenanthren-17-yl)-2-(2H-1,2,3-triazol-2-yl)ethan-1-one (9.2 mg, yield: 15.7%) were obtained.

Example 93

MS m/z (ESI): 414.3[M+H]$^+$.

$^1$H NMR (400 MHz, $CDCl_3$) δ 7.77 (s, 1H), 7.67 (s, 1H), 5.37-5.09 (m, 2H), 2.62 (t, J=9.2 Hz, 1H), 2.28-1.20 (m, 25H), 1.16-1.05 (m, 2H), 0.85 (t, J=7.3 Hz, 3H), 0.80 (s, 3H).

Example 94

MS m/z (ESI): 414.3[M+H]$^+$.

$^1$H NMR (400 MHz, $CDCl_3$) δ 7.68 (s, 2H), 5.28-5.20 (m, 2H), 2.54 (t, J=8.0 Hz, 1H), 1.99-1.23 (m, 25H), 1.13-1.06 (m, 2H), 0.88-0.78 (m, 6H).

Example 95

1-(2-((3R,5R,8R,9R,10S,13S,14S,15R,17S)-15-Ethyl-3-hydroxy-3,13-dimethylhexadecahydro-1H-cyclopenta[a]phenanthren-17-yl)-2-oxoethyl)-1H-pyrazole-3,5-dicarbonitrile

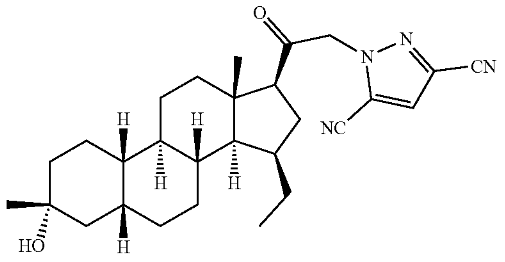

Step 1: Preparation of 1-(2-((3R,5R,8R,9R,10S,13S,14S,15R,17S)-15-ethyl-3-hydroxy-3,13-dimethylhexadecahydro-1H-cyclopenta[a]phenanthren-17-yl)-2-oxoethyl)-1H-pyrazole-3,5-dicarbonitrile

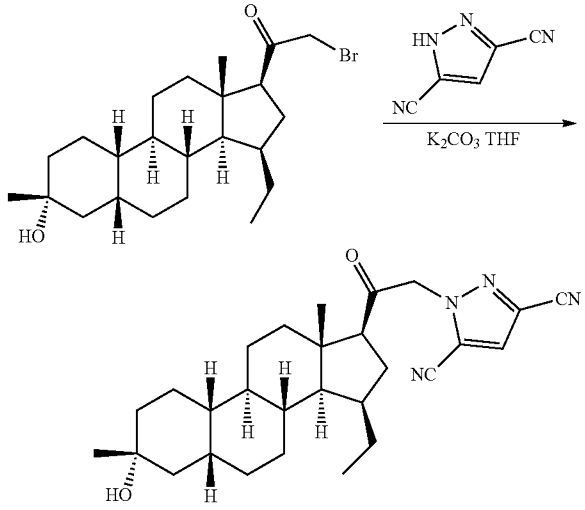

In accordance with Example 5, 2-bromo-1-((3R,5R,8R,9R,10S,13S,14S,15R,17S)-15-ethyl-3-hydroxy-3,13-dimethylhexadecahydro-1H-cyclopenta[a]phenanthren-17-yl)ethan-1-one was used as the starting material, accordingly, the product 1-(2-((3R,5R,8R,9R,10S,13S,14S,15R,17S)-15-ethyl-3-hydroxy-3,13-dimethylhexadecahydro-1H-cyclopenta[a]phenanthren-17-yl)-2-oxoethyl)-1H-pyrazole-3,5-dicarbonitrile (5 mg, yield: 9.2%) was obtained.

MS m/z (ESI): 463.2[M+H]$^+$.

$^1$H NMR (400 MHz, $CDCl_3$) δ 7.21 (s, 1H), 5.29-5.02 (m, 2H), 2.61 (t, J=9.3 Hz, 1H), 2.24-1.34 (m, 19H), 1.28 (s, 3H), 1.26-1.02 (m, 5H), 0.92-0.76 (m, 6H).

Example 96

1-(2-((3R,5R,8R,9R,10S,13S,14S,15S,17S)-15-Cyclopropyl-3-hydroxy-3,13-dimethylhexadecahydro-1H-cyclopenta[a]phenanthren-17-yl)-2-oxoethyl)-1H-pyrazole-3,5-dicarbonitrile

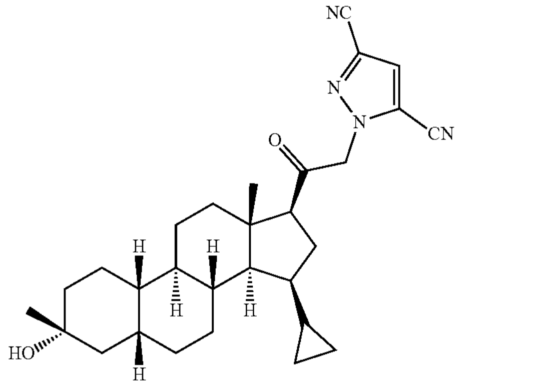

Step 1: Preparation of 1-(2-((3R,5R,8R,9R,10S,13S,14S,15S,17S)-15-cyclopropyl-3-hydroxy-3,13-dimethylhexadecahydro-1H-cyclopenta[a]phenanthren-17-yl)-2-oxoethyl)-1H-pyrazole-3,5-dicarbonitrile

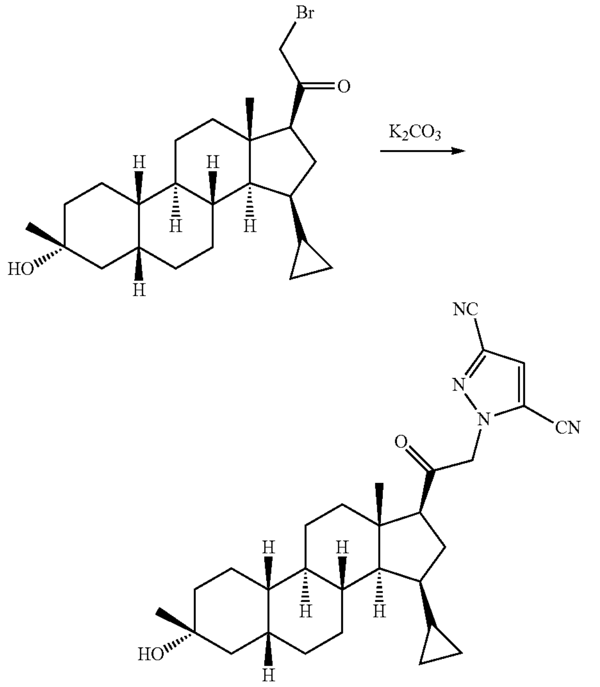

In accordance with Example 3, 1-((3R,5R,8R,9R,10S,13S,14S,15S,17S)-15-cyclopropyl-3-hydroxy-3,13-dimethylhexadecahydro-1H-cyclopenta[a]phenanthren-17-yl)ethan-1-one was used as the starting material, accordingly, 1-(2-((3R,5R,8R,9R,10S,13S,14S,15S,17S)-15-cyclopropyl-3-hydroxy-3,13-dimethylhexadecahydro-1H-cyclopenta[a]phenanthren-17-yl)-2-oxoethyl)-1H-pyrazole-3,5-dicarbonitrile (19.6 mg, yield: 18%) was obtained.

MS m/z (ESI): 473.2[M−H]$^-$ $^1$H NMR (400 MHz, $CDCl_3$) δ 7.20 (s, 1H), 5.24-5.09 (m, 2H), 2.58-2.50 (m, 1H), 2.26-2.07 (m, 2H), 2.06-1.95 (m, 2H), 1.90-1.80 (m, 2H), 1.78-1.66 (m, 2H), 1.58-1.22 (m, 16H), 1.19-1.06 (m, 2H), 0.94 (s, 3H), 0.87-0.78 (m, 1H), 0.64-0.56 (m, 1H), 0.45-0.39 (m, 1H), 0.18-0.02 (m, 2H).

Example 97

1-((3R,5R,8R,9R,10S,13S,14S,15S,17S)-15-Cyclopropyl-3-hydroxy-3,13-dimethylhexadecahydro-1H-cyclopenta[a]phenanthren-17-yl)-2-(3-(trifluoromethyl)-1H-pyrazol-1-yl)ethan-1-one

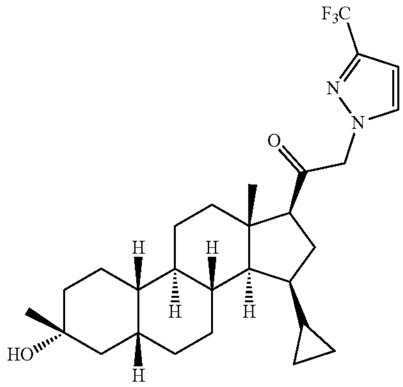

Step 1: Preparation of 1-((3R,5R,8R,9R,10S,13S,14S,15S,17S)-15-cyclopropyl-3-hydroxy-3,13-dimethylhexadecahydro-1H-cyclopenta[a]phenanthren-17-yl)-2-(3-(trifluoromethyl)-1H-pyrazol-1-yl)ethan-1-one

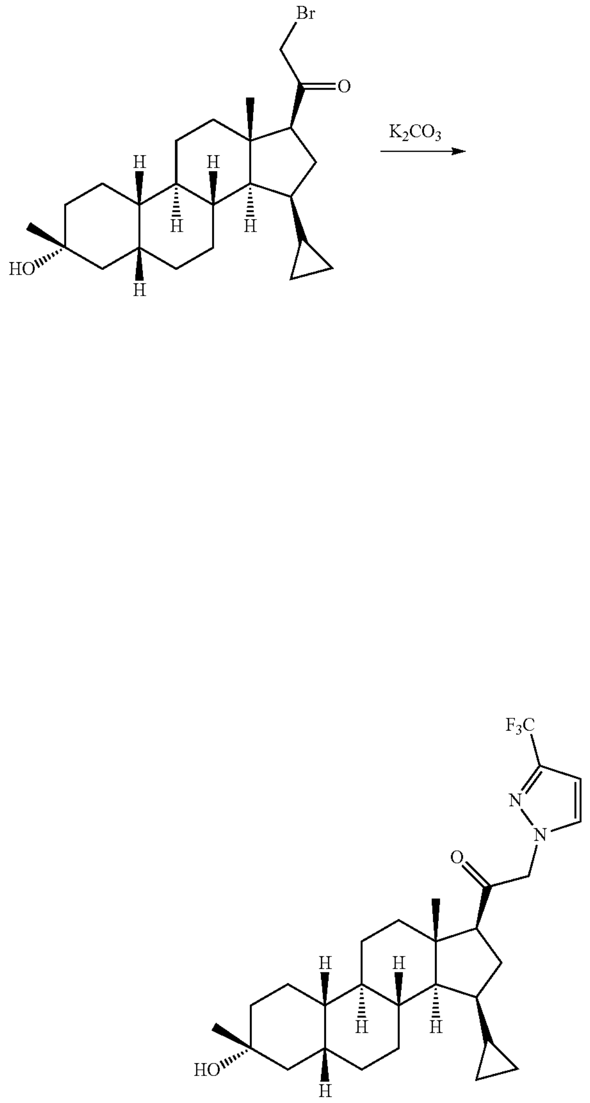

In accordance with Example 3, 1-((3R,5R,8R,9R,10S,13S,14S,15S,17S)-15-cyclopropyl-3-hydroxy-3,13-dimethylhexadecahydro-1H-cyclopenta[a]phenanthren-17-yl)ethan-1-one was used as the starting material, accordingly, 1-((3R,5R,8R,9R,10S,13S,14S,15S,17S)-15-cyclopropyl-3-hydroxy-3,13-dimethylhexadecahydro-1H-cyclopenta[a]phenanthren-17-yl)-2-(3-(trifluoromethyl)-1H-pyrazol-1-yl)ethan-1-one (18.0 mg, yield: 23%) was obtained.

MS m/z (ESI): 491.3[M−H]$^-$ $^1$H NMR (400 MHz, $CDCl_3$) δ 7.47 (d, J=2.0 Hz, 1H), 6.59 (d, J=2.0 Hz, 1H), 5.08-4.90 (m, 2H), 2.53-2.42 (m, 1H), 2.24-1.94 (m, 4H), 1.91-1.79 (m, 3H), 1.78-1.66 (m, 2H), 1.52-1.22 (m, 15H), 1.18-1.02 (m, 2H), 0.91 (s, 3H), 0.88-0.76 (m, 1H), 0.65-0.54 (m, 1H), 0.48-0.36 (m, 1H), 0.18-0.00 (m, 2H).

Example 98

1-((3R,5R,8R,9R,10S,13S,14S,15S,17S)-15-Cyclopropyl-3-hydroxy-3,13-dimethylhexadecahydro-1H-cyclopenta[a]phenanthren-17-yl)-2-(2H-tetrazol-2-yl)ethan-1-one

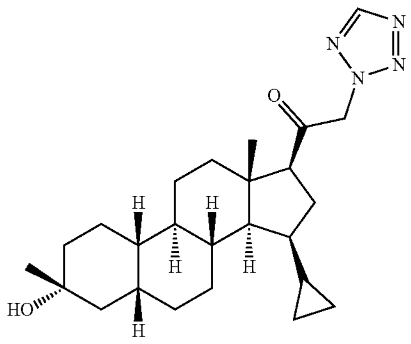

Step 1: Preparation of 1-((3R,5R,8R,9R,10S,13S,14S,15S,17S)-15-cyclopropyl-3-hydroxy-3,13-dimethylhexadecahydro-1H-cyclopenta[a]phenanthren-17-yl)-2-(2H-tetrazol-2-yl)ethan-1-one

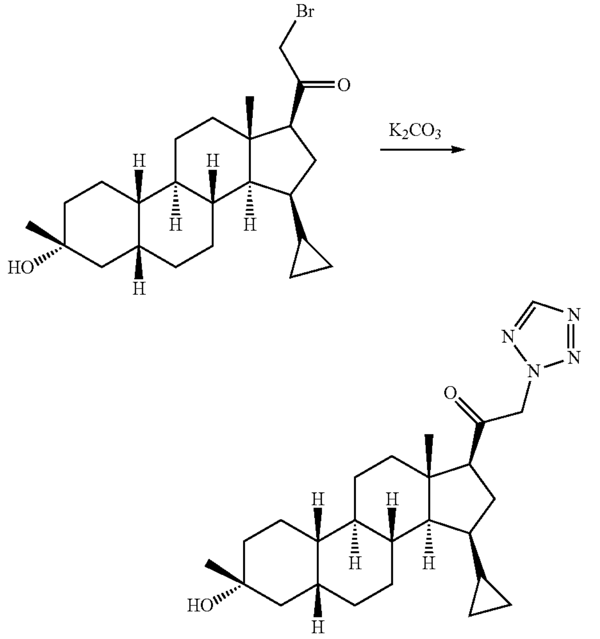

In accordance with Example 3, 1-((3R,5R,8R,9R,10S,13S,14S,15S,17S)-15-cyclopropyl-3-hydroxy-3,13-dimethylhexadecahydro-1H-cyclopenta[a]phenanthren-17-yl)ethan-1-one was used as the starting material, accordingly, 1-((3R,5R,8R,9R,10S,13S,14S,15S,17S)-15-cyclopropyl-3-hydroxy-3,13-dimethylhexadecahydro-1H-cyclopenta[a]phenanthren-17-yl)-2-(2H-tetrazol-2-yl)ethan-1-one (12.9 mg, yield: 13.2%) was obtained.

MS m/z (ESI): 409.3[M−$H_2O$+H]$^+$ $^1$H NMR (400 MHz, $CDCl_3$) δ 8.57 (s, 1H), 5.46 (s, 2H), 2.58-2.47 (m, 1H), 2.24-1.94 (m, 4H), 1.93-1.80 (m, 3H), 1.77-1.66 (m, 2H), 1.50-1.21 (m, 15H), 1.18-1.06 (m, 2H), 0.95 (s, 3H), 0.87-0.78 (m, 11H), 0.64-0.55 (m, 11H), 0.46-0.38 (m, 1H), 0.17-0.01 (m, 2H).

Example 99

3-Chloro-1-(2-((3R,5R,8R,9R,10S,13S,14S,15S,17S)-15-cyclopropyl-3-hydroxy-3,13-dimethylhexadecahydro-1H-cyclopenta[a]phenanthren-17-yl)-2-oxoethyl)-1H-pyrazole-4-carbonitrile

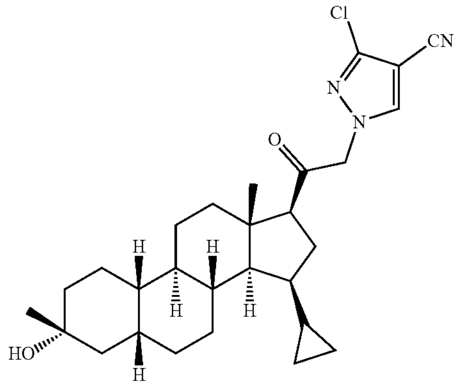

Step 1: Preparation of 3-chloro-1-(2-((3R,5R,8R,9R,10S,13S,14S,15S,17S)-15-cyclopropyl-3-hydroxy-3,13-dimethylhexadecahydro-1H-cyclopenta[a]phenanthren-17-yl)-2-oxoethyl)-1H-pyrazole-4-carbonitrile

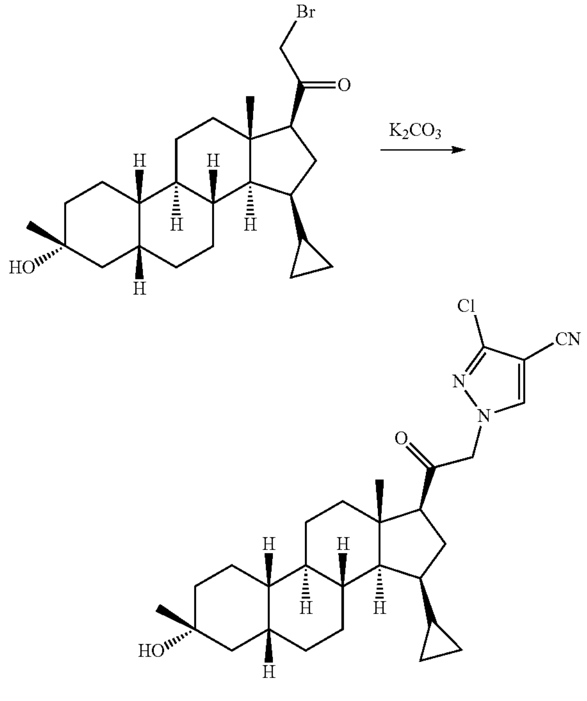

In accordance with Example 5, 1-((3R,5R,8R,9R,10S,13S,14S,15S,17S)-15-cyclopropyl-3-hydroxy-3,13-dimethylhexadecahydro-1H-cyclopenta[a]phenanthren-17-yl)ethan-1-one was used as the starting material, accordingly, 3-chloro-1-(2-((3R,5R,8R,9R,10S,13S,14S,15S,17S)-15-cyclopropyl-3-hydroxy-3,13-dimethylhexadecahydro-1H-cyclopenta[a]phenanthren-17-yl)-2-oxoethyl)-1H-pyrazole-4-carbonitrile (13.5 mg, yield: 17.4%) was obtained.

MS m/z (ESI): 482.2[M−H]$^-$ $^1$H NMR (400 MHz, $CDCl_3$) δ 7.82 (s, 1H), 5.01-4.76 (m, 2H), 2.55-2.41 (m, 1H), 2.22-1.94 (m, 4H), 1.91-1.77 (m, 3H), 1.76-1.66 (m, 2H), 1.56-1.24 (m, 15H), 1.18-1.04 (m, 2H), 0.90 (s, 3H), 0.87-0.75 (m, 1H), 0.64-0.53 (m, 1H), 0.46-0.38 (m, 1H), 0.17-0.02 (m, 2H).

Example 100

1-((3R,5R,8R,9R,10S,13S,14S,15R,17S)-15-Ethyl-3-hydroxy-3,13-dimethylhexadecahydro-1H-cyclopenta[a]phenanthren-17-yl)-2-(2H-tetrazol-2-yl)ethan-1-one

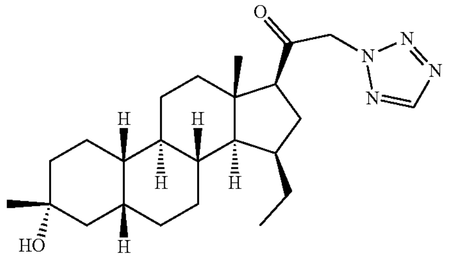

Step 1: Preparation of 1-((3R,5R,8R,9R,10S,13S,14S,15R,17S)-15-ethyl-3-hydroxy-3,13-dimethylhexadecahydro-1H-cyclopenta[a]phenanthren-17-yl)-2-(2H-tetrazol-2-yl)ethan-1-one

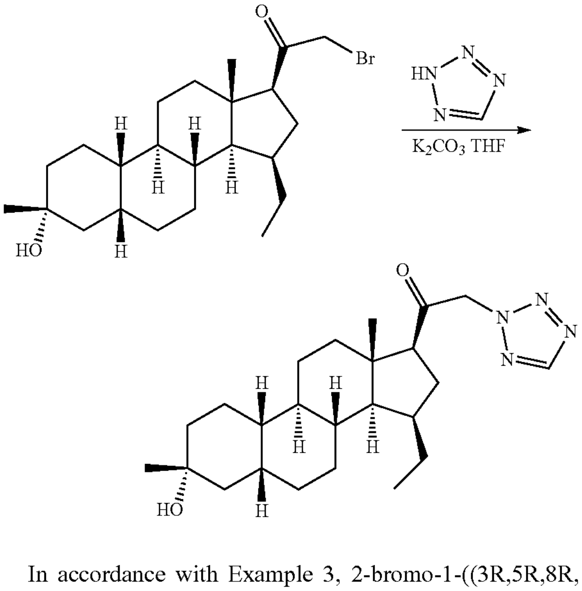

In accordance with Example 3, 2-bromo-1-((3R,5R,8R,9R,10S,13S,14S,15R,17S)-15-ethyl-3-hydroxy-3,13-dimethylhexadecahydro-1H-cyclopenta[a]phenanthren-17-yl)ethan-1-one was used as the starting material, accordingly, the product 1-((3R,5R,8R,9R,10S,13S,14S,15R,17S)-15- ethyl-3-hydroxy-3,13-dimethylhexadecahydro-1H-cyclopenta[a]phenanthren-17-yl)-2-(2H-tetrazol-2-yl)ethan-1-one (11 mg, white solid, yield: 18.8%) was obtained.

MS m/z (ESI): 397.2[M-$H_2O$+H]$^+$ $^1$H NMR (400 MHz, $CDCl_3$) δ 8.57 (s, 1H), 5.50-5.41 (m, 2H), 2.62 (t, J=8.5 Hz, 1H), 2.29-1.30 (m, 20H), 1.28 (s, 3H), 1.27-1.05 (m, 4H), 0.85-0.82 (m, 6H).

Example 103

(3R,5R,8R,9R,10S,13S,14S,16R,17S)-3-Hydroxy-3,13-dimethyl-17-(2-(4-(trifluoromethyl)-1H-pyrazol-1-yl)acetyl)hexadecahydro-1H-cyclopenta[a]phenanthrene-16-carbonitrile

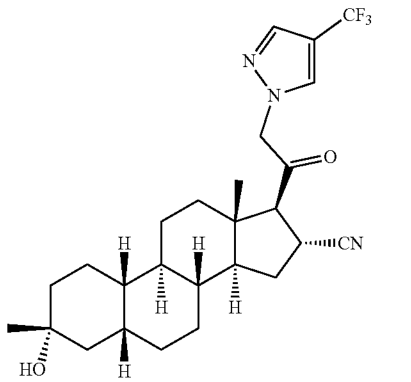

Step 1: Preparation of (3R,5R,8R,9R,10S,13S,14S,16R,17S)-17-(2-bromoacetyl)-3-hydroxy-3,13-dimethylhexadecahydro-1H-cyclopenta[a]phenanthrene-16-carbonitrile

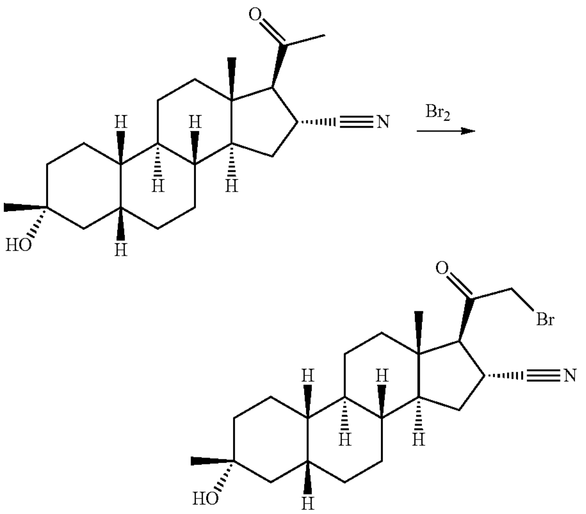

(3R,5R,8R,9R,10S,13S,14S,16R,17S)-17-Acetyl-3-hydroxy-3,13-dimethylhexadecahydro-1H-cyclopenta[a]phenanthrene-16-carbonitrile (120 mg, 0.349 mmol) was dissolved in methanol (3 mL). Liquid bromine (83 mg, 0.524 mmol) and a drop of hydrogen bromide were added, and then the reaction solution was stirred at room temperature for 5 hours. Water (30 mL) was added, and then the reaction solution was extracted with ethyl acetate (20 mL×3). The organic phases were combined, washed with saturated saline (30 mL), dried over anhydrous sodium sulfate and filtrated. The filtrate was concentrated under reduced pressure to dryness to obtain (3R,5R,8R,9R,10S,13S,14S,16R,17S)-17-(2-bromoacetyl)-3-hydroxy-3,13-dimethylhexadecahydro-1H-cyclopenta[a]phenanthrene-16-carbonitrile (140 mg, crude product).

Step 2: Preparation of (3R,5R,8R,9R,10S,13S,14S,16R,17S)-3-hydroxy-3,13-dimethyl-17-(2-(4-(trifluoromethyl)-1H-pyrazol-1-yl)acetyl)hexadecahydro-1H-cyclopenta[a]phenanthrene-16-carbonitrile

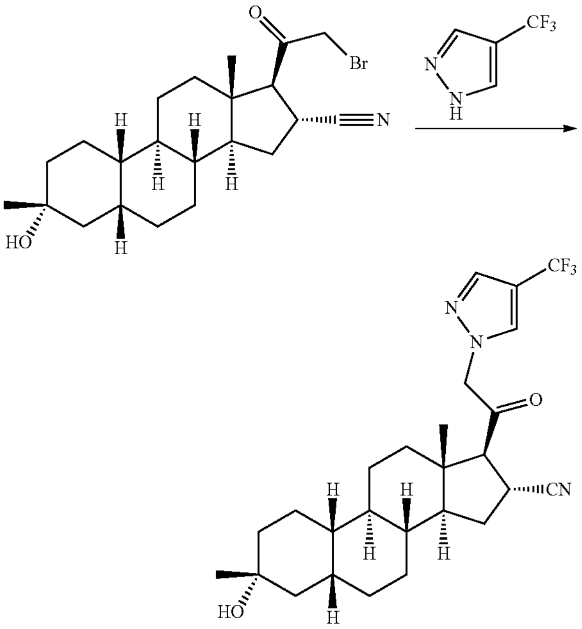

A mixture of (3R,5R,8R,9R,10S,13S,14S,16R,17S)-17-(2-bromoacetyl)-3-hydroxy-3,13-dimethylhexadecahydro-1H-cyclopenta[a]phenanthrene-16-carbonitrile (100 mg, 0.23 mmol), 4-(trifluoromethyl)-1H-pyrazole (63 mg, 0.46 mmol), potassium carbonate (95 mg, 0.69 mmol) and tetrahydrofuran (5 mL) was stirred at room temperature for 16 hours. Water (20 mL) was added, and then the reaction solution was extracted with ethyl acetate (20 mL×3). The organic phases were combined, washed with saturated saline (30 mL), dried over anhydrous sodium sulfate and filtrated. The filtrate was concentrated under reduced pressure to dryness, and the resulting crude product was purified by high performance liquid chromatography to obtain (3R,5R,8R,9R,10S,13S,14S,16R,17S)-3-hydroxy-3,13-dimethyl-17-(2-(4-(trifluoromethyl)-1H-pyrazol-1-yl)acetyl)hexadecahydro-1H-cyclopenta[a]phenanthrene-16-carbonitrile (25 mg, yield: 23%).

MS m/z (ESI): 478.2[M+H]$^+$.

$^1$H NMR (400 MHz, $CDCl_3$) δ 7.76 (s, 1H), 7.74 (s, 1H), 5.01 (dd, J=77.6, 18.0 Hz, 2H), 3.65-3.36 (m, 1H), 2.96 (d, J=8.7 Hz, 1H), 2.18-2.04 (m, 2H), 1.89-1.71 (m, 5H), 1.69-1.60 (m, 5H), 1.46-1.39 (m, 5H), 1.32-1.25 (m, 5H), 1.24-1.03 (m, 3H), 0.65 (s, 3H).

Biological Assay and Evaluation of the Compounds

The present invention is further described below in combination with the following test examples, which are not intended to limit the scope of the present invention.

1. $GABA_A$ Receptor Binding Ability Assay of the Compounds of the Present Invention 1.1 Experimental objective: The objective of this test example is to measure the ability of the compounds to allosterically inhibit the binding of the ion channel blocker (tert-butylbicyclophosphorothionate (TBPS)) to the GABA-A receptor.

Experimental Instruments:

| Instruments/Consumables | Supplier | Model |
|---|---|---|
| Vortex mixer | IKA | MS3 basic |
| Electric thermostat incubator | Shanghai Yiheng Instrument Co., Ltd. | DHP-9032 |
| TopCount | PerkinElmer | NTX |
| Universal Harvester | Perkin Elmer | UNIFILTER-96 |
| High-speed floor-standing centrifuge | Thermo | LYNX 4000 |
| Glass tissue homogenizer | Nanjing Luanyu Glass Instrument Co., Ltd. | 50 mL |
| Sprague-Dawley Rat | Pharmaron | |
| Protease inhibitor | roche | 11836170001 |
| 1.1 mL deep 96-well plate, round bottom | Axygen | P-DW-11-C |
| ULTIMA GOLD | Perkin Elmer | 77-16061 |
| UNIFILTER-96 GF/B filter plate | Perkin Elmer | 6005177 |
| Polyethylenimine (PEI), branched | Sigma | 408727 |

1.2 Experimental Procedures 1.2.1 Extraction of Cerebral Cortex Cell Membrane:

1. The cerebral cortex of male Sprague-Dawley rat was isolated.

2. A pre-chilled 0.32 M sucrose solution (one tablet of protease inhibitor was added per 100 mL) was added to the cerebral cortex (the volume of sucrose solution was 10 times the volume of the cerebral cortex). The mixture was crushed with a 50 mL glass tissue homogenizer in batches and mixed well.

3. The mixture was centrifuged at 1,500 g, 4° C. for 10 minutes, and the supernatant was collected.

4. The mixture was centrifuged at 20,000 g, 4° C. for 30 minutes, and the supernatant was discarded.

5. The precipitate was resuspended with the pre-chilled phosphate buffer saline (PBS) (one tablet of protease inhibitor was added per 100 mL). An average of 4 mL of PBS was added per rat, and the mixture was mixed well with a glass tissue homogenizer.

6. The mixture was centrifuged at 10,000 g, 4° C. for 10 minutes, and the supernatant was discarded.

7. Steps 5 and 6 were repeated three times.

8. Finally, the precipitate was resuspended with 4 volumes of PBS. The resulting solution was dispensed, frozen in liquid nitrogen, and stored at −80° C.

9. The protein concentration was measured by the bicinchoninic acid (BCA) method.

1.2.2 35S-TBPS Binding Assay 1. 230 μL of PBS was added to each well of a well plate with 1.1 mL volume.

2. 60 μL of the cerebral cortex cell membrane (5 μg/μL) solution was added to each well, and the mixture was mixed well.

3. The test compound (3 μL per well) was added, and the plate was incubated at 25° C. for 5 minutes. The DMSO concentration was 1%. The initial compound concentration was 1 M, and a 3-fold dilution in gradient was carried out to obtain a total of 8 gradients and 2 replicates. 1% DMSO was used as a negative control, and 10 μM P026-2 was used as a positive control.

4. GABA was added at a final concentration of 5 μM, and incubated at 25° C. for 5 minutes. 1 mM GABA solution was formulated, and 1.5 μL of the solution was added to each well.

5. 35S-TBPS was added at a final concentration of 2 nM. The concentration of isotope mother solution was 9.7 μM. After dilution with PBS for 100 times, 6 μL of the diluted isotope solution was added to each well.

6. The plate was incubated at 4° C. for 20 hours.

7. The FilterMate GF/C plate was pre-treated with 0.5% PEI, and incubated at 4° C. for 1 hour.

8. The FilterMate GF/C plate was washed with Universal Harvester twice, 50 mL PBS each time.

9. The reaction solution was transferred to the GF/C plate, and each well was washed 4 times with 900 μL of PBS.

10. The washed GF/C plate was placed at 55° C. and dried for 10 minutes.

11. 40 μL of scintillation solution was added to each well, and the CPM value was read with TopCount.

1.2.3 Experimental Data Processing Method:

In the experiment, the CPM (counts per minute) value was read with TopCount. According to the readings of the High control (DMSO) and the Low control (10 μM of the positive compound) experimental groups, the % inhibition was calculated based on the following formula:

$$\% \text{ Inhibition}=100\times(CPM_{High\ control}-CPM_{sample})/(CPM_{High\ control}-CPM_{Low\ control})$$

The $IC_{50}$ of the compound was calculated according to the following 4-parameter nonlinear logic formula:

$$Y=\text{Bottom}+(\text{Top}-\text{Bottom})/(1+10\hat{}((\text{Log } IC50-X)*\text{HillSlope})),$$

wherein:

X represents the log of compound concentration,

Y represents the % Inhibition.

The effect of the compound of the present invention on the TBPS binding activity was determined by the above test, and the measured $IC_{50}$ values are shown in Table 5.

TABLE 5

$IC_{50}$ of the compounds of the present invention on inhibiting the TBPS binding activity

| Example No. | 35S-TBPS bindng assay (nM) |
|---|---|
| 1 | 24.3 |
| 2 | 14.9 |
| 3 | 13.5 |
| 4 | 3.1 |
| 5 | 14.7 |
| 7 | 21.3 |
| 9 | 4.6 |
| 14 | 6.4 |
| 24 | 18.3 |
| 25 | 28.1 |
| 28 | 15.4 |
| 29 | 15.4 |
| 30 | 28.7 |
| 35 | 5.0 |
| 39 | 6.2 |

TABLE 5-continued

| IC$_{50}$ of the compounds of the present invention on inhibiting the TBPS binding activity | |
|---|---|
| Example No. | 35S-TBPS bindng assay (nM) |
| 40 | 8.2 |
| 42 | 24.6 |
| 43 | 5.4 |
| 44 | 6.1 |
| 47 | 7.6 |
| 48 | 7.5 |
| 68 | 9.6 |
| 71 | 11.4 |
| 73 | 10.2 |
| 80 | 18.3 |
| 84 | 6.1 |
| 85 | 15.8 |
| 86 | 8.0 |
| 87 | 17.8 |
| 88 | 6.7 |
| 89 | 4.3 |
| 90 | 16.2 |
| 91 | 25.2 |
| 92 | 27.0 |
| 94 | 23.9 |
| 95 | 16.2 |
| 96 | 28.5 |
| 97 | 18.6 |
| 98 | 21.4 |
| 99 | 24.4 |
| 100 | 25.6 |

Conclusion: The compounds of the examples of the present invention have a significant inhibitory effect on the TBPS binding activity.

2. Pharmacokinetic Assay in Balb/C Mice 2.1 Test Objective:

Balb/C mice were used as test animals. The pharmacokinetic behavior in mice (plasma and brain tissue) of the compounds of Examples 1 to 4, 7, 9, 39 to 41, 44, 48 to 52, 59, 73, 88 to 91, 93 to 94, 96 and 98 orally administered at a dose of 5 mg/kg was studied.

2.2 Test Scheme 2.2.1 Test Compounds:

Compounds of Examples 1 to 4, 7, 9, 39 to 41, 44, 48 to 52, 59, 73, 88 to 90, 93 to 94, 96 and 98 of the present invention, prepared by the applicant.

2.2.2 Test Animals:

Male Balb/C mice were purchased from Shanghai Jiesijie Laboratory Animal Co., LTD, with Certificate No.: SCXK (Shanghai) 2013-0006 N0.311620400001794.

2.2.3 Administration:

Each group had 24 male Balb/C mice. After an overnight fast, Balb/C mice were administered p.o. with the test compound at an administration dose of 5 mg/kg and an administration volume of 10 mL/kg.

2.2.4 Sample Collection:

0.2 ml of blood was taken from the heart before administration and at 0, 0.5, 1, 2, 4, 6, 8 and 24 hours after administration. The samples were stored in EDTA-$K_2$ tubes, and centrifuged for 6 minutes at 4° C., 6000 rpm to separate the plasma. The plasma samples were stored at −80° C. The mice were sacrificed with $CO_2$, and the whole brain tissue was taken out, weighed, placed in a 2 mL centrifuge tube and stored at −80° C.

2.2.5 Sample Process:

1) 160 μL of acetonitrile was added to 40 μL of the plasma sample for precipitation, and then the mixture was centrifuged for 5-20 minutes at 3500×g.

2) 90 μL of acetonitrile containing the internal standard (100 ng/mL) was added to 30 μL of the plasma and brain homogenate samples for precipitation, and then the mixture was centrifuged for 8 minutes at 13000 rpm.

3) 70 μL of the treated supernatant was taken and added to 70 μL of water, and mixed by vortex for 10 minutes. 20 μL of the mixture was taken to analyze the concentration of the test compound by LC/MS/MS. LC/MS/MS analysis instrument: AB Sciex API 4000 Qtrap.

2.2.6 Liquid Chromatography Analysis

Liquid chromatography condition: Shimadzu LC-20AD pump

Chromatographic column: Agilent ZORBAX XDB-C18 (50×2.1 mm, 3.5 μm)

Mobile phase: Eluent A was 0.1% formic acid in water, and Eluent B was acetonitrile Flow rate: 0.4 mL/min Elution time: 0-4.0 minutes, the eluent is as follows:

| Time/minute | Eluent A | Eluent B |
|---|---|---|
| 0.01 | 90% | 10% |
| 0.5 | 90% | 10% |
| 0.8 | 5% | 95% |
| 2.4 | 5% | 95% |
| 2.5 | 90% | 10% |
| 4.0 | Stop | |

2.3. Test Results and Analysis

The main parameters of pharmacokinetics were calculated by WinNonlin 6.1. The results of pharmacokinetic experiment in mice are shown in Table 6 below:

TABLE 6

| Results of pharmacokinetic experiment in mice | | | | | | |
|---|---|---|---|---|---|---|
| | Pharmacokinetic experiment (5 mg/kg) | | | | | |
| Example No. | Peak time $t_{max}$(ng/mL) | Plasma. concentration $C_{max}$(ng/mL) | Area under curve $AUC_{0-t}$(ng/mL × h) | Area under curve $AUC_{0-\infty}$(ng/mL × h) | Half-life $t_{1/2}$(h) | Mean residence time MRT(h) |
| 1 plasma | 0.5 | 1099.3 | 1360.5 | 1374.2 | 0.54 | 1.21 |
| 1 brain tissue | 0.5 | 636.7 | 839.7 | 913.0 | 2.84 | 2.39 |
| 2 plasma | 0.5 | 673.3 | 569.7 | 573.8 | 0.50 | 1.01 |
| 2 brain tissue | 0.5 | 690.3 | 718.9 | 721.8 | 0.50 | 1.10 |

TABLE 6-continued

| Results of pharmacokinetic experiment in mice | | | | | | |
|---|---|---|---|---|---|---|
| | Pharmacokinetic experiment (5 mg/kg) | | | | | |
| Example No. | Peak time $t_{max}$(ng/mL) | Plasma. concentration $C_{max}$(ng/mL) | Area under curve $AUC_{0-t}$(ng/mL × h) | Area under curve $AUC_{0-\infty}$(ng/mL × h) | Half-life $t_{1/2}$(h) | Mean residence time MRT(h) |
| 3 plasma | 0.5 | 461.0 | 1241.5 | 1254.2 | 5.12 | 4.80 |
| 3 brain tissue | 0.5 | 1406.3 | 2303.0 | 3067.4 | 4.72 | 5.53 |
| 4 plasma | 0.5 | 219.0 | 409.0 | 483.8 | 3.19 | 4.03 |
| 4 brain tissue | 0.5 | 464.0 | 917.2 | 964.3 | 1.90 | 2.40 |
| 7 plasma | 0.5 | 663.7 | 774.9 | 778.0 | 0.9 | 1.1 |
| 7 brain tissue | 0.5 | 605.3 | 677.0 | 679.9 | 0.5 | 0.9 |
| 9 plasma | 1.0 | 1210 | 5057.2 | 5065.8 | 2.5 | 3.6 |
| 9 brain tissue | 1.0 | 1060.0 | 4731.4 | 4744.7 | 2.5 | 3.9 |
| 39 plasma | 0.5 | 553.7 | 1305.0 | 1316.9 | 2.99 | 4.15 |
| 39 brain tissue | 1.0 | 678.0 | 2642.7 | 2680.6 | 3.18 | 4.81 |
| 40 plasma | 0.5 | 719.7 | 1704.9 | 1772.1 | 1.64 | 1.43 |
| 40 brain tissue | 1.0 | 998.0 | 2403.0 | 2498.4 | 2.37 | 2.35 |
| 41 plasma | 0.5 | 524.7 | 588.5 | 604.6 | 3.27 | 1.48 |
| 41 brain tissue | 0.5 | 710.7 | 657.1 | 676.0 | 3.95 | 1.41 |
| 48 plasma | 1.0 | 508.3 | 1577.3 | 1758.8 | 2.04 | 3.50 |
| 48 brain tissue | 1.0 | 382.7 | 1127.8 | 1275.4 | 2.00 | 3.66 |
| 49 plasma | 0.5 | 1146.3 | 2967.0 | 2972.0 | 2.79 | 3.71 |
| 49 brain tissue | 0.5 | 723.7 | 2051.0 | 2237.3 | 2.12 | 3.17 |
| 50 plasma | 0.5 | 1303.3 | 2430.5 | 2482.0 | 1.40 | 2.06 |
| 50 brain tissue | 0.5 | 635.7 | 1098.1 | 1117.6 | 1.31 | 1.91 |
| 51 plasma | 1.0 | 2986.7 | 13411.8 | 13415.2 | 1.75 | 3.47 |
| 51 brain tissue | 1.0 | 1480.0 | 4821.6 | 5273.3 | 2.09 | 3.40 |
| 52 plasma | 0.5 | 2136.7 | 7156.4 | 8601.3 | 3.06 | 4.59 |
| 52 brain tissue | 1.0 | 1523.3 | 5846.2 | 6511.2 | 2.28 | 3.82 |
| 59 plasma | 1.0 | 1146.7 | 4643.8 | 5922.3 | 2.64 | 4.96 |
| 59 brain tissue | 1.0 | 296.2 | 1439.7 | 2234.7 | 5.59 | 7.97 |
| 73 plasma | 1.0 | 386 | 1034.8 | 1060.9 | 1.19 | 2.12 |
| 73 brain tissue | 1.0 | 626.3 | 1676.2 | 1706.2 | 1.12 | 2.07 |
| 88 plasma | 0.5 | 1750.0 | 4627.3 | 5132.2 | 1.78 | 3.31 |
| 88 brain tissue | 1.0 | 892.0 | 3205.7 | 3501.3 | 1.59 | 3.22 |
| 89 plasma | 2.0 | 640.3 | 4103.8 | 4110.3 | 2.06 | 4.38 |
| 89 brain tissue | 2.0 | 724.0 | 3736.7 | 4450.7 | 2.82 | 4.71 |
| 90 plasma | 1.0 | 762.7 | 2785.0 | 3792.4 | 3.85 | 5.88 |
| 90 brain tissue | 1.0 | 613.0 | 2126.5 | 3162.6 | 6.02 | 7.58 |
| 93 plasma | 0.5 | 2483.3 | 5982.0 | 6106.9 | 1.19 | 2.22 |

TABLE 6-continued

Results of pharmacokinetic experiment in mice

| Example No. | Pharmacokinetic experiment (5 mg/kg) Peak time $t_{max}$(ng/mL) | Plasma. concentration $C_{max}$(ng/mL) | Area under curve $AUC_{0-t}$(ng/mL × h) | Area under curve $AUC_{0-\infty}$(ng/mL × h) | Half-life $t_{1/2}$(h) | Mean residence time MRT(h) |
|---|---|---|---|---|---|---|
| 93 brain tissue | 0.5 | 1738.0 | 4327.1 | 4539.1 | 1.21 | 2.10 |
| 94 plasma | 0.5 | 1633.3 | 3545.3 | 3634.6 | 1.35 | 2.55 |
| 94 brain tissue | 0.5 | 1048.0 | 2153.2 | 2251.2 | 1.68 | 2.68 |
| 96 plasma | 0.5 | 1650.0 | 6287.8 | 6492.4 | 1.70 | 3.08 |
| 96 brain tissue | 2.0 | 812.0 | 8818.0 | 9215.1 | 3.95 | 7.81 |
| 98 plasma | 1.0 | 2086.7 | 7785.5 | 8000.6 | 1.45 | 2.97 |
| 98 brain tissue | 1.0 | 1966.0 | 8677.8 | 12488.1 | 4.66 | 6.73 |

It can be seen from the results of the pharmacokinetic experiment in mice in the table that the compounds of the examples of the present invention showed good metabolic properties, and both the exposure AUC and the maximum blood drug concentration $C_{max}$ performed well. Compared with the existing compound SAGE-217, the compounds of the present invention can significantly increase the exposure in mice, while the maximum tolerated dose is equivalent or even better than that of SAGE-217. Therefore, the compounds of the present invention have good tolerance, wide safety window and high safety.

3. In Vivo Pharmacodynamic Experiment in the Forced Swimming Model in Mice 3.1 Experimental Objective The antidepressant effect of the compound was evaluated by the forced swimming model in mice.

3.2 Main Instruments and Reagents of the Experiment 3.2.1 Instruments

Forced swimming device (JLBehv-FSC-4, Shanghai Jiliang Software Technology Co., Ltd.).

3.2.2 Reagents

Sodium carboxymethyl cellulose (CMC-Na, SLBV9664, Sigma)

Tween 80 (BCBV8843, Sigma)

3.2.3 Test Compounds

Compounds of Examples 1 to 3, Example 9, Example 40, Example 41, Examples 48 to 52, Example 90 and Example 98 of the present invention, prepared by the applicant.

3.3 Experimental Procedures 3.3.1 Adaptation:

Male ICR mice (25-35 g) were adapted in the experiment environment for 3 days before the forced swimming test.

3.3.2 Grouping and Administration:

According to the experiment design, the mice were randomly grouped on the day before the experiment according to body weight, with 12 mice in each group. Before the test, the compounds of each example were administered intragastrically according to the Tmax thereof in the brain in mice pharmacokinetic experiment.

Respectively:

1) Model group (0.5% CMC-Na-1% Tween 80 solution, p.o., 10 mL/kg);
2) Compounds of Examples 1 to 3, Example 40, Example 41, Examples 48 to 51, Example 90 and Example 98 (10 mg/kg, p.o., 10 mL/kg); Example 9 and Example 52 (5 mg/kg, p.o., 5 mL/kg).

When being administered, the compounds of each example were suspended in 0.5% CMC-Na+1% Tween 80 solution to the desired concentration.

3.3.2 Forced Swimming Test:

0.5-1 hour after administration, ICR mice were placed in a forced swimming device (transparent glass drum (water depth 18 cm, water temperature 25-26° C.), one mouse per tank) and forced to swim for 6 minutes. The forced swimming device recorded the floating time of the ICR mice during the entire 6 minutes, and the data of the latter four minutes were used for data analysis. The mice were taken out immediately after the swimming experiment, wiped dry and put back in their original cages.

Note: The criterion for determining the immobility time is that the mouse stops struggling in water and floats, and there are only slight limb movements to keep the head floating on the water.

3.4 Data Analysis

Floating time percentage=100*floating time/240 s.

3.5 Test Data:

TABLE 7

Results of the forced swimming experiment in mice

| Example No. | Dose (mpk) | Mean (immobility, s) | Mean (immobility, %) |
|---|---|---|---|
| Vehicle | / | 163.70 | 68.22 |
| Example 1 | 10 | 130.22 | 54.26 |
| Example 2 | 10 | 68.39 | 28.50 |
| Example 3 | 10 | 143.81 | 59.93 |
| Example 9 | 5 | 138.22 | 57.60 |
| Example 40 | 10 | 84.90 | 35.30 |
| Example 41 | 10 | 85.8 | 35.75 |
| Example 48 | 10 | 134.21 | 55.92 |
| Example 49 | 10 | 85.77 | 35.74 |
| Example 50 | 10 | 70.96 | 29.57 |
| Example 51 | 5 | 73.72 | 30.72 |
| Example 52 | 5 | 91.21 | 38.00 |
| Example 90 | 10 | 88.61 | 36.92 |
| Example 98 | 5 | 80.5 | 33.54 |

3.6 Experimental Results

It can be seen from the above results that the compounds of the examples of the present application can significantly shorten the cumulative immobility time of the forced-swimming mice, and have a significant antidepressant effect.

The immobility time during the latter four minutes of the compounds of Example 2, Example 40, Example 41, Example 49, Example 50, Example 90 and Example 98 was very significantly different compared with that of the model group.

4. In Vivo Pharmacodynamic Test in the PTZ-Induced Epilepsy Model in Mice 4.1 Test Objective The PTZ-induced epilepsy model in CD-1 mice was established, and the antiepileptic effect of the compounds of Example 2, Example 40, Example 41 and Example 52 was evaluated using this model.

4.2 Test Method 4.2.1 Test Animals 50 male CD-1 mice were purchased from Beijing Vital River Laboratory Animal Technology Co. Ltd. The test animals were adapted at the animal room in the third building of Shanghai ChemPartner Co., Ltd for 7 days before the experiment. The average body weight of the animals on the test day was 32.2±0.2 grams. Feeding environment: 5 animals/cage, room temperature 23±2° C., 12/12 hours of light and dark cycle, free access to food and water.

The mice were randomly grouped for the experiment on the test day.

4.2.2 Test Compounds

Compounds of Example 2, Example 40, Example 41 and Example 52 (prepared by the applicant). The test compounds were stored in a refrigerator at 4° C.

4.2.4 Test Animal Grouping

1) Vehicle/PTZ: 0.5% CMC-Na+1% Tween-80 (10 ml/kg, p.o.), administered 0.5 hr before the PTZ administration; PTZ (120 ml/kg, s.c.), administered before the experiment;

2) 3 mg/kg of the compounds of Examples/PTZ: the compounds of Example 2, Example 40, Example 41 and Example 52 (3 mg/kg, 10 ml/kg, p.o.), administered 0.5 hr before the PTZ administration; PTZ (120 ml/kg, s.c.), administered before the experiment.

4.3 Experimental Procedures 4.3.1 Solvent Formulation 1) 0.5% CMC-Na+1% Tween-80 (administration volume: 10 mL/kg):

1 g of sodium carboxymethyl cellulose was precisely weighed and added to a 250 mL solvent bottle, then 150 mL of double-distilled water was added. The mixture was stirred at room temperature for 4 hours with a magnetic stirrer to obtain a uniform and clear solution. 2 mL of Tween-80 was slowly added, and the mixture was stirred at room temperature for 3 hours to obtain a uniform and clear solution. The solution was slowly transferred to a 200 mL volumetric flask, and double distilled water was added to the constant volume of 200 mL. The solution was transferred to a 250 mL solvent bottle, and stirred for 1 hour with a magnetic stirrer to obtain a uniform and clear solution.

2) 30% hydroxypropyl-p-cyclodextrin:

30.6122 g of hydroxypropyl-p-cyclodextrin (purity: 98%) was precisely weighed and added to a 100 mL solvent bottle, then 60 mL of double-distilled water was added. The mixture was mixed by vortex for 3 minutes, and treated by ultrasound at room temperature for 15 minutes to obtain a uniform and clear solution. Double distilled water was added to the constant volume of 100 mL, mixed by vortex for 1 minute, and treated by ultrasound at room temperature for 5 minutes to obtain a uniform and clear solution.

TABLE 8

Test reagent information

| Name | Article number | Batch number | Property | Supplier | Total weight | Purity | Store condition |
|---|---|---|---|---|---|---|---|
| Pentylenetetrazol (PTZ) | P6500 | SLBD3876V | White crystal | Sigma | 25 g | 100% | −20° C. refrigeration |
| Sodium carboxymethyl cellulose | 9004-32-4 | LAB0R36 | White solid | Beijing J&K Scientific Co., Ltd. | 100 G | 800 cps | Room temperature/dry/in the dark |
| Tween-80 | 9005-65-6 | P1279207 | Transparent liquid | GENERAL-REAGENT ® | 500 mL | 100% | Room temperature/dry |
| Hydroxypropyl β-cyclodextrin | 19184C | OP1901A | White powder | Seebio Biotech | 500 g | ≥98% | 2-8° C. refrigeration |
| 0.9% sodium chloride injection | H37022749 | H18010314 | Transparent liquid | Shandong Hualu Pharmaceutical Co., Ltd. | 500 mL | 100% | Room temperature/dry |

4.2.3 Test Equipments 1 ml sterile disposable syringe with needle (purchased from Zhejiang Kangdelai Medical Devices Co., Ltd.)

Pipette: Eppendorf Research Plus (100-1000 μL)

Vortex mixer: Kylin-Bell Vortex 5

Ultrasonic instrument: JL-360 ultrasonic cleaner

Balance: METTLER TOLEDO XS204 precision balance

Balance: METTLER TOLEDO XS6002S electronic balance

Plexiglass box: 25 cm length*15 cm width*15 cm height with one opaque side wall, custom made by Suzhou Fengshi Laboratory Animal Equipment Co., Ltd 3-channel timer: Oregon/Model NO. WB-388.

4.3.2 Test Compound Formulation 1) 12 mg/mL PTZ (dose: 120 mg/kg; administration volume: 10 mL/kg):

248 mg of PTZ was precisely weighed and added to a 40 mL brown flask, then 20.667 mL of physiological saline was added. The mixture was mixed by vortex for 2 minutes, and treated by ultrasound at room temperature for 2 minutes to obtain a uniform and clear solution (concentration: 12 mg/mL).

2) 0.3 mg/mL of the compounds of Example 5 or Example 23 (dose: 3 mg/kg; administration volume: 10 mL/kg):

A certain amount of 0.5% CMC-Na+1% Tween-80 was taken and added to a flask containing a certain amount of the compounds of Example 5 or Example 23. The mixture was mixed by vortex for 3 minutes, and treated by ultrasound at room temperature for 15 minutes to obtain a uniform suspension (concentration: 0.3 mg/mL).

4.3.3 Test Method

1) The test animals were transferred to the operating room to adapt to the environment 1 hour before the test;
2) The animals were randomly grouped, marked and weighed;
3) The compounds of Example 2, Example 40, Example 41 and Example 52 were administered respectively 1 hour before the PTZ administration, or 0.5% CMC-Na+1% Tween-80, the compounds of Example 2, Example 40, Example 41 and Example 52 were administered respectively 0.5 hour before the PTZ administration;
4) PTZ (120 mg/kg) was administrated subcutaneously before the experiment observation, and this time point was recorded as the observation start point;
5) After the administration of PTZ, the animal was immediately placed in the observation box and observed for 30 minutes, and the followings were recorded: a) the incubation period of the first clonic seizure, b) the incubation period of the first generalized tonic seizure, c) the number of clonic seizures, d) the number of generalized tonic seizures, e) the time when the animal died, 6) if the animal did not have seizures during the 30-minute observation period, the incubation period was recorded as 1800 see and the number of seizures was recorded as 0.

Clonic seizure: generalized clonic seizure in animals lasts for more than 3 seconds, and is accompanied by a fall;

Tonic seizure: the limbs straightens 90° to the body;

6) The possible side effects induced by the drug after the administration were observed and recorded, which can be divided into four levels:

None: normal
Mild sedation
Moderate sedation
Severe sedation

7) The test was carried out from 12:00 am to 16:30 pm.

4.4 Adaptation to the Environment

The test animals were transferred to the operating room to adapt to the environment 1 hour before the test.

4.5 Grouping and Administration

The mice were randomly grouped, marked and weighed; 10 mice per group. The test compound was administered orally at an administration volume of 10 mL/kg 30-60 minutes before the PTZ administration.

4.6 PTZ Modeling and Testing

PTZ (120 mg/kg) was administrated subcutaneously before the experiment observation, and this time point was recorded as the observation start point; after the administration of PTZ, the animal was immediately placed in the observation box and observed for 30 minutes, and the followings were recorded: a) the incubation period of the first clonic seizure, b) the incubation period of the first generalized tonic seizure, c) the number of clonic seizures, d) the number of generalized tonic seizures, e) the time when the animal died. If the animal did not have seizures during the 30-minute observation period, the incubation period was recorded as 1800 sec and the number of seizures was recorded as 0.

4.7 Data Analysis

All measurement data were expressed as Mean±SEM, and analysed with Prism 6.0 statistical software.

4.8 Test Data:

TABLE 9

Results of the in vivo pharmacodynamic experiment in the epilepsy model in mice

| Example No. | Dose (mpk) | Incubation period of the clonic seizure (sec) Mean ± SEM | Number of clonic seizures Mean | Incubation period of the generalized tonic seizure (sec) Mean | Number of generalized tonic seizures Mean | Time when the animal died (sec) Mean | Mortality rate (%) |
|---|---|---|---|---|---|---|---|
| Vehicle | / | 331.4 ± 61.2 | 2.1 ± 0.2 | 821.6 ± 107.7 | 1.0 ± 0.0 | 839.8 ± 108.0 | 100% |
| 2 | 3 | 902.9 ± 200.8 | 1.3 ± 0.3 | 1736.0 ± 63.2 | 0.1 ± 0.1 | 1739.8 ± 60.2 | 10% |
| 40 | 3 | 1308.1 ± 170.1 | 0.5 ± 0.2 | 1800.0 ± 0.0 | 0.0 ± 0.0 | 1800.0 ± 0.0 | 0% |
| 41 | 3 | 841.4 ± 179.8 | 1.9 ± 0.4 | 1497.4 ± 124.3 | 0.5 ± 0.2 | 1573.1 ± 117.9 | 40% |
| 52 | 3 | 635.4 ± 149.9 | 1.8 ± 0.3 | 1506.8 ± 149.8 | 0.3 ± 0.2 | 1618.1 ± 121.3 | 30% |

4.9 Experimental Results

The compounds of the examples significantly prolonged the incubation period of clonic seizure and generalized tonic seizure and reduced the number of clonic seizures and generalized tonic seizures compared with the control group. The compounds of the examples can protect 60%-100% of animals from death, significantly prolong the incubation period of death, and have a good antiepileptic effect.

5. Positive Regulatory Effect of the Compounds of the Present Invention on $GABA_A$ Receptor 5.1 Experimental Objective:

The objective of this test example is to determine the positive regulatory effect of the compound on $GABA_A$ receptor by the electrophysiological manual patch clamp method.

5.2 Experimental Instruments:

Manual patch clamp system HEKA EPC10 USB signal amplifier and digital conversion system (purchased from HEKA Electronics, Germany), centrifuge (Eppendorf, etc.), carbon dioxide incubator (purchased from Thermo, etc.), biological safety cabinet (Thermo, etc.), pipette (purchased from Eppendorf, etc.).

5.3 Experimental Method:

The cells used in this experiment came from the HEK293T cell line which was transfected with human $GABA_A$ receptor α1, β2 and γ2 subunit cDNA and stably exhibited normal $GABA_A$ receptor function. The cells were grown in a culture dish with DMEM medium (purchased from Invitrogen), and cultured in an incubator at 37° C. and 5% $CO_2$. Before the electrophysiological experiment, the cells were transferred to a round glass slide placed in the culture dish, and grown in the same culture medium and under the same culture condition as above. The density of cells on each round glass slide should meet the requirement that most cells were independent and individual.

Each test compound was diluted in gradient with DMSO to obtain a stock solution, which was then diluted with extracellular fluid by 1,000-fold to obtain the final test concentration. The final concentration of DMSO in the compound solution with each concentration was 0.1%. The experiment used the manual patch clamp system HEKA EPC10 USB signal amplifier and digital conversion system for whole cell current recording. The round glass slide with HEK293T $GABA_A$ cells grown on the surface was taken out of the culture dish, and placed in the electrophysiological recording tank under the inverted microscope. The recording tank was continuously perfused with extracellular fluid. During the experiment, the whole-cell current recording technology was used to record the chloride current of the $GABA_A$ channel. 1 μM GABA was used to activate the chloride current of the $GABA_A$ channel of each cell as an initial control. 1 μM GABA acted on the cell through the drug perfusion system to induce the chloride current of the $GABA_A$ channel, the action time was about 3 to 5 seconds, and the current value was used as the initial control value. The test concentration of compound was perfused and incubated for 2 to 5 minutes. 1 M GABA solution (mixed with the test concentration of compound) was given to the cells to observe the enhancement effect of the test compound on the current induced by 1 μM GABA. When the cell state was stable, the test compound acted on the same cell from low to high concentration to record the enhancement effect of the induced current.

5.4 Processing Method of the Experimental Data:

The experimental data was analyzed by HEKA Patchmaster, Microsoft Excel and the data analysis software provided by Graphpad Prism.

5.5 Experimental Conclusion:

The biological activity of the compounds of the present invention in the in vitro cell activity test obtained according to the above scheme is shown in Table 10:

TABLE 10

EC50 values (nM) of the positive regulatory effect of GABA-A current

| Example No. | EC50: nM | Example No. | EC50: nM |
|---|---|---|---|
| 9 | 60 | 86 | 74 |
| 40 | 57 | 88 | 49 |
| 41 | 130 | 89 | 43 |
| 52 | 150 | 96 | 84 |

Conclusion: The compounds of the examples of the present invention have an obvious positive regulatory effect on GABA-A current.

Screening Study on the Salt and Crystal Form of the Compound

1. Preparation of Different Crystal Forms of the Free Base of Formula (VI)

Figure 2:
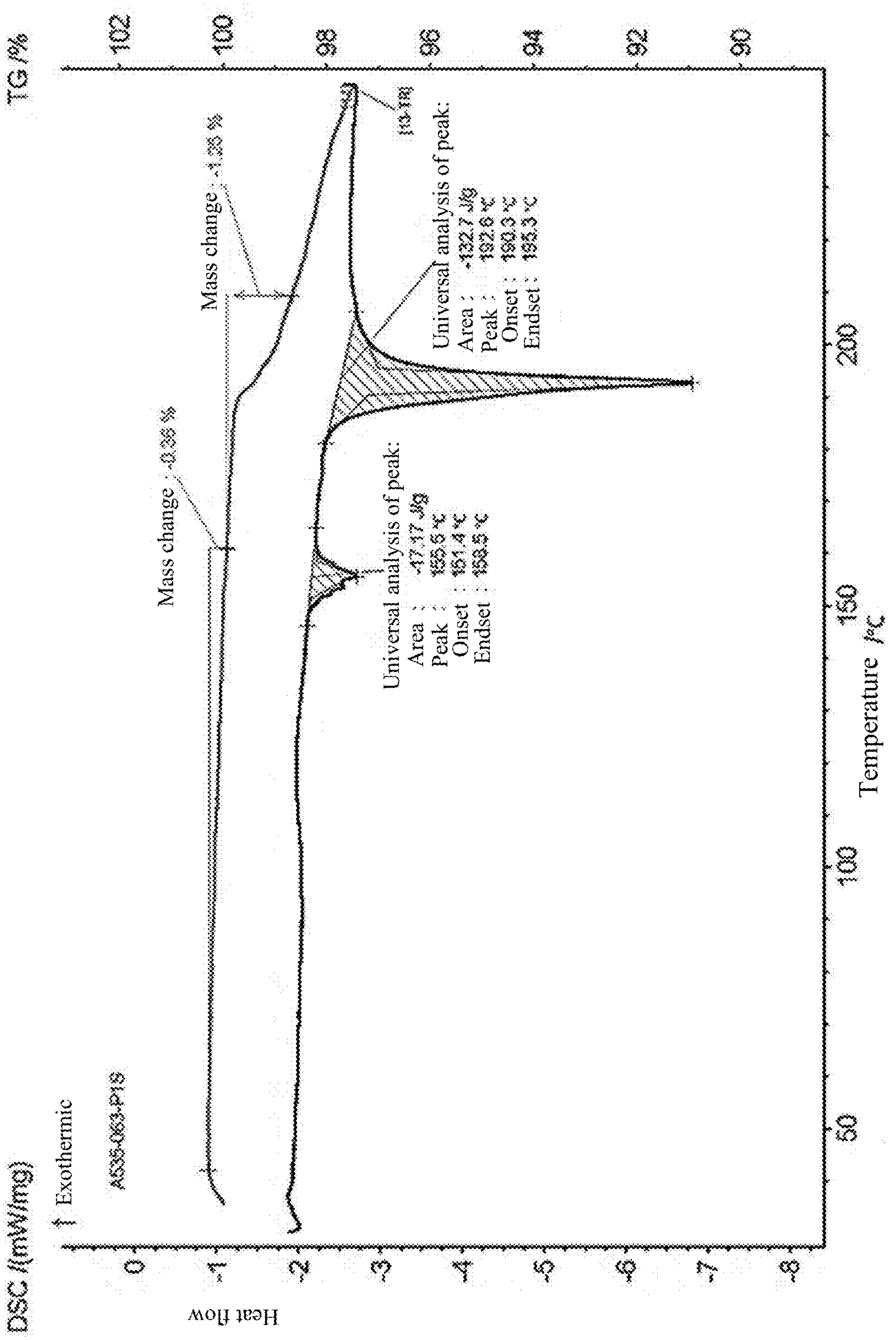
FIG. 2 is the TGA-DSC spectrum of crystal form I of the free base of formula (VI) (i.e., crystal form I of the free base of Example 40).
Figure 8:
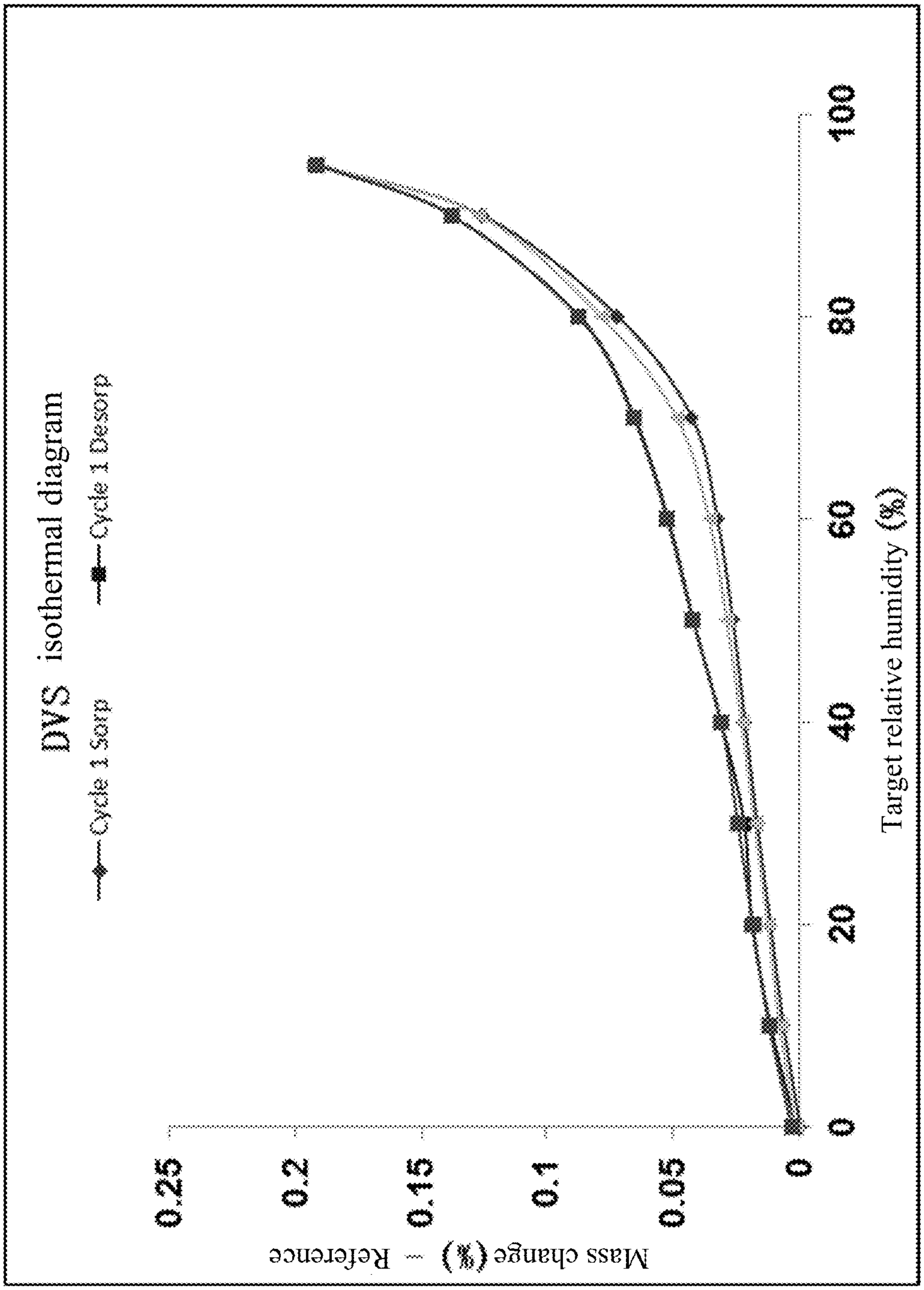
FIG. 8 is the DVS spectrum of crystal form I of the free base of formula (VI) (i.e., crystal form I of the free base of Example 40).

1.1 Preparation of Crystal Form I of the Free Base:

20.5 g of the free base compound of Example 40 (purity: ~95%) was dissolved in 125 mL of ethyl acetate, and the resulting solution was refluxed to clear. 125 mL of n-heptane was added dropwise, and granular solids precipitated during the addition process. The mixture was naturally cooled to 20° C. in the oil bath, and then stirred at 10 to 20° C. for 1 hour. The mixture was filtered, and the filter cake was dried to obtain 16.7 g of white solid. After detection and analysis, the solid was crystal form I of the free base, having the XRPD pattern as shown in FIG. 1, the TGA-DSC spectrum as shown in FIG. 2, and the DVS spectrum as shown in FIG. 8.

Figure 3:
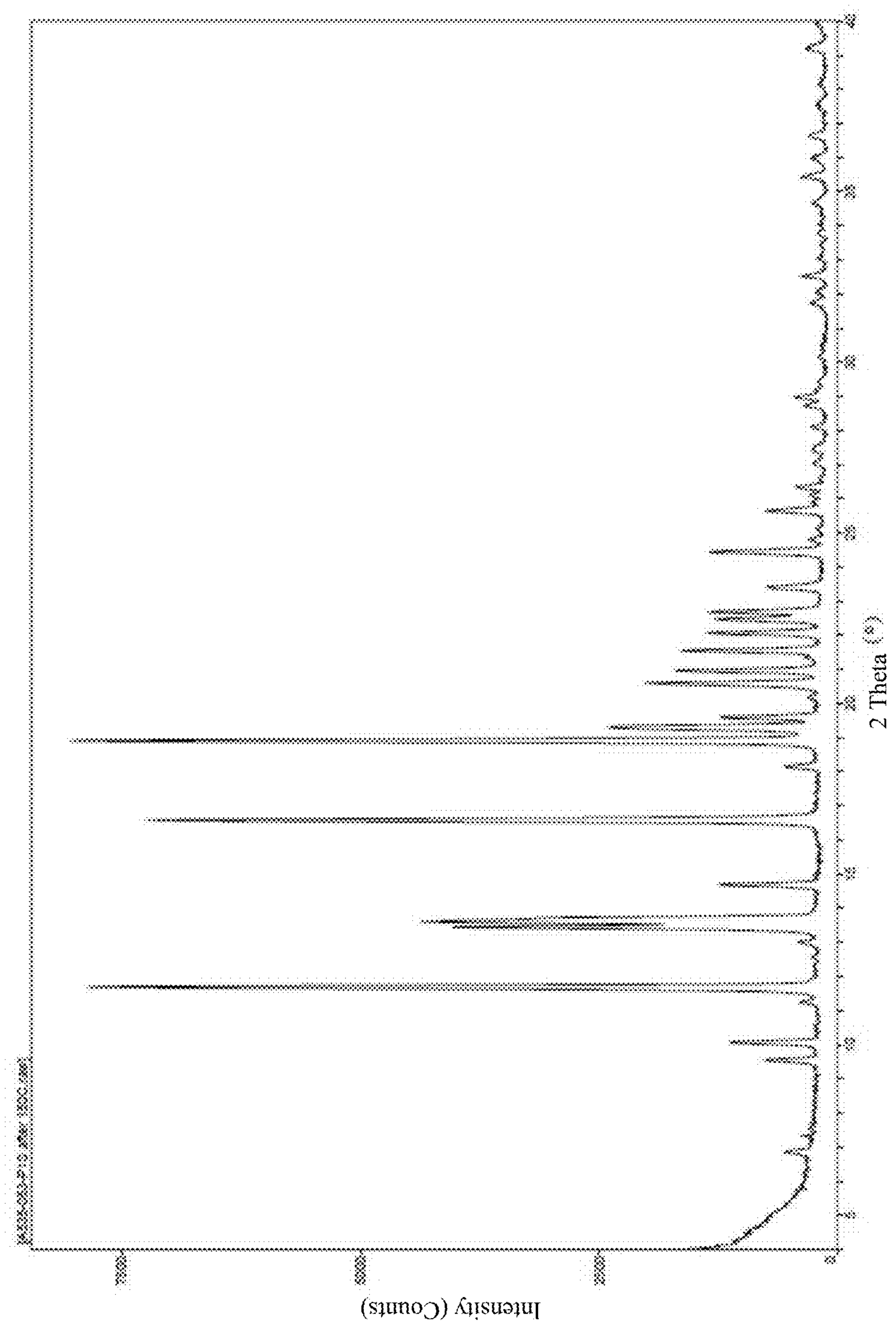
FIG. 3 is the XRPD pattern of crystal form II of the free base of formula (VI) (i.e., crystal form II of the free base of Example 40).
Figure 4:
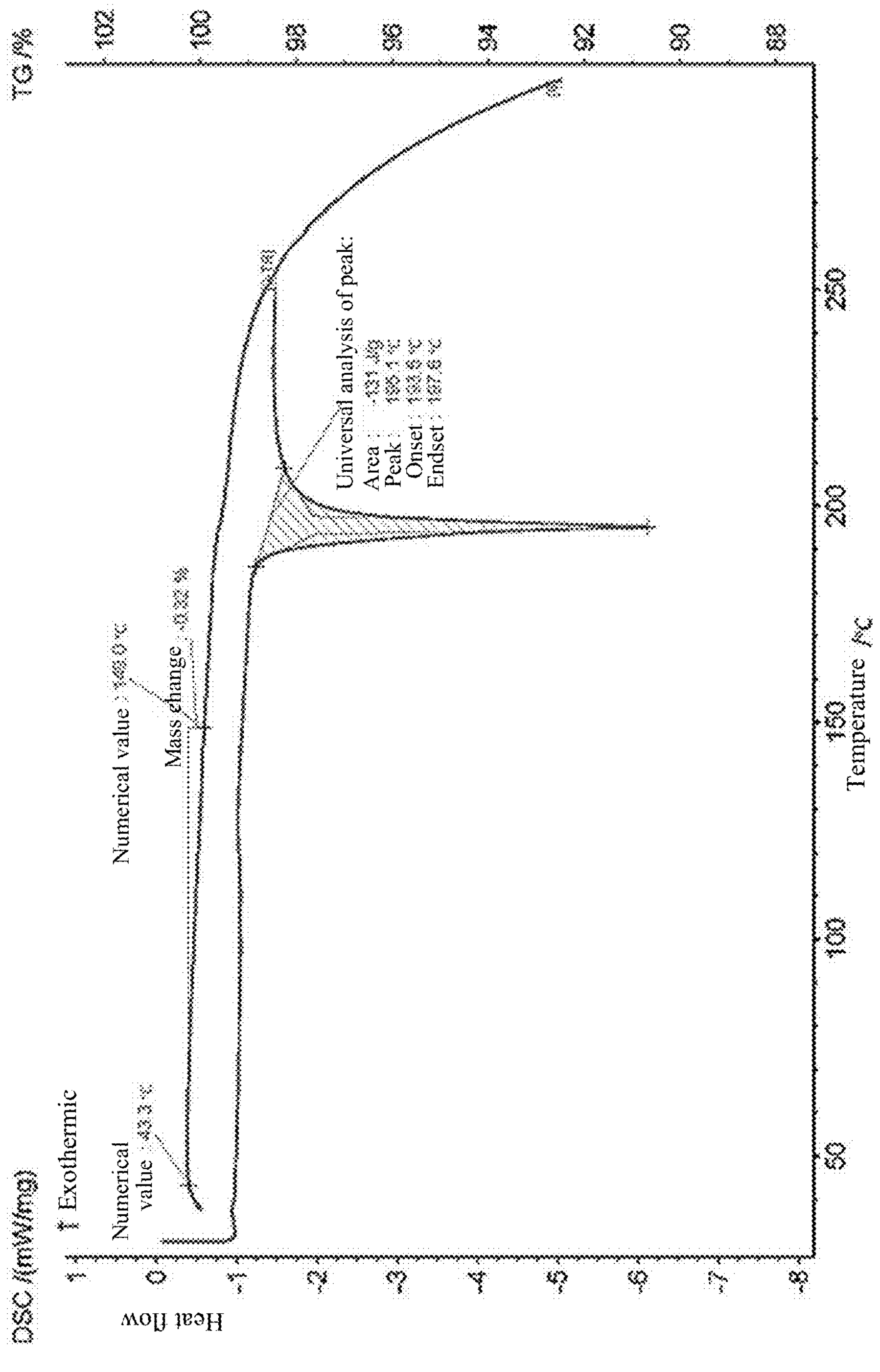
FIG. 4 is the TGA-DSC spectrum of crystal form II of the free base of formula (VI) (i.e., crystal form II of the free base of Example 40).
Figure 9:
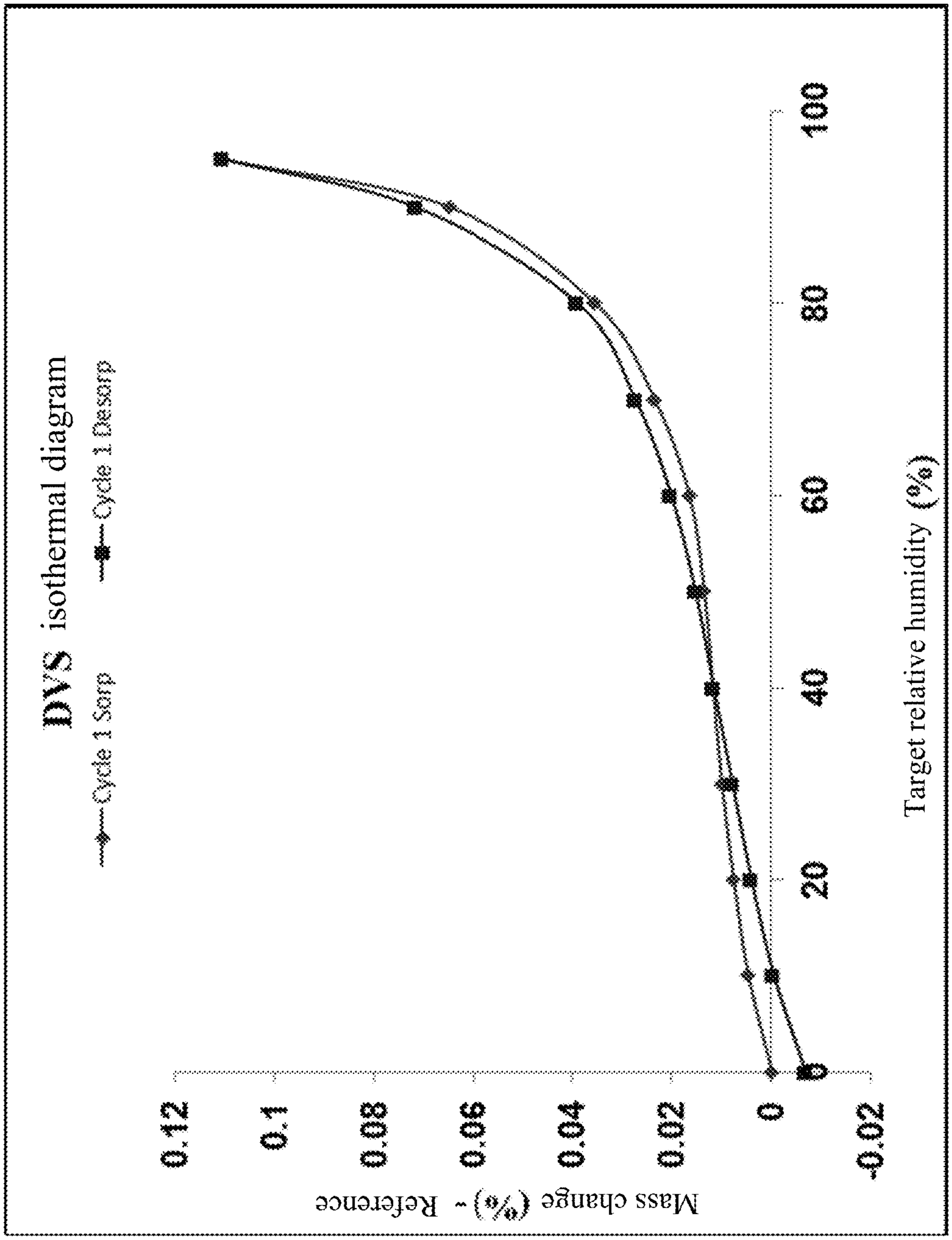
FIG. 9 is the DVS spectrum of crystal form II of the free base of formula (VI) (i.e., crystal form II of the free base of Example 40).

1.2 Preparation of Crystal Form II of the Free Base:

0.2 g of crystal form I of the free base of Example 40 was added to a 20 mL dry clean glass flask, heated to 160° C. for 5 minutes, and a sample was taken. After detection and analysis, the sample was crystal form II of the free base, having the XRPD pattern as shown in FIG. 3, the TGA-DSC spectrum as shown in FIG. 4, and the DVS spectrum as shown in FIG. 9.

Figure 5:
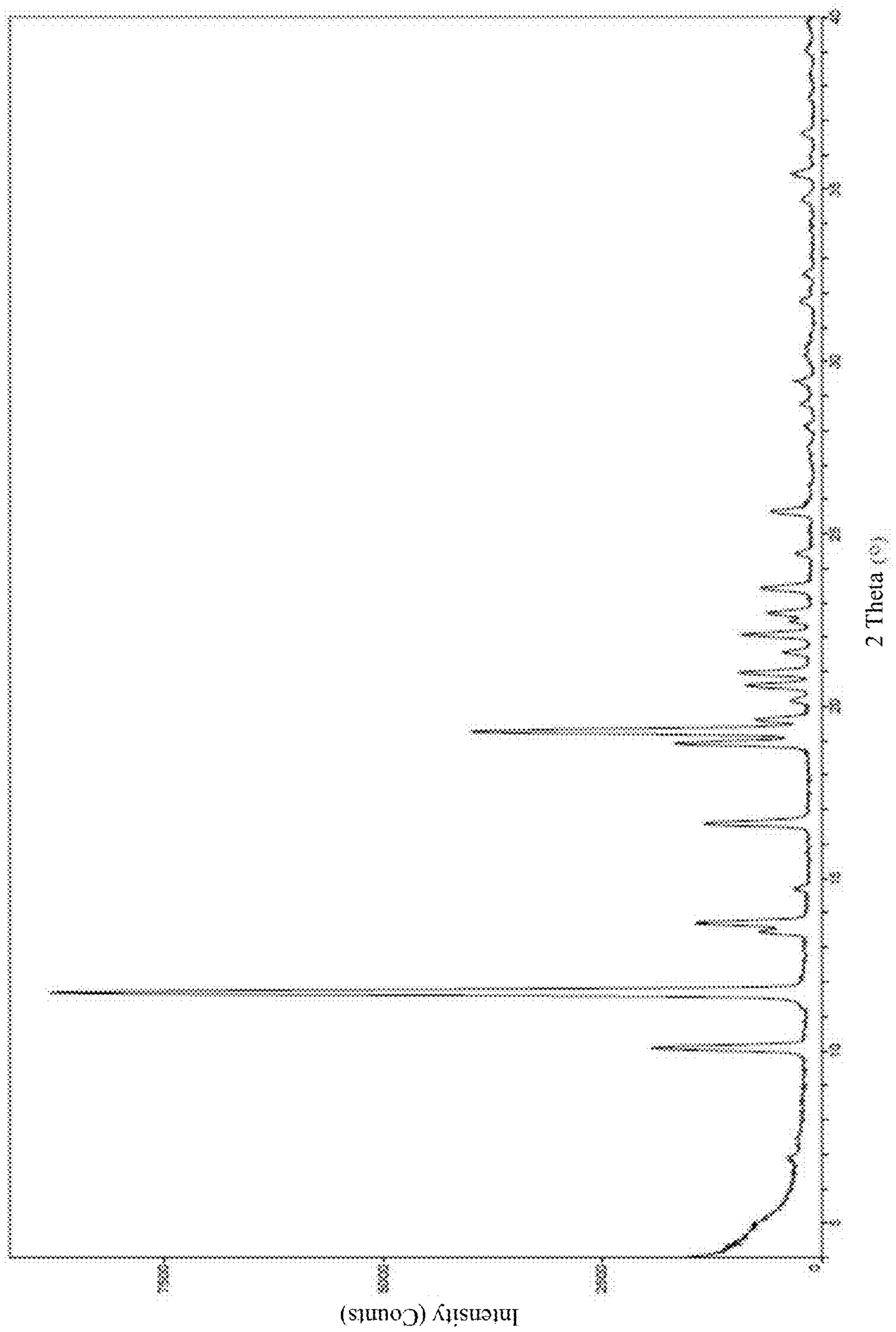
FIG. 5 is the XRPD pattern of crystal form III of the free base of formula (VI) (i.e., crystal form III of the free base of Example 40).
Figure 6:
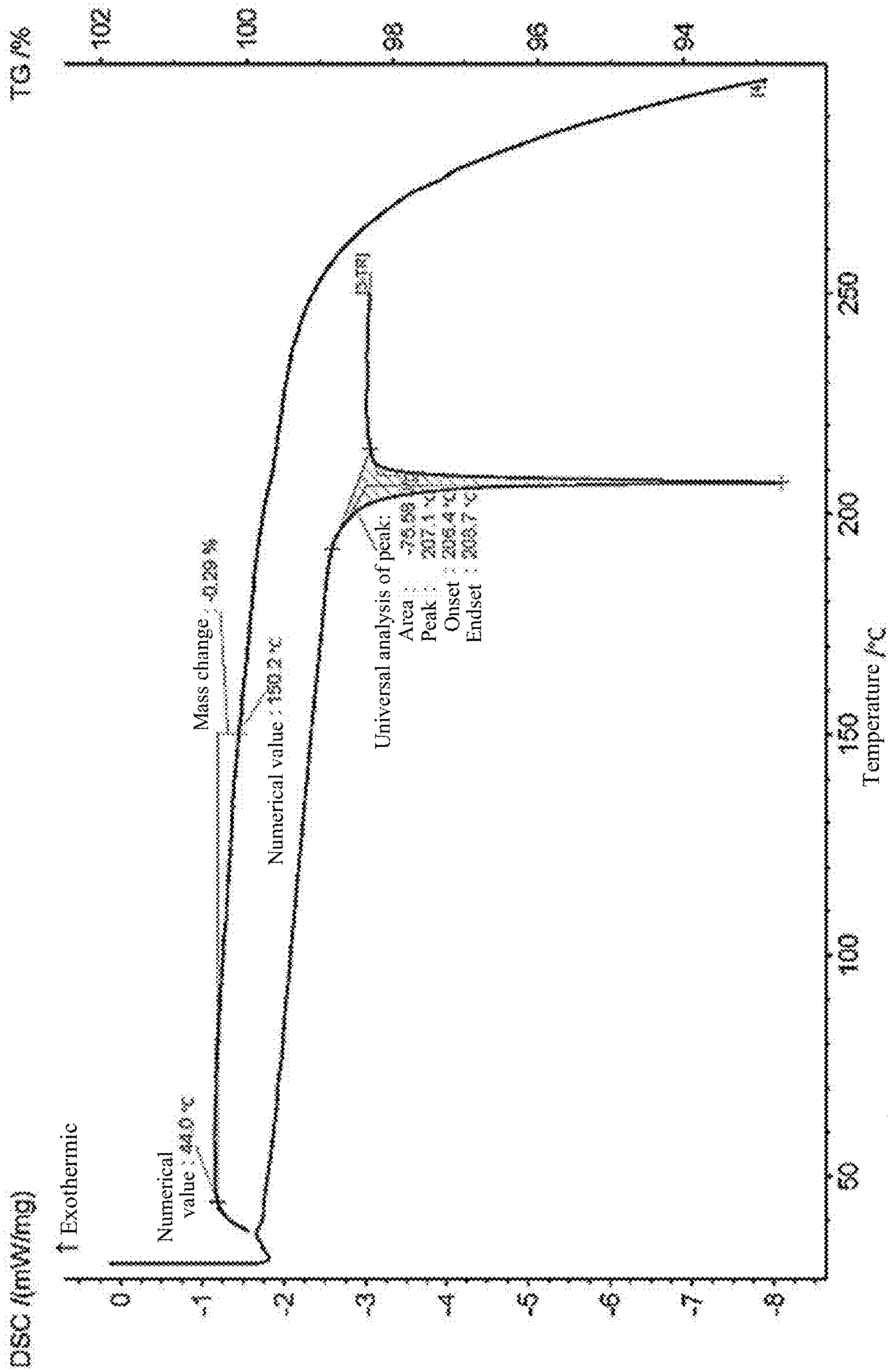
FIG. 6 is the TGA-DSC spectrum of crystal form III of the free base of formula (VI) (i.e., crystal form III of the free base of Example 40).
Figure 10:
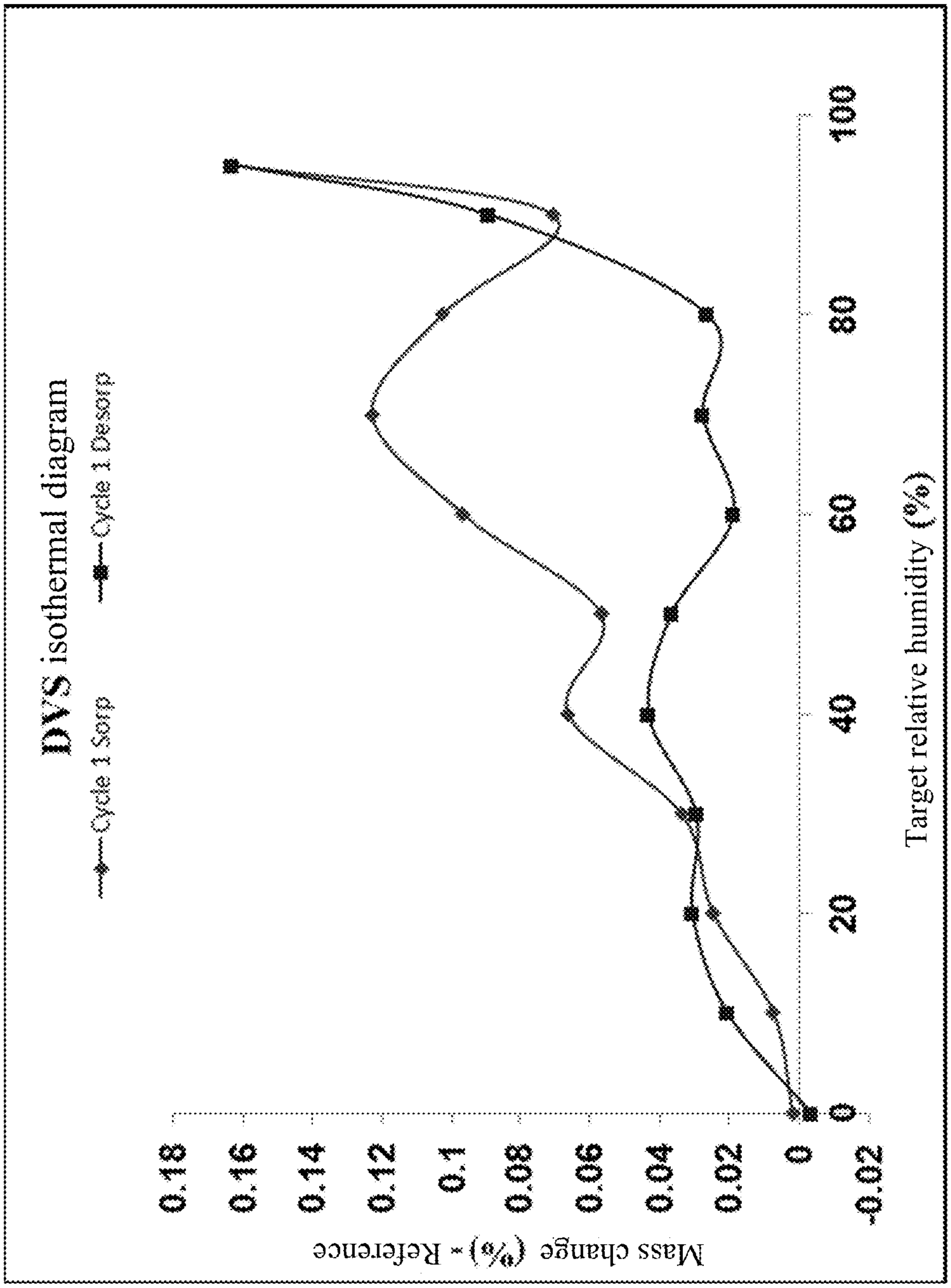
FIG. 10 is the DVS spectrum of crystal form III of the free base of formula (VI) (i.e., crystal form III of the free base of Example 40).

1.3 Preparation of Crystal Form III of the Free Base:

17.5 g of the free base compound of Example 40 (purity: ~86%) was dissolved in 96 mL of ethyl acetate, and the resulting solution was refluxed to clear. 96 mL of n-heptane was added dropwise. Flocculent solids precipitated during the addition process, and the precipitation rate was rapid. The mixture was naturally cooled to 20° C. in the oil bath, and then stirred at 10 to 20° C. for 1 hour. The mixture was filtered, and the filter cake was dried to obtain 12.1 g of white flocculent solid. After detection and analysis, the solid was crystal form III of the free base, having the XRPD pattern as shown in FIG. 5, the TGA spectrum as shown in FIG. 6, and the DSC spectrum as shown in FIG. 10.

2. Screening of Crystal Form of the Compound Salt Form 2.1 Experimental Objective:

Different salts in crystal form were prepared with different counter ion acid by crystallization methods such as natural evaporation, solution crystallization, anti-solvent crystallization and the like.

2.2 Experimental Instruments:

| Instrument name | Model | Manufacturer |
|---|---|---|
| Analytical Balance | BSA224S-CW | Sartorius |
| Analytical Balance | XPR2 | Mettler Toledo |
| Ultrasonic cleaner | SK5200LHC | Shanghai Kudos Ultrasonic instrument Co., Ltd |
| Pipette | 5000 μL, 1000 μL, 200 μL, 20 μL | Eppendorf |

2.3 Screening of Salt Form of the Compound of Formula (VI)

0.5 mL of good solvent was added to 50 mg of the free base of Example 40 (by an 1 mL pipette), and the resulting mixture was subjected to ultrasound to obtain a solution of the free base (concentration: 100 mg/mL). Corresponding counter ion acids were weighed (the amount of the counter ion acid was 1 to 1.2 equivalents), and dissolved by 200 μL of the same good solvent (by an 1 mL pipette) respectively. The counter ion acids were added to the suspension of the free base respectively under stirring, and stirred overnight. If there was no precipitation, then an anti-solvent was added to precipitate a precipitation. The mixture was centrifuged at high speed, the supernatant was removed, and the resulting solid precipitate was vacuum dried at 40° C. to obtain the corresponding salt of the compound.

The above good solvent was selected from the group consisting of methanol, ethanol, acetone, tetrahydrofuran, dichloromethane and 1,4-dioxane, and preferably ethyl acetate and ethanol.

The above poor solvent was selected from the group consisting of heptane, methyl tert-butyl ether, toluene, isopropyl ether and ethyl acetate, and preferably methyl tert-butyl ether and isopropyl ether.

The good solvent and poor solvent were miscible when used.

TABLE 10

Screening experimental results of crystal form of salt form of Example 40

| No. | Counter ion acid name | Counter ion acid weight mg (μL) | Solid state | XRPD result | FIG. |
|---|---|---|---|---|---|
| 1 | Sulfuric acid | 14.85 mg | Dark brown oil | / | / |
| 2 | p-Toluenesulfonic acid | 26.87 mg | Dark brown oil | / | / |
| 3 | Methanesulfonic acid | 14.02 mg | White solid | Crystal form | 7 |
| 4 | 1,5-Naphthalenedisulfonic acid | 51.57 mg | Dark brown oil | / | / |

3. Solubility Experiment 3.1 Experimental Objective:

The solubility of the free base and salt of the compound in water, Fasted State Simulated Gastric Fluid (FaSGF), Fasted State Simulated Intestinal Fluid (FaSSIF) and Fed State Simulated Intestinal Fluid (FeSSIF) was compared, so as to provide a basis for evaluating the druggability of the crystal form and salt.

3.2 Experimental Scheme:

About 2 to 3 mg of crystal forms I, II and III of the free base of Example 40 were weighed, suspended in 1 mL of Fasted State Simulated Gastric Fluid (FaSSGF), Fasted State Simulated Intestinal Fluid (FaSSIF), Fed State Simulated Intestinal Fluid (FeSSIF) and pure water respectively, and shaked for 24 hours. Thermodynamic solubility of the compound at 37° C. was determined using HPLC by external standard method.

3.3 Experimental Results:

3.3.1 Solubility results of crystal forms I, II and III of the free base of Example 40 are as shown in Table 11 below:

TABLE 11

Solubility experimental results of crystal form of the free base and salt of Example 40

| Medium | Solubility (μg/mL) | | |
|---|---|---|---|
| | Crystal form I | Crystal form II | Crystal form III |
| Water | <1 | <1 | <1 |
| FaSSGF | <1 | <1 | <1 |
| FaSSIF | 3.262 | 3.705 | 4.914 |
| FeSSIF | 18.213 | 18.495 | 28.166 |

It can be seen from the solubility results of crystal forms I, II and III of the free base of Example 40 in the four media that the solubility of the three crystal forms of the free base of Example 40 is low, wherein the solubility of crystal form I of the free base is the lowest, indicating that crystal form I of the free base is the most stable crystal form under the current temperature condition.

4. Hygroscopicity Experiment 4.1 Experimental Objective:

The hygroscopicity of crystal forms I, II and III of the free base of Example 40 under different relative humidity conditions was investigated, so as to provide a basis for screening of the crystal form and salt of the compound, production and storage.

4.2 Experimental Scheme:

10 to 15 mg of the free base of Example 40 was placed in the sample chamber of DVS. DVS was carried out, and the vapour sorption weight gain percentage of the compound at 80% RH was recorded at the same time.

4.3 Instrument Parameters:

The DVS experiment parameters are as follows:

| | |
|---|---|
| Test temperature | 25° C. |
| Mass change rate | dm/dt = 0.02%, |
| Stable duration | Minimum 10 min, maximum 180 min |
| Drying duration | Equilibrating at 0% RH for 120 min |
| RH (%) measuring gradient | 10% |
| RH (%) measuring range | 0-95-0% |
| Cycles | 2 |

4.4 Experimental Results:

4.4.1 Hygroscopicity results of crystal forms I, II and III of the free base of Example 40 are as shown in Table 12 below:

TABLE 12

Hygroscopicity experimental results of different crystal forms of the free base of Example 40

| No. | Free base | Hygroscopicity (25° C./80% RH) | FIG. |
|---|---|---|---|
| 1 | Crystal form I | 0.07% | 8 |
| 2 | Crystal form II | 0.03% | 9 |
| 3 | Crystal form III | 0.10% | 10 |

Crystal forms 1, II and III of the free base of Example 40 had no hygroscopicity.

5. Competitive Experiment of Different Crystal Forms of the Free Base 5.1 Experimental Objective:

The stability among crystal forms I, II and III of the free base of Example 40 was investigated, so as to select the stable crystal form.

5.2 Experimental Scheme:

Multiple portions of about 20 mg of crystal forms I, II and III of the free base of Example 40 were accurately weighed, and mixed in pairs in equal amounts. Methyl tert-butyl ether and n-heptane were added respectively, and the resulting mixture was stirred at 40° C. for 7 days. The mixture was centrifuged at high speed, the supernatant was removed, and the resulting solid precipitate was vacuum dried in an oven at 40° C. and characterized by XRPD.

5.3 Experimental Results:

The competitive results of crystal forms I, II and III of the free base of Example 40 are as shown in Table 13 below:

TABLE 13

Competitive test results of different crystal forms of the free base of Example 40

| | XRPD result | | |
|---|---|---|---|
| Solvent | Crystal form I + crystal form II | Crystal form I + crystal form III | Crystal form II + crystal form III |
| n-heptane | Crystal form I + crystal form II | Crystal form I + crystal form III | Crystal form II + crystal form III |
| Methyl tert-butyl ether | Crystal form I | Crystal form 1 | Crystal form 1 |

It can be seen from the results in the table that crystal forms I, II and III of the free base of Example 40 were almost insoluble in n-heptane, and no crystal form conversion had occurred; in methyl tert-butyl ether, the other two crystal forms were eventually converted to crystal form I, indicating that crystal form I of the free base is the stable crystal form.

6. Solid Stability Experiment 6.1 Experimental Objective:

The physicochemical stability of candidate crystal forms I, II and III of the free base of Example 40 under influencing factors such as high temperature, high humidity and strong light was investigated, so as to provide a basis for the production and storage of the compound.

6.2 Experimental Scheme:

About 5 mg of crystal form I of the free base of Example 40 was accurately weighed, and placed in a 60° C. oven (sealed) or light box (5000±500 lux, sealed), or placed under room temperature/90% RH (saturated aqueous $KNO_3$ solution, open) or high temperature and high humidity (50° C./75% RH, saturated aqueous sodium chloride solution, open) respectively to investigate for 5 and 10 days. The related substance change of the free base was calculated by chromatographic peak area normalization method.

6.3 Experimental Results:

1) The physicochemical stability results of crystal form I of the free base of Example 40 are as shown in Table 14 below:

TABLE 14

Stability experimental results of the free base of Example 40

| | Sample name | | | | | | | | |
|---|---|---|---|---|---|---|---|---|---|
| | Initial sample | 60° C. Sealed | | RT/90% RH Open | | Light 5k lux Sealed | | 50° C./75% RH Open | |
| Investigated factor | 0 d Total impurities (%) | 5 d Total impurities (%) | 10 d Total impurities (%) | 5 d Total impurities (%) | 5 d Total impurities (%) | 10 d Total impurities (%) | 10 d Total impurities (%) | 5 d Total impurities (%) | 10 d Total impurities (%) |
| Crystal form I of the free base | 0.59 | 0.55 | 0.56 | 0.56 | 0.56 | 0.57 | 0.56 | 0.56 | 0.59 |

After crystal form I of the free base was placed under influencing factors of high temperature, high humidity and light for 10 days, the impurities did not increase, indicating that it has good physicochemical stability.

7. Crystal Form Stability Experiment 7.1 Experimental Objective:

The crystal form stability of crystal form I of the free base of Example 40 under influencing factors such as high temperature, high humidity and strong light was investigated.

7.2 Experimental Scheme:

About 5 mg of crystal form I of the free base of Example 40 was accurately weighed, and placed under influencing factors of light, 40° C., 60° C., 25° C./RH75% or 25° C./RH90% respectively for 5, 10 and 30 days. X-ray powder diffraction assay was carried out, and the obtained data was compared with the initial data.

7.3 Experimental Results:

1) The crystal form stability results of crystal form I of the free base of Example 40 are as shown in Table 15 below:

TABLE 15

Crystal form stability experimental results of crystal form I of the free base of Example 40

| Condition | | No. 1 | 2 | 3 | 4 | 5 | 6 | 7 | 8 | 9 | 10 | 11 |
|---|---|---|---|---|---|---|---|---|---|---|---|---|
| / | 0 day | 7.3 | 11.1 | 11.9 | 12.6 | 16.7 | 17.4 | 20.2 | 20.6 | 21.9 | 23.9 | 38.4 |
| Light | 5 days | 7.3 | 11.0 | 11.9 | 12.5 | 16.6 | 17.3 | 20.1 | 20.6 | 22.1 | 23.9 | 38.3 |
| | 10 days | 7.3 | 11.1 | 11.9 | 12.5 | 16.7 | 17.3 | 20.2 | 20.5 | 21.9 | 23.9 | 38.3 |
| 40° C. | 5 days | 7.2 | 11.0 | 11.8 | 12.5 | 16.6 | 17.3 | 20.1 | 20.5 | 22.1 | 23.8 | 38.3 |
| | 10 days | 7.3 | 11.0 | 11.8 | 12.5 | 16.6 | 17.3 | 20.2 | 20.5 | 21.9 | 23.8 | 38.2 |
| | 30 days | 7.2 | 11.0 | 11.8 | 12.5 | 16.6 | 17.3 | 20.1 | 20.5 | 22.0 | 23.7 | 38.2 |
| 60° C. | 5 days | 7.1 | 10.9 | 11.7 | 12.4 | 16.5 | 17.2 | 20.0 | 20.7 | 22.0 | 24.0 | 38.2 |
| | 10 days | 7.2 | 10.9 | 11.7 | 12.4 | 16.5 | 17.2 | 20.1 | 20.7 | 22.0 | 24.0 | 38.2 |
| | 30 days | 7.2 | 11.0 | 11.8 | 12.5 | 16.6 | 17.3 | 20.1 | 20.4 | 21.8 | 23.8 | 38.2 |
| 25° C. RH75% | 5 days | 7.3 | 11.0 | 11.8 | 12.5 | 16.6 | 17.3 | 20.1 | 20.5 | 21.7 | 24.1 | 38.2 |
| | 10 days | 7.3 | 11.0 | 11.8 | 12.5 | 16.6 | 17.3 | 20.1 | 20.5 | 21.8 | 24.1 | 38.2 |
| | 30 days | 7.1 | 11.2 | 11.7 | 12.4 | 16.5 | 17.2 | 20.0 | 20.7 | 22.0 | 24.0 | 38.2 |
| 25° C. RH90% | 5 days | 7.2 | 11.0 | 11.8 | 12.5 | 16.5 | 17.3 | 20.1 | 20.5 | 21.7 | 24.1 | 38.3 |
| | 10 days | 7.2 | 11.0 | 11.8 | 12.5 | 16.6 | 17.3 | 20.2 | 20.5 | 21.8 | 23.8 | 38.3 |
| | 30 days | 7.2 | 11.0 | 11.8 | 12.5 | 16.6 | 17.3 | 20.1 | 20.5 | 21.8 | 24.0 | 38.2 |

The results show that under different influencing factors, the X-ray powder diffraction assay data are consistent with the initial data. No crystal form conversion had occurred, indicating that crystal form I of the free base is stable. It should be emphasized that those skilled in the art know that the general diffraction angle error of a crystal form is within the range of ±0.2°. Individual peaks of a crystal form not within the scope of the present invention do not mean that such crystal form is a new crystal form. Those skilled in the art know that a crystal form still belongs to the crystal form of the present invention if there are differences in individual peaks.

8. Single Crystal Culture 8.1 Experimental Objective:

A single crystal was cultured to resolve the structure of the free base of Example 40.

8.2 Experimental Scheme:

About 20 mg of the free base of Example 40 was added into a 1.5 mL of glass flask, to which 1 mL of toluene was added. The mixture was heated to 50° C. to dissolve the compound, and filtered through a 0.45 μm organic nylon membrane. The resulting filtrate was placed in a clean glass flask preheated to 50° C., and slowly cooled at room temperature. After about one day, colorless crystal particles, namely the single crystal of crystal form I of the free base of Example 40, were precipitated.

8.3 Experimental Results:

The single crystal data of crystal form I of the free base of Example 40 is shown in Table 18 below:

TABLE 16

Single crystal data of crystal form I of the free base of Example 40

| | |
|---|---|
| $C_{26}H_{37}N_3O_2$ | $D_x$ = 1.181 Mg $m^{-3}$ |
| $M_r$ = 423.58 | Cu K□ radiation, □ = 1.54178 Å |
| Orthorhombic, $P2_12_12_1$ | Cell parameters from 9852 reflections |
| a = 9.376 (2) Å | □ = 4.6-74.4° |
| b = 10.533 (3) Å | □ = 0.59 $mm^{-1}$ |
| c = 24.117 (4) Å | T = 110K |
| V = 2381.6 (9) $Å^3$ | Block, colourless |
| Z = 4 | 0.19 × 0.08 × 0.03 mm |
| F(000) = 920 | |

Figure 11:
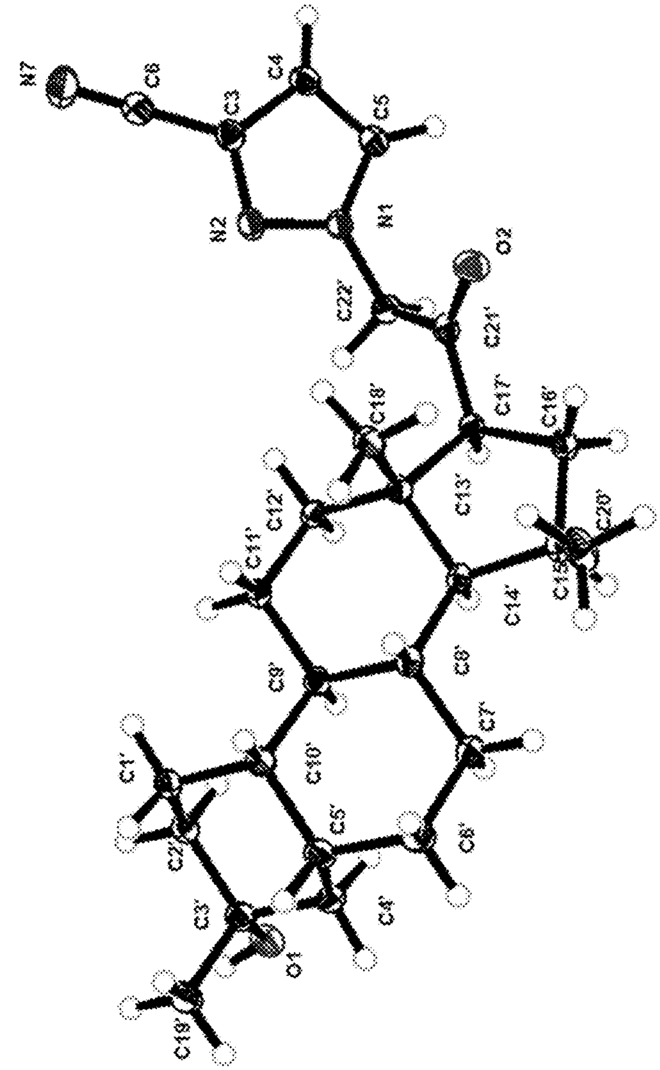
FIG. 11 is the schematic diagram of the single crystal structure of crystal form I of the free base of formula (VI) (i.e., crystal form I of the free base of Example 40).

The single crystal results show that:

The unit cell structure of the single crystal of crystal form I of the free base of Example 40 is orthogonal, each unit cell contains 4 molecules, and the chiral molecular configuration optimized with single crystal characterization is consistent with the theoretical structure of chemical synthesis. The XRD pattern fitted from the single crystal data is consistent with that of crystal form I of the free base of Example 40, indicating that the single crystal of Example 40 formed at room temperature is crystal form I of the free base. The specific structure is shown in FIG. 11.

What is claimed is:

1. A crystal form of formula (VI), having the following structure:

(VI)

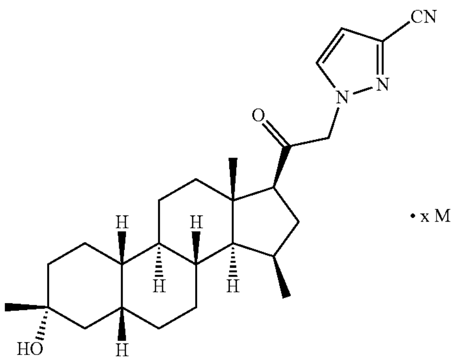

wherein x is 0, the crystal form is crystal form I of free base, the X-ray powder diffraction pattern thereof has any 3 to 11 of the diffraction peaks at 2θ (±0.2°) of 16.7, 12.6, 17.4, 7.3, 20.2, 20.6, 11.9, 11.1, 23.9, 21.9 and 38 or, wherein x is 0, the crystal form is crystal form II of free base, the X-ray powder diffraction pattern thereof has diffraction peaks at 2θ (±0.2°) of 11.7, 13.4, 13.6, 16.6 and 18.9;

or, wherein x is 0, the crystal form is crystal form III of free base, the X-ray powder diffraction pattern thereof has diffraction peaks at 2θ (±0.2°) of 10.0, 11.7, 13.7, 16.6, 18.9 and 19.2:

or, wherein M is methanesulfonic acid, x is 1, the X-ray powder diffraction pattern thereof has diffraction peaks at 2θ (±0.2°) of 12.5, 13.5, 194 and 19.9.

2. The crystal form according to claim 1, wherein, the DSC spectrum of the crystal form I of free base has an endothermic peak at 151.4±0.5° C.;

or, the DSC spectrum of the crystal form II of free base has an endothermic peak at 193.5±0.5° C.;

or, the DSC spectrum of the crystal form III of free base has an endothermic peak at 206.4±0.5° C.

3. The crystal form according to claim 1, wherein the crystal form is crystal form I of free base and the X-ray powder diffraction pattern of the crystal form comprises any 5 to 8 or 6 to 8 of the diffraction peaks.

4. The crystal form according to claim 1, wherein the crystal form is crystal form I of free base and the X-ray powder diffraction pattern of the crystal form comprises any 3, 6, 8, 10 or 11 of the diffraction peaks.

5. The crystal form according to claim 1, wherein the crystal form is crystal form I of free base and the X-ray powder diffraction pattern of the crystal form has diffraction peaks at 2θ (±0.2°) of 16.7, 12.6 and 17.4;

the crystal form is crystal form II of free base and the X-ray powder diffraction pattern further has diffraction peaks at 2θ (±0.2°) of 9.5, 10.1, 14.7 and 19.3;

the crystal form is crystal form III of free base and the X-ray powder diffraction pattern further has diffraction peaks at 2θ (±0.2°) of 13.4, 19.6, 20.6, 20.9, 22.0, 22.7, 23.4 and 25.6;

or the X-ray powder diffraction pattern of the methanesulfonic acid crystal form further has diffraction peaks at 2θ (±0.2°) of 15.1, 15.8, 16.5, 17.3, 18.7 and 23.1.

6. The crystal form according to claim 5, wherein the crystal form is crystal form I of free base and the X-ray powder diffraction pattern of the crystal form further comprises one or more diffraction peaks at 2θ (±0.2°) of 7.3, 20.2, 20.6, 11.9, 11.1, 23.9, 21.9 and 38.4;

the crystal form is crystal form II of free base and the X-ray powder diffraction pattern further has diffraction peaks at 2θ (±0.2°) of 19.6, 20.6, 20.9, 21.6, 22.1, 22.5, 22.7 and 24.4;

or the crystal form is crystal form of methanesulfonic acid and the X-ray powder diffraction pattern further has diffraction peaks at 2θ (±0.2°) of 11.1, 11.5, 13.9, 18.5, 213, 21.7, 26.5 and 28.9.

7. The crystal form according to claim 1, wherein the crystal form is crystal form I of free base and the X-ray powder diffraction pattern of the crystal form has diffraction peaks at 2θ (±0.2°) of 16.7, 12.6, 17.4, 7.3, 20.2 and 20.6.

8. The crystal form according to claim 1, wherein the crystal form is crystal form I of free base and the X-ray powder diffraction pattern of the crystal form has diffraction peaks at 2θ (±0.2°) of 16.7, 12.6, 17.4, 73, 20.2, 20.6, 11.9 and 11.1.

9. The crystal form according to claim 1, wherein the crystal form is crystal form I of free base and the X-ray powder diffraction pattern of the crystal form has diffraction peaks at 2θ (±0.2°) of 16.7, 12.6, 17.4, 7.3, 20.2, 20.6, 11.9, 11.1, 23.9 and 21.9.

10. The crystal form according to claim 1, wherein the crystal form is crystal form I of free base, and the X-ray powder diffraction pattern of the crystal form has diffraction peaks at 2θ (±0.2°) of 16.7, 12.6, 17.4, 7.3, 20.2, 20.6, 11.9, 11.1, 23.9, 21.9 and 38.4.

Figure 7:
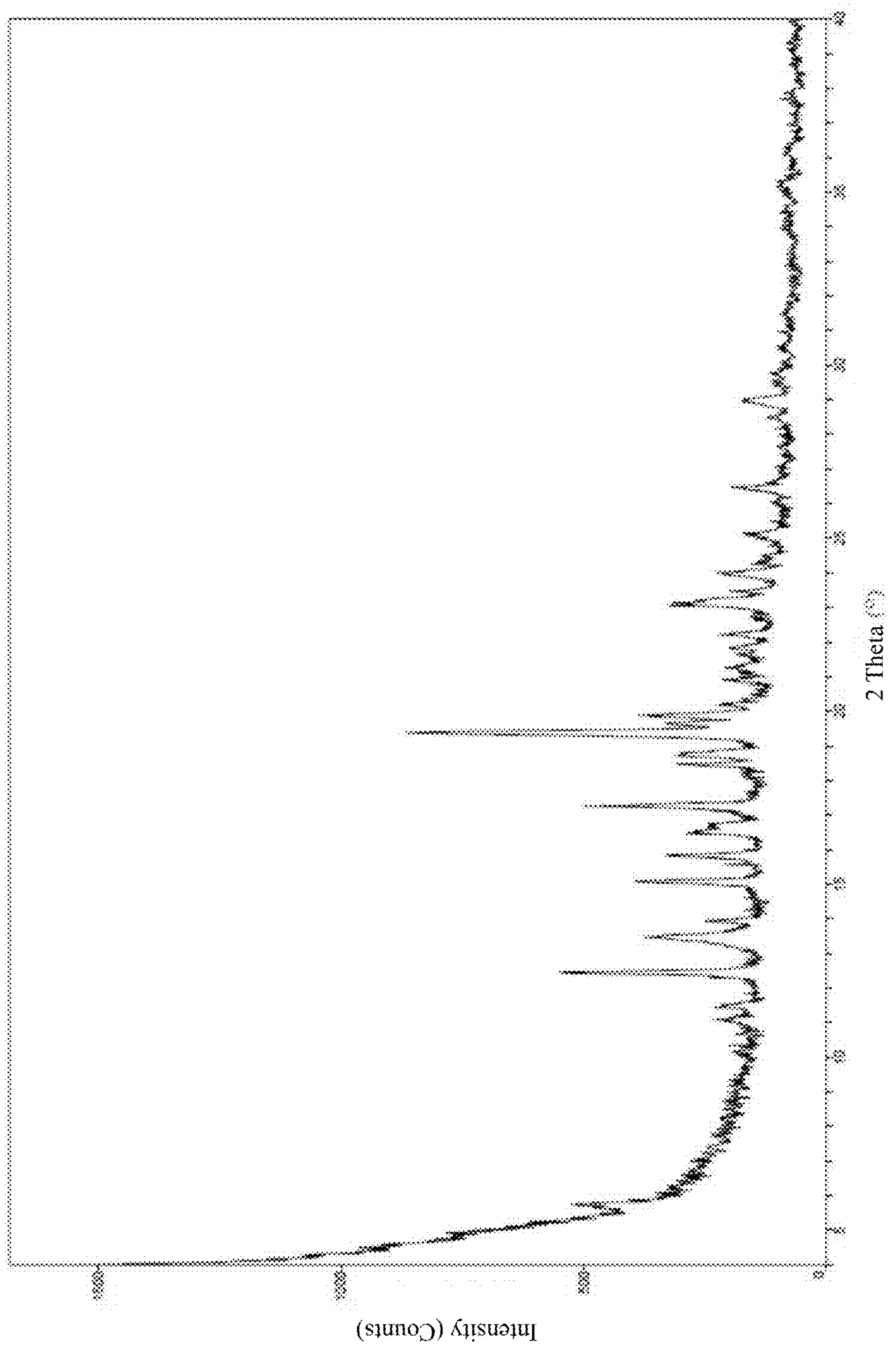
FIG. 7 is the XRPD pattern of the mesylate of formula (VI) (i.e., the mesylate of Example 40).

11. The crystal form according to claim 1, wherein the crystal form is crystal form I of free base and the X-ray powder diffraction pattern of the crystal form is substantially as shown in FIG. 1;

the crystal form is crystal form II of free base and the X-ray powder diffraction pattern thereof is substantially as shown in FIG. 3;

the crystal form is crystal form III of free base and the X-ray powder diffraction pattern thereof is substantially as shown in FIG. 5; or the crystal form is crystal form of methanesulfonic acid and the X-ray powder diffraction pattern thereof is substantially as shown in FIG. 7.

12. A pharmaceutical composition, comprising a therapeutically effective amount of the crystal form of the compound of formula (VI) according to claim 1, and one or more pharmaceutically acceptable carriers.

13. A crystal form of a compound of formula (VI), having the following structure, (VI)

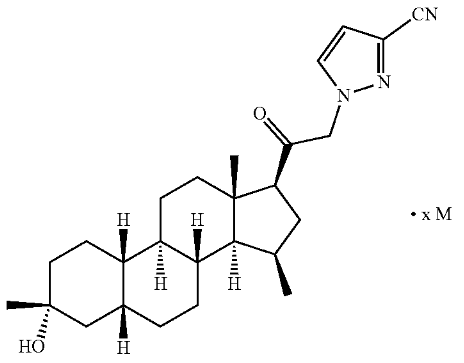

wherein x is 0, the crystal form is crystal form I of free base and the X-ray powder diffraction pattern thereof has diffraction peaks at 2θ (±0.2°) of 16.7, 12.6 and 14.6;

the crystal form I of free base has diffraction peaks at 2θ (±0.2°) of 7.3, 13.2, 17.4, 19.4, 20.2 and 20.6; or the crystal form I of free base has diffraction peaks at 2θ (±0.2°) of 9.2, 11.1, 11.9, 19.6, 22.3 and 25.5.

14. A pharmaceutical composition, comprising a therapeutically effective amount of the crystal form of the compound of formula (VI) according to claim 13, and one or more pharmaceutically acceptable carriers.

* * * * *